US 7,074,414 B2
(12) United States Patent
Dowling et al.

(10) Patent No.: US 7,074,414 B2
(45) Date of Patent: *Jul. 11, 2006

(54) COLD-ADAPTED EQUINE INFLUENZA VIRUSES

(75) Inventors: Patricia W. Dowling, Pittsburgh, PA (US); Julius S. Youngner, Pittsburgh, PA (US)

(73) Assignee: The University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 269 days.

This patent is subject to a terminal disclaimer.

(21) Appl. No.: 10/181,585

(22) PCT Filed: Feb. 16, 2001

(86) PCT No.: PCT/US01/05048

§ 371 (c)(1),
(2), (4) Date: Nov. 25, 2002

(87) PCT Pub. No.: WO01/60849

PCT Pub. Date: Aug. 23, 2001

(65) Prior Publication Data

US 2005/0175985 A1    Aug. 11, 2005

Related U.S. Application Data

(63) Continuation-in-part of application No. 09/506,286, filed on Feb. 16, 2000, now Pat. No. 6,482,414.

(51) Int. Cl.
*A61K 39/145* (2006.01)
*A61K 39/12* (2006.01)
*C07K 14/11* (2006.01)

(52) U.S. Cl. .............................. 424/209.1; 424/204.1; 424/186.1; 530/350

(58) Field of Classification Search ................ 530/350; 435/235.1
See application file for complete search history.

(56) References Cited

U.S. PATENT DOCUMENTS

| 3,518,347 | A | 6/1970 | Pavilanis et al. ............. 424/89 |
| 4,631,191 | A | 12/1986 | Dale et al. ..................... 424/88 |
| 4,683,137 | A | 7/1987 | Coggins et al. .............. 424/89 |
| 4,693,893 | A | 9/1987 | Campbell et al. ............ 424/89 |
| 4,920,213 | A | 4/1990 | Dale et al. ..................... 536/27 |
| 5,149,531 | A | 9/1992 | Youngner et al. ............ 424/89 |
| 5,690,937 | A | 11/1997 | Parkin et al. ............ 424/199.1 |
| 2004/0137015 | A1* | 7/2004 | Dowling et al. ......... 424/209.1 |

FOREIGN PATENT DOCUMENTS

| WO | WO83/03546 | 10/1983 |
| WO | WO 92/00097 | 1/1992 |
| WO | WO 93/21310 | 10/1993 |
| WO | WO 00/09702 | 2/2000 |

OTHER PUBLICATIONS

Brundage-Anguish, et al., 1982, *Am J Vet Res*, 43(5), pp. 869-874.
Enami, et al., 1990, *PNAS*, vol. 87, pp. 3802-3805.
Estola, et al., 1976, *Nord Vet med* vol. 28(7-8), pp. 353-356.
Hannant, et al., Feb. 6, 1988, *Vet Rec*, pp. 125-128.
Holmes, et al., 1992, *Equine Infectious Diseases VI: Proceedings of the Sixth International Conference*, Jul. 7-11, 1991, pp. 253-258.
Ilobi, et al., 1998, *Arch Virol*, vol. 143, pp. 891-901.
Kucera, et al., 1977, *Can J Comp Med*, 41(3), pp. 326-331.

(Continued)

*Primary Examiner*—Scott D. Priebe
*Assistant Examiner*—Michael Burkhart
(74) *Attorney, Agent, or Firm*—Heska Corporation

(57) ABSTRACT

The present invention provides experimentally-generated cold-adapted equine influenza viruses, and reassortant influenza A viruses comprising at least one genome segment of such an equine influenza virus, wherein the equine influenza virus genome segment confers at least one identifying phenotype of the cold-adapted equine influenza virus, such as cold-adaptation, temperature sensitivity, dominant interference, or attenuation. Such viruses are formulated into therapeutic compositions to protect animals from diseases caused by influenza A viruses, and in particular, to protect horses from disease caused by equine influenza virus. The present invention also includes methods to protect animals from diseases caused by influenza A virus utilizing the claimed therapeutic compositions. Such methods include using a therapeutic composition as a vaccine to generate a protective immune response in an animal prior to exposure to a virulent virus, and using a therapeutic composition as a treatment for an animal that has been recently infected with a virulent virus, or is likely to be subsequently exposed to virulent viruses in a few days whereby the therapeutic composition interferes with the growth of the virulent virus, even in the absence of immunity. The present invention also provides methods to produce cold-adapted equine influenza viruses, and reassortant influenza A viruses having at least one genome segment of an equine influenza virus generated by cold-adaptation.

2 Claims, No Drawings

OTHER PUBLICATIONS

Mumford, et al., 1983, *J Hyg (Lond)*, vol. 90(3), pp. 385-395.
Noble, et al., 1994, *J Gen Virol* vol. 75, pp. 3485-3491.
Reed, et al., 1938, *The American Journal of Hygiene*, vol. 27, pp. 493-497.
Timoney, P.J., 1996, *Comp Immunol Microbiol Infect Dis*, vol. 19(3), pp. 205-211.
USDA, 9 CFR 113.2XX, Oct. 28, 1994, Supplemental Assay Method for Conducting the Hemagglutination Inhibition Assay for Equine Influenza Antibody.
Van Maanen, et al., 1992, *Vet Q*, vol. 14(1), pp. 13-17.
Van Oirschot, et al., 1991, *Zentralbl Veterinarmed [B]*, vol. 38(5), pp. 391-396.
Wood, et al., 1983, *J Hyg (Lond)* vol. 90(3), pp. 371-384.
Wilson, et al., 1993, *Vet Clin North Am Equine Practi*, vol. 9(2), pp. 257-282.
Youngner, et al., 1994, *J. of Clinical of Microbiology*, vol. 32(3), pp. 750-754.
Lunn et al., 1999, *Vaccine*, vol. 17, pp. 2245-2258.
Romanova et al., 1997, *Vaccine*, vol. 15, No. 6/7, pp. 653-658.
Talon et al., 2000, *PNAS*, vol. 97, No. 8, pp. 4309-4314.
Daly, et al., 1996, *Journal of General Virology*, vol. 77, pp. 661-671.
Lindstrom, et al., 1998, *Archives of Virology*, vol. 143, No. 8, pp. 1585-1598.

* cited by examiner

COLD-ADAPTED EQUINE INFLUENZA VIRUSES

CROSS-REFERENCE TO RELATED APPLICATION

This application is a 35 U.S.C. 371 of International PCT Application No. PCT/US01/05048, filed Feb. 16, 2001; which is a continuation-in-part of U.S. patent application Ser. No. 09/506,286, filed Feb. 16, 2000, now issued as U.S. Pat. No. 6,482,414 B1; all entitled "COLD-ADAPTED EQUINE INFLUENZA VIRUSES" and incorporated herein by reference in their entirety.

FIELD OF THE INVENTION

The present invention relates to nucleic acids and proteins of experimentally-generated cold-adapted equine influenza viruses, and particularly to cold-adapted equine influenza viruses having additional phenotypes, such as attenuation, dominant interference, or temperature sensitivity. The invention also includes reassortant influenza A viruses which contain at least one genome segment from such an equine influenza virus, such that the reassortant virus includes certain phenotypes of the donor equine influenza virus. The invention further includes genetically-engineered equine influenza viruses, produced through reverse genetics, which comprise certain identifying phenotypes of a cold-adapted equine influenza virus of the present invention. The present invention also relates to the use of these viruses in therapeutic compositions to protect animals from diseases caused by influenza viruses.

BACKGROUND OF THE INVENTION

Equine influenza virus has been recognized as a major respiratory pathogen in horses since about 1956. Disease symptoms caused by equine influenza virus can be severe, and are often followed by secondary bacterial infections. Two subtypes of equine influenza virus are recognized, namely subtype-1, the prototype being A/Equine/Prague/1/56 (H7N7), and subtype-2, the prototype being A/Equine/Miami/1/63 (H3N8). Presently, the predominant virus subtype is subtype-2, which has further diverged among Eurasian and North American isolates in recent years. The currently licensed vaccine for equine influenza is an inactivated (killed) virus vaccine. This vaccine provides minimal, if any, protection for horses, and can produce undesirable side effects, for example, inflammatory reactions at the site of injection. See, e.g., Mumford, 1987, *Equine Infectious Disease IV,* 207–217, and Mumford, et al., 1993, *Vaccine* 11, 1172–1174. Furthermore, current modalities cannot be used in young foals, because they cannot overcome maternal immunity, and can induce tolerance in a younger animal. Based on the severity of disease, there remains a need for safe, effective therapeutic compositions to protect horses against equine influenza disease.

Production of therapeutic compositions comprising cold-adapted human influenza viruses is described, for example, in Maassab, et al., 1960, *Nature* 7,612–614, and Maassab, et al., 1969, *J. Immunol.* 102, 728–732. Furthermore, these researchers noted that cold-adapted human influenza viruses, i.e., viruses that have been adapted to grow at lower than normal temperatures, tend to have a phenotype wherein the virus is temperature sensitive; that is, the virus does not grow well at certain higher, non-permissive temperatures at which the wild-type virus will grow and replicate. Various cold-adapted human influenza A viruses, produced by reassortment with existing cold-adapted human influenza A viruses, have been shown to elicit good immune responses in vaccinated individuals, and certain live attenuated cold-adapted reassortant human influenza A viruses have proven to protect humans against challenge with wild-type virus. See, e.g., Clements, et al., 1986, *J. Clin. Microbiol.* 23, 73–76. In U.S. Pat. No. 5,149,531, by Youngner, et al., issued Sep. 22, 1992, the inventors of the present invention further demonstrated that certain reassortant cold-adapted human influenza A viruses also possess a dominant interference phenotype, i.e., they inhibit the growth of their corresponding parental wild-type strain, as well as heterologous influenza A viruses.

U.S. Pat. No. 4,683,137, by Coggins et al., issued Jul. 28, 1987, and U.S. Pat. No. 4,693,893, by Campbell, issued Sep. 15, 1987, disclose attenuated therapeutic compositions produced by reassortment of wild-type equine influenza viruses with attenuated, cold-adapted human influenza A viruses. Although these therapeutic compositions appear to be generally safe and effective in horses, they pose a significant danger of introducing into the environment a virus containing both human and equine influenza genes.

SUMMARY OF THE INVENTION

The present invention provides nucleic acids and proteins of experimentally-generated cold-adapted equine influenza viruses, and reassortant influenza A viruses.

Examples of cold-adapted equine influenza viruses of the present invention include EIV-P821, identified by accession No. ATCC VR-2625; EIV-P824, identified by accession No. ATCC VR-2624; EIV-MSV+5, identified by accession No. ATCC VR-627; and progeny of such viruses. Cold-adapted equine influenza viruses of the invention, and their methods of making, are disclosed in related U.S. Pat. No. 6,177,082, by Dowling et al., issued Jan. 23, 2001; and WO 00/09702, by Dowling et al., published Feb. 24, 2000, both of which are incorporated herein by reference in their entirety.

The present invention also describes nucleic acid molecules encoding wild-type and cold-adapted equine influenza proteins PB2, NS, PB1, PA and NA. One embodiment of the present invention is an isolated equine nucleic acid molecule having a nucleic acid sequence selected from a group consisting of SEQ ID NO:5, SEQ ID NO:7, SEQ ID NO:8, SEQ ID NO:10, SEQ ID NO:13, SEQ ID NO:19, SEQ ED NO:20, SEQ ID NO:21, SEQ ID NO:23, SEQ ID NO:24, SEQ ID NO:26, SEQ ID NO:27, SEQ ID NO:29, SEQ ID NO:32, SEQ ID NO:34, SEQ ID NO:35, SEQ ID NO:36, SEQ ID NO:38, SEQ ID NO:39, SEQ ID NO:41, SEQ ID NO:42, SEQ ID NO:44, SEQ ID NO:45, SEQ ID NO:47, SEQ ID NO:48, SEQ ID NO:50, SEQ ID NO:51, SEQ ID NO:53, SEQ ID NO:60, SEQ ID NO:61, SEQ ID NO:63, SEQ ID NO:65, SEQ ID NO:66, SEQ ID NO:68, SEQ ID NO:70, SEQ ID NO:71, SEQ ID NO:73, SEQ ID NO:76, SEQ ID NO:82, SEQ ID NO:83, SEQ ID NO:84, SEQ ID NO:86, SEQ ID NO:87, SEQ ID NO:89, SEQ ID NO:94, SEQ ID NO:95, SEQ ID NO:97, SEQ ID NO:98, SEQ ID NO:100 and SEQ ID NO:102 and a nucleic acid molecule comprising a nucleic acid sequence which is fully complementary to any of such nucleic acid sequences. Another embodiment of the present invention is an isolated equine nucleic acid molecule that encodes a protein comprising an amino acid sequence selected from the group consisting of SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103. Another embodiment is an isolated equine influenza protein that comprises an amino acid sequence selected from a group consisting of SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103. Also included in the present invention is a virus that include any of these nucleic acid molecules or proteins. In one embodiment, such a virus is equine influenza virus or a reassortant virus.

DETAILED DESCRIPTION OF THE INVENTION

The present invention provides nucleic acids and proteins of experimentally-generated cold-adapted equine influenza viruses comprising certain defined phenotypes, which are disclosed herein. It is to be noted that the term "a" or "an" entity, refers to one or more of that entity; for example, "a cold-adapted equine influenza virus" can include one or more cold-adapted equine influenza viruses. As such, the terms "a" (or "an"), "one or more," and "at least one" can be used interchangeably herein. It is also to be noted that the terms "comprising," "including," and "having" can be used interchangeably. Furthermore, an item "selected from the group consisting of" refers to one or more of the items in that group, including combinations thereof.

A cold-adapted equine influenza virus of the present invention is a virus that has been generated in the laboratory, and as such, is not a virus as occurs in nature. Since the present invention also includes those viruses having the identifying phenotypes of such a cold-adapted equine influenza virus, an equine influenza virus isolated from a mixture of naturally-occurring viruses, i.e., removed from its natural milieu, but having the claimed phenotypes, is included in the present invention. A cold-adapted equine influenza virus of the present invention does not require any specific level of purity. For example, a cold-adapted equine influenza virus grown in embryonated chicken eggs may be in a mixture with the allantoic fluid (AF), and a cold-adapted equine influenza virus grown in tissue culture cells may be in a mixture with disrupted cells and tissue culture medium.

As used herein, an "equine influenza virus" is an influenza virus that infects and grows in equids, e.g., horses or ponies. As used herein, "growth" of a virus denotes the ability of the virus to reproduce or "replicate" itself in a permissive host cell. As such, the terms, "growth of a virus" and "replication of a virus" are used interchangeably herein. Growth or replication of a virus in a particular host cell can be demonstrated and measured by standard methods well-known to those skilled in the art of virology. For example, samples containing infectious virus, e.g., as contained in nasopharyngeal secretions from an infected horse, are tested for their ability to cause cytopathic effect (CPE), e.g., virus plaques, in tissue culture cells. Infectious virus may also be detected by inoculation of a sample into the allantoic cavity of embryonated chicken eggs, and then testing the AF of eggs thus inoculated for its ability to agglutinate red blood cells, i.e., cause hemagglutination, due to the presence of the influenza virus hemagglutinin (HA) protein in the AF.

Cold-adapted equine influenza viruses of the present invention are characterized primarily by one or more of the following identifying phenotypes: cold-adaptation, temperature sensitivity, dominant interference, and/or attenuation. As used herein, the phrase "an equine influenza virus comprises the identifying phenotype(s) of cold-adaptation, temperature sensitivity, dominant interference, and/or attenuation" refers to a virus having such a phenotype(s). Examples of such viruses include, but are not limited to, EIV-P821, identified by accession No. ATCC VR-2625, EIV-P824, identified by accession No. ATCC VR-2624, and EIV-MSV+5, identified by accession No. ATCC VR-2627, as well as EIV-MSV0, EIV, MSV+1, EIV-MSV+2, EIV-MSV+3, and EIV-MSV+4.

Pursuant to 37 CFR § 1.802 (a–c), cold-adapted equine influenza viruses, designated herein as EIV-P821, an EIV-P824 were deposited with the American Type Culture Collection (ATCC, 10801 University Boulevard, Manassas, Va. 20110-2209) under the Budapest Treaty as ATCC Accession Nos. ATCC VR-2625, and ATCC VR-2624, respectively, on Jul. 11, 1998. Cold-adapted equine influenza virus EIV-MSV+5 was deposited with the ATCC as ATCC Accession No. ATCC VR-2627 on Aug. 3, 1998. Pursuant to 37 CFR§ 1.806, the deposits are made for a term of at least thirty (30) years and at least five (5) years after the most recent request for the furnishing of a sample of the deposit was received by the depository. Pursuant to 37 CFR § 1.808 (a)(2), all restrictions imposed by the depositor on the availability to the public will be irrevocably removed upon the granting of the patent.

The present invention includes nucleic acid molecules isolated from equine influenza virus wild type strain A/equine/Kentucky/1/91 (H3N8), and cold-adapted equine influenza virus EIV-P821.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified.

The present invention includes nucleic acid molecules encoding wild-type and cold-adapted equine influenza virus proteins. Nucleic acid molecules of the present invention can be prepared by methods known to one skilled in the art. Proteins of the present invention can be prepared by methods known to one skilled in the art, i.e., recombinant DNA technology. Preferred nucleic acid molecules have coding strands comprising nucleic acid sequences SEQ ID NO:5, SEQ ID NO:7, SEQ ID NO:8, SEQ ID NO:10, SEQ ID NO:13, SEQ ID NO:19, SEQ ID NO:20, SEQ ID NO:21, SEQ ID NO:23, SEQ ID NO:24, SEQ ID NO:26, SEQ ID NO:27, SEQ ID NO:29, SEQ ID NO:32, SEQ ID NO:34, SEQ ID NO:35, SEQ ID NO:36, SEQ ID NO:38, SEQ ID NO:39, SEQ ID NO:41, SEQ ID NO:42, SEQ ID NO:44, SEQ ID NO:45, SEQ ID NO:47, SEQ ID NO:48, SEQ ID NO:50, SEQ ID NO:51, SEQ ID NO:53, SEQ ID NO:60, SEQ ID NO:61, SEQ ID NO:63, SEQ ID NO:65, SEQ ID NO:66, SEQ ID NO:68, SEQ ID NO:70, SEQ ID NO:71, SEQ ID NO:73, SEQ ID NO:76, SEQ ID NO:82, SEQ ID NO:83, SEQ ID NO:84, SEQ ID NO:86, SEQ ID NO:87, SEQ ID NO:89, SEQ ID NO:94, SEQ ID NO:95, SEQ ID NO:97, SEQ ID NO:98, SEQ ID NO:100 and SEQ ID NO:102 and/or a complement thereof. Complements are defined as two single strands of nucleic acid in which the nucleotide sequence is such that they will hybridize as a result of base pairing throughout their full length. Given a nucleotide sequence, one of ordinary skill in the art can deduce the complement.

Preferred nucleic acid molecules encoding equine influenza PB2 proteins are $nei_{wt1}PB2_{2341}$, $nei_{wt1}PB2_{2277}$, $nei_{ca1}PB2_{2341}$, and/or $nei_{ca1}PB2_{2277}$, the coding strands of which are represented by SEQ ID NO:24, SEQ ID NO:26, SEQ ID NO:27, and/or SEQ ID NO:29.

Preferred nucleic acid molecules encoding equine influenza NS proteins are $nei_{wt1}NS_{891}$, $nei_{wt1}NS_{690}$, $nei_{wt3}NS_{888}$, $nei_{wt4}NS_{468}$, $nei_{wt4}NS_{293}$, $nei_{ca1}NS_{888}$, and/or $nei_{ca1}NS_{690}$, the coding strands of which are represented by SEQ ID NO:32, SEQ ID NO:34, SEQ ID NO:35, SEQ ID NO:36, SEQ ID NO:38, SEQ ID NO:39 and/or SEQ ID NO:41.

Preferred nucleic acid molecules encoding equine influenza PB1-N proteins are $nei_{wt1}PB1-N_{1229}$, $nei_{wt1}PB1-N_{1194}$, $nei_{wt2}PB1-N_{673}$, $nei_{wt2}PB1-N_{636}$, $nei_{ca1}PB1-N_{1225}$, $nei_{ca1}PB1-N_{1185}$, $nei_{ca2}PB1-N_{1221}$, and/or $nei_{ca2}PB1-N_{1185}$, the coding strands of which are represented by SEQ ID NO:42, SEQ ID NO:44, SEQ ID NO:45, SEQ ID NO:47, SEQ ID NO:48, SEQ ID NO:50, and/or SEQ ID NO:51.

Preferred nucleic acid molecules encoding equine influenza PB1-C proteins are $nei_{wt1}PB1-C_{1234}$, $nei_{wt1}PB1-C_{1188}$, $nei_{wt2}PB1-C_{1240}$, $nei_{ca1}PB1-C_{1241}$, $nei_{ca1}PB1-C_{1188}$, and/or $nei_{ca2}PB1-C_{1241}$, the coding strands of which are represented by SEQ ID NO:53, SEQ ID NO:60, SEQ ID NO:61, SEQ ID NO:63, SEQ ID NO:65, SEQ ID NO:66, and/or SEQ ID NO:94.

Preferred nucleic acid molecules encoding equine influenza PB1 proteins are $nei_{wt}PB1_{2341}$, $nei_{wt}PB1_{2271}$, $nei_{ca1}PB1_{2341}$, $nei_{ca1}PB1_{2271}$, the coding strands of which are represented by SEQ ID NO:68, SEQ ID NO:70, SEQ ID NO:71, and/or SEQ ID NO:73.

Preferred nucleic acid molecules encoding equine influenza PA-C proteins are $nei_{wt1}PA-C_{1228}$, $nei_{wt1}PA-C_{1164}$, $nei_{wt2}PA-C_{1223}$, $nei_{ca1}PA-C_{1233}$, and $nei_{ca1}PA-C_{1170}$, the coding strands of which are represented by SEQ ID NO:76, SEQ ID NO:82, SEQ ID NO:83, SEQ ID NO:84, and/or SEQ ID NO:86.

Preferred nucleic acid molecules encoding equine influenza PA-N proteins are $nei_{wt}PA-N_{1216}$, $nei_{wt}PA-N_{1193}$, $nei_{ca}PA-N_{1217}$, and $nei_{ca}PA-N_{1193}$, the coding strands of which are represented by SEQ ID NO:94, SEQ ID NO:95, SEQ ID NO:97 and SEQ ID NO:98.

Preferred nucleic acid molecules encoding equine influenza PA proteins are $nei_{wt}PA_{2148}$ and $nei_{ca}PA_{2148}$, the coding strands of which are represented by SEQ ID NO:100 and SEQ ID NO:102.

Preferred nucleic acid molecules encoding equine influenza NA proteins are $nei_{ca}NA_{1478}$ and $nei_{ca}NA_{1410}$, the coding strands of which are represented by SEQ ID NO:87 and SEQ ID NO:89.

The present invention includes proteins comprising SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103 as well as nucleic acid molecules encoding such proteins.

Preferred equine influenza PB2-N proteins of the present invention include proteins encoded by a nucleic acid molecule comprising $nei_{wt}PB2-N_{1241}$, $nei_{wt}PB2-N_{1214}$, $nei_{ca1}PB2-N_{1241}$, $nei_{ca1}PB2-N_{1214}$ $nei_{ca2}$, and/or $PB2-N_{1214}$. Preferred equine influenza PB2-N proteins are $P_{wt}PB2-N_{404}$, $P_{ca1}PB2-N_{404}$, and/or $P_{ca2}PB2-N_{404}$. In one embodiment, a preferred equine influenza PB2-N protein of the present invention is encoded by SEQ ID NO:5, SEQ ID NO:7, SEQ ID NO:8, and/or SEQ ID NO:10, and, as such, has an amino acid sequence that includes SEQ ID NO:6 and/or SEQ ID NO:9.

Preferred equine influenza PB2-C proteins of the present invention include proteins encoded by a nucleic acid molecule comprising $nei_{wt1}PB2C-_{1233}$, $nei_{wt2}PB2-C_{1232}$, $nei_{wt}PB2-C_{1194}$, $nei_{ca1}PB2-C_{1232}$, and/or $nei_{ca1}PB2-C_{1194}$. In one embodiment, a preferred equine influenza PB2-C protein of the present invention is encoded by SEQ ID NO:13, SEQ ID NO:20, SEQ ID NO:19, SEQ ID NO:21, and/or SEQ ID NO:23, and, as such, has an amino acid sequence that includes SEQ ID NO:14 and/or SEQ ID NO:22.

Preferred equine influenza PB2 proteins of the present invention include proteins encoded by a nucleic acid molecule comprising $nei_{wt}PB2_{2341}$, $nei_{wt}PB2_{2277}$, $nei_{ca1}PB2_{2341}$, and or $nei_{ca1}PB2_{2277}$. In one embodiment, a preferred equine influenza PB2 protein of the present invention is encoded by SEQ ID NO:24, SEQ ID NO:26, SEQ ID NO:27, and/or SEQ ID NO:29, and, as such, has an amino acid sequence that includes SEQ ID NO:25 and/or SEQ ID NO:28.

Preferred equine influenza NS proteins of the present invention include proteins encoded by a nucleic acid molecule comprising $nei_{wt1}NS_{891}$, $nei_{wt1}NS_{690}$, $nei_{wt3}NS_{888}$, $nei_{wt4}NS_{468}$, $nei_{wt4}NS_{293}$, $nei_{ca1}NS_{888}$, and/or $nei_{ca1}NS_{690}$. Preferred equine influenza NS proteins are $Pei_{wt}NS_{230}$, $Pei_{wt4}NS_{97}$, and/or $Pei_{ca1}NS_{230}$. In one embodiment, a preferred equine influenza NS protein of the present invention is encoded by SEQ ID NO:32, SEQ ID NO:34, SEQ ID NO:35, SEQ ID NO:36, SEQ ID NO:38, SEQ ID NO:39 and/or SEQ ID NO:41, and, as such, has an amino acid sequence that includes SEQ ID NO:33, SEQ ID NO:37 and/or SEQ ID NO:40.

Preferred equine influenza PB1-N proteins of the present invention include proteins encoded by a nucleic acid molecule comprising $nei_{wt1}PB1-N_{1229}$, $nei_{wt1}PB1-N_{1194}$, $nei_{wt2}PB1-N_{673}$, $nei_{wt2}PB1-N_{636}$, $nei_{ca1}PB21-N_{1225}$, $nei_{ca1}PB1-N_{1185}$, and/or $nei_{ca2}PB1-N_{1221}$. Preferred equine influenza PB1-N proteins are $Pei_{wt1}PB1-N_{398}$, $P_{wt2}PB1-N_{212}$ and/or $P_{ca1}PB1-N_{395}$. In one embodiment, a preferred equine influenza PB1-N protein of the present invention is encoded by SEQ ID NO:42, SEQ ID NO:44, SEQ ID NO:45, SEQ ID NO:47, SEQ ID NO:48, SEQ ID NO:50, and/or SEQ ID NO:51, and, as such, has an amino acid sequence that includes SEQ ID NO:43, SEQ ID NO:46 and/or SEQ ID NO:49.

Preferred equine influenza PB1-C proteins of the present invention include proteins encoded by a nucleic acid molecule comprising $nei_{wt1}PB1-C_{1234}$, $nei_{wt1}PB1-C_{1188}$, $nei_{wt2}PB1-C_{1240}$, $nei_{ca1}PB1-C_{1241}$, $nei_{ca1}PB1-C_{1188}$, and/or $nei_{ca2}PB1-C_{1241}$. Preferred equine influenza PB1-C proteins are $Pei_{wt1}PB1-C_{396}$, $Pei_{wt2}PB1-C_{396}$ $Pei_{ca1}PB1-C_{396}$, and/or $Pei_{ca2}PB1-C_{396}$. In one embodiment, a preferred equine influenza PB1-C protein of the present invention is encoded by SEQ ID NO:53, SEQ ID NO:60, SEQ ID NO:61, SEQ ID NO:63, SEQ ID NO:65, and/or SEQ ID NO:66, and, as such, has an amino acid sequence that includes SEQ ID NO:54, SEQ ID NO:62, SEQ ID NO:64, and/or SEQ ID NO:67.

Preferred equine influenza PB1 proteins of the present invention include proteins encoded by a nucleic acid molecule comprising $nei_{wt}PB1_{2341}$, $nei_{wt}PB1_{2271}$, $nei_{ca1}PB1_{2341}$, $nei_{ca1}PB1_{2271}$. Preferred equine influenza PB1 proteins are $Pei_{wt}PB1_{757}$, and/or $Pei_{ca1}PB1_{757}$. In one embodiment, a preferred equine influenza PB1 protein of the present invention is encoded by SEQ ID NO:68, SEQ ID NO:70, SEQ ID NO:71, and/or SEQ ID NO:73, and, as such, has an amino acid sequence that includes SEQ ID NO:69 and/or SEQ ID NO:72.

Preferred equine influenza PA-C proteins of the present invention include proteins encoded by a nucleic acid molecule comprising $nei_{wt1}PA-C_{1228}$, $nei_{wt1}PA-C_{1164}$, $nei_{wt2}PA-C_{1223}$, $nei_{ca1}PA-C_{1233}$, and/or $nei_{ca1}PA-C_{1170}$. Preferred equine influenza PA-C proteins are $Pei_{wt1}PA-C_{388}$, and/or $Pei_{ca1}PA-C_{390}$. In one embodiment, a preferred equine influenza PA-C protein of the present invention is encoded by SEQ ID NO:76, SEQ ID NO:82, SEQ ID NO:83, SEQ ID NO:84, and/or SEQ ID NO:86, and, as such, has an amino acid sequence that includes SEQ ID NO:77 and/or SEQ ID NO:85.

Preferred equine influenza PA-N proteins of the present invention include proteins encoded by a nucleic acid molecule comprising $nei_{wt}PA-N_{1216}$, $nei_{wt}PA-N_{1193}$, $nei_{ca}PA-N_{1217}$ and $nei_{ca}PA-N_{1193}$. Preferred equine influenza PA-N proteins are $Pei_{wt}PA-N_{397}$ and/or $Pei_{ca}PA-N_{397}$. In one embodiment, a preferred equine influenza PA-N protein of the present invention is encoded by SEQ ID NO:94, SEQ ID NO:95, SEQ ID NO:97, and/or SEQ ID NO:98, and, as such, has an amino acid sequence that includes SEQ ID NO:96 and/or SEQ ID NO:99.

Preferred equine influenza PA proteins of the present invention include proteins encoded by a nucleic acid molecule comprising $nei_{wt}PA_{1248}$ and $nei_{ca}PA_{1248}$. Preferred equine influenza PA proteins are $Pei_{wt}PA_{716}$ and/or $Pei_{ca}PA_{716}$. In one embodiment, a preferred equine influenza PA protein of the present invention is encoded by SEQ ID NO:100 and/or SEQ ID NO:102, and, as such, has an amino acid sequence that includes SEQ ID NO:101 and/or SEQ ID NO:103.

Preferred equine influenza NA proteins of the present invention include proteins encoded by a nucleic acid molecule comprising $nei_{ca}NA_{1478}$ and $nei_{ca}NA_{1410}$. A preferred equine influenza NA protein is $Pei_{ca}NA_{470}$. In one embodiment, a preferred equine influenza NA protein of the present invention is encoded by SEQ ID NO:87 and/or SEQ ID NO:89, and, as such, has an amino acid sequence that includes SEQ ID NO:88.

The present invention includes a nucleic acid molecule comprising a cold-adapted equine influenza virus encoding a PB2-N protein having an amino acid sequence comprising SEQ ID NO:9. Another embodiment of the present invention includes a nucleic acid molecule comprising a cold-adapted equine influenza virus encoding a PB2-C protein having an amino acid sequence comprising SEQ ID NO:22. Another embodiment of the present invention includes a nucleic acid molecule comprising a cold-adapted equine influenza virus encoding a PB2 protein having an amino acid sequence comprising SEQ ID NO:28. Another embodiment of the present invention includes a nucleic acid molecule comprising a cold-adapted equine influenza virus encoding a NS protein having an amino acid sequence comprising SEQ ID NO:40. Another embodiment of the present invention includes a nucleic acid molecule comprising a cold-adapted equine influenza virus encoding a PB1-N protein having an amino acid sequence comprising SEQ ID NO:49. Another embodiment of the present invention includes a nucleic acid molecule comprising a cold-adapted equine influenza virus encoding a PA-C protein having an amino acid sequence comprising SEQ ID NO:85. Another embodiment of the present invention includes a nucleic acid molecule comprising a cold-adapted equine influenza virus encoding a PB1-C protein having an amino acid sequence comprising SEQ ID NO:64 and/or SEQ ID NO:67. Another embodiment of the present invention includes a nucleic acid molecule comprising a cold-adapted equine influenza virus encoding a PB1 protein having an amino acid sequence comprising SEQ ID NO:72. Another embodiment of the present invention includes a nucleic acid molecule comprising a cold-adapted equine influenza virus encoding a PA-N protein having an amino acid sequence comprising SEQ ID NO:99. Another embodiment of the present invention includes a nucleic acid molecule comprising a cold-adapted equine influenza virus encoding a PA protein having an amino acid sequence comprising SEQ ID NO:103. Another embodiment of the present invention includes a nucleic acid molecule comprising a cold-adapted equine influenza virus encoding a NA protein having an amino acid sequence comprising SEQ ID NO:88. It should be noted that since nucleic acid sequencing technology is not entirely error-free, the nucleic acid sequences and amino acid sequences presented herein represent, respectively, apparent nucleic acid sequences of nucleic acid molecules of the present invention and apparent amino acid sequences of PB2-N, PB2-C, PB2, NS, PB1-N, PB1-C, PB1, PA-C, PA-N, PA, and NA proteins of the present invention.

Another embodiment of the present invention is an antibody that selectively binds to an wild-type virus PB2-N, PB2-C, PB2, NS, PB1-N, PB1-C, PB1, PA-C, PA-N, PA and NA protein of the present invention. Another embodiment of the present invention is an antibody that selectively binds to a cold-adapted virus PB2-N, PB2-C, PB2, NS, PB1-N, PB1-C, PB1, PA-C, PA-N, PA and NA protein of the present invention. Preferred antibodies selectively bind to SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103.

The following examples are provided for the purposes of illustration and are not intended to limit the scope of the present invention.

EXAMPLE 1

This example describes the cloning and sequencing of equine influenza PB2 protein (RNA-directed RNA polymerase) nucleic acid molecules corresponding to the N-terminal portion of the protein, for wild type or cold-adapted equine influenza viruses.

A. Nucleic acid molecules encoding wild type or cold-adapted equine influenza virus PB2-N proteins were produced as follows. A PCR product containing a N-terminal portion of the equine PB2 gene was produced by PCR amplification from equine influenza virus DNA, and primers w570 and w571, designated SEQ ID NO:36 and SEQ ID NO:37, respectively. A nucleic acid molecule of 1241 nucleotides encoding a wild type PB2-N protein, denoted $nei_{wt}PB2-N_{1241}$, with a coding strand having a nucleic acid sequence designated SEQ ID NO:13 was produced by further PCR amplification using the above described PCR product as a template and cloned into pCR 2.1®TA cloning vector, available from Invitrogen, Carlsbad, Calif., using standard procedures recommended by the manufacturer. The primers used were the T7 primer, designated by SEQ ID NO:29 and the REV primer, designated by SEQ ID NO:28.

Plasmid DNA was purified using a mini-prep method available from Qiagen, Valencia, Calif. PCR products were prepared for sequencing using a PRISM™ Dye Terminator Cycle Sequencing Ready Reaction kit, a PRISM™ dRhodamine Terminator Cycle Sequencing Ready Reaction kit, or a PRISM™ BigDye™ Terminator Cycle Sequencing Ready Reaction kit, all available from PE Applied Biosystems, Foster City, Calif., following the manufacturer's protocol. Specific PCR conditions used with the kit were a rapid ramp to 95° C., hold for 10 seconds followed by a rapid ramp to 50° C. with a 5 second hold then a rapid ramp to 60° C. with a 4 minute hold, repeating for 25 cycles. T7 and REV primers were used in one reaction. PCR products were purified by ethanol/magnesium chloride precipitation. Automated sequencing of DNA samples was performed using an ABI PRISM™ Model 377 with XL upgrade DNA Sequencer, available from PE Applied Biosystems.

Translation of SEQ ID NO:13 indicates that nucleic acid molecule $nei_{wt}PB2-N_{1241}$ encodes a N-terminal portion of influenza PB2 protein of about 404 amino acids, referred to herein as $P_{wt}PB2-N_{404}$, having amino acid sequence SEQ ID NO:14, assuming an open reading frame in which the initiation codon spans from nucleotide 28 through nucleotide 30 of SEQ ID NO:13, and the last codon spans from nucleotide 1237 through nucleotide 1239. The region encoding $P_{wt}PB2-N_{404}$, designated $nei_{wt}PB2-N_{1214}$, and having a coding strand comprising nucleotides 28 to 1239 of SEQ ID NO:13 is represented by SEQ ID NO:15.

B. A nucleic acid molecule of 1239 nucleotides encoding a N-terminal portion of influenza PB2 cold-adapted equine influenza virus PB2-N protein, denoted $nei_{ca1}PB2-N_{1241}$, with a coding strand having a sequence designated SEQ ID NO:16 was produced, and sequenced as described in part A.

Translation of SEQ ID NO:16 indicates that nucleic acid molecule $nei_{ca1}PB2-N_{1241}$ encodes a—terminal portion of equine influenza PB-2 protein of about 404 amino acids, referred to herein as $P_{ca1}PB2-N_{404}$, having amino acid sequence SEQ ID NO:17, assuming an open reading frame in which the initiation codon spans from nucleotide 28 through nucleotide 30 of SEQ ID NO:16, and the last codon spans from nucleotide 1237 through nucleotide 1239. The region encoding $P_{ca1}PB2-N_{404}$, designated $nei_{ca1}PB2-N_{1214}$, and having a coding strand comprising nucleotides 28 to 1239 of SEQ ID NO:16, is represented by SEQ ID NO:18.

PCR amplification of a second nucleic acid molecule encoding a cold-adapted equine influenza PB2-N protein in the same manner resulted in molecules $nei_{ca2}PB2-N_{1241}$, identical to $nei_{ca1}PB2-N_{1241}$, and $nei_{ca2}PB2-N_{1214}$, identical to $nei_{ca1}PB2-N_{1214}$.

C. Comparison of the nucleic acid sequences of the coding strands of $nei_{wt}PB2-N_{1241}$ (SEQ ID NO:13) and $nei_{ca1}PB2-N_{1241}$ (SEQ ID NO:16) by DNA alignment reveals the following difference: a T to C base shift at base 370. Comparison of the amino acid sequences of proteins $P_{wt}PB2-N_{404}$ (SEQ ID NO:14) and $P_{ca1}PB2-N_{404}$ (SEQ ID NO:17) reveals the following difference: a Y to H shift at amino acid 124 relating to the a T to C shift at base 370 in the DNA sequence.

EXAMPLE 2

This example describes the cloning and sequencing of equine influenza PB2 protein (RNA-directed RNA polymerase) nucleic acid molecules corresponding to the C-terminal portion of the protein, for wild type or cold-adapted equine influenza viruses.

A. Nucleic acid molecules encoding wild type or cold-adapted equine influenza virus PB2-C proteins were produced as follows. A PCR product containing the C-terminal portion of the equine PB2 gene was produced by PCR amplification using from equine influenza virus DNA and primers w572 and w573, designated SEQ ID NO:38 and SEQ ID NO:39, respectively. A nucleic acid molecule of 1233 nucleotides encoding a wild type PB2-C protein, denoted $nei_{wt}PB2-C_{1233}$, with a coding strand having a nucleic acid sequence designated SEQ ID NO:19 was produced by further PCR amplification using the above-described PCR product as a template and cloned as described in Example 1B. Plasmid DNA was purified and sequenced as in Example 1A, except that different primers were used in the sequencing kits. T7 and REV were used in one instance; efPB2-a1, designated SEQ ID NO:40 and efPB2-s1, designated SEQ ID NO:41 were used in another instance, and efPB2-a2, designated SEQ ID NO:42 and efPB2-s2, designated SEQ ID NO:43 were used in another instance.

Translation of SEQ ID NO:19 indicates that nucleic acid molecule $nei_{wt1}PB2-C_{1233}$ encodes a C-terminal portion of influenza PB2 protein of about 398 amino acids, referred to herein as $P_{wt}PB2-C_{398}$, having amino acid sequence SEQ ID NO:20, assuming an open reading frame having a first codon spans from nucleotide 3 through nucleotide 5 and a termination codon which spans from nucleotide 1197 through nucleotide 1199 of SEQ ID NO:19. Because SEQ ID NO:19 is only a partial gene sequence, it does not contain an initiation codon. The region encoding $P_{wt}PB2-C_{398}$, designated $nei_{wt}PB2-C_{1194}$, and having a coding strand comprising nucleotides 3 to 1196 of SEQ ID NO:19 is represented by SEQ ID NO:21.

PCR amplification of a second nucleic acid molecule encoding a wild type equine influenza PB2-N protein in the same manner resulted in a nucleic acid molecule of 1232 nucleotides denoted $nei_{wt2}PB2-N_{1232}$ with a coding strand with a sequence designated SEQ ID NO:22. $nei_{wt2}PB2-N_{1232}$ is identical to $nei_{wt1}PB2-C_{1233}$, expect that $nei_{wt2}PB2-N_{1232}$ lacks one nucleotide on the 5'-end. Translation of SEQ ID NO:22 indicates that nucleic acid molecule $nei_{wt1}PB2-C_{1233}$ also encodes $P_{wt}PB2-C_{398}$ (SEQ ID NO:20), assuming an open reading frame having a first codon which spans from nucleotide 2 through nucleotide 4 and a termination codon spans from nucleotide 1196 through nucleotide 1198 of SEQ ID NO:22. Because SEQ ID NO:22 is only a partial gene sequence, it does not contain an initiation codon. The nucleic acid molecule having a coding strand comprising nucleotides 2 to 1195 of SEQ ID NO:22, denoted $nei_{wt2}PB2-C_{1194}$, is identical to SEQ ID NO:21.

B. A nucleic acid molecule of 1232 nucleotides encoding a C-terminal portion of influenza PB2 cold-adapted equine influenza virus protein, denoted $nei_{ca1}PB2-C_{1232}$, and having a coding strand having a sequence designated SEQ ID NO:23 was produced as described in part A, except that the pCR®-Blunt cloning vector was used.

Translation of SEQ ID NO:23 indicates that nucleic acid molecule $nei_{ca1}PB2-C_{1232}$ encodes a C-terminal portion of equine influenza PB-2 protein of about 398 amino acids, referred to herein as $P_{ca1}PB2-C_{398}$, having amino acid sequence SEQ ID NO:24, assuming an open reading frame having a first codon which spans from nucleotide 2 through nucleotide 4 and a termination codon spans from nucleotide 1196 through nucleotide 1198 of SEQ ID NO:23. Because SEQ ID NO:23 is only a partial gene sequence, it does not contain an initiation codon. The region encoding $P_{ca1}PB2-C_{398}$, designated $nei_{ca1}PB2-C1194$, and having a coding strand comprising nucleotides 2 to 1195 of SEQ ID NO:23, is represented by SEQ ID NO:25.

PCR amplification of a second nucleic acid molecule encoding a cold-adapted equine influenza PB2-C protein in the same manner resulted in molecules $nei_{ca2}PB2\text{-}C_{1231}$, containing one less nucleotide at the 3'end than $nei_{ca1}PB2\text{-}N_{1241}$; and $nei_{ca2}PB2\text{-}N_{1214}$, identical to $nei_{ca1}PB2\text{-}N_{1214}$.

C. Comparison of the nucleic acid sequences of the coding strands of $nei_{wt1}PB2\text{-}C_{1233}$ (SEQ ID NO:19) and $nei_{ca1}PB2\text{-}C_{1232}$ (SEQ ID NO:23) by DNA alignment reveals the following differences: an A to C base shift at base 153 of SEQ ID NO:19, and a G to A base shift at base 929 of SEQ ID NO:19. Comparison of the amino acid sequences of proteins $P_{wt}PB2\text{-}C_{398}$ (SEQ ID NO:20) and $P_{ca1}PB2\text{-}_{398}$ (SEQ ID NO:24) reveals the following difference: a K to Q shift at amino acid 51 when relating to the an A to C base shift at base 153 in the DNA sequences. There is no amino acid shift resulting from the G to A base shift at base 929.

EXAMPLE 3

This example describes the cloning and sequencing of equine influenza PB2 protein (RNA-directed RNA polymerase) nucleic acid molecules for wild type or cold-adapted equine influenza viruses.

A. Nucleic acid molecules encoding wild type or cold-adapted equine influenza virus PB2 proteins were produced as follows. The wild type or cold-adapted equine influenza genes were cloned in two fragments, the N-terminal portion was produced as in Example 1 and the C-terminal portion of the gene was produced as in Example 2. The DNA sequence for the wild type equine influenza PB2 gene was generated by combining the consensus sequences for the wild type PB2-N protein, denoted $nei_{wt}PB2\text{-}N_{1241}$, (SEQ ID NO:13) with the gene fragments for the wild type PB2-C protein, denoted $nei_{wt1}PB2\text{-}C_{1233}$ (SEQ ID NO:19) and $nei_{wt2}PB2\text{-}C_{1232}$ (SEQ ID NO:22). The result of combining the consensus sequences from the N-terminal and C-terminal portions of the PB2 wild type influenza virus yielded a complete DNA sequence denoted $nei_{wt}PB2_{2341}$ (SEQ ID NO:44). Translation of SEQ ID NO:44 indicates that the nucleic acid molecule $nei_{wt}PB2_{2341}$ encodes a full length equine influenza PB2 protein of about 759 amino acids referred to herein as $Pei_{wt}PB2_{759}$, having amino acid sequence SEQ ID NO: 45, assuming an open reading frame in which the initiation codon spans from nucleotide 28 through nucleotide 30 of SEQ ID NO: 44 and the termination codon spans from nucleotide 2305 through nucleotide 2307 of SEQ ID NO: 44. The region encoding $Pei_{wt}PB2_{759}$, designated $nei_{wt}PB2_{2277}$, and having a coding strand comprising nucleotides 28 to 2304 of SEQ ID NO: 44, is SEQ ID NO: 46.

B. A DNA sequence of 2341 nucleotides encoding a cold-adapted equine influenza virus PB2, denoted $nei_{ca1}PB2_{2341}$, with a sequence denoted SEQ ID NO: 47 was produced by combining the sequences for the N-terminal and C-terminal portions of the PB2 cold-adapted equine influenza gene. The clones for the N-terminal sequences are denoted $nei_{ca1}PB2\text{-}N_{1241}$, and $nei_{ca2}PB2\text{-}N_{1241}$, which are identical and are represented by SEQ ID NO:16. The clones for the C-terminal sequences are denoted $nei_{ca1}PB2\text{-}C_{1232}$ and $nei_{ca2}PB2\text{-}C_{1231}$, represented by SEQ ID NO:23.

Translation of SEQ ID NO:47 indicates that nucleic acid molecule $nei_{ca1}PB2_{2341}$ encodes a full-length equine influenza PB2 protein of about 759 amino acids, referred to herein as $Pei_{ca1}PB2_{759}$, having amino acid sequence SEQ ID NO:48, assuming an open reading frame in which the initiation codon spans from nucleotide 28 through nucleotide 30 of SEQ ID NO: 47 and the termination codon spans from nucleotide 2305 through nucleotide 2307 of SEQ ID NO:47. The region encoding $Pei_{ca1}PB2_{759}$ designated $nei_{ca1}PB2_{2277}$ and having a coding strand comprising nucleotides 28 to 2304 of SEQ ID NO:49.

C. Comparison of the nucleic acid sequences of the coding strands of $nei_{wt}PB2_{2341}$ (SEQ ID NO:44) and $nei_{ca1}PB2_{2341}$ (SEQ ID NO:47) by DNA alignment reveals the following differences: a T to C base shift at base 370, a A to C base shift at base 1261, and a G to A base shift at base 2037. Comparison of the amino acid sequences of proteins $Pei_{wt}PB2_{759}$ (SEQ ID NO:45) and $Pei_{ca1}PB2_{759}$ (SEQ ID NO:48) reveals the following differences: a Y to H shift at amino acid 124 relating to the a T to C shift at base 370 in the DNA sequence, a K to Q shift at amino acid 421 relating to the A to C shift at base 1261 in the DNA sequence. The third nucleotide shift at base 2037 does not result in an amino acid shift.

EXAMPLE 4

This example describes the cloning and sequencing of equine influenza NS (nonstructural) protein nucleic acid molecules for wild type or cold-adapted equine influenza viruses.

A. Nucleic acid molecules encoding wild type or cold-adapted equine influenza virus NS proteins were produced as follows. A PCR product containing an equine NS gene was produced by PCR amplification from equine influenza virus DNA and primers w586 and w587, designated SEQ ID NO:59 and SEQ ID NO:60, respectively. A nucleic acid molecule of 891 nucleotides encoding a wild-type NS protein, denoted $nei_{wt}NS_{891}$, with a coding strand having a nucleic acid sequence designated SEQ ID NO:50 was produced by further PCR amplification using the above-described PCR product as a template and cloned into pCR 2.1®TA cloning vector as described in Example 1A. Plasmid DNA was purified and sequenced as in Example 1A, except that primers used in the sequencing kits were only T7 and REV.

Translation of SEQ ID NO:50 indicates that nucleic acid molecule $nei_{wt}NS_{891}$ encodes a full-length equine influenza NS protein of about 230 amino acids, referred to herein as $Pei_{wt1}NS_{230}$, having amino acid sequence SEQ ID NO:51, assuming an open reading frame in which the initiation codon spans from nucleotide 27 through nucleotide 29 of SEQ ID NO:50 and the termination codon spans from nucleotide 717 through nucleotide 719 of SEQ ID NO:50. The region encoding $Pei_{wt1}NS_{230}$, designated $nei_{wt1}NS_{690}$, and having a coding strand comprising nucleotides 27 to 716 of SEQ ID NO:50 is represented by SEQ ID NO:52.

PCR amplification of a second nucleic acid molecule encoding a wild type equine influenza NS protein in the same manner resulted in molecules $nei_{wt2}NS_{891}$, identical to $nei_{wt1}NS_{891}$, in the coding region, i.e. $nei_{wt2}NS_{690}$, is identical to $nei_{wt1}NS_{690}$. $nei_{wt2}NS_{891}$ differs from $nei_{wt1}NS_{891}$ in one nucleotide at base 827 (G to A) which is 111 bases downstream from the stop codon. PCR amplification of a third nucleic acid encoding a wild type equine influenza NS protein in the same manner resulted in a nucleic acid molecule of 888 nucleotides denoted $nei_{wt3}NS_{888}$, with a coding strand with a nucleic acid sequence designated SEQ ID NO: 53. $nei_{wt3}NS_{888}$ is identical to $nei_{wt1}NS_{891}$, except that $nei_{wt3}NS_{888}$, lacks two nucleotides on the 5' end and one nucleotide on the 3' end. Translation of SEQ ID NO:53 indicates that nucleic acid molecule $nei_{wt3}NS_{888}$ also encodes $Pei_{wt1}NS_{230}$ (SEQ ID NO:51), assuming an open reading frame having an initiation codon which spans from nucleotide 25 through nucleotide 27 of SEQ ID NO:53 and a termination codon which spans from nucleotide 715 through nucleotide 717 of SEQ ID NO:53. The nucleic acid molecule having a coding strand comprising nucleotides 25 to 714 of SEQ ID 53, denoted $nei_{wt3}NS_{690}$, is identical to SEQ ID NO:52.

PCR amplification of a fourth nucleic acid of 468 nucleotides encoding a C-terminal portion of the wild type equine influenza NS protein, denoted $nei_{wt4}NS468$ and having a coding sequence designated SEQ ID NO:54 was produced. Translation of SEQ ID NO:54 indicates that nucleic acid molecule $nei_{wt4}NS_{468}$ encodes a C-terminal portion of equine influenza NS protein of about 97 amino acids, referred to herein as $Pei_{wt4}NS_{97}$, having amino acid sequence SEQ ID NO:55, assuming an open reading frame having a first codon which spans from nucleotide 3 to 5 of SEQ ID NO: 54, and a termination codon spans from nucleotide 294 through 296 of SEQ ID NO:54. Because SEQ ID NO:54 is only a partial gene sequence, it does not contain an initiation codon. The region encoding $Pei_{wt4}NS_{97}$, designated $nei_{wt4}NS_{293}$, and having a coding strand comprising nucleotides 1 to 293 of SEQ ID NO:54, is represented by SEQ ID NO: 64.

B. A nucleic acid molecule of 888 nucleotides encoding a cold-adapted equine influenza virus NS protein, denoted $nei_{ca1}NS_{888}$, with a coding strand having a sequence designated SEQ ID NO:57 was produced and sequenced as described in part A.

Translation of SEQ ID NO:57 indicates that nucleic acid molecule $nei_{ca1}NS_{888}$ encodes a full-length equine influenza NS protein of about 230 amino acids, referred to herein as $Pei_{ca1}NS_{230}$, having amino acid sequence SEQ ID NO:58, assuming an open reading frame in which the initiation codon spans from nucleotide 27 through nucleotide 29 of SEQ ID NO:57 and the termination codon spans from nucleotide 717 through nucleotide 719 of SEQ ID NO:57. The region encoding $Pei_{ca1}NS_{230}$, designated $nei_{ca1}NS_{690}$, and having a coding strand comprising nucleotides 27 to 716 of SEQ ID NO:57, is represented by SEQ ID NO:59.

PCR amplification of a second nucleic acid molecule encoding a cold-adapted equine influenza NS protein in the same manner resulted in molecules $nei_{ca2}NS_{887}$, containing one less nucleotide at the 3' end than $nei_{ca1}NS_{888}$; the coding region $nei_{ca2}NS690$ is identical to $nei_{ca1}NS_{690}$.

C. Comparison of the nucleic acid sequences of the coding strands of $nei_{wt}NS_{891}$ (SEQ ID NO:50) and $nei_{ca1}NS_{888}$ (SEQ ID NO:57) by DNA alignment reveals the following difference: a A to G shift at base 827 which is 111 bases downstream from the stop codon. The 3' fragment encoding $nei_{wt4}NS_{468}$ (SEQ ID NO:54) has one shift T to C found at base 633 relative to the full-length consensus sequence. Comparison of the amino acid sequences of proteins $Pei_{wt}NS_{230}$ (SEQ ID NO:51) and $Pei_{ca1}NS_{230}$ (SEQ ID NO:58) reveals that there are no differences between amino acid sequences of the wild type and cold-adapted proteins.

EXAMPLE 5

This example describes the cloning and sequencing of equine influenza PB1 protein (RNA-directed RNA polymerase 1) nucleic acid molecules corresponding to the N-terminal portion of the protein, for wild type or cold-adapted equine influenza viruses.

A. Nucleic acid molecules encoding wild type or cold-adapted equine influenza virus PB1-N proteins were produced as follows. A PCR product containing a N-terminal portion of the equine PB1 gene was produced by PCR amplification from equine influenza virus DNA, and primers T7 and REV. A nucleic acid molecule of 1229 nucleotides encoding a wild type PB1-N protein, denoted $nei_{wt1}PB1-N_{1229}$, with a coding strand having a nucleic acid sequence designated SEQ ID NO:62 was produced by further PCR amplification using the above described PCR product as a template and cloned as described in Example 1B. Plasmid DNA was purified and sequenced as in Example 1B, except that only T7 and REV primers were used in the sequencing kits.

Translation of SEQ ID NO:62 indicates that nucleic acid molecule $nei_{wt1}PB1-N_{1229}$ encodes a N-terminal portion of influenza PB1 protein of about 398 amino acids, referred to herein as $Pei_{wt1}PB1-N_{398}$, having amino acid sequence SEQ ID NO:63, assuming an open reading frame in which the initiation codon spans from nucleotide 36 through nucleotide 38 of SEQ ID NO:62, and the last codon spans from nucleotide 1227 through nucleotide 1229 of SEQ ID NO:62. The region encoding $Pei_{wt1}PB1-N_{398}$, designated $nei_{wt1}PB1-N_{1194}$, and having a coding strand comprising nucleotides 36 to 1229 of SEQ ID NO:62 is represented by SEQ ID NO:64.

PCR amplification of a second nucleic acid molecule encoding a wild type equine influenza PB1-N protein in the same manner resulted in a nucleic acid molecule of 673 nucleotides denoted $nei_{wt2}PB1-N_{673}$, with a coding strand with a sequence designated SEQ ID NO:65. Translation of SEQ ID NO:65 indicates that nucleic acid molecule $nei_{wt2}PB1-N_{673}$ encodes $Pei_{wt2}PB1-N_{212}$ (SEQ ID NO:66), assuming an open reading frame having an initiation codon which spans from nucleotide 36 through nucleotide 38 of SEQ ID NO:65 and a last codon which spans from nucleotide 671 through nucleotide 673 of SEQ ID NO:65. Because SEQ ID NO:65 is only a partial gene sequence, it does not contain a stop codon. The nucleic acid molecule having a coding strand comprising nucleotides 36 to 671 of SEQ ID NO:65, denoted $nei_{wt2}PB1-N_{636}$, is designated SEQ ID NO:67.

B. A nucleic acid molecule of 1225 nucleotides encoding a N-terminal portion of influenza PB1 cold-adapted equine influenza virus PB1-N protein, denoted $nei_{ca1}PB1-N_{1225}$, with a coding strand having a sequence designated SEQ ID NO:68 was produced, and sequenced as described in part A.

Translation of SEQ ID NO:68 indicates that nucleic acid molecule $nei_{ca1}PB1-N_{1225}$ encodes a N-terminal portion of equine influenza PB-1 protein of about 395 amino acids, referred to herein as $Pei_{ca1}PB1-N_{395}$, having amino acid sequence SEQ ID NO:69, assuming an open reading frame in which the initiation codon spans from nucleotide 34 through nucleotide 36 of SEQ ID NO:68, and a last codon which spans from nucleotide 1216 through nucleotide 1218 of SEQ ID NO:68. The region encoding $Pei_{ca1}PB1-N_{395}$, designated $nei_{ca1}PB1-N_{1185}$, and having a coding strand comprising nucleotides 34 to 1218 of SEQ ID NO:68, is represented by SEQ ID NO:70.

PCR amplification of a second nucleic acid molecule encoding a cold-adapted equine influenza PB1-N protein in the same manner resulted in molecules $nei_{ca2}PB1-N_{1221}$, designated SEQ ID NO:71, containing four less nucleotides at the 5' end than $nei_{ca1}PB1-N_{1225}$; the coding region $nei_{ca2}PB1-N_{1185}$, is identical to $nei_{ca1}PB1-N_{1185}$.

C. Comparison of the nucleic acid sequences of the coding strands of $nei_{wt}PB1-N_{1229}$ (SEQ ID NO:62) and $nei_{ca1}PB1-N_{1225}$ (SEQ ID NO:68) by DNA alignment reveals no differences in the coding regions. Comparison of the amino acid sequences of proteins $Pei_{wt1}PB1-N_{395}$ (SEQ ID NO:63) and $Pei_{ca1}PB1-N_{395}$ (SEQ ID NO:69) also reveals no differences.

EXAMPLE 6

This example describes the cloning and sequencing of equine influenza PB1 protein (RNA-directed RNA polymerase 1) nucleic acid molecules corresponding to the C-terminal portion of the protein, for wild type or cold-adapted equine influenza viruses.

A. Nucleic acid molecules encoding wild type or cold-adapted equine influenza virus PB1-C proteins were produced as follows. A PCR product containing an C-terminal portion of the equine PB1 gene was produced by PCR amplification from equine influenza virus DNA, and primer w569 designated SEQ ID NO:102. A nucleic acid molecule of 1234 nucleotides encoding a wild type PB1-C protein, denoted $nei_{wt1}PB1-C_{1234}$, with a coding strand having a nucleic acid sequence designated SEQ ID NO:85 was produced by further PCR amplification using the above described PCR product as a template and cloned as described in Example 1B. Plasmid DNA was purified and sequenced as in Example 1A, except that different primers were used in the sequencing kits. T7, REV, w569, efPB1-a1, designated SEQ ID NO:97, efPB1-a2, designated SEQ. ID NO:98, efPB1-s1, designated SEQ ID NO: 99, efPB1-s2, designated SEQ ID NO: 100, and efPB1-s3, designated SEQ ID NO:101 were used in one instance, T7, REV, efPB1-a1, efPB1-a2, efPB1-s1, efPB1-s2, and efPB1-s3 were used in another instance and T7 and REV were used in another instance.

Translation of SEQ ID NO:85 indicates that nucleic acid molecule $nei_{wt1}PB1-C_{1234}$ encodes an C-terminal portion of influenza PB1 protein of about 396 amino acids, referred to herein as $Pei_{wt1}PB1-C_{396}$, having amino acid sequence SEQ ID NO:86, assuming an open reading frame in which the first codon spans from nucleotide 1 through nucleotide 3 of SEQ ID NO:85 and a termination codon which spans from nucleotide 1189 through nucleotide 1191 of SEQ ID NO:85. Because SEQ ID NO:85 is only a partial gene sequence, it does not contain an initiation codon. The region encoding $Pei_{wt1}PB1-C_{396}$, designated $nei_{wt1}PB1-C_{1188}$, and having a coding strand comprising nucleotides 1 to 1188 of SEQ ID NO:85 is represented by SEQ ID NO:87.

PCR amplification of a second nucleic acid molecule encoding a wild type equine influenza PB1-C protein in the same manner resulted in a nucleic acid molecule of 1240 nucleotides denoted $nei_{wt2}PB1-C_{1240}$, with a coding strand with a sequence designated SEQ ID NO:88. Translation of SEQ ID NO:88 indicates that nucleic acid molecule $nei_{wt2}PB1-N_{1240}$ encodes a molecule designated $Pei_{wt2}PB1-C_{396}$ (SEQ ID NO: 89) which differs from $Pei_{wt1}PB1-C_{396}$ (SEQ ID NO:85) in one nucleotide. Nucleotide 382 of $nei_{wt1}PB1-C_{1234}$, i.e. nucleotide 382 of $nei_{wt1}PB1-C_{1188}$ was A, while nucleotide 389 of $nei_{wt2}PB1-C_{1240}$, i.e. nucleotide 382 of $nei_{wt2}PB1-C_{1188}$ was T. Translation of $nei_{wt2}PB1-C_{1240}$ results in an amino acid change of T to S.

B. A nucleic acid molecule of 1241 nucleotides encoding an C-terminal portion of influenza PB1 cold-adapted equine influenza virus PB1-C protein, denoted $nei_{ca1}PB1-C_{1241}$, with a coding strand having a sequence designated SEQ ID NO:91 was produced, and sequenced as described in part A.

Translation of SEQ ID NO:91 indicates that nucleic acid molecule $nei_{ca1}PB1-C_{1241}$ encodes an C-terminal portion of equine influenza PB-1 protein of about 396 amino acids, referred to herein as $Pei_{ca1}PB1-C_{396}$, having amino acid sequence SEQ ID NO:92, assuming an open reading frame in which the first codon spans from nucleotide 8 through nucleotide 10 of SEQ ID NO:91 and a termination codon that spans from nucleotide 1196 through nucleotide 1198 of SEQ ID NO:91. Because SEQ ID NO:91 is only a partial gene sequence, it does not contain an initiation codon. The region encoding $Pei_{ca1}PB1-C_{396}$, designated $nei_{ca1}PB1-C_{1188}$, and having a coding strand comprising nucleotides 8 to 1195 of SEQ ID NO:91, is represented by SEQ ID NO:93.

PCR amplification of a second nucleic acid molecule encoding a cold-adapted equine influenza PB1-C protein in the same manner resulted in a nucleic acid molecule of 1241 nucleotides denoted $nei_{ca2}PB1-C_{1241}$, with a coding strand with a sequence designated SEQ ID NO:94. Translation of SEQ ID NO:94 indicates that nucleic acid molecule $nei_{ca2}PB1-C_{1241}$ encodes a molecule designated $Pei_{ca2}PB1-C_{396}$ (SEQ ID NO:95) which differs from $Pei_{ca1}PB1-C_{396}$ (SEQ ID NO:92) in one nucleotide. Nucleotide 1044 of $nei_{ca1}PB1-C_{1241}$, i.e. nucleotide 1037 of $nei_{ca1}PB1-N_{1188}$ was A, while nucleotide 1044 of $nei_{ca2}PB1-C_{1241}$, i.e. nucleotide 1037 of $nei_{ca2}PB1-C_{1188}$ was G. Translation of $nei_{ca2}PB1-C_{1241}$ results in an amino acid change of R to K.

C. Comparison of the nucleic acid sequences of the coding strands of $nei_{wt1}PB1-C_{1234}$ (SEQ ID NO:85) and $nei_{ca1}PB1-C_{1241}$ (SEQ ID NO:91) by DNA alignment reveals the following differences: a C to T shift at base 600 of SEQ ID NO:85, and a T to A shift at base 603 of SEQ ID NO:85. Comparison of the amino acid sequences of proteins $Pei_{wt1}PB1-C_{396}$ (SEQ ID NO:86) and $Pei_{ca1}PB1-N_{396}$ (SEQ ID NO:92) reveals the following difference: a H to Q amino acid shift 203 when relating to the T to A base shift at base 603 in the DNA sequences. There is no amino acid shift resulting from the C to T base shift at base 600.

EXAMPLE 7

This example describes the cloning and sequencing of equine influenza PB1 protein (RNA-directed RNA polymerase) nucleic acid molecules for wild type or cold-adapted equine influenza viruses.

A. Nucleic acid molecules encoding wild type or cold-adapted equine influenza virus PB1 proteins were produced as follows. The wild type or cold-adapted equine influenza genes were cloned in two fragments, the N-terminal portion was produced as in Example 5 and the C-terminal portion of the gene was produced as in Example 6.

The DNA sequence for the wild type equine influenza PB1 gene was generated by combining the sequences for the wild type PB1-N protein, $nei_{wt1}PB1-N_{1229}$ (SEQ ID NO:62) and $nei_{wt2}PB1-N_{673}$ (SEQ ID NO:65) with the gene fragments for the wild type PB1-C protein, denoted $nei_{wt1}PB1-C_{1234}$ (SEQ ID NO:85) and $nei_{wt2}PB1-C_{1240}$ (SEQ ID NO: 88). The result of combining the N-terminal and C-terminal portions of the PB1 wild type influenza virus yielded a complete DNA sequence of 2341 nucleotides denoted $nei_{wt}PB1_{2341}$ (SEQ ID NO:103). Translation of SEQ ID NO:103 indicates that the nucleic acid molecule $nei_{wt}PB2_{2341}$ encodes a full length equine influenza PB1 protein of about 757 amino acids referred to herein as $Pei_{wt}PB1_{757}$, having amino acid sequence SEQ ID NO:104, assuming an open reading frame in which the initiation codon spans from nucleotide 25 through nucleotide 27 of SEQ ID NO: 103 and the termination codon spans from nucleotide 2293 through nucleotide 2295 of SEQ ID NO: 103. The region encoding, $Pei_{wt}PB1_{757}$ designated $nei_{wt}PB1_{2271}$, and having a coding strand comprising nucleotides 25 to 2292 of SEQ ID NO: 103, is SEQ ID NO:105.

B. A DNA sequence of 2341 nucleotides encoding a cold-adapted equine influenza virus PB1, denoted $nei_{ca1}PB1_{2341}$, with a sequence denoted SEQ ID NO: 106 was produced by combining the sequences for the N-terminal and C-terminal portions of the PB1 cold-adapted equine influenza gene. The clones for the N-terminal sequences are denoted $nei_{ca1}PB1-N_{1225}$ (SEQ ID NO: 68) and $nei_{ca2}PB1-N_{1221}$ (SEQ ID NO: 71). The clones for the C-terminal sequences are denoted $nei_{ca1}PB1-C_{1241}$ (SEQ ID NO:91) and $nei_{ca2}PB1-C_{1241}$, (SEQ ID NO: 94).

Translation of SEQ ID NO:106 indicates that nucleic acid molecule $nei_{ca1}PB1_{2341}$ encodes a fill-length equine influenza PB1 protein of about 757 amino acids, referred to herein as $Pei_{ca1}PB1_{757}$, having amino acid sequence SEQ ID NO:107, assuming an open reading frame in which the initiation codon spans from nucleotide 25 through nucleotide 27 SEQ ID NO: 106 and the termination codon spans from nucleotide 2296 through nucleotide 2298 of SEQ ID NO:106. The region encoding $Pei_{ca1}PB1_{757}$ designated $nei_{ca1}PB1_{2271}$ and having a coding strand comprising nucleotides 25 to 2295 of SEQ ID NO:108.

C. Comparison of the nucleic acid sequences of the coding strands of $nei_{wt}PB1_{2341}$ (SEQ ID NO:103) and $nei_{ca1}PB1_{2341}$ (SEQ ID NO:106) by DNA alignment reveals the following differences: a C to T base shift at base 1683, and a T to A base shift at base 1686. Comparison of the amino acid sequences of proteins $Pei_{wt}PB1_{757}$ (SEQ ID NO:104) and $Pei_{ca1}PB1_{757}$ (SEQ ID NO:107) reveals the following differences: no shift in base C at amino acid 561 relating to the C to T shift at base 1683, and a H to Q shift at amino acid 562 relating to the a T to A shift at base 1683 in the DNA sequence.

EXAMPLE 8

This example describes the cloning and sequencing of equine influenza PA protein ( RNA polymerase A) nucleic acid molecules corresponding to the C-terminal portion of the protein, for wild type or cold-adapted equine influenza viruses.

A. Nucleic acid molecules encoding wild type or cold-adapted equine influenza virus PA-C proteins were produced as follows. A PCR product containing the C-terminal portion of the equine PA gene was produced by PCR amplification using from equine influenza virus DNA and primers C+PA and C−PA, designated SEQ ID NO:83 and SEQ ID NO:84 respectively. A nucleic acid molecule of 1228 nucleotides encoding a wild type PA-C protein, denoted $nei_{wt1}PA-C_{1228}$, with a coding strand having a nucleic acid sequence designated SEQ ID NO:76 was produced by further PCR amplification using the above-described PCR product as a template and cloned as described in Example 1B. Plasmid DNA was purified and sequenced as in Example 1A, except that different primers were used in the sequencing kits. T7 and REV were used in one instance; PAC-1,designated SEQ ID NO:72, PAC-2, designated SEQ ID NO:73, PAC-3, designated SEQ ID NO:74, PAC-4, designated SEQ ID NO: 75, T7 and REV were used in another instance; and PAC-1, PAC-2, T7 and REV were used in another instance.

Translation of SEQ ID NO:76 indicates that nucleic acid molecule $nei_{wt1}PA-C_{1228}$ encodes a C-terminal portion of influenza PA protein of about 388 amino acids, referred to herein as $Pei_{wt1}PA-C_{388}$, having amino acid sequence SEQ ID NO:77, assuming an open reading frame having a first codon spans from nucleotide 3 through nucleotide 5 of SEQ ID NO:76 and a termination codon which spans from nucleotide 1167 through nucleotide 1169 of SEQ ID NO:76. Because SEQ ID NO:76 is only a partial gene sequence, it does not contain an initiation codon. The region encoding $Pei_{wt1}PA-C_{388}$, designated $nei_{wt1}PA-C_{1164}$, and having a coding strand comprising nucleotides 3 to 1166 of SEQ ID NO:76 is represented by SEQ ID NO:78.

PCR amplification of a second nucleic acid molecule encoding a wild type equine influenza PA-C protein in the same manner resulted in a nucleic acid molecule of 1223 nucleotides denoted $nei_{wt2}PA-C_{1223}$, with a coding strand with a sequence designated SEQ ID NO:79. $nei_{wt2}PA-C_{1223}$ is identical to $nei_{wt1}PA-C_{1228}$, with the exception of a T to C base shift at base 753 and that $nei_{wt2}PA-C_{1223}$ lacks five nucleotides on the 3'-end. Translation of SEQ ID NO:79 indicates that nucleic acid molecule $nei_{wt2}PA-C_{1223}$ also encodes $Pei_{wt1}PA-C_{388}$ (SEQ ID NO:77), assuming an open reading frame having a first codon which spans from nucleotide 3 through nucleotide 5 of SEQ ID NO:79 and a termination codon which spans from nucleotide 1167 through nucleotide 1169 of SEQ ID NO:79. Because SEQ ID NO:79 is only a partial gene sequence, it does not contain an initiation codon. The nucleic acid molecule having a coding strand comprising nucleotides 3 to 1166 of SEQ ID NO:79, denoted $nei_{wt2}PA-C_{1223}$, is identical to SEQ ID NO 78.

B. A nucleic acid molecule of 1233 nucleotides encoding a C-terminal portion of influenza PA-C cold-adapted equine influenza virus protein, denoted $nei_{ca1}PA-C_{1233}$, and having a coding strand having a sequence designated SEQ ID NO:80 was produced as described in part A, except that the pCR®-Blunt cloning vector was used.

Translation of SEQ ID NO:80 indicates that nucleic acid molecule $nei_{ca1}PA-C_{1233}$ encodes a C-terminal portion of equine influenza PA protein of about 390 amino acids, referred to herein as $Pei_{ca1}PA-C_{390}$, having amino acid sequence SEQ ID NO:81, assuming an open reading frame having a first codon which spans from nucleotide 3 through nucleotide 5 of SEQ ID NO:80 and a termination codon which spans from nucleotide 1173 through nucleotide 1175 of SEQ ID NO:80. Because SEQ ID NO:80 is only a partial gene sequence, it does not contain an initiation codon. The region encoding $Pei_{ca1}PA-C_{390}$, designated $nei_{ca1}PA-C_{1170}$, and having a coding strand comprising nucleotides 3 to 1172 of SEQ ID NO:80, is represented by SEQ ID NO:82.

PCR amplification of a second nucleic acid molecule encoding a cold-adapted equine influenza PA-C protein in the same manner resulted in molecule $nei_{ca2}PA-C_{1233}$, containing one A to G base shift at base 953 as compared to $nei_{ca1}PA-C_{1233}$; this base shift does not result in an amino acid change so $Pei_{ca2}PA-C_{390}$, is identical to $Pei_{ca1}PA-C_{390}$ (SEQ ID NO:81.)

C. Comparison of the nucleic acid sequences of the coding strands of $nei_{wt1}PA-C_{1228}$ (SEQ ID NO:76) and $nei_{ca1}PA-C_{1233}$ (SEQ ID NO:80) by DNA alignment reveals the following difference: an C to T base shift at base 753 of SEQ ID NO:80. Comparison of the amino acid sequences of proteins $Pei_{wt1}PA-C_{388}$ (SEQ ID NO:77) and $Pei_{ca1}PA-_{390}$ (SEQ ID NO:81) reveals the following difference: a W to R shift at amino acid 251 when relating to the C to T base shift at base 753 in the DNA sequences.

EXAMPLE 9

This example describes the cloning and sequencing of equine influenza PA protein nucleic acid molecules corresponding to the N-terminal portion of the protein, for wild type or cold-adapted equine influenza viruses.

A. Nucleic acid molecules encoding wild type or cold-adapted equine influenza virus PA-N proteins were produced as follows. A PCR product containing the N-terminal portion of the equine influenza PA gene was produced using equine influenza virus DNA and primers REV (SEQ ID NO:1), T7 (SEQ ID NO:2), PAN-2 (SEQ ID NO:90), PAN-3 (SEQ ID NO:91), PAN-4 (SEQ ID NO:92), and PAN-5 (SEQ ID NO:93). Plasmid DNA was purified and sequenced as in Example 1.

A nucleic acid molecule of 1216 nucleotides encoding a wild type PA-N protein, denoted $nei_{wt}PA-N_{1216}$, with a coding strand having a nucleic acid sequence designated SEQ ID NO:X5.

Translation of SEQ ID NO:X5 indicates that nucleic acid molecule $nei_{wt}PA-N_{1216}$ encodes a N-terminal portion of influenza PA protein of about 397 amino acids, referred to herein as $Pei_{wt}PA-N_{397}$, having amino acid sequence SEQ ID NO:X7, assuming an open reading frame from the starting methionine (M) through glutamic acid (E) at amino acid 397. The region encoding $Pei_{wt}PA-N_{397}$ designated $nei_{wt}PA-N_{1193}$ and having a coding strand comprising nucleotides 24 to 1214 of SEQ ID NO:X5, is herein designated SEQ ID NO:X6.

B. A nucleic acid molecule of 1217 nucleotides encoding an N-terminal portion of influenza PA-N cold-adapted equine influenza virus protein, denoted $nei_{ca}PA-N_{1217}$, with a coding strand having a nucleic acid sequence designated SEQ ID NO:X8.

Translation of SEQ ID NO:X9 indicates that nucleic acid molecule $nei_{ca}PA-N_{1217}$ encodes a N-terminal portion of influenza PA protein of about 397 amino acids, referred to herein as $Pei_{ca}PA-N_{397}$, having amino acid sequence SEQ ID NO:X10, assuming an open reading frame from the starting methionine (M) through glutamic acid (E) at amino acid 397. The region encoding $Pei_{ca}PA-N_{397}$, designated $nei_{ca}PA-N_{1193}$ and having a coding strand comprising nucleotides 25 to 1215 of SEQ ID NO:X8, is designated herein as SEQ ID NO:X9.

C. Comparison of the amino acid sequences of proteins $Pei_{wt}PA-N_{397}$ (SEQ ID NO:X7) and $Pei_{ca}PA-N_{397}$ (SEQ ID NO:X10) reveals the following differences: a glutamic acid (E) to lysine (K) at amino acid 59 and an alanine (A) to threonine (T) at amino acid 156.

EXAMPLE 10

This example describes the cloning and sequencing of equine influenza PA protein nucleic acid molecules, for wild type or cold-adapted equine influenza viruses.

A. The nucleic acid sequences encoding wild type or cold-adapted equine influenza virus PA proteins were compiled as follows. The open reading frame DNA sequence is 2148 nucleotides long for both stains. There is a 214 nucleotide overlap from the C-terminal and N-terminal fragments generated in Examples 8 and 9, respectively. The open reading frame sequences encode the RNA Polymerase A, otherwise known as RNA Polymerase 2 gene, which has 716 amino acid residues from the starting methionine (M) through lysine (K) at amino acid 716.

A nucleic acid molecule of 2148 nucleotides encoding the wild type protein is designed $nei_{wt}PA_{2148}$, and has the coding strand of nucleic acid sequence SEQ ID NO:X11.

Translation of SEQ ID NO:X11 indicates that nucleic acid molecule $nei_{wt}PA_{2148}$ encodes the equine influenza virus PA protein of about 716 amino acids, referred to herein as $Pei_{wt}PA_{716}$, having amino acid sequence SEQ ID NO:X12.

B. A nucleic acid molecule of 2148 nucleotides encoding the cold-adapted protein is designated $nei_{ca}PA_{2148}$, and has the coding strand of nucleic acid sequence SEQ ID NO:X13.

Translation of SEQ ID NO:X13 indicates that nucleic acid molecule $nei_{ca}PA_{2148}$ encodes a protein of about 716 amino acids, referred to herein as $PEI_{ca}PA_{716}$, having amino acid sequence SEQ ID NO:X14.

C. Comparison of the wild type and cold-adapted virus sequences reveals three discrepancies: a G to A base shift at base 175, base 466, and base 870. The base change at base 175 results in a glutamic acid (E) to lysine (K) change at amino acid 59. The base change at 466 results in an alanine (A) to threonine (T) change at amino acid 156. The base change at 870 does not result in an amino acid change at amino acid 290.

EXAMPLE 11

This example describes the cloning and sequencing of equine influenza Neuraminidase (NA) protein nucleic acid molecules for cold-adapted equine influenza viruses.

A. Nucleic acid molecules encoding cold-adapted equine influenza virus NA proteins were produced as follows. A PCR product was produced by PCR amplification using equine influenza virus DNA and primers M13 reverse primer (REV) and T7 primer (T7), designated SEQ ID NO:1 and SEQ ID NO:2, respectively. A nucleic acid molecule of 1478 molecules encoding the cold-adapted NA protein, denoted $nei_{ca}NA_{1478}$ with a coding strand having a nucleic acid sequence designated SEQ ID NO:87 was produced.

Translation of SEQ ID NO:87 indicates that nucleic acid molecule $nei_{ca}NA_{1478}$ encodes a full-length protein of 470 amino acids, referred to herein as $Pei_{ca}NA_{470}$, having amino acid sequence SEQ ID NO:88, assuming an open reading frame in which the initiation codons spans from nucleotide 29 through 31 of SEQ ID NO:87 and the termination codon spans from nucleotide 1439 through 1441 of SEQ ID NO:87. The region encoding $Pei_{ca}NA_{470}$, designated $nei_{ca}NA_{1412}$, and having a coding strand comprising nucleotide 29 to 1441 of SEQ ID NO:87, is represented by SEQ ID NO:89.

EXAMPLE 12

This example describes the cloning and sequencing of the N-terminal and C-terminal regions of the equine influenza nucleoprotein (NP) nucleic acid molecules for wild type and cold adapted equine influenza virus.

A. Nucleic acid molecules encoding wild type and cold adapted equine influenza virus NP proteins were produced as follows. Wild-type strains 1 and 2 were cloned into pCR2.1 (Invitrogen), and cold-adapted strains 1 and 2 were cloned into pCR-Blunt cloning vector (Invitrogen). All strains were sequenced using M13 REV and T7 primers, SEQ ID NO: 1 and SEQ ID NO: 2, respectively.

B. N-Terminal Regions

A nucleic acid molecule of 738 nucleotides encoding the N-terminus of the wild-type strain 1 NP protein, denoted $nei_{wt1}$ NP-$N_{738}$, with a coding strand having a nucleic acid sequence designated SEQ ID NO:104, was produced. Translation of SEQ ID NO:104 indicates that nucleic acid molecule $nei_{wt1}$ NP-$N_{738}$ encodes the N-terminal 246 amino acids of NP protein, designated $Pei_{wt1}$ NP-$N_{246}$, having amino acid sequence SEQ ID NO:105.

A nucleic acid molecule of 693 nucleotides encoding the N-terminus of the wild-type strain 1 NP protein, denoted $nei_{wt1}$ NP-$N_{693}$, with a coding strand having a nucleic acid sequence designated SEQ ID NO:106 was produced. Translation of SEQ ID NO:106 indicates that nucleic acid molecule $nei_{wt1}$ NP-$N_{693}$ encodes the N-terminal 231 amino acids of NP protein, designated Pei$w_{t1}$ NP-$N_{231}$, having amino acid sequence SEQ ID NO:107.

A nucleic acid molecule of 738 nucleotides encoding the N-terminus of the wild-type strain 2 NP protein, denoted $nei_{wt2}$ NP-$N_{738}$, with a coding strand having a nucleic acid sequence designated SEQ ID NO:108, was produced. Translation of SEQ ID NO:108 indicates that nucleic acid molecule $nei_{wt2}$ NP-$N_{738}$ encodes the N-terminal 246 amino acids of NP protein, designated Pei$_{wt2}$ NP-$N_{246}$, having amino acid sequence SEQ ID NO:109.

A nucleic acid molecule of 693 nucleotides encoding the N-terminus of the wild-type strain 2 NP protein, denoted $nei_{wt2}$ NP-$N_{693}$, with a coding strand having a nucleic acid sequence designated SEQ ID NO:110, was produced. Translation of SEQ ID NO:110 indicates that nucleic acid molecule $nei_{wt2}$ NP-$N_{693}$ encodes the N-terminal 231 amino acids of NP protein, designated Pei$_{wt2}$ NP-$N_{231}$, having amino acid sequence SEQ ID NO:111.

An N-terminal protein fragment of 245 amino acids of NP protein, designated Pei$_{ca1}$ NP-$N_{245}$, having amino acid sequence SEQ ID NO:112, was generated.

A nucleic acid molecule of 690 nucleotides encoding the N-terminus of the cold-adapted strain 1 NP protein, denoted $nei_{ca1}$ NP-$N_{690}$, with a coding strand having a nucleic acid sequence designated SEQ ID NO:113, was produced. Translation of SEQ ID NO:113 indicates that nucleic acid molecule $nei_{ca1}$ NP-$N_{690}$ encodes the N-terminal 230 amino acids of NP protein, designated Pei$_{ca1}$ NP-$N_{230}$, having amino acid sequence SEQ ID NO:114.

A nucleic acid molecule of 735 nucleotides encoding the N-terminus of the cold-adapted strain 2 Np protein, denoted $nei_{ca2}$ NP-$N_{735}$, with a coding strand having a nucleic acid sequence designated SEQ ID NO:115 was produced. Translation of SEQ ID NO:115 indicates that nucleic acid molecule $nei_{ca2}$ NP-$N_{735}$ encodes the N-terminal 245 amino acids of NP protein, designated Pei$_{ca2}$ NP-$N_{245}$, having amino acid sequence SEQ ID NO:116.

A nucleic acid molecule of 690 nucleotides encoding the N-terminus of the cold-adapted strain 2, denoted $nei_{ca2}$ NP-$N_{690}$, with a coding strand having a nucleic acid sequence designated SEQ ID NO:117, was produced. Translation of SEQ ID NO:117 indicates that nucleic acid molecule $nei_{ca2}$ NP-$N_{690}$ encodes the N-terminal 230 amino acids of NP protein, designated Pei$_{ca2}$ NP-$N_{230}$, having amino acid sequence SEQ ID NO:118.

C. C-Terminal Regions

A nucleic acid molecule of 679 nucleotides encoding the C-terminal of the wild type strain 1, denoted $nei_{wt1}$ NP-$C_{679}$, with a coding strand having a nucleic acid sequence designated SEQ ID NO:119, was produced. Translation of SEQ ID NO:119 indicates that nucleic acid molecule $nei_{wt1}$ NP-$C_{679}$ encodes the C-terminal 226 amino acids of NP protein, designated Pei$_{wt1}$ NP-$C_{226}$, having amino acid sequence SEQ ID NO:120.

A nucleic acid molecule of 656 nucleotides encoding the C-terminal of the wild type strain 1, denoted $nei_{wt1}$ NP-$C_{656}$, with a coding strand having a nucleic acid sequence designated SEQ ID NO:121, was produced. Translation of SEQ ID NO:121 indicates that nucleic acid molecule $nei_{wt1}$ NP-$C_{656}$ encodes the C-terminal 218 amino acids of NP protein, designated Pei$_{wt1}$ NP-$C_{218}$, having amino acid sequence SEQ ID NO:122.

A nucleic acid molecule of 679 nucleotides encoding the C-terminal of the wild type strain 1, denoted $nei_{wt2}$ NP-$C_{679}$, with a coding strand having a nucleic acid sequence designated SEQ ID NO:123, was produced. Translation of SEQ ID NO:123 indicates that nucleic acid molecule $nei_{wt2}$ NP-$C_{679}$ encodes the C-terminal 226 amino acids of NP protein, designated Pei$_{wt2}$ NP-$C_{226}$, having amino acid sequence SEQ ID NO:124.

A nucleic acid molecule of 656 nucleotides encoding the C-terminal of the wild type strain 2, denoted $nei_{wt2}$ NP-$C_{656}$, with a coding strand having a nucleic acid sequence designated SEQ ID NO:125, was produced. Translation of SEQ ID NO:125 indicates that nucleic acid molecule $nei_{wt2}$ NP-$C_{656}$ encodes the C-terminal 218 amino acids of NP protein, designated Pei$_{wt2}$ NP-$C_{218}$, having amino acid sequence SEQ ID NO:126.

A nucleic acid molecule of 656 nucleotides encoding the C-terminal of the cold-adapted strain 1, denoted $nei_{ca1}$ NP-$C_{665}$, with a coding strand having a nucleic acid sequence designated SEQ ID NO:127, was produced. Translation of SEQ ID NO:127 indicates that nucleic acid molecule $nei_{ca1}$ NP-$C_{665}$ encodes the C-terminal 222 amino acids of NP protein, designated Pei$_{ca1}$ NP-$C_{222}$, having amino acid sequence SEQ ID NO:128.

A nucleic acid molecule of 642 nucleotides encoding the C-terminal of the cold-adapted strain 1, denoted $nei_{ca1}$ NP-$C_{642}$, with a coding strand having a nucleic acid sequence designated SEQ ID NO:129 was produced. Translation of SEQ ID NO:129 indicates that nucleic acid molecule $nei_{ca1}$ NP-$C_{642}$ encodes the C-terminal 214 amino acids of NP protein, designated Pei$_{ca1}$ NP-$C_{214}$, having amino acid sequence SEQ ID NO:130.

D. Comparisons

Consensus sequences for the 5' and 3' ends of the NP gene were generated, but there is an approximately 148 base pair gap in the data that prevents the formation of a contiguous sequence when compared to protein and DNA data currently in the GenBank databases (a nucleoprotein from GenBank named flanpg; Gorman et al, J. Virol. 64, 1487 (1990)). The flanpg sequences were used to compare the 5' and 3' fragments of the present NP genes to get relative positions that are used to designate position for the various differences in the bases between the Wild Type and the ca strains. The flanpg sequence allows for the approximately 148 base pairs that are missing between the 5' and 3' fragments needed to construct the entire gene.

The DNA codes for the N-terminal 735–738 bases and the C-terminal 665–679 bases with a gap of approximately 149–166 bases between the two fragments of the Wild Type and cold-adapted (ca) strains, respectively. There are seven discrepancies between the wild type and ca strains. The ca strains have discrepancies at base 146 (G to T) and at base 228 (A to G). At base 492, the wt1 only has a discrepancy versus the other strains of (A to C). At base 541, the ca1 only has a discrepancy versus the other strains of (C to A). There is a base discrepancy at position 645 in the DNA (G to A). At base 670, the ca strains have a discrepancy (G to A). At base 1019, the wt1 only has a discrepancy versus the other strains of (G to A). There are no other points of discrepancy between the full-length Wild Type and ca strains.

The full-length sequence is proposed to consist of 1497 bases, however there is no overlap between the 5' and 3' ends of the DNA sequences generated. The sequences listed are for the 5' end and the 3' end of the open reading frame of the gene. The gene is missing approximately 148 base pairs between these two fragment sequences that would generate the complete gene sequence.

A comparison of all the Wild Type and ca strain clones (wt1, wt2, ca1, and ca2) by amino acid translation for the protein sequence coding only for the open reading frame (ORF) from the 5' and 3' DNA fragments was compared to the GenBank nucleoprotein noted above. The DNA codes for the N-terminal 230 amino acids and the C-terminal 214 amino acids with a gap of approximately 55 amino acids between the two fragments. There are seven discrepancies between the ca and Wild Type strains. The ca strains have a discrepancy (G to V) at amino acid 34, and at amino acid 61 (I to M). At amino acid 149, the wt1 only has a discrepancy versus the other strains of (Q to H). At amino acid 166, ca1 only has a discrepancy versus the other strains of (L to M). Although there is a base discrepancy at position 600 in the DNA sequence, there is no change in the corresponding amino acid sequence. At amino acid 209, the ca strains have a discrepancy (G to S). At amino acid 325, the wt1 only has a discrepancy versus the other strains of R to K). There are no other points of discrepancy between the fill-length Wild Type and ca strains.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated equine influenza protein that comprises the amino acid sequence of SEQ ID NO:28.

2. A composition comprising the isolated equine influenza protein of claim 1 and an excipient.

* * * * *

SEQUENCE LISTING

```
<160> NUMBER OF SEQ ID NOS: 130

<210> SEQ ID NO 1
<211> LENGTH: 18
<212> TYPE: DNA
<213> ORGANISM: Artificial
<220> FEATURE:
<223> OTHER INFORMATION: Synthetic Primer

<400> SEQUENCE: 1
caggaaacag ctatgacc                                                   18

<210> SEQ ID NO 2
<211> LENGTH: 20
<212> TYPE: DNA
<213> ORGANISM: Artificial
<220> FEATURE:
<223> OTHER INFORMATION: Synthetic Primer

<400> SEQUENCE: 2
taatacgact cactataggg                                                 20

<210> SEQ ID NO 3
<211> LENGTH: 25
<212> TYPE: DNA
<213> ORGANISM: Artificial
<220> FEATURE:
<223> OTHER INFORMATION: Synthetic Primer

<400> SEQUENCE: 3
agcaaaagca ggtcaaatat attca                                           25

<210> SEQ ID NO 4
<211> LENGTH: 26
<212> TYPE: DNA
<213> ORGANISM: Artificial
<220> FEATURE:
<223> OTHER INFORMATION: Synthetic Primer

<400> SEQUENCE: 4
gaaaacacca tggctacaat tattgc                                          26

<210> SEQ ID NO 5
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)

<400> SEQUENCE: 5
```

```
agcaaaagca ggtcaaatat attcaat atg gag aga ata aaa gaa ctg aga gat        54
                            Met Glu Arg Ile Lys Glu Leu Arg Asp
                             1               5 cta atg tca caa tcc cgc acc cgc gag ata cta aca aaa act act gtg         102
Leu Met Ser Gln Ser Arg Thr Arg Glu Ile Leu Thr Lys Thr Thr Val
 10              15                  20                  25 gac cac atg gcc ata atc aag aaa tac aca tca gga aga caa gag aag         150
Asp His Met Ala Ile Ile Lys Lys Tyr Thr Ser Gly Arg Gln Glu Lys
                 30                  35                  40 aac ccc gca ctt agg atg aag tgg atg atg gca atg aaa tac cca att         198
Asn Pro Ala Leu Arg Met Lys Trp Met Met Ala Met Lys Tyr Pro Ile
             45                  50                  55 aca gca gat aag agg ata atg gaa atg att cct gag aga aat gaa cag         246
Thr Ala Asp Lys Arg Ile Met Glu Met Ile Pro Glu Arg Asn Glu Gln
                 60                  65                  70 ggg caa acc ctt tgg agc aaa acg aac gat gct ggc tca gac cgc gta         294
Gly Gln Thr Leu Trp Ser Lys Thr Asn Asp Ala Gly Ser Asp Arg Val
 75                  80                  85 atg gta tca cct ctg gca gtg aca tgg tgg aat agg aat gga cca aca         342
Met Val Ser Pro Leu Ala Val Thr Trp Trp Asn Arg Asn Gly Pro Thr
 90                  95                 100                 105 acg agc aca att cat tat cca aaa gtc tac aaa act tat ttt gaa aaa         390
Thr Ser Thr Ile His Tyr Pro Lys Val Tyr Lys Thr Tyr Phe Glu Lys
                110                 115                 120 gtt gaa aga tta aaa cac gga acc ttt ggc ccc gtt cat ttt agg aat         438
Val Glu Arg Leu Lys His Gly Thr Phe Gly Pro Val His Phe Arg Asn
            125                 130                 135 caa gtc aag ata aga cgg aga gtt gat gta aac cct ggt cac gcg gac         486
Gln Val Lys Ile Arg Arg Arg Val Asp Val Asn Pro Gly His Ala Asp
            140                 145                 150 ctc agt gcc aaa gaa gca caa gat gtg atc atg gaa gtt gtt ttc cca         534
Leu Ser Ala Lys Glu Ala Gln Asp Val Ile Met Glu Val Val Phe Pro
155                 160                 165 aat gaa gtg gga gcc aga att cta aca tcg gaa tca caa cta aca ata         582
Asn Glu Val Gly Ala Arg Ile Leu Thr Ser Glu Ser Gln Leu Thr Ile
170                 175                 180                 185 acc aaa gag aaa aaa gaa gaa ctt cag gac tgc aaa att gcc ccc ttg         630
Thr Lys Glu Lys Lys Glu Glu Leu Gln Asp Cys Lys Ile Ala Pro Leu
                190                 195                 200 atg gta gca tac atg cta gaa aga gag ttg gtc cga aaa aca aga ttc         678
Met Val Ala Tyr Met Leu Glu Arg Glu Leu Val Arg Lys Thr Arg Phe
            205                 210                 215 ctc cca gtg gct ggc gga aca agc agt gta tac att gaa gtg ttg cat         726
Leu Pro Val Ala Gly Gly Thr Ser Ser Val Tyr Ile Glu Val Leu His
            220                 225                 230 ctg act cag gga aca tgc tgg gaa caa atg tac acc cca gga gga gaa         774
Leu Thr Gln Gly Thr Cys Trp Glu Gln Met Tyr Thr Pro Gly Gly Glu
235                 240                 245 gtt aga aac gat gac att gat caa agt tta att att gct gcc cgg aac         822
Val Arg Asn Asp Asp Ile Asp Gln Ser Leu Ile Ile Ala Ala Arg Asn
250                 255                 260                 265 ata gtg aga aga gcg aca gta tca gca gat cca cta gca tcc ctg ctg         870
Ile Val Arg Arg Ala Thr Val Ser Ala Asp Pro Leu Ala Ser Leu Leu
                270                 275                 280 gaa atg tgc cac agt aca cag att ggt gga ata agg atg gta gac atc         918
Glu Met Cys His Ser Thr Gln Ile Gly Gly Ile Arg Met Val Asp Ile
            285                 290                 295 ctt aag cag aat cca aca gag gaa caa gct gtg gat ata tgc aaa gca         966
Leu Lys Gln Asn Pro Thr Glu Glu Gln Ala Val Asp Ile Cys Lys Ala
            300                 305                 310
```

```
gca atg ggg tta aga att agc tca tca ttc agc ttt ggt gga ttc acc         1014
Ala Met Gly Leu Arg Ile Ser Ser Ser Phe Ser Phe Gly Gly Phe Thr
315                 320                 325 ttt aag aga aca agt gga tca tca gtc aag aga gaa gaa gaa atg ctt         1062
Phe Lys Arg Thr Ser Gly Ser Ser Val Lys Arg Glu Glu Glu Met Leu
330                 335                 340                 345 acg ggc aac ctt caa aca ttg aaa ata aga gtg cat gaa ggc tat gaa         1110
Thr Gly Asn Leu Gln Thr Leu Lys Ile Arg Val His Glu Gly Tyr Glu
            350                 355                 360 gaa ttc aca atg gtc gga aga aga gca aca gcc att ctc aga aag gca         1158
Glu Phe Thr Met Val Gly Arg Arg Ala Thr Ala Ile Leu Arg Lys Ala
        365                 370                 375 acc aga aga ttg att caa ttg ata gta agt ggg aga gat gaa caa tca         1206
Thr Arg Arg Leu Ile Gln Leu Ile Val Ser Gly Arg Asp Glu Gln Ser
    380                 385                 390 att gct gaa gca ata att gta gcc atg gtg ttt tc                          1241
Ile Ala Glu Ala Ile Ile Val Ala Met Val Phe
395                 400
```

<210> SEQ ID NO 6
<211> LENGTH: 404
<212> TYPE: PRT
<213> ORGANISM: Equine influenza virus H3N8

<400> SEQUENCE: 6

```
Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
```

```
                   245                 250                 255
Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
            275                 280                 285

Ile Gly Gly Ile Arg Met Val Asp Ile Leu Lys Gln Asn Pro Thr Glu
            290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
            355                 360                 365

Arg Ala Thr Ala Ile Leu Arg Lys Ala Thr Arg Arg Leu Ile Gln Leu
            370                 375                 380

Ile Val Ser Gly Arg Asp Glu Gln Ser Ile Ala Glu Ala Ile Ile Val
385                 390                 395                 400

Ala Met Val Phe

<210> SEQ ID NO 7
<211> LENGTH: 1214
<212> TYPE: DNA
<213> ORGANISM: Equine influenza virus H3N8

<400> SEQUENCE: 7
atggagagaa taaagaact  gagagatcta atgtcacaat cccgcacccg cgagatacta      60
acaaaaacta ctgtggacca catggccata atcaagaaat acacatcagg aagacaagag    120
aagaaccccg cacttaggat gaagtggatg atggcaatga ataccccaat tacagcagat    180
aagaggataa tggaaatgat tcctgagaga atgaacagg  ggcaaaccct ttggagcaaa    240
acgaacgatg ctggctcaga ccgcgtaatg gtatcacctc tggcagtgac atggtggaat    300
aggaatggac caacaacgag cacaattcat tatccaaaag tctacaaaac ttattttgaa    360
aaagttgaaa gattaaaaca cggaaccttt ggccccgttc attttaggaa tcaagtcaag    420
ataagacgga gagttgatgt aaaccctggt cacgcggacc tcagtgccaa agaagcacaa    480
gatgtgatca tggaagttgt tttcccaaat gaagtgggag ccagaattct aacatcggaa    540
tcacaactaa caataaccaa agagaaaaaa gaagaacttc aggactgcaa aattgccccc    600
ttgatggtag catacatgct agaaagagag ttggtccgaa aaacaagatt cctcccagtg    660
gctggcggaa caagcagtgt atacattgaa gtgttgcatc tgactcaggg aacatgctgg    720
gaacaaatgt acacccccag aggagaagtt gaaacgatg  acattgatca agtttaattt    780
attgctgccc ggaacatagt gagaagagcg acagtatcag cagatccact agcatccctg    840
ctggaaatgt gccacagtac acagattggt ggaataagga tggtagacat ccttaagcag    900
aatccaacag aggaacaagc tgtggatata tgcaaagcag caatggggtt aagaattagc    960
tcatcattca gctttggtgg attcaccttt aagagaacaa gtggatcatc agtcaagaga   1020
gaagaagaaa tgcttacggg caaccttcaa acattgaaaa taagagtgca tgaaggctat   1080
gaagaattca atggtcgg   aagaagagca acagccattc tcagaaaggc aaccagaaga   1140
ttgattcaat tgatagtaag tgggagagat gaacaatcaa ttgctgaagc aataattgta   1200
```

```
gccatggtgt tttc                                                      1214
```

<210> SEQ ID NO 8
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)

<400> SEQUENCE: 8

```
agcaaaagca ggtcaaatat attcaat atg gag aga ata aaa gaa ctg aga gat      54
                             Met Glu Arg Ile Lys Glu Leu Arg Asp
                               1               5 cta atg tca caa tcc cgc acc cgc gag ata cta aca aaa act act gtg      102
Leu Met Ser Gln Ser Arg Thr Arg Glu Ile Leu Thr Lys Thr Thr Val
 10              15                  20                  25 gac cac atg gcc ata atc aag aaa tac aca tca gga aga caa gag aag      150
Asp His Met Ala Ile Ile Lys Lys Tyr Thr Ser Gly Arg Gln Glu Lys
             30                  35                  40 aac ccc gca ctt agg atg aag tgg atg atg gca atg aaa tac cca att      198
Asn Pro Ala Leu Arg Met Lys Trp Met Met Ala Met Lys Tyr Pro Ile
         45                  50                  55 aca gca gat aag agg ata atg gaa atg att cct gag aga aat gaa cag      246
Thr Ala Asp Lys Arg Ile Met Glu Met Ile Pro Glu Arg Asn Glu Gln
     60                  65                  70 ggg caa acc ctt tgg agc aaa acg aac gat gct ggc tca gac cgc gta      294
Gly Gln Thr Leu Trp Ser Lys Thr Asn Asp Ala Gly Ser Asp Arg Val
 75                  80                  85 atg gta tca cct ctg gca gtg aca tgg tgg aat agg aat gga cca aca      342
Met Val Ser Pro Leu Ala Val Thr Trp Trp Asn Arg Asn Gly Pro Thr
 90                  95                 100                 105 acg agc aca att cat tat cca aaa gtc cac aaa act tat ttt gaa aaa      390
Thr Ser Thr Ile His Tyr Pro Lys Val His Lys Thr Tyr Phe Glu Lys
                110                 115                 120 gtt gaa aga tta aaa cac gga acc ttt ggc ccc gtt cat ttt agg aat      438
Val Glu Arg Leu Lys His Gly Thr Phe Gly Pro Val His Phe Arg Asn
            125                 130                 135 caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150 ctc agt gcc aaa gaa gca caa gat gtg atc atg gaa gtt gtt ttc cca      534
Leu Ser Ala Lys Glu Ala Gln Asp Val Ile Met Glu Val Val Phe Pro
    155                 160                 165 aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185 acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200 atg gta gca tac atg cta gaa aga gag ttg gtc cga aaa aca aga ttc      678
Met Val Ala Tyr Met Leu Glu Arg Glu Leu Val Arg Lys Thr Arg Phe
            205                 210                 215 ctc cca gtg gct ggc gga aca agc agt gta tac att gaa gtg ttg cat      726
Leu Pro Val Ala Gly Gly Thr Ser Ser Val Tyr Ile Glu Val Leu His
        220                 225                 230 ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245 gtt aga aac gat gac att gat caa agt tta att att gct gcc cgg aac      822
Val Arg Asn Asp Asp Ile Asp Gln Ser Leu Ile Ile Ala Ala Arg Asn
```

-continued

```
ata gtg aga aga gcg aca gta tca gca gat cca cta gca tcc ctg ctg    870
Ile Val Arg Arg Ala Thr Val Ser Ala Asp Pro Leu Ala Ser Leu Leu
            270                 275                 280 gaa atg tgc cac agt aca cag att ggt gga ata agg atg gta gac atc    918
Glu Met Cys His Ser Thr Gln Ile Gly Gly Ile Arg Met Val Asp Ile
                285                 290                 295 ctt aag cag aat cca aca gag gaa caa gct gtg gat ata tgc aaa gca    966
Leu Lys Gln Asn Pro Thr Glu Glu Gln Ala Val Asp Ile Cys Lys Ala
            300                 305                 310 gca atg ggg tta aga att agc tca tca ttc agc ttt ggt gga ttc acc   1014
Ala Met Gly Leu Arg Ile Ser Ser Ser Phe Ser Phe Gly Gly Phe Thr
315                 320                 325 ttt aag aga aca agt gga tca tca gtc aag aga gaa gaa gaa atg ctt   1062
Phe Lys Arg Thr Ser Gly Ser Ser Val Lys Arg Glu Glu Glu Met Leu
330                 335                 340                 345 acg ggc aac ctt caa aca ttg aaa ata aga gtg cat gaa ggc tat gaa   1110
Thr Gly Asn Leu Gln Thr Leu Lys Ile Arg Val His Glu Gly Tyr Glu
            350                 355                 360 gaa ttc aca atg gtc gga aga aga gca aca gcc att ctc aga aag gca   1158
Glu Phe Thr Met Val Gly Arg Arg Ala Thr Ala Ile Leu Arg Lys Ala
                365                 370                 375 acc aga aga ttg att caa ttg ata gta agt ggg aga gat gaa caa tca   1206
Thr Arg Arg Leu Ile Gln Leu Ile Val Ser Gly Arg Asp Glu Gln Ser
            380                 385                 390 att gct gaa gca ata att gta gcc atg gtg ttt tc                    1241
Ile Ala Glu Ala Ile Ile Val Ala Met Val Phe
395                 400

<210> SEQ ID NO 9
<211> LENGTH: 404
<212> TYPE: PRT
<213> ORGANISM: Equine influenza virus H3N8

<400> SEQUENCE: 9

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val His Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175
```

```
Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
            245                 250                 255

Gln Ser Leu Ile Ile Ala Ala Arg Asn Ile Val Arg Arg Ala Thr Val
        260                 265                 270

Ser Ala Asp Pro Leu Ala Ser Leu Leu Glu Met Cys His Ser Thr Gln
    275                 280                 285

Ile Gly Gly Ile Arg Met Val Asp Ile Leu Lys Gln Asn Pro Thr Glu
290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
            325                 330                 335

Ser Val Lys Arg Glu Glu Glu Met Leu Thr Gly Asn Leu Gln Thr Leu
        340                 345                 350

Lys Ile Arg Val His Glu Gly Tyr Glu Glu Phe Thr Met Val Gly Arg
    355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe

<210> SEQ ID NO 10
<211> LENGTH: 1214
<212> TYPE: DNA
<213> ORGANISM: Equine influenza virus H3N8

<400> SEQUENCE: 10
atggagagaa taaagaact gagagatcta atgtcacaat cccgcacccg cgagatacta      60
acaaaaacta ctgtggacca catggccata atcaagaaat acacatcagg aagacaagag     120
aagaaccccg cacttaggat gaagtggatg atggcaatga ataccccaat tacagcagat    180
aagaggataa tggaaatgat tcctgagaga atgaacaggg gcaaaccct ttggagcaaa     240 acgaacgatg ctggctcaga ccgcgtaatg gtatcacctc tggcagtgac atggtggaat    300
aggaatggac caacaacgag cacaattcat tatccaaaag tccacaaaac ttattttgaa    360
aaagttgaaa gattaaaaca cggaaccttt ggccccgttc attttaggaa tcaagtcaag    420
ataagacgga gagttgatgt aaaccctggt cacgcggacc tcagtgccaa gaagcacaa    480 gatgtgatca tggaagttgt tttcccaaat gaagtgggag ccagaattct aacatcggaa    540
tcacaactaa caataaccaa agagaaaaaa gaagaacttc aggactgcaa aattgccccc    600
ttgatggtag catacatgct agaaagagag ttggtccgaa aaacaagatt cctcccagtg    660
gctggcggaa caagcagtgt atacattgaa gtgttgcatc tgactcaggg aacatgctgg    720
gaacaaatgt acaccccagg aggagaagtt agaaacgatg acattgatca agtttaatt    780 attgctgccc ggaacatagt gagaagagcg acagtatcag cagatccact agcatccctg    840
```

```
ctggaaatgt gccacagtac acagattggt ggaataagga tggtagacat ccttaagcag    900
aatccaacag aggaacaagc tgtggatata tgcaaagcag caatggggtt aagaattagc    960
tcatcattca gctttggtgg attcaccttt aagagaacaa gtggatcatc agtcaagaga   1020
gaagaagaaa tgcttacggg caaccttcaa acattgaaaa taagagtgca tgaaggctat   1080
gaagaattca caatggtcgg aagaagagca acagccattc tcagaaaggc aaccagaaga   1140
ttgattcaat tgatagtaag tgggagagat gaacaatcaa ttgctgaagc aataattgta   1200
gccatggtgt tttc                                                     1214
```

<210> SEQ ID NO 11
<211> LENGTH: 27
<212> TYPE: DNA
<213> ORGANISM: Artificial
<220> FEATURE:
<223> OTHER INFORMATION: Synthetic Primer

<400> SEQUENCE: 11
agaattcaca atggtcggaa gaagagc                                         27

<210> SEQ ID NO 12
<211> LENGTH: 27
<212> TYPE: DNA
<213> ORGANISM: Artificial
<220> FEATURE:
<223> OTHER INFORMATION: Synthetic Primer

<400> SEQUENCE: 12
agtagaaaca aggtcgtttt taaacaa                                         27

<210> SEQ ID NO 13
<211> LENGTH: 1233
<212> TYPE: DNA
<213> ORGANISM: Equine influenza virus H3N8
<220> FEATURE:
<221> NAME/KEY: CDS
<222> LOCATION: (3)..(1196)

<400> SEQUENCE: 13

```
ta gaa ttc aca atg gtc gga aga aga gca aca gcc att ctc aga aag      47
   Glu Phe Thr Met Val Gly Arg Arg Ala Thr Ala Ile Leu Arg Lys
   1               5                  10                  15 gca acc aga aga ttg att caa ttg ata gta agt ggg aga gat gaa caa     95
Ala Thr Arg Arg Leu Ile Gln Leu Ile Val Ser Gly Arg Asp Glu Gln
             20                  25                  30 tca att gct gaa gca ata att gta gcc atg gtg ttt tcg caa gaa gat    143
Ser Ile Ala Glu Ala Ile Ile Val Ala Met Val Phe Ser Gln Glu Asp
         35                  40                  45 tgc atg ata aaa gca gtt cga ggc gat ttg aac ttc gtt aat aga gca    191
Cys Met Ile Lys Ala Val Arg Gly Asp Leu Asn Phe Val Asn Arg Ala
     50                  55                  60 aat cag cgc ttg aac ccc atg cat caa ctc ttg agg cat ttc caa aaa    239
Asn Gln Arg Leu Asn Pro Met His Gln Leu Leu Arg His Phe Gln Lys
 65                  70                  75 gat gca aaa gtg ctt ttc cag aat tgg ggg att gaa ccc atc gac aat    287
Asp Ala Lys Val Leu Phe Gln Asn Trp Gly Ile Glu Pro Ile Asp Asn
 80                  85                  90                  95 gtg atg gga atg att gga ata ttg cct gac atg acc cca agc acc gag    335
Val Met Gly Met Ile Gly Ile Leu Pro Asp Met Thr Pro Ser Thr Glu
                100                 105                 110 atg tca ttg aga gga gtg aga gtc agc aaa atg gga gtg gat gag tac    383
Met Ser Leu Arg Gly Val Arg Val Ser Lys Met Gly Val Asp Glu Tyr
```

|  |  |  |
|---|---|---|
| Met Ser Leu Arg Gly Val Arg Val Ser Lys Met Gly Val Asp Glu Tyr<br>115                      120                125 |  |  |
| tcc agc act gag aga gtg gtg gtg agc att gac cgt ttt tta aga gtt<br>Ser Ser Thr Glu Arg Val Val Val Ser Ile Asp Arg Phe Leu Arg Val<br>        130                  135              140 | 431 |
| cgg gat caa agg gga aac ata cta ctg tcc cct gaa gag gtc agt gaa<br>Arg Asp Gln Arg Gly Asn Ile Leu Leu Ser Pro Glu Glu Val Ser Glu<br>145                      150                155 | 479 |
| aca caa gga acg gaa aag ctg aca ata att tat tca tca tca atg atg<br>Thr Gln Gly Thr Glu Lys Leu Thr Ile Ile Tyr Ser Ser Ser Met Met<br>160                165              170              175 | 527 |
| tgg gag att aat ggt ccc gaa tca gtg ttg gtc aat act tat caa tgg<br>Trp Glu Ile Asn Gly Pro Glu Ser Val Leu Val Asn Thr Tyr Gln Trp<br>                180                185              190 | 575 |
| atc atc agg aac tgg gaa att gtg aaa att caa tgg tca cag gat ccc<br>Ile Ile Arg Asn Trp Glu Ile Val Lys Ile Gln Trp Ser Gln Asp Pro<br>                195                200              205 | 623 |
| aca atg tta tac aat aag ata gaa ttt gag cca ttc cag tcc ctg gtc<br>Thr Met Leu Tyr Asn Lys Ile Glu Phe Glu Pro Phe Gln Ser Leu Val<br>210                      215                220 | 671 |
| cct agg gcc acc aga agc caa tac agc ggt ttc gta aga acc ctg ttt<br>Pro Arg Ala Thr Arg Ser Gln Tyr Ser Gly Phe Val Arg Thr Leu Phe<br>225                      230                235 | 719 |
| cag caa atg cga gat gta ctt gga aca ttt gat act gct caa ata ata<br>Gln Gln Met Arg Asp Val Leu Gly Thr Phe Asp Thr Ala Gln Ile Ile<br>240                245              250              255 | 767 |
| aaa ctc ctc cct ttt gcc gct gct cct ccg gaa cag agt agg atg cag<br>Lys Leu Leu Pro Phe Ala Ala Ala Pro Pro Glu Gln Ser Arg Met Gln<br>                260                265              270 | 815 |
| ttc tct tct ttg act gtt aat gta aga gga tcg gga atg agg ata ctt<br>Phe Ser Ser Leu Thr Val Asn Val Arg Gly Ser Gly Met Arg Ile Leu<br>                275                280              285 | 863 |
| gta aga ggc aat tcc cca gtg ttc aac tac aat aaa gcc act aag agg<br>Val Arg Gly Asn Ser Pro Val Phe Asn Tyr Asn Lys Ala Thr Lys Arg<br>290                      295                300 | 911 |
| ctc aca gtc ctc gga aag gat gca ggt gcg ctt act gaa gac cca gat<br>Leu Thr Val Leu Gly Lys Asp Ala Gly Ala Leu Thr Glu Asp Pro Asp<br>305                      310                315 | 959 |
| gaa ggt acg gct gga gta gaa tct gct gtt cta aga ggg ttt ctc att<br>Glu Gly Thr Ala Gly Val Glu Ser Ala Val Leu Arg Gly Phe Leu Ile<br>320                      325                330              335 | 1007 |
| tta ggt aaa gaa aac aag aga tat ggc cca gca cta agc atc aat gaa<br>Leu Gly Lys Glu Asn Lys Arg Tyr Gly Pro Ala Leu Ser Ile Asn Glu<br>                340                345              350 | 1055 |
| ctg agc aaa ctt gca aaa ggg gag aaa gct aat gtg cta att ggg caa<br>Leu Ser Lys Leu Ala Lys Gly Glu Lys Ala Asn Val Leu Ile Gly Gln<br>                355                360              365 | 1103 |
| ggg gac gtg gtg ttg gta atg aaa cgg aaa cgt gac tct agc ata ctt<br>Gly Asp Val Val Leu Val Met Lys Arg Lys Arg Asp Ser Ser Ile Leu<br>                370                375              380 | 1151 |
| act gac agc cag aca gcg acc aaa agg att cgg atg gcc atc aat<br>Thr Asp Ser Gln Thr Ala Thr Lys Arg Ile Arg Met Ala Ile Asn<br>385                      390                395 | 1196 |
| tagtgttgaa ttgtttaaaa acgaccttgt ttctact | 1233 |

<210> SEQ ID NO 14
<211> LENGTH: 398
<212> TYPE: PRT
<213> ORGANISM: Equine influenza virus H3N8

<400> SEQUENCE: 14

```
Glu Phe Thr Met Val Gly Arg Arg Ala Thr Ala Ile Leu Arg Lys Ala
1               5                   10                  15
Thr Arg Arg Leu Ile Gln Leu Ile Val Ser Gly Arg Asp Glu Gln Ser
            20                  25                  30
Ile Ala Glu Ala Ile Ile Val Ala Met Val Phe Ser Gln Glu Asp Cys
        35                  40                  45
Met Ile Lys Ala Val Arg Gly Asp Leu Asn Phe Val Asn Arg Ala Asn
    50                  55                  60
Gln Arg Leu Asn Pro Met His Gln Leu Leu Arg His Phe Gln Lys Asp
65                  70                  75                  80
Ala Lys Val Leu Phe Gln Asn Trp Gly Ile Glu Pro Ile Asp Asn Val
                85                  90                  95
Met Gly Met Ile Gly Ile Leu Pro Asp Met Thr Pro Ser Thr Glu Met
            100                 105                 110
Ser Leu Arg Gly Val Arg Val Ser Lys Met Gly Val Asp Glu Tyr Ser
        115                 120                 125
Ser Thr Glu Arg Val Val Ser Ile Asp Arg Phe Leu Arg Val Arg
    130                 135                 140
Asp Gln Arg Gly Asn Ile Leu Leu Ser Pro Glu Glu Val Ser Glu Thr
145                 150                 155                 160
Gln Gly Thr Glu Lys Leu Thr Ile Ile Tyr Ser Ser Met Met Trp
                165                 170                 175
Glu Ile Asn Gly Pro Glu Ser Val Leu Val Asn Thr Tyr Gln Trp Ile
            180                 185                 190
Ile Arg Asn Trp Glu Ile Val Lys Ile Gln Trp Ser Gln Asp Pro Thr
        195                 200                 205
Met Leu Tyr Asn Lys Ile Glu Phe Glu Pro Phe Gln Ser Leu Val Pro
    210                 215                 220
Arg Ala Thr Arg Ser Gln Tyr Ser Gly Phe Val Arg Thr Leu Phe Gln
225                 230                 235                 240
Gln Met Arg Asp Val Leu Gly Thr Phe Asp Thr Ala Gln Ile Ile Lys
                245                 250                 255
Leu Leu Pro Phe Ala Ala Pro Pro Glu Gln Ser Arg Met Gln Phe
            260                 265                 270
Ser Ser Leu Thr Val Asn Val Arg Gly Ser Gly Met Arg Ile Leu Val
        275                 280                 285
Arg Gly Asn Ser Pro Val Phe Asn Tyr Asn Lys Ala Thr Lys Arg Leu
    290                 295                 300
Thr Val Leu Gly Lys Asp Ala Gly Ala Leu Thr Glu Asp Pro Asp Glu
305                 310                 315                 320
Gly Thr Ala Gly Val Glu Ser Ala Val Leu Arg Gly Phe Leu Ile Leu
                325                 330                 335
Gly Lys Glu Asn Lys Arg Tyr Gly Pro Ala Leu Ser Ile Asn Glu Leu
            340                 345                 350
Ser Lys Leu Ala Lys Gly Glu Lys Ala Asn Val Leu Ile Gly Gln Gly
        355                 360                 365
Asp Val Val Leu Val Met Lys Arg Lys Arg Asp Ser Ser Ile Leu Thr
    370                 375                 380
Asp Ser Gln Thr Ala Thr Lys Arg Ile Arg Met Ala Ile Asn
385                 390                 395
```

<210> SEQ ID NO 15

-continued

<211> LENGTH: 19
<212> TYPE: DNA
<213> ORGANISM: Artificial
<220> FEATURE:
<223> OTHER INFORMATION: Synthetic Primer

<400> SEQUENCE: 15
agccgtacct tcatctggg 19

<210> SEQ ID NO 16
<211> LENGTH: 19
<212> TYPE: DNA
<213> ORGANISM: Artificial
<220> FEATURE:
<223> OTHER INFORMATION: Synthetic Primer

<400> SEQUENCE: 16
agcactgaga gagtggtgg 19

<210> SEQ ID NO 17
<211> LENGTH: 19
<212> TYPE: DNA
<213> ORGANISM: Artificial
<220> FEATURE:
<223> OTHER INFORMATION: Synthetic Primer

<400> SEQUENCE: 17
gtaagaggca attccccag 19

<210> SEQ ID NO 18
<211> LENGTH: 18
<212> TYPE: DNA
<213> ORGANISM: Artificial
<220> FEATURE:
<223> OTHER INFORMATION: Synthetic Primer

<400> SEQUENCE: 18
cagcttttcc gttccttg 18

<210> SEQ ID NO 19
<211> LENGTH: 1194
<212> TYPE: DNA
<213> ORGANISM: Equine influenza virus H3N8

<400> SEQUENCE: 19
gaattcacaa tggtcggaag aagagcaaca gccattctca gaaaggcaac cagaagattg 60
attcaattga tagtaagtgg gagagatgaa caatcaattg ctgaagcaat aattgtagcc 120
atggtgtttt cgcaagaaga ttgcatgata aaagcagttc gaggcgattt gaacttcgtt 180
aatagagcaa atcagcgctt gaaccccatg catcaactct tgaggcattt ccaaaaagat 240
gcaaaagtgc ttttccagaa ttgggggatt gaacccatcg acaatgtgat gggaatgatt 300
ggaatattgc ctgacatgac cccaagcacc gagatgtcat tgagaggagt gagagtcagc 360
aaaatgggag tggatgagta ctccagcact gagagagtgg tggtgagcat tgaccgtttt 420
ttaagagttc gggatcaaag gggaaacata ctactgtccc ctgaagaggt cagtgaaaca 480
caaggaacgg aaaagctgac aataatttat tcatcatcaa tgatgtggga gattaatggt 540
cccgaatcag tgttggtcaa tacttatcaa tggatcatca ggaactggga aattgtgaaa 600
attcaatggt cacaggatcc cacaatgtta tacaataaga tagaatttga gccattccag 660
tccctggtcc ctagggccac cagaagccaa tacagcggtt tcgtaagaac cctgtttcag 720
caaatgcgag atgtacttgg aacatttgat actgctcaaa taataaaact cctccctttt 780

```
gccgctgctc ctccggaaca gagtaggatg cagttctctt ctttgactgt taatgtaaga      840
ggatcgggaa tgaggatact tgtaagaggc aattccccag tgttcaacta caataaagcc      900
actaagaggc tcacagtcct cggaaaggat gcaggtgcgc ttactgaaga cccagatgaa      960
ggtacggctg gagtagaatc tgctgttcta agagggtttc tcattttagg taaagaaaac     1020
aagagatatg gcccagcact aagcatcaat gaactgagca aacttgcaaa agggagaaa     1080 gctaatgtgc taattgggca aggggacgtg gtgttggtaa tgaaacggaa acgtgactct     1140
agcatactta ctgacagcca gacagcgacc aaaaggattc ggatggccat caat           1194

<210> SEQ ID NO 20
<211> LENGTH: 1232
<212> TYPE: DNA
<213> ORGANISM: Equine influenza virus H3N8

<400> SEQUENCE: 20
agaattcaca atggtcggaa gaagagcaac agccattctc agaaaggcaa ccagaagatt       60
gattcaattg atagtaagtg ggagagatga acaatcaatt gctgaagcaa taattgtagc      120
catggtgttt tcgcaagaag attgcatgat aaaagcagtt cgaggcgatt tgaacttcgt      180
taatagagca aatcagcgct tgaaccccat gcatcaactc ttgaggcatt tccaaaaaga      240
tgcaaaagtg cttttccaga attggggat tgaacccatc gacaatgtga tgggaatgat      300
tggaatattg cctgacatga ccccaagcac cgagatgtca ttgagaggag tgagagtcag      360
caaaatggga gtggatgagt actccagcac tgagagagtg gtggtgagca ttgaccgttt      420
tttaagagtt cgggatcaaa ggggaaacat actactgtcc cctgaagagg tcagtgaaac      480
acaaggaacg gaaaagctga caataatttta ttcatcatca atgatgtggg agattaatgg      540
tcccgaatca gtgttggtca atacttatca atggatcatc aggaactggg aaattgtgaa      600
aattcaatgg tcacaggatc ccacaatgtt atacaataag atagaatttg agccattcca      660
gtccctggtc cctagggcca ccagaagcca atacagcggt ttcgtaagaa ccctgttca       720 gcaaatgcga gatgtacttg gaacatttga tactgctcaa ataataaaac tcctccctt       780 tgccgctgct cctccggaac agagtaggat gcagttctct ctttgactg ttaatgtaag       840 aggatcggga tgaggatac ttgtaagagg caattcccca gtgttcaact acaataaagc      900
cactaagagg ctcacagtcc tcggaaagga tgcaggtgcg cttactgaag cccagatga      960 aggtacggct ggagtagaat ctgctgttct aagagggttt ctcattttag gtaaagaaaa     1020
caagagatat ggcccagcac taagcatcaa tgaactgagc aaacttgcaa aagggagaa     1080 agctaatgtg ctaattgggc aaggggacgt ggtgttggta atgaaacgga acgtgactc     1140 tagcatactt actgacagcc agacagcgac caaaaggatt cggatggcca tcaattagtg     1200
ttgaattgtt taaaaacgac cttgtttcta ct                                   1232

<210> SEQ ID NO 21
<211> LENGTH: 1232
<212> TYPE: DNA
<213> ORGANISM: Equine influenza virus H3N8
<220> FEATURE:
<221> NAME/KEY: CDS
<222> LOCATION: (2)..(1195)

<400> SEQUENCE: 21 a gaa ttc aca atg gtc gga aga aga gca aca gcc att ctc aga aag gca       49
  Glu Phe Thr Met Val Gly Arg Arg Ala Thr Ala Ile Leu Arg Lys Ala
  1               5                   10                  15
```

-continued

| | |
|---|---|
| acc aga aga ttg att caa ttg ata gta agt ggg aga gat gaa caa tca<br>Thr Arg Arg Leu Ile Gln Leu Ile Val Ser Gly Arg Asp Glu Gln Ser<br>20                        25                   30 | 97 |
| att gct gaa gca ata att gta gcc atg gtg ttt tcg caa gaa gat tgc<br>Ile Ala Glu Ala Ile Ile Val Ala Met Val Phe Ser Gln Glu Asp Cys<br>35                       40                     45 | 145 |
| atg ata caa gca gtt cga ggc gat ttg aac ttc gtt aat aga gca aat<br>Met Ile Gln Ala Val Arg Gly Asp Leu Asn Phe Val Asn Arg Ala Asn<br>50                       55                    60 | 193 |
| cag cgc ttg aac ccc atg cat caa ctc ttg agg cat ttc caa aaa gat<br>Gln Arg Leu Asn Pro Met His Gln Leu Leu Arg His Phe Gln Lys Asp<br>65                    70                   75                   80 | 241 |
| gca aaa gtg ctt ttc cag aat tgg ggg att gaa ccc atc gac aat gtg<br>Ala Lys Val Leu Phe Gln Asn Trp Gly Ile Glu Pro Ile Asp Asn Val<br>85                     90                   95 | 289 |
| atg gga atg att gga ata ttg cct gac atg acc cca agc acc gag atg<br>Met Gly Met Ile Gly Ile Leu Pro Asp Met Thr Pro Ser Thr Glu Met<br>100                    105                  110 | 337 |
| tca ttg aga gga gtg aga gtc agc aaa atg gga gtg gat gag tac tcc<br>Ser Leu Arg Gly Val Arg Val Ser Lys Met Gly Val Asp Glu Tyr Ser<br>115                   120                  125 | 385 |
| agc act gag aga gtg gtg gtg agc att gac cgt ttt tta aga gtt cgg<br>Ser Thr Glu Arg Val Val Val Ser Ile Asp Arg Phe Leu Arg Val Arg<br>130                   135                  140 | 433 |
| gat caa agg gga aac ata cta ctg tcc cct gaa gag gtc agt gaa aca<br>Asp Gln Arg Gly Asn Ile Leu Leu Ser Pro Glu Glu Val Ser Glu Thr<br>145                   150                  155                  160 | 481 |
| caa gga acg gaa aag ctg aca ata att tat tca tca tca atg atg tgg<br>Gln Gly Thr Glu Lys Leu Thr Ile Ile Tyr Ser Ser Ser Met Met Trp<br>165                   170                  175 | 529 |
| gag att aat ggt ccc gaa tca gtg ttg gtc aat act tat caa tgg atc<br>Glu Ile Asn Gly Pro Glu Ser Val Leu Val Asn Thr Tyr Gln Trp Ile<br>180                    185                  190 | 577 |
| atc agg aac tgg gaa att gtg aaa att caa tgg tca cag gat ccc aca<br>Ile Arg Asn Trp Glu Ile Val Lys Ile Gln Trp Ser Gln Asp Pro Thr<br>195                   200                  205 | 625 |
| atg tta tac aat aag ata gaa ttt gag cca ttc cag tcc ctg gtc cct<br>Met Leu Tyr Asn Lys Ile Glu Phe Glu Pro Phe Gln Ser Leu Val Pro<br>210                   215                  220 | 673 |
| agg gcc acc aga agc caa tac agc ggt ttc gta aga acc ctg ttt cag<br>Arg Ala Thr Arg Ser Gln Tyr Ser Gly Phe Val Arg Thr Leu Phe Gln<br>225                   230                  235                  240 | 721 |
| caa atg cga gat gta ctt gga aca ttt gat act gct caa ata ata aaa<br>Gln Met Arg Asp Val Leu Gly Thr Phe Asp Thr Ala Gln Ile Ile Lys<br>245                   250                  255 | 769 |
| ctc ctc cct ttt gcc gct gct cct ccg gaa cag agt agg atg cag ttc<br>Leu Leu Pro Phe Ala Ala Ala Pro Pro Glu Gln Ser Arg Met Gln Phe<br>260                   265                  270 | 817 |
| tct tct ttg act gtt aat gta aga gga tcg gga atg agg ata ctt gta<br>Ser Ser Leu Thr Val Asn Val Arg Gly Ser Gly Met Arg Ile Leu Val<br>275                   280                  285 | 865 |
| aga ggc aat tcc cca gtg ttc aac tac aat aaa gcc act aag agg ctc<br>Arg Gly Asn Ser Pro Val Phe Asn Tyr Asn Lys Ala Thr Lys Arg Leu<br>290                   295                  300 | 913 |
| aca gtc ctc gga aaa gat gca ggt gcg ctt act gaa gac cca gat gaa<br>Thr Val Leu Gly Lys Asp Ala Gly Ala Leu Thr Glu Asp Pro Asp Glu<br>305                   310                  315                  320 | 961 |
| ggt acg gct gga gta gaa tct gct gtt cta aga ggg ttt ctc att tta<br>Gly Thr Ala Gly Val Glu Ser Ala Val Leu Arg Gly Phe Leu Ile Leu | 1009 |

```
                         325                 330                 335
ggt aaa gaa aac aag aga tat ggc cca gca cta agc atc aat gaa ctg    1057
Gly Lys Glu Asn Lys Arg Tyr Gly Pro Ala Leu Ser Ile Asn Glu Leu
            340                 345                 350 agc aaa ctt gca aaa ggg gag aaa gct aat gtg cta att ggg caa ggg    1105
Ser Lys Leu Ala Lys Gly Glu Lys Ala Asn Val Leu Ile Gly Gln Gly
        355                 360                 365 gac gtg gtg ttg gta atg aaa cgg aaa cgt gac tct agc ata ctt act    1153
Asp Val Val Leu Val Met Lys Arg Lys Arg Asp Ser Ser Ile Leu Thr
    370                 375                 380 gac agc cag aca gcg acc aaa agg att cgg atg gcc atc aat             1195
Asp Ser Gln Thr Ala Thr Lys Arg Ile Arg Met Ala Ile Asn
385                 390                 395 tagtgttgaa ttgtttaaaa acgaccttgt ttctact                            1232

<210> SEQ ID NO 22
<211> LENGTH: 398
<212> TYPE: PRT
<213> ORGANISM: Equine influenza virus H3N8

<400> SEQUENCE: 22

Glu Phe Thr Met Val Gly Arg Arg Ala Thr Ala Ile Leu Arg Lys Ala
1               5                   10                  15

Thr Arg Leu Ile Gln Leu Ile Val Ser Gly Arg Asp Glu Gln Ser
            20                  25                  30

Ile Ala Glu Ala Ile Ile Val Ala Met Val Phe Ser Gln Glu Asp Cys
        35                  40                  45

Met Ile Gln Ala Val Arg Gly Asp Leu Asn Phe Val Asn Arg Ala Asn
    50                  55                  60

Gln Arg Leu Asn Pro Met His Gln Leu Leu Arg His Phe Gln Lys Asp
65                  70                  75                  80

Ala Lys Val Leu Phe Gln Asn Trp Gly Ile Glu Pro Ile Asp Asn Val
                85                  90                  95

Met Gly Met Ile Gly Ile Leu Pro Asp Met Thr Pro Ser Thr Glu Met
            100                 105                 110

Ser Leu Arg Gly Val Arg Val Ser Lys Met Gly Val Asp Glu Tyr Ser
        115                 120                 125

Ser Thr Glu Arg Val Val Ser Ile Asp Arg Phe Leu Arg Val Arg
    130                 135                 140

Asp Gln Arg Gly Asn Ile Leu Leu Ser Pro Glu Glu Val Ser Glu Thr
145                 150                 155                 160

Gln Gly Thr Glu Lys Leu Thr Ile Ile Tyr Ser Ser Met Met Trp
                165                 170                 175

Glu Ile Asn Gly Pro Glu Ser Val Leu Val Asn Thr Tyr Gln Trp Ile
            180                 185                 190

Ile Arg Asn Trp Glu Ile Val Lys Ile Gln Trp Ser Gln Asp Pro Thr
        195                 200                 205

Met Leu Tyr Asn Lys Ile Glu Phe Glu Pro Phe Gln Ser Leu Val Pro
    210                 215                 220

Arg Ala Thr Arg Ser Gln Tyr Ser Gly Phe Val Arg Thr Leu Phe Gln
225                 230                 235                 240

Gln Met Arg Asp Val Leu Gly Thr Phe Asp Thr Ala Gln Ile Ile Lys
                245                 250                 255

Leu Leu Pro Phe Ala Ala Ala Pro Pro Glu Gln Ser Arg Met Gln Phe
            260                 265                 270
```

-continued

```
Ser Ser Leu Thr Val Asn Val Arg Gly Ser Gly Met Arg Ile Leu Val
        275                 280                 285

Arg Gly Asn Ser Pro Val Phe Asn Tyr Asn Lys Ala Thr Lys Arg Leu
    290                 295                 300

Thr Val Leu Gly Lys Asp Ala Gly Ala Leu Thr Glu Asp Pro Asp Glu
305                 310                 315                 320

Gly Thr Ala Gly Val Glu Ser Ala Val Leu Arg Gly Phe Leu Ile Leu
                325                 330                 335

Gly Lys Glu Asn Lys Arg Tyr Gly Pro Ala Leu Ser Ile Asn Glu Leu
            340                 345                 350

Ser Lys Leu Ala Lys Gly Glu Lys Ala Asn Val Leu Ile Gly Gln Gly
        355                 360                 365

Asp Val Val Leu Val Met Lys Arg Lys Arg Asp Ser Ser Ile Leu Thr
370                 375                 380

Asp Ser Gln Thr Ala Thr Lys Arg Ile Arg Met Ala Ile Asn
385                 390                 395
```

<210> SEQ ID NO 23
<211> LENGTH: 1194
<212> TYPE: DNA
<213> ORGANISM: Equine influenza virus H3N8

<400> SEQUENCE: 23

```
gaattcacaa tggtcggaag aagagcaaca gccattctca gaaaggcaac cagaagattg      60
attcaattga tagtaagtgg gagagatgaa caatcaattg ctgaagcaat aattgtagcc     120
atggtgtttt cgcaagaaga ttgcatgata caagcagttc gaggcgattt gaacttcgtt     180
aatagagcaa atcagcgctt gaacccatg catcaactct tgaggcattt ccaaaaagat      240
gcaaaagtgc ttttccagaa ttgggggatt gaacccatcg acaatgtgat gggaatgatt     300
ggaatattgc ctgacatgac cccaagcacc gagatgtcat tgagaggagt gagagtcagc     360
aaaatgggag tggatgagta ctccagcact gagagagtgg tggtgagcat tgaccgtttt     420
ttaagagttc gggatcaaag gggaaacata ctactgtccc ctgaagaggt cagtgaaaca     480
caaggaacgg aaaagctgac aataatttat tcatcatcaa tgatgtggga gattaatggt     540
cccgaatcag tgttggtcaa tacttatcaa tggatcatca ggaactggga aattgtgaaa     600
attcaatggt cacaggatcc cacaatgtta tacaataaga tagaatttga gccattccag     660
tccctggtcc ctaggccac cagaagccaa tacagcggtt tcgtaagaac cctgttttcag     720
caaatgcgag atgtacttgg aacatttgat actgctcaaa taataaaact cctccctttt     780
gccgctgctc ctccggaaca gagtaggatg cagttctctt ctttgactgt taatgtaaga     840
ggatcgggaa tgaggatact tgtaagaggc aattccccag tgttcaacta caataaagcc     900
actaagaggc tcacagtcct cggaaaagat gcaggtgcgc ttactgaaga cccagatgaa     960
ggtacggctg gagtagaatc tgctgttcta agagggtttc tcatttaggg taagaaaac     1020
aagagatatg gcccagcact aagcatcaat gaactgagca acttgcaaa gggagaaa      1080
gctaatgtgc taattgggca aggggacgtg gtgttggtaa tgaaacggaa acgtgactct     1140
agcatactta ctgacagcca gacagcgacc aaaaggattc ggatggccat caat          1194
```

<210> SEQ ID NO 24
<211> LENGTH: 2341
<212> TYPE: DNA
<213> ORGANISM: Equine influenza virus H3N8
<220> FEATURE:
<221> NAME/KEY: CDS -continued

<222> LOCATION: (28)..(2304)

<400> SEQUENCE: 24

```
agcaaaagca ggtcaaatat attcaat atg gag aga ata aaa gaa ctg aga gat      54
                                Met Glu Arg Ile Lys Glu Leu Arg Asp
                                 1               5 cta atg tca caa tcc cgc acc cgc gag ata cta aca aaa act act gtg       102
Leu Met Ser Gln Ser Arg Thr Arg Glu Ile Leu Thr Lys Thr Thr Val
 10              15                  20                  25 gac cac atg gcc ata atc aag aaa tac aca tca gga aga caa gag aag       150
Asp His Met Ala Ile Ile Lys Lys Tyr Thr Ser Gly Arg Gln Glu Lys
             30                  35                  40 aac ccc gca ctt agg atg aag tgg atg atg gca atg aaa tac cca att       198
Asn Pro Ala Leu Arg Met Lys Trp Met Met Ala Met Lys Tyr Pro Ile
         45                  50                  55 aca gca gat aag agg ata atg gaa atg att cct gag aga aat gaa cag       246
Thr Ala Asp Lys Arg Ile Met Glu Met Ile Pro Glu Arg Asn Glu Gln
 60                  65                  70 ggg caa acc ctt tgg agc aaa acg aac gat gct ggc tca gac cgc gta       294
Gly Gln Thr Leu Trp Ser Lys Thr Asn Asp Ala Gly Ser Asp Arg Val
     75                  80                  85 atg gta tca cct ctg gca gtg aca tgg tgg aat agg aat gga cca aca       342
Met Val Ser Pro Leu Ala Val Thr Trp Trp Asn Arg Asn Gly Pro Thr
 90                  95                 100                 105 acg agc aca att cat tat cca aaa gtc tac aaa act tat ttt gaa aaa       390
Thr Ser Thr Ile His Tyr Pro Lys Val Tyr Lys Thr Tyr Phe Glu Lys
                 110                 115                 120 gtt gaa aga tta aaa cac gga acc ttt ggc ccc gtt cat ttt agg aat       438
Val Glu Arg Leu Lys His Gly Thr Phe Gly Pro Val His Phe Arg Asn
             125                 130                 135 caa gtc aag ata aga cgg aga gtt gat gta aac cct ggt cac gcg gac       486
Gln Val Lys Ile Arg Arg Arg Val Asp Val Asn Pro Gly His Ala Asp
         140                 145                 150 ctc agt gcc aaa gaa gca caa gat gtg atc atg gaa gtt gtt ttc cca       534
Leu Ser Ala Lys Glu Ala Gln Asp Val Ile Met Glu Val Val Phe Pro
     155                 160                 165 aat gaa gtg gga gcc aga att cta aca tcg gaa tca caa cta aca ata       582
Asn Glu Val Gly Ala Arg Ile Leu Thr Ser Glu Ser Gln Leu Thr Ile
170                 175                 180                 185 acc aaa gag aaa aaa gaa gaa ctt cag gac tgc aaa att gcc ccc ttg       630
Thr Lys Glu Lys Lys Glu Glu Leu Gln Asp Cys Lys Ile Ala Pro Leu
                 190                 195                 200 atg gta gca tac atg cta gaa aga gag ttg gtc cga aaa aca aga ttc       678
Met Val Ala Tyr Met Leu Glu Arg Glu Leu Val Arg Lys Thr Arg Phe
             205                 210                 215 ctc cca gtg gct ggc gga aca agc agt gta tac att gaa gtg ttg cat       726
Leu Pro Val Ala Gly Gly Thr Ser Ser Val Tyr Ile Glu Val Leu His
         220                 225                 230 ctg act cag gga aca tgc tgg gaa caa atg tac acc cca gga gga gaa       774
Leu Thr Gln Gly Thr Cys Trp Glu Gln Met Tyr Thr Pro Gly Gly Glu
     235                 240                 245 gtt aga aac gat gac att gat caa agt tta att att gct gcc cgg aac       822
Val Arg Asn Asp Asp Ile Asp Gln Ser Leu Ile Ile Ala Ala Arg Asn
250                 255                 260                 265 ata gtg aga aga gcg aca gta tca gca gat cca cta gca tcc ctg ctg       870
Ile Val Arg Arg Ala Thr Val Ser Ala Asp Pro Leu Ala Ser Leu Leu
                 270                 275                 280 gaa atg tgc cac agt aca cag att ggt gga ata agg atg gta gac atc       918
Glu Met Cys His Ser Thr Gln Ile Gly Gly Ile Arg Met Val Asp Ile
             285                 290                 295
```

```
ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310 gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325 ttt aag aga aca agt gga tca tca gtc aag aga gaa gaa gaa atg ctt     1062
Phe Lys Arg Thr Ser Gly Ser Ser Val Lys Arg Glu Glu Glu Met Leu
330                 335                 340                 345 acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
            350                 355                 360 gaa ttc aca atg gtc gga aga aga gca aca gcc att ctc aga aag gca     1158
Glu Phe Thr Met Val Gly Arg Arg Ala Thr Ala Ile Leu Arg Lys Ala
        365                 370                 375 acc aga aga ttg att caa ttg ata gta agt ggg aga gat gaa caa tca     1206
Thr Arg Arg Leu Ile Gln Leu Ile Val Ser Gly Arg Asp Glu Gln Ser
    380                 385                 390 att gct gaa gca ata att gta gcc atg gtg ttt tcg caa gaa gat tgc     1254
Ile Ala Glu Ala Ile Ile Val Ala Met Val Phe Ser Gln Glu Asp Cys
395                 400                 405 atg ata aaa gca gtt cga ggc gat ttg aac ttc gtt aat aga gca aat     1302
Met Ile Lys Ala Val Arg Gly Asp Leu Asn Phe Val Asn Arg Ala Asn
410                 415                 420                 425 cag cgc ttg aac ccc atg cat caa ctc ttg agg cat ttc caa aaa gat     1350
Gln Arg Leu Asn Pro Met His Gln Leu Leu Arg His Phe Gln Lys Asp
            430                 435                 440 gca aaa gtg ctt ttc cag aat tgg ggg att gaa ccc atc gac aat gtg     1398
Ala Lys Val Leu Phe Gln Asn Trp Gly Ile Glu Pro Ile Asp Asn Val
        445                 450                 455 atg gga atg att gga ata ttg cct gac atg acc cca agc acc gag atg     1446
Met Gly Met Ile Gly Ile Leu Pro Asp Met Thr Pro Ser Thr Glu Met
    460                 465                 470 tca ttg aga gga gtg aga gtc agc aaa atg gga gtg gat gag tac tcc     1494
Ser Leu Arg Gly Val Arg Val Ser Lys Met Gly Val Asp Glu Tyr Ser
475                 480                 485 agc act gag aga gtg gtg gtg agc att gac cgt ttt tta aga gtt cgg     1542
Ser Thr Glu Arg Val Val Val Ser Ile Asp Arg Phe Leu Arg Val Arg
490                 495                 500                 505 gat caa agg gga aac ata cta ctg tcc cct gaa gag gtc agt gaa aca     1590
Asp Gln Arg Gly Asn Ile Leu Leu Ser Pro Glu Glu Val Ser Glu Thr
            510                 515                 520 caa gga acg gaa aag ctg aca ata att tat tca tca tca atg atg tgg     1638
Gln Gly Thr Glu Lys Leu Thr Ile Ile Tyr Ser Ser Ser Met Met Trp
        525                 530                 535 gag att aat ggt ccc gaa tca gtg ttg gtc aat act tat caa tgg atc     1686
Glu Ile Asn Gly Pro Glu Ser Val Leu Val Asn Thr Tyr Gln Trp Ile
    540                 545                 550 atc agg aac tgg gaa att gtg aaa att caa tgg tca cag gat ccc aca     1734
Ile Arg Asn Trp Glu Ile Val Lys Ile Gln Trp Ser Gln Asp Pro Thr
555                 560                 565 atg tta tac aat aag ata gaa ttt gag cca ttc cag tcc ctg gtc cct     1782
Met Leu Tyr Asn Lys Ile Glu Phe Glu Pro Phe Gln Ser Leu Val Pro
570                 575                 580                 585 agg gcc acc aga agc caa tac agc ggt ttc gta aga acc ctg ttt cag     1830
Arg Ala Thr Arg Ser Gln Tyr Ser Gly Phe Val Arg Thr Leu Phe Gln
            590                 595                 600 caa atg cga gat gta ctt gga aca ttt gat act gct caa ata ata aaa     1878
Gln Met Arg Asp Val Leu Gly Thr Phe Asp Thr Ala Gln Ile Ile Lys
```

-continued

```
                  605                 610                 615
ctc ctc cct ttt gcc gct gct cct ccg gaa cag agt agg atg cag ttc    1926
Leu Leu Pro Phe Ala Ala Ala Pro Pro Glu Gln Ser Arg Met Gln Phe
            620                 625                 630 tct tct ttg act gtt aat gta aga gga tcg gga atg agg ata ctt gta    1974
Ser Ser Leu Thr Val Asn Val Arg Gly Ser Gly Met Arg Ile Leu Val
        635                 640                 645 aga ggc aat tcc cca gtg ttc aac tac aat aaa gcc act aag agg ctc    2022
Arg Gly Asn Ser Pro Val Phe Asn Tyr Asn Lys Ala Thr Lys Arg Leu
650                 655                 660                 665 aca gtc ctc gga aag gat gca ggt gcg ctt act gaa gac cca gat gaa    2070
Thr Val Leu Gly Lys Asp Ala Gly Ala Leu Thr Glu Asp Pro Asp Glu
                670                 675                 680 ggt acg gct gga gta gaa tct gct gtt cta aga ggg ttt ctc att tta    2118
Gly Thr Ala Gly Val Glu Ser Ala Val Leu Arg Gly Phe Leu Ile Leu
            685                 690                 695 ggt aaa gaa aac aag aga tat ggc cca gca cta agc atc aat gaa ctg    2166
Gly Lys Glu Asn Lys Arg Tyr Gly Pro Ala Leu Ser Ile Asn Glu Leu
        700                 705                 710 agc aaa ctt gca aaa ggg gag aaa gct aat gtg cta att ggg caa ggg    2214
Ser Lys Leu Ala Lys Gly Glu Lys Ala Asn Val Leu Ile Gly Gln Gly
    715                 720                 725 gac gtg gtg ttg gta atg aaa cgg aaa cgt gac tct agc ata ctt act    2262
Asp Val Val Leu Val Met Lys Arg Lys Arg Asp Ser Ser Ile Leu Thr
730                 735                 740                 745 gac agc cag aca gcg acc aaa agg att cgg atg gcc atc aat             2304
Asp Ser Gln Thr Ala Thr Lys Arg Ile Arg Met Ala Ile Asn
                750                 755 tagtgttgaa ttgtttaaaa acgaccttgt ttctact                            2341

<210> SEQ ID NO 25
<211> LENGTH: 759
<212> TYPE: PRT
<213> ORGANISM: Equine influenza virus H3N8

<400> SEQUENCE: 25

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
```

-continued

```
                165                 170                 175
Leu Thr Ser Glu Ser Gln Leu Thr Ile Thr Lys Glu Lys Glu Glu
            180                 185                 190
Leu Gln Asp Cys Lys Ile Ala Pro Leu Met Val Ala Tyr Met Leu Glu
            195                 200                 205
Arg Glu Leu Val Arg Lys Thr Arg Phe Leu Pro Val Ala Gly Gly Thr
210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Ile Asp
                245                 250                 255
Gln Ser Leu Ile Ile Ala Ala Arg Asn Ile Val Arg Arg Ala Thr Val
            260                 265                 270
Ser Ala Asp Pro Leu Ala Ser Leu Leu Glu Met Cys His Ser Thr Gln
            275                 280                 285
Ile Gly Gly Ile Arg Met Val Asp Ile Leu Lys Gln Asn Pro Thr Glu
            290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Met Leu Thr Gly Asn Leu Gln Thr Leu
            340                 345                 350
Lys Ile Arg Val His Glu Gly Tyr Glu Glu Phe Thr Met Val Gly Arg
            355                 360                 365
Arg Ala Thr Ala Ile Leu Arg Lys Ala Thr Arg Leu Ile Gln Leu
370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
            435                 440                 445
Trp Gly Ile Glu Pro Ile Asp Asn Val Met Gly Met Ile Gly Ile Leu
            450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Ile Leu
            500                 505                 510
Leu Ser Pro Glu Glu Val Ser Glu Thr Gln Gly Thr Glu Lys Leu Thr
            515                 520                 525
Ile Ile Tyr Ser Ser Ser Met Met Trp Glu Ile Asn Gly Pro Glu Ser
            530                 535                 540
Val Leu Val Asn Thr Tyr Gln Trp Ile Ile Arg Asn Trp Glu Ile Val
545                 550                 555                 560
Lys Ile Gln Trp Ser Gln Asp Pro Thr Met Leu Tyr Asn Lys Ile Glu
                565                 570                 575
Phe Glu Pro Phe Gln Ser Leu Val Pro Arg Ala Thr Arg Ser Gln Tyr
            580                 585                 590
```

-continued

```
Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

```
<210> SEQ ID NO 26
<211> LENGTH: 2277
<212> TYPE: DNA
<213> ORGANISM: Equine influenza virus H3N8

<400> SEQUENCE: 26
atggagagaa taaaagaact gagagatcta atgtcacaat cccgcacccg cgagatacta      60
acaaaaacta ctgtggacca catggccata atcaagaaat acacatcagg aagacaagag     120
aagaaccccg cacttaggat gaagtggatg atggcaatga atacccaat tacagcagat      180 aagaggataa tggaaatgat tcctgagaga atgaacagg ggcaaaccct ttggagcaaa      240
acgaacgatg ctggctcaga ccgcgtaatg gtatcacctc tggcagtgac atggtggaat    300
aggaatggac caacaacgag cacaattcat tatccaaaag tctacaaaac ttatttttgaa    360 aaagttgaaa gattaaaaca cggaaccttt ggccccgttc attttaggaa tcaagtcaag    420
ataagacgga gagttgatgt aaaccctggt cacgcgacc tcagtgccaa agaagcacaa     480
gatgtgatca tggaagttgt tttcccaaat gaagtgggag ccagaattct aacatcggaa    540
tcacaactaa caataaccaa agagaaaaaa gaagaacttc aggactgcaa aattgccccc    600
ttgatggtag catacatgct agaaagagag ttggtccgaa aaacaagatt cctcccagtg    660
gctggcggaa caagcagtgt atacattgaa gtgttgcatc tgactcaggg aacatgctgg    720
gaacaaatgt acaccccagg aggagaagtt agaaacgatg acattgatca agtttaatt     780 attgctgccc ggaacatagt gagaagagcg acagtatcag cagatccact agcatccctg    840
ctggaaatgt gccacagtac acagattggt ggaataagga tggtagacat ccttaagcag    900
aatccaacag aggaacaagc tgtggatata tgcaaagcag caatgggggtt aagaattagc    960 tcatcattca gctttggtgg attcacccttt aagagaacaa gtggatcatc agtcaagaga   1020
gaagaagaaa tgcttacggg caaccttcaa acattgaaaa taagagtgca tgaaggctat    1080
gaagaattca atggtcgg aagaagagca acagccattc tcagaaaggc aaccagaaga    1140
```

-continued

```
ttgattcaat tgatagtaag tgggagagat gaacaatcaa ttgctgaagc aataattgta   1200
gccatggtgt tttcgcaaga agattgcatg ataaaagcag ttcgaggcga tttgaacttc   1260
gttaatagag caaatcagcg cttgaacccc atgcatcaac tcttgaggca tttccaaaaa   1320
gatgcaaaag tgcttttcca gaattggggg attgaaccca tcgacaatgt gatgggaatg   1380
attggaatat tgcctgacat gacccccaag ccgagatgt cattgagagg agtgagagtc    1440
agcaaaatgg gagtggatga gtactccagc actgagagag tggtggtgag cattgaccgt   1500 ttttaagag ttcgggatca aaggggaaac atactactgt cccctgaaga ggtcagtgaa    1560
acacaaggaa cggaaaagct gacaataatt tattcatcat caatgatgtg ggagattaat   1620
ggtcccgaat cagtgttggt caatacttat caatggatca tcaggaactg ggaaattgtg   1680
aaaattcaat ggtcacagga tcccacaatg ttatacaata agatagaatt tgagccattc   1740
cagtccctgg tccctagggc caccagaagc aatacagcg gtttcgtaag aaccctgttt   1800
cagcaaatgc gagatgtact tggaacattt gatactgctc aaataataaa actcctccct   1860
tttgccgctg ctcctccgga acagagtagg atgcagttct cttctttgac tgttaatgta   1920
agaggatcgg gaatgaggat acttgtaaga ggcaattccc cagtgttcaa ctacaataaa   1980
gccactaaga ggctcacagt cctcggaaaa gatgcaggtg cgcttactga agacccagat   2040
gaaggtacgg ctggagtaga atctgctgtt ctaagagggt ttctcatttt aggtaaagaa   2100
aacaagagat atggcccagc actaagcatc aatgaactga gcaaacttgc aaaaggggag   2160
aaagctaatg tgctaattgg gcaagggac gtggtgttgg taatgaaacg gaaacgtgac    2220
tctagcatac ttactgacag ccagacagcg accaaaagga ttcggatggc catcaat       2277
```

<210> SEQ ID NO 27
<211> LENGTH: 2341
<212> TYPE: DNA
<213> ORGANISM: Equine influenza virus H3N8
<220> FEATURE:
<221> NAME/KEY: CDS
<222> LOCATION: (28)..(2304)

<400> SEQUENCE: 27

```
agcaaaagca ggtcaaatat attcaat atg gag aga ata aaa gaa ctg aga gat    54
                                Met Glu Arg Ile Lys Glu Leu Arg Asp
                                 1               5 cta atg tca caa tcc cgc acc cgc gag ata cta aca aaa act act gtg     102
Leu Met Ser Gln Ser Arg Thr Arg Glu Ile Leu Thr Lys Thr Thr Val
 10              15                  20                  25 gac cac atg gcc ata atc aag aaa tac aca tca gga aga caa gag aag     150
Asp His Met Ala Ile Ile Lys Lys Tyr Thr Ser Gly Arg Gln Glu Lys
                 30                  35                  40 aac ccc gca ctt agg atg aag tgg atg atg gca atg aaa tac cca att     198
Asn Pro Ala Leu Arg Met Lys Trp Met Met Ala Met Lys Tyr Pro Ile
             45                  50                  55 aca gca gat aag agg ata atg gaa atg att cct gag aga aat gaa cag     246
Thr Ala Asp Lys Arg Ile Met Glu Met Ile Pro Glu Arg Asn Glu Gln
         60                  65                  70 ggg caa acc ctt tgg agc aaa acg aac gat gct ggc tca gac cgc gta     294
Gly Gln Thr Leu Trp Ser Lys Thr Asn Asp Ala Gly Ser Asp Arg Val
 75                  80                  85 atg gta tca cct ctg gca gtg aca tgg tgg aat agg aat gga cca aca    342
Met Val Ser Pro Leu Ala Val Thr Trp Trp Asn Arg Asn Gly Pro Thr
 90                  95                 100                 105 acg agc aca att cat tat cca aaa gtc cac aaa act tat ttt gaa aaa    390
```

```
                Thr Ser Thr Ile His Tyr Pro Lys Val His Lys Thr Tyr Phe Glu Lys
                            110                 115                 120 gtt gaa aga tta aaa cac gga acc ttt ggc ccc gtt cat ttt agg aat                  438
Val Glu Arg Leu Lys His Gly Thr Phe Gly Pro Val His Phe Arg Asn
            125                 130                 135 caa gtc aag ata aga cgg aga gtt gat gta aac cct ggt cac gcg gac                  486
Gln Val Lys Ile Arg Arg Arg Val Asp Val Asn Pro Gly His Ala Asp
            140                 145                 150 ctc agt gcc aaa gaa gca caa gat gtg atc atg gaa gtt gtt ttc cca                  534
Leu Ser Ala Lys Glu Ala Gln Asp Val Ile Met Glu Val Val Phe Pro
        155                 160                 165 aat gaa gtg gga gcc aga att cta aca tcg gaa tca caa cta aca ata                  582
Asn Glu Val Gly Ala Arg Ile Leu Thr Ser Glu Ser Gln Leu Thr Ile
170                 175                 180                 185 acc aaa gag aaa aaa gaa gaa ctt cag gac tgc aaa att gcc ccc ttg                  630
Thr Lys Glu Lys Lys Glu Glu Leu Gln Asp Cys Lys Ile Ala Pro Leu
                190                 195                 200 atg gta gca tac atg cta gaa aga gag ttg gtc cga aaa aca aga ttc                  678
Met Val Ala Tyr Met Leu Glu Arg Glu Leu Val Arg Lys Thr Arg Phe
            205                 210                 215 ctc cca gtg gct ggc gga aca agc agt gta tac att gaa gtg ttg cat                  726
Leu Pro Val Ala Gly Gly Thr Ser Ser Val Tyr Ile Glu Val Leu His
        220                 225                 230 ctg act cag gga aca tgc tgg gaa caa atg tac acc cca gga gga gaa                  774
Leu Thr Gln Gly Thr Cys Trp Glu Gln Met Tyr Thr Pro Gly Gly Glu
    235                 240                 245 gtt aga aac gat gac att gat caa agt tta att att gct gcc cgg aac                  822
Val Arg Asn Asp Asp Ile Asp Gln Ser Leu Ile Ile Ala Ala Arg Asn
250                 255                 260                 265 ata gtg aga aga gcg aca gta tca gca gat cca cta gca tcc ctg ctg                  870
Ile Val Arg Arg Ala Thr Val Ser Ala Asp Pro Leu Ala Ser Leu Leu
                270                 275                 280 gaa atg tgc cac agt aca cag att ggt gga ata agg atg gta gac atc                  918
Glu Met Cys His Ser Thr Gln Ile Gly Gly Ile Arg Met Val Asp Ile
            285                 290                 295 ctt aag cag aat cca aca gag gaa caa gct gtg gat ata tgc aaa gca                  966
Leu Lys Gln Asn Pro Thr Glu Glu Gln Ala Val Asp Ile Cys Lys Ala
        300                 305                 310 gca atg ggg tta aga att agc tca tca ttc agc ttt ggt gga ttc acc                 1014
Ala Met Gly Leu Arg Ile Ser Ser Ser Phe Ser Phe Gly Gly Phe Thr
    315                 320                 325 ttt aag aga aca agt gga tca tca gtc aag aga gaa gaa gaa atg ctt                 1062
Phe Lys Arg Thr Ser Gly Ser Ser Val Lys Arg Glu Glu Glu Met Leu
330                 335                 340                 345 acg ggc aac ctt caa aca ttg aaa ata aga gtg cat gaa ggc tat gaa                 1110
Thr Gly Asn Leu Gln Thr Leu Lys Ile Arg Val His Glu Gly Tyr Glu
                350                 355                 360 gaa ttc aca atg gtc gga aga aga gca aca gcc att ctc aga aag gca                 1158
Glu Phe Thr Met Val Gly Arg Arg Ala Thr Ala Ile Leu Arg Lys Ala
            365                 370                 375 acc aga aga ttg att caa ttg ata gta agt ggg aga gat gaa caa tca                 1206
Thr Arg Arg Leu Ile Gln Leu Ile Val Ser Gly Arg Asp Glu Gln Ser
        380                 385                 390 att gct gaa gca ata att gta gcc atg gtg ttt tcg caa gaa gat tgc                 1254
Ile Ala Glu Ala Ile Ile Val Ala Met Val Phe Ser Gln Glu Asp Cys
    395                 400                 405 atg ata caa gca gtt cga ggc gat ttg aac ttc gtt aat aga gca aat                 1302
Met Ile Gln Ala Val Arg Gly Asp Leu Asn Phe Val Asn Arg Ala Asn
410                 415                 420                 425
```

```
                                                    -continued cag cgc ttg aac ccc atg cat caa ctc ttg agg cat ttc caa aaa gat    1350
Gln Arg Leu Asn Pro Met His Gln Leu Leu Arg His Phe Gln Lys Asp
            430                 435                 440 gca aaa gtg ctt ttc cag aat tgg ggg att gaa ccc atc gac aat gtg    1398
Ala Lys Val Leu Phe Gln Asn Trp Gly Ile Glu Pro Ile Asp Asn Val
        445                 450                 455 atg gga atg att gga ata ttg cct gac atg acc cca agc acc gag atg    1446
Met Gly Met Ile Gly Ile Leu Pro Asp Met Thr Pro Ser Thr Glu Met
    460                 465                 470 tca ttg aga gga gtg aga gtc agc aaa atg gga gtg gat gag tac tcc    1494
Ser Leu Arg Gly Val Arg Val Ser Lys Met Gly Val Asp Glu Tyr Ser
475                 480                 485 agc act gag aga gtg gtg gtg agc att gac cgt ttt tta aga gtt cgg    1542
Ser Thr Glu Arg Val Val Val Ser Ile Asp Arg Phe Leu Arg Val Arg
490                 495                 500                 505 gat caa agg gga aac ata cta ctg tcc cct gaa gag gtc agt gaa aca    1590
Asp Gln Arg Gly Asn Ile Leu Leu Ser Pro Glu Glu Val Ser Glu Thr
                510                 515                 520 caa gga acg gaa aag ctg aca ata att tat tca tca tca atg atg tgg    1638
Gln Gly Thr Glu Lys Leu Thr Ile Ile Tyr Ser Ser Ser Met Met Trp
            525                 530                 535 gag att aat ggt ccc gaa tca gtg ttg gtc aat act tat caa tgg atc    1686
Glu Ile Asn Gly Pro Glu Ser Val Leu Val Asn Thr Tyr Gln Trp Ile
        540                 545                 550 atc agg aac tgg gaa att gtg aaa att caa tgg tca cag gat ccc aca    1734
Ile Arg Asn Trp Glu Ile Val Lys Ile Gln Trp Ser Gln Asp Pro Thr
    555                 560                 565 atg tta tac aat aag ata gaa ttt gag cca ttc cag tcc ctg gtc cct    1782
Met Leu Tyr Asn Lys Ile Glu Phe Glu Pro Phe Gln Ser Leu Val Pro
570                 575                 580                 585 agg gcc acc aga agc caa tac agc ggt ttc gta aga acc ctg ttt cag    1830
Arg Ala Thr Arg Ser Gln Tyr Ser Gly Phe Val Arg Thr Leu Phe Gln
                590                 595                 600 caa atg cga gat gta ctt gga aca ttt gat act gct caa ata ata aaa    1878
Gln Met Arg Asp Val Leu Gly Thr Phe Asp Thr Ala Gln Ile Ile Lys
            605                 610                 615 ctc ctc cct ttt gcc gct gct cct ccg gaa cag agt agg atg cag ttc    1926
Leu Leu Pro Phe Ala Ala Ala Pro Pro Glu Gln Ser Arg Met Gln Phe
        620                 625                 630 tct tct ttg act gtt aat gta aga gga tcg gga atg agg ata ctt gta    1974
Ser Ser Leu Thr Val Asn Val Arg Gly Ser Gly Met Arg Ile Leu Val
    635                 640                 645 aga ggc aat tcc cca gtg ttc aac tac aat aaa gcc act aag agg ctc    2022
Arg Gly Asn Ser Pro Val Phe Asn Tyr Asn Lys Ala Thr Lys Arg Leu
650                 655                 660                 665 aca gtc ctc gga aaa gat gca ggt gcg ctt act gaa gac cca gat gaa    2070
Thr Val Leu Gly Lys Asp Ala Gly Ala Leu Thr Glu Asp Pro Asp Glu
                670                 675                 680 ggt acg gct gga gta gaa tct gct gtt cta aga ggg ttt ctc att tta    2118
Gly Thr Ala Gly Val Glu Ser Ala Val Leu Arg Gly Phe Leu Ile Leu
            685                 690                 695 ggt aaa gaa aac aag aga tat ggc cca gca cta agc atc aat gaa ctg    2166
Gly Lys Glu Asn Lys Arg Tyr Gly Pro Ala Leu Ser Ile Asn Glu Leu
        700                 705                 710 agc aaa ctt gca aaa ggg gag aaa gct aat gtg cta att ggg caa ggg    2214
Ser Lys Leu Ala Lys Gly Glu Lys Ala Asn Val Leu Ile Gly Gln Gly
    715                 720                 725 gac gtg gtg ttg gta atg aaa cgg aaa cgt gac tct agc ata ctt act    2262
Asp Val Val Leu Val Met Lys Arg Lys Arg Asp Ser Ser Ile Leu Thr
730                 735                 740                 745
```

```
gac agc cag aca gcg acc aaa agg att cgg atg gcc atc aat         2304
Asp Ser Gln Thr Ala Thr Lys Arg Ile Arg Met Ala Ile Asn
            750                 755 tagtgttgaa ttgtttaaaa acgaccttgt ttctact                         2341
```

<210> SEQ ID NO 28
<211> LENGTH: 759
<212> TYPE: PRT
<213> ORGANISM: Equine influenza virus H3N8

<400> SEQUENCE: 28

```
Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val His Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
```

-continued

```
                340                 345                 350
Lys Ile Arg Val His Glu Gly Tyr Glu Phe Thr Met Val Gly Arg
            355                 360                 365
Arg Ala Thr Ala Ile Leu Arg Lys Ala Thr Arg Leu Ile Gln Leu
        370                 375                 380
Ile Val Ser Gly Arg Asp Glu Gln Ser Ile Ala Glu Ala Ile Val
385                 390                 395                 400
Ala Met Val Phe Ser Gln Glu Asp Cys Met Ile Gln Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
        435                 440                 445
Trp Gly Ile Glu Pro Ile Asp Asn Val Met Gly Met Ile Gly Ile Leu
        450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Ile Leu
            500                 505                 510
Leu Ser Pro Glu Glu Val Ser Glu Thr Gln Gly Thr Glu Lys Leu Thr
        515                 520                 525
Ile Ile Tyr Ser Ser Ser Met Met Trp Glu Ile Asn Gly Pro Glu Ser
        530                 535                 540
Val Leu Val Asn Thr Tyr Gln Trp Ile Ile Arg Asn Trp Glu Ile Val
545                 550                 555                 560
Lys Ile Gln Trp Ser Gln Asp Pro Thr Met Leu Tyr Asn Lys Ile Glu
                565                 570                 575
Phe Glu Pro Phe Gln Ser Leu Val Pro Arg Ala Thr Arg Ser Gln Tyr
                580                 585                 590
Ser Gly Phe Val Arg Thr Leu Phe Gln Gln Met Arg Asp Val Leu Gly
            595                 600                 605
Thr Phe Asp Thr Ala Gln Ile Ile Lys Leu Leu Pro Phe Ala Ala Ala
        610                 615                 620
Pro Pro Glu Gln Ser Arg Met Gln Phe Ser Ser Leu Thr Val Asn Val
625                 630                 635                 640
Arg Gly Ser Gly Met Arg Ile Leu Val Arg Gly Asn Ser Pro Val Phe
                645                 650                 655
Asn Tyr Asn Lys Ala Thr Lys Arg Leu Thr Val Leu Gly Lys Asp Ala
                660                 665                 670
Gly Ala Leu Thr Glu Asp Pro Asp Glu Gly Thr Ala Gly Val Glu Ser
            675                 680                 685
Ala Val Leu Arg Gly Phe Leu Ile Leu Gly Lys Glu Asn Lys Arg Tyr
        690                 695                 700
Gly Pro Ala Leu Ser Ile Asn Glu Leu Ser Lys Leu Ala Lys Gly Glu
705                 710                 715                 720
Lys Ala Asn Val Leu Ile Gly Gln Gly Asp Val Val Leu Val Met Lys
                725                 730                 735
Arg Lys Arg Asp Ser Ser Ile Leu Thr Asp Ser Gln Thr Ala Thr Lys
            740                 745                 750
Arg Ile Arg Met Ala Ile Asn
            755
```

<210> SEQ ID NO 29
<211> LENGTH: 2277
<212> TYPE: DNA
<213> ORGANISM: Equine influenza virus H3N8

<400> SEQUENCE: 29

| | | | | | |
|---|---|---|---|---|---|
| atggagagaa | taaaagaact | gagagatcta | atgtcacaat | cccgcacccg | cgagatacta | 60 |
| acaaaaacta | ctgtggacca | catggccata | atcaagaaat | acacatcagg | aagacaagag | 120 |
| aagaaccccg | cacttaggat | gaagtggatg | atggcaatga | aatacccaat | tacagcagat | 180 |
| aagaggataa | tggaaatgat | tcctgagaga | aatgaacagg | ggcaaaccct | tggagcaaaa | 240 |
| acgaacgatg | ctggctcaga | ccgcgtaatg | gtatcacctc | tggcagtgac | atggtggaat | 300 |
| aggaatggac | caacaacgag | cacaattcat | tatccaaaag | tccacaaaac | ttattttgaa | 360 |
| aaagttgaaa | gattaaaaca | cggaaccttt | ggccccgttc | attttaggaa | tcaagtcaag | 420 |
| ataagacgga | gagttgatgt | aaaccctggt | cacgcggacc | tcagtgccaa | agaagcacaa | 480 |
| gatgtgatca | tggaagttgt | tttcccaaat | gaagtgggag | ccagaattct | aacatcggaa | 540 |
| tcacaactaa | caataaccaa | agagaaaaaa | gaagaacttc | aggactgcaa | aattgccccc | 600 |
| ttgatggtag | catacatgct | agaaagagag | ttggtccgaa | aaacaagatt | cctcccagtg | 660 |
| gctggcggaa | caagcagtgt | atacattgaa | gtgttgcatc | tgactcaggg | aacatgctgg | 720 |
| gaacaaatgt | acaccccagg | aggagaagtt | agaaacgatg | acattgatca | agtttaatt | 780 |
| attgctgccc | ggaacatagt | gagaagagcg | acagtatcag | cagatccact | agcatccctg | 840 |
| ctggaaatgt | gccacagtac | acagattggt | ggaataagga | tggtagacat | ccttaagcag | 900 |
| aatccaacag | aggaacaagc | tgtggatata | tgcaaagcag | caatgggtt | aagaattagc | 960 |
| tcatcattca | gctttggtgg | attcacccttt | aagagaacaa | gtggatcatc | agtcaagaga | 1020 |
| gaagaagaaa | tgcttacggg | caaccttcaa | acattgaaaa | taagagtgca | tgaaggctat | 1080 |
| gaagaattca | caatggtcgg | aagaagagca | acagccattc | tcagaaaggc | aaccagaaga | 1140 |
| ttgattcaat | tgatagtaag | tgggagagat | gaacaatcaa | ttgctgaagc | aataattgta | 1200 |
| gccatggtgt | tttcgcaaga | agattgcatg | atacaagcag | ttcgaggcga | tttgaacttc | 1260 |
| gttaatagag | caaatcagcg | cttgaacccc | atgcatcaac | tcttgaggca | tttccaaaaa | 1320 |
| gatgcaaaag | tgcttttcca | gaattggggg | attgaaccca | tcgacaatgt | gatgggaatg | 1380 |
| attggaatat | tgcctgacat | gaccccaagc | accgagatgt | cattgagagg | agtgagagtc | 1440 |
| agcaaaatgg | gagtggatga | gtactccagc | actgagagag | tggtggtgag | cattgaccgt | 1500 |
| tttttaagag | ttcgggatca | aaggggaaac | atactactgt | ccctgaaga | ggtcagtgaa | 1560 |
| acacaaggaa | cggaaaagct | gacaataatt | tattcatcat | caatgatgtg | ggagattaat | 1620 |
| ggtcccgaat | cagtgttggt | caatacttat | caatggatca | tcaggaactg | ggaaattgtg | 1680 |
| aaaattcaat | ggtcacagga | tcccacaatg | ttatacaata | agatagaatt | tgagccattc | 1740 |
| cagtccctgg | tccctaggc | caccagaagc | caatacagcg | gtttcgtaag | aaccctgttt | 1800 |
| cagcaaatgc | gagatgtact | tggaacattt | gatactgctc | aaataataaa | actcctccct | 1860 |
| tttgccgctg | ctcctccgga | acagagtagg | atgcagttct | cttctttgac | tgttaatgta | 1920 |
| agaggatcgg | gaatgaggat | acttgtaaga | ggcaattccc | cagtgttcaa | ctacaataaa | 1980 |
| gccactaaga | ggctcacagt | cctcggaaaa | gatgcaggtg | cgcttactga | agacccagat | 2040 |
| gaaggtacgg | ctggagtaga | atctgctgtt | ctaagagggt | ttctcatttt | aggtaaagaa | 2100 |

```
aacaagagat atggcccagc actaagcatc aatgaactga gcaaacttgc aaaaggggag    2160
aaagctaatg tgctaattgg gcaagggac gtggtgttgg taatgaaacg gaaacgtgac     2220
tctagcatac ttactgacag ccagacagcg accaaaagga ttcggatggc catcaat       2277
```

<210> SEQ ID NO 30
<211> LENGTH: 21
<212> TYPE: DNA
<213> ORGANISM: Artificial
<220> FEATURE:
<223> OTHER INFORMATION: Synthetic Primer

<400> SEQUENCE: 30

```
agcaaagcag gtgacaaaaa c                                              21
```

<210> SEQ ID NO 31
<211> LENGTH: 19
<212> TYPE: DNA
<213> ORGANISM: Artificial
<220> FEATURE:
<223> OTHER INFORMATION: Synthetic Primer

<400> SEQUENCE: 31

```
agtagaaaca agggtgttt                                                 19
```

<210> SEQ ID NO 32
<211> LENGTH: 891
<212> TYPE: DNA
<213> ORGANISM: Equine influenza virus H3N8
<220> FEATURE:
<221> NAME/KEY: CDS
<222> LOCATION: (27)..(716)

<400> SEQUENCE: 32

```
agcaaaagca gggtgacaaa aacata atg gat tcc aac act gtg tca agc ttt     53
                              Met Asp Ser Asn Thr Val Ser Ser Phe
                              1               5 cag gta gac tgt ttt ctt tgg cat gtc cgc aaa cga ttt gca gac caa     101
Gln Val Asp Cys Phe Leu Trp His Val Arg Lys Arg Phe Ala Asp Gln
10              15                  20                  25 gaa ctg ggt gat gcc cca ttc ctt gac cgg ctt cgc cga gac cag aag     149
Glu Leu Gly Asp Ala Pro Phe Leu Asp Arg Leu Arg Arg Asp Gln Lys
                30                  35                  40 tcc cta aaa gga aga ggt agc act ctt ggt ctg gac atc gaa aca gcc    197
Ser Leu Lys Gly Arg Gly Ser Thr Leu Gly Leu Asp Ile Glu Thr Ala
            45                  50                  55 act cgt gca gga aag cag ata gtg gag cag att ctg gaa gag gaa tca    245
Thr Arg Ala Gly Lys Gln Ile Val Glu Gln Ile Leu Glu Glu Glu Ser
        60                  65                  70 gat gag gca ctt aaa atg acc att gcc tct gtt cct gct tca cgc tac    293
Asp Glu Ala Leu Lys Met Thr Ile Ala Ser Val Pro Ala Ser Arg Tyr
    75                  80                  85 tta act gac atg act ctt gat gag atg tca aga gac tgg ttc atg ctc    341
Leu Thr Asp Met Thr Leu Asp Glu Met Ser Arg Asp Trp Phe Met Leu
90                  95                  100                 105 atg ccc aag cag aaa gta aca ggc tcc cta tgt ata aga atg gac cag    389
Met Pro Lys Gln Lys Val Thr Gly Ser Leu Cys Ile Arg Met Asp Gln
                110                 115                 120 gca atc atg gat aag aac atc ata ctt aaa gca aac ttt agt gtg att    437
Ala Ile Met Asp Lys Asn Ile Ile Leu Lys Ala Asn Phe Ser Val Ile
            125                 130                 135 ttc gaa agg ctg gag aca cta ata cta ctt aga gcc ttc acc gaa gaa    485
Phe Glu Arg Leu Glu Thr Leu Ile Leu Leu Arg Ala Phe Thr Glu Glu
```

-continued

```
                140                 145                 150
gga gca gtc gtt ggc gaa att tca cca ttg cct tct ctt cca gga cat    533
Gly Ala Val Val Gly Glu Ile Ser Pro Leu Pro Ser Leu Pro Gly His
    155                 160                 165 act aat gag gat gtc aaa aat gca att ggg gtc ctc atc gga gga ctt    581
Thr Asn Glu Asp Val Lys Asn Ala Ile Gly Val Leu Ile Gly Gly Leu
170                 175                 180                 185 aaa tgg aat gat aat acg gtt aga atc tct gaa act cta cag aga ttc    629
Lys Trp Asn Asp Asn Thr Val Arg Ile Ser Glu Thr Leu Gln Arg Phe
                190                 195                 200 gct tgg aga agc agt cat gag aat ggg aga cct tca ttc cct cca aag    677
Ala Trp Arg Ser Ser His Glu Asn Gly Arg Pro Ser Phe Pro Pro Lys
            205                 210                 215 cag aaa cga aaa atg gag aga aca att gag cca gaa gtt tgaagaaata     726
Gln Lys Arg Lys Met Glu Arg Thr Ile Glu Pro Glu Val
        220                 225                 230 agatggttga ttgaagaagt gcgacataga ttgaaaaata cagaaaatag ttttgaacaa   786
ataacattta tgcaagcctt acaactattg cttgaagtag gacaagagat aagaactttc   846
tcgtttcagc ttatttaatg ataaaaaaca cccttgtttc tacta                   891
```

<210> SEQ ID NO 33
<211> LENGTH: 230
<212> TYPE: PRT
<213> ORGANISM: Equine influenza virus H3N8

<400> SEQUENCE: 33

```
Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asp Ile Glu Thr Ala Thr Arg Ala Gly Lys Gln Ile
    50                  55                  60

Val Glu Gln Ile Leu Glu Glu Ser Asp Glu Ala Leu Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Pro Lys Gln Lys Arg Lys Met Glu Arg
    210                 215                 220

Thr Ile Glu Pro Glu Val
225                 230
```

<210> SEQ ID NO 34
<211> LENGTH: 690
<212> TYPE: DNA
<213> ORGANISM: Equine influenza virus H3N8

<400> SEQUENCE: 34

| | | | | | |
|---|---|---|---|---|---|
| atggattcca | acactgtgtc | aagctttcag | gtagactgtt | ttctttggca | tgtccgcaaa | 60 |
| cgatttgcag | accaagaact | gggtgatgcc | ccattccttg | accggcttcg | ccgagaccag | 120 |
| aagtccctaa | aggaagagg | tagcactctt | ggtctggaca | tcgaaacagc | cactcgtgca | 180 |
| ggaaagcaga | tagtggagca | gattctggaa | gaggaatcag | atgaggcact | taaaatgacc | 240 |
| attgcctctg | ttcctgcttc | acgctactta | actgacatga | ctcttgatga | gatgtcaaga | 300 |
| gactggttca | tgctcatgcc | caagcagaaa | gtaacaggct | ccctatgtat | aagaatggac | 360 |
| caggcaatca | tggataagaa | catcatactt | aaagcaaact | ttagtgtgat | tttcgaaagg | 420 |
| ctggagacac | taatactact | tagagccttc | accgaagaag | gagcagtcgt | tggcgaaatt | 480 |
| tcaccattgc | cttctcttcc | aggacatact | aatgaggatg | tcaaaatgc | aatttggggtc | 540 |
| ctcatcggag | gacttaaatg | gaatgataat | acggttagaa | tctctgaaac | tctacagaga | 600 |
| ttcgcttgga | gaagcagtca | tgagaatggg | agaccttcat | tccctccaaa | gcagaaacga | 660 |
| aaaatggaga | gaacaattga | gccagaagtt | | | | 690 |

<210> SEQ ID NO 35
<211> LENGTH: 888
<212> TYPE: DNA
<213> ORGANISM: Equine influenza virus H3N8

<400> SEQUENCE: 35

| | | | | | |
|---|---|---|---|---|---|
| caaaagcagg | gtgacaaaaa | catgatggat | tccaacactg | tgtcaagctt | tcaggtagac | 60 |
| tgttttcttt | ggcatgtccg | caaacgattt | gcagaccaag | aactgggtga | tgccccattc | 120 |
| cttgaccggc | ttcgccgaga | ccagaagtcc | ctaaaaggaa | gaggtagcac | tcttggtctg | 180 |
| gacatcgaaa | cagccactcg | tgcaggaaag | cagatagtgg | agcagattct | ggaagaggaa | 240 |
| tcagatgagg | cacttaaaat | gaccattgcc | tctgttcctg | cttcacgcta | cttaactgac | 300 |
| atgactcttg | atgagatgtc | aagagactgg | ttcatgctca | tgcccaagca | gaaagtaaca | 360 |
| ggctccctat | gtataagaat | ggaccaggca | atcatggata | gaacatcat | acttaaagca | 420 |
| aactttagtg | tgattttcga | aaggctggag | acactaatac | tacttagagc | cttcaccgaa | 480 |
| gaaggagcag | tcgttggcga | aatttcacca | ttgccttctc | ttccaggaca | tactaatgag | 540 |
| gatgtcaaaa | atgcaattgg | ggtcctcatc | ggaggactta | aatggaatga | taatacggtt | 600 |
| agaatctctg | aaactctaca | gagattcgct | tggagaagca | gtcatgagaa | tgggagacct | 660 |
| tcattccctc | caaagcagaa | acgaaaaatg | gagagaacaa | ttgagccaga | gtttgaaga | 720 |
| aataagatgg | ttgattgaag | aagtgcgaca | tagattgaaa | atacagaaa | atagttttga | 780 |
| acaaataaca | tttatgcaag | ccttacaact | attgcttgaa | gtagaacaag | agataagaac | 840 |
| tttctcgttt | cagcttattt | aatgataaaa | aacacccttg | tttctact | | 888 |

<210> SEQ ID NO 36
<211> LENGTH: 468
<212> TYPE: DNA
<213> ORGANISM: Equine influenza virus H3N8
<220> FEATURE:
<221> NAME/KEY: CDS

<222> LOCATION: (3)..(293)

<400> SEQUENCE: 36

| | | |
|---|---|---|
| ac ttt agt gtg att ttc gaa agg ctg gag aca cta ata cta ctt aga<br>   Phe Ser Val Ile Phe Glu Arg Leu Glu Thr Leu Ile Leu Leu Arg<br>   1               5                   10                  15 | | 47 |
| gcc ttc acc gaa gaa gga gca gtc gtt ggc gaa att tca cca ttg cct<br>Ala Phe Thr Glu Glu Gly Ala Val Val Gly Glu Ile Ser Pro Leu Pro<br>                20                  25                  30 | | 95 |
| tct ctt cca gga cat act aat gag gat gtc aaa aat gca att ggg gtc<br>Ser Leu Pro Gly His Thr Asn Glu Asp Val Lys Asn Ala Ile Gly Val<br>            35                  40                  45 | | 143 |
| ctc atc gga gga ctt aaa tgg aat gat aat acg gtt aga atc tct gaa<br>Leu Ile Gly Gly Leu Lys Trp Asn Asp Asn Thr Val Arg Ile Ser Glu<br>        50                  55                  60 | | 191 |
| act cta cag aga ttc gct cgg aga agc agt cat gag aat ggg aga cct<br>Thr Leu Gln Arg Phe Ala Arg Arg Ser Ser His Glu Asn Gly Arg Pro<br>    65                  70                  75 | | 239 |
| tca ttc cct cca aag cag aaa cga aaa atg gag aga aca att gag cca<br>Ser Phe Pro Pro Lys Gln Lys Arg Lys Met Glu Arg Thr Ile Glu Pro<br>80                  85                  90                  95 | | 287 |
| gaa gtt tgaagaaata agatggttga ttgaagaagt gcgacataga ttgaaaaata<br>Glu Val | | 343 |
| cagaaatag ttttgaacaa ataacattta tgcaagcctt acaactattg cttgaagtag | | 403 |
| aacaagagat aagaactttc tcgtttcagc ttatttaatg ataaaaaaca cccttgtttc | | 463 |
| tacta | | 468 |

<210> SEQ ID NO 37
<211> LENGTH: 97
<212> TYPE: PRT
<213> ORGANISM: Equine influenza virus H3N8

<400> SEQUENCE: 37

Phe Ser Val Ile Phe Glu Arg Leu Glu Thr Leu Ile Leu Leu Arg Ala
1               5                   10                  15

Phe Thr Glu Glu Gly Ala Val Val Gly Glu Ile Ser Pro Leu Pro Ser
            20                  25                  30

Leu Pro Gly His Thr Asn Glu Asp Val Lys Asn Ala Ile Gly Val Leu
        35                  40                  45

Ile Gly Gly Leu Lys Trp Asn Asp Asn Thr Val Arg Ile Ser Glu Thr
    50                  55                  60

Leu Gln Arg Phe Ala Arg Arg Ser Ser His Glu Asn Gly Arg Pro Ser
65                  70                  75                  80

Phe Pro Pro Lys Gln Lys Arg Lys Met Glu Arg Thr Ile Glu Pro Glu
                85                  90                  95

Val

<210> SEQ ID NO 38
<211> LENGTH: 293
<212> TYPE: DNA
<213> ORGANISM: Equine influenza virus H3N8

<400> SEQUENCE: 38

| | |
|---|---|
| actttagtgt gattttcgaa aggctggaga cactaatact acttagagcc ttcaccgaag | 60 |
| aaggagcagt cgttggcgaa atttcaccat tgccttctct tccaggacat actaatgagg | 120 |
| atgtcaaaaa tgcaattggg gtcctcatcg gaggacttaa atggaatgat aatacggtta | 180 |

-continued

```
gaatctctga aactctacag agattcgctc ggagaagcag tcatgagaat gggagacctt      240
cattccctcc aaagcagaaa cgaaaaatgg agagaacaat tgagccagaa gtt            293
```

<210> SEQ ID NO 39
<211> LENGTH: 888
<212> TYPE: DNA
<213> ORGANISM: Equine influenza virus H3N8
<220> FEATURE:
<221> NAME/KEY: CDS
<222> LOCATION: (27)..(716)

<400> SEQUENCE: 39

```
agcaaaagca gggtgacaaa aacata atg gat tcc aac act gtg tca agc ttt       53
                              Met Asp Ser Asn Thr Val Ser Ser Phe
                                1               5 cag gta gac tgt ttt ctt tgg cat gtc cgc aaa cga ttt gca gac caa       101
Gln Val Asp Cys Phe Leu Trp His Val Arg Lys Arg Phe Ala Asp Gln
 10              15                  20                  25 gaa ctg ggt gat gcc cca ttc ctt gac cgg ctt cgc cga gac cag aag       149
Glu Leu Gly Asp Ala Pro Phe Leu Asp Arg Leu Arg Arg Asp Gln Lys
             30                  35                  40 tcc cta aaa gga aga ggt agc act ctt ggt ctg gac atc gaa aca gcc       197
Ser Leu Lys Gly Arg Gly Ser Thr Leu Gly Leu Asp Ile Glu Thr Ala
         45                  50                  55 act cgt gca gga aag cag ata gtg gag cag att ctg gaa gag gaa tca       245
Thr Arg Ala Gly Lys Gln Ile Val Glu Gln Ile Leu Glu Glu Glu Ser
     60                  65                  70 gat gag gca ctt aaa atg acc att gcc tct gtt cct gct tca cgc tac       293
Asp Glu Ala Leu Lys Met Thr Ile Ala Ser Val Pro Ala Ser Arg Tyr
 75                  80                  85 tta act gac atg act ctt gat gag atg tca aga gac tgg ttc atg ctc       341
Leu Thr Asp Met Thr Leu Asp Glu Met Ser Arg Asp Trp Phe Met Leu
 90                  95                 100                 105 atg ccc aag cag aaa gta aca ggc tcc cta tgt ata aga atg gac cag       389
Met Pro Lys Gln Lys Val Thr Gly Ser Leu Cys Ile Arg Met Asp Gln
                110                 115                 120 gca atc atg gat aag aac atc ata ctt aaa gca aac ttt agt gtg att       437
Ala Ile Met Asp Lys Asn Ile Ile Leu Lys Ala Asn Phe Ser Val Ile
            125                 130                 135 ttc gaa agg ctg gag aca cta ata cta ctt aga gcc ttc acc gaa gaa       485
Phe Glu Arg Leu Glu Thr Leu Ile Leu Leu Arg Ala Phe Thr Glu Glu
        140                 145                 150 gga gca gtc gtt ggc gaa att tca cca ttg cct tct ctt cca gga cat       533
Gly Ala Val Val Gly Glu Ile Ser Pro Leu Pro Ser Leu Pro Gly His
    155                 160                 165 act aat gag gat gtc aaa aat gca att ggg gtc ctc atc gga gga ctt       581
Thr Asn Glu Asp Val Lys Asn Ala Ile Gly Val Leu Ile Gly Gly Leu
170                 175                 180                 185 aaa tgg aat gat aat acg gtt aga atc tct gaa act cta cag aga ttc       629
Lys Trp Asn Asp Asn Thr Val Arg Ile Ser Glu Thr Leu Gln Arg Phe
                190                 195                 200 gct tgg aga agc agt cat gag aat ggg aga cct tca ttc cct cca aag       677
Ala Trp Arg Ser Ser His Glu Asn Gly Arg Pro Ser Phe Pro Pro Lys
            205                 210                 215 cag aaa cga aaa atg gag aga aca att gag cca gaa gtt tgaagaaata       726
Gln Lys Arg Lys Met Glu Arg Thr Ile Glu Pro Glu Val
        220                 225                 230 agatggttga ttgaagaagt gcgacataga ttgaaaaata cagaaaatag ttttgaacaa      786
ataacattta tgcaagcctt acaactattg cttgaagtag aacaagagat aagaactttc      846
```
tcgtttcagc ttatttaatg ataaaaaaca cccttgtttc ta            888

<210> SEQ ID NO 40
<211> LENGTH: 230
<212> TYPE: PRT
<213> ORGANISM: Equine influenza virus H3N8

<400> SEQUENCE: 40

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asp Ile Glu Thr Ala Thr Arg Ala Gly Lys Gln Ile
    50                  55                  60

Val Glu Gln Ile Leu Glu Glu Ser Asp Glu Ala Leu Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Pro Lys Gln Lys Arg Lys Met Glu Arg
    210                 215                 220

Thr Ile Glu Pro Glu Val
225                 230

<210> SEQ ID NO 41
<211> LENGTH: 690
<212> TYPE: DNA
<213> ORGANISM: Equine influenza virus H3N8

<400> SEQUENCE: 41
atggattcca acactgtgtc aagctttcag gtagactgtt ttctttggca tgtccgcaaa      60
cgatttgcag accaagaact gggtgatgcc ccattccttg accggcttcg ccgagaccag     120
aagtccctaa aaggaagagg tagcactctt ggtctggaca tcgaaacagc cactcgtgca     180
ggaaagcaga tagtggagca gattctggaa gaggaatcag atgaggcact taaaatgacc     240
attgcctctg ttcctgcttc acgctactta actgacatga ctcttgatga gatgtcaaga     300
gactggttca tgctcatgcc caagcagaaa gtaacaggct ccctatgtat aagaatggac     360
caggcaatca tggataagaa catcatactt aaagcaaact ttagtgtgat tttcgaaagg     420
ctggagacac taatactact tagagccttc accgaagaag gagcagtcgt tggcgaaatt     480

| | | |
|---|---|---|
| tcaccattgc cttctcttcc aggacatact aatgaggatg tcaaaaatgc aattggggtc | 540 | |
| ctcatcggag gacttaaatg gaatgataat acggttagaa tctctgaaac tctacagaga | 600 | |
| ttcgcttgga gaagcagtca tgagaatggg agaccttcat tccctccaaa gcagaaacga | 660 | |
| aaaatggaga gaacaattga gccagaagtt | 690 | |

<210> SEQ ID NO 42
<211> LENGTH: 1229
<212> TYPE: DNA
<213> ORGANISM: Equine influenza virus H3N8
<220> FEATURE:
<221> NAME/KEY: CDS
<222> LOCATION: (36)..(1229)

<400> SEQUENCE: 42

| | | |
|---|---|---|
| gaattcggct tagcaaaagc aggcaaacta tttga atg gat gtc aat ccg act<br>                                                      Met Asp Val Asn Pro Thr<br>                                                      1               5 | 53 | |
| cta ctc ttc tta aag gtg cca gcg caa aat gct ata agc aca aca ttc<br>Leu Leu Phe Leu Lys Val Pro Ala Gln Asn Ala Ile Ser Thr Thr Phe<br>               10                    15                   20 | 101 | |
| cct tat act gga gat cct ccc tac agt cat gga aca ggg aca gga tac<br>Pro Tyr Thr Gly Asp Pro Pro Tyr Ser His Gly Thr Gly Thr Gly Tyr<br>         25                    30                   35 | 149 | |
| acc atg gat act gtc aac aga aca cat caa tac tca gaa aag ggg aaa<br>Thr Met Asp Thr Val Asn Arg Thr His Gln Tyr Ser Glu Lys Gly Lys<br>40                         45                   50 | 197 | |
| tgg aca aca aac act gag att gga gca cca caa ctt aat cca atc gat<br>Trp Thr Thr Asn Thr Glu Ile Gly Ala Pro Gln Leu Asn Pro Ile Asp<br>55                     60                    65                   70 | 245 | |
| gga ccg ctt cct gaa gac aat gaa cca agt ggg tac gcc caa aca gat<br>Gly Pro Leu Pro Glu Asp Asn Glu Pro Ser Gly Tyr Ala Gln Thr Asp<br>               75                    80                   85 | 293 | |
| tgt gta ttg gaa gca atg gct ttc ctt gaa gaa tcc cat ccc gga atc<br>Cys Val Leu Glu Ala Met Ala Phe Leu Glu Glu Ser His Pro Gly Ile<br>               90                    95                  100 | 341 | |
| ttt gaa aat tcg tgt ctt gaa aca atg gag gtg gtt cag cag aca aga<br>Phe Glu Asn Ser Cys Leu Glu Thr Met Glu Val Val Gln Gln Thr Arg<br>         105                    110                  115 | 389 | |
| gtg gac aaa cta aca caa ggc cga caa act tac gat tgg acc ttg aat<br>Val Asp Lys Leu Thr Gln Gly Arg Gln Thr Tyr Asp Trp Thr Leu Asn<br>    120                    125                  130 | 437 | |
| agg aat caa cct gcc gca aca gca ctt gct aat aca att gaa gtg ttc<br>Arg Asn Gln Pro Ala Ala Thr Ala Leu Ala Asn Thr Ile Glu Val Phe<br>135                    140                  145                  150 | 485 | |
| aga tca aat gat ctg act tcc agt gag tca ggg aga tta atg gac ttc<br>Arg Ser Asn Asp Leu Thr Ser Ser Glu Ser Gly Arg Leu Met Asp Phe<br>               155                    160                  165 | 533 | |
| ctc aaa gat gtc atg gag tcc atg aac aag gaa gaa atg gaa ata aca<br>Leu Lys Asp Val Met Glu Ser Met Asn Lys Glu Glu Met Glu Ile Thr<br>               170                    175                  180 | 581 | |
| aca cac ttc caa cgg aag aga aga gta aga gac aac atg aca aag aga<br>Thr His Phe Gln Arg Lys Arg Arg Val Arg Asp Asn Met Thr Lys Arg<br>         185                    190                  195 | 629 | |
| atg gtg aca cag aga acc ata ggg aag aaa aaa caa cga tta aac aga<br>Met Val Thr Gln Arg Thr Ile Gly Lys Lys Lys Gln Arg Leu Asn Arg<br>200                         205                    210 | 677 | |
| aag agc tat ctg atc agg gca tta acc tta aac aca atg acc aag gac<br>Lys Ser Tyr Leu Ile Arg Ala Leu Thr Leu Asn Thr Met Thr Lys Asp<br>215                    220                  225                  230 | 725 | |

```
gct gag aga ggg aaa ttg aaa cga cga gca att gca acc cca gga atg      773
Ala Glu Arg Gly Lys Leu Lys Arg Arg Ala Ile Ala Thr Pro Gly Met
            235                 240                 245 cag ata aga ggg ttt gta tat ttt gtt gaa aca tta gcc cga aga ata      821
Gln Ile Arg Gly Phe Val Tyr Phe Val Glu Thr Leu Ala Arg Arg Ile
        250                 255                 260 tgt gaa aag ctt gaa caa tca gga ttg cca gtt ggc ggt aat gag aaa      869
Cys Glu Lys Leu Glu Gln Ser Gly Leu Pro Val Gly Gly Asn Glu Lys
    265                 270                 275 aag gcc aaa ctg gct aat gtc gtc aga aaa atg atg act aat tcc caa      917
Lys Ala Lys Leu Ala Asn Val Val Arg Lys Met Met Thr Asn Ser Gln
280                 285                 290 gac act gaa ctc tcc ttc acc atc act ggg gac aat acc aaa tgg aat      965
Asp Thr Glu Leu Ser Phe Thr Ile Thr Gly Asp Asn Thr Lys Trp Asn
295                 300                 305                 310 gaa aat cag aac cca cgc atg ttc ctg gca atg atc aca tac ata act     1013
Glu Asn Gln Asn Pro Arg Met Phe Leu Ala Met Ile Thr Tyr Ile Thr
                315                 320                 325 aga aac cag cca gaa tgg ttc aga aat gtt cta agc att gca ccg att     1061
Arg Asn Gln Pro Glu Trp Phe Arg Asn Val Leu Ser Ile Ala Pro Ile
            330                 335                 340 atg ttc tca aat aaa atg gca aga ctg ggg aaa gga tat atg ttt gaa     1109
Met Phe Ser Asn Lys Met Ala Arg Leu Gly Lys Gly Tyr Met Phe Glu
        345                 350                 355 agc aaa agt atg aaa ttg aga act caa ata cca gca gaa atg ctc gca     1157
Ser Lys Ser Met Lys Leu Arg Thr Gln Ile Pro Ala Glu Met Leu Ala
    360                 365                 370 agc att gat ctg aaa tat ttc aat gat tca aca aaa aag aaa att gag     1205
Ser Ile Asp Leu Lys Tyr Phe Asn Asp Ser Thr Lys Lys Lys Ile Glu
375                 380                 385                 390 aag ata cga cca caa gcc gaa ttc                                     1229
Lys Ile Arg Pro Gln Ala Glu Phe
                395
```

<210> SEQ ID NO 43
<211> LENGTH: 398
<212> TYPE: PRT
<213> ORGANISM: Equine influenza virus H3N8

<400> SEQUENCE: 43

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140
```

-continued

```
Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
                260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
        370                 375                 380

Thr Lys Lys Lys Ile Glu Lys Ile Arg Pro Gln Ala Glu Phe
385                 390                 395
```

<210> SEQ ID NO 44
<211> LENGTH: 1194
<212> TYPE: DNA
<213> ORGANISM: Equine influenza virus H3N8

<400> SEQUENCE: 44

```
atggatgtca atccgactct actcttctta aaggtgccag cgcaaaatgc tataagcaca      60
acattccctt atactggaga tcctccctac agtcatggaa cagggacagg atacaccatg     120
gatactgtca acagaacaca tcaatactca gaaaagggga atggacaac aaacactgag      180 attggagcac acaacttaa tccaatcgat ggaccgcttc ctgaagacaa tgaaccaagt     240
gggtacgccc aaacagattg tgtattggaa gcaatggctt ccttgaaga tcccatccc     300 ggaatctttg aaaattcgtg tcttgaaaca atggaggtgg ttcagcagac aagagtggac     360
aaactaacac aaggccgaca aacttacgat tggaccttga ataggaatca acctgccgca     420
acagcacttg ctaatacaat tgaagtgttc agatcaaatg atctgacttc cagtgagtca     480
gggagattaa tggacttcct caaagatgtc atggagtcca tgaacaagga agaaatggaa     540
ataacaacac acttccaacg gaagagaaga gtaagagaca catgacaaa gagaatggtg      600 acacagagaa cctagggaa gaaaaaacaa cgattaaaca gaaagagcta tctgatcagg      660 gcattaaccct taaacacaat gaccaaggac gctgagagag ggaaattgaa cgacgagca      720
```

```
attgcaaccc caggaatgca gataagaggg tttgtatatt ttgttgaaac attagcccga    780
agaatatgtg aaaagcttga acaatcagga ttgccagttg gcggtaatga aaaaaggcc    840 aaactggcta atgtcgtcag aaaaatgatg actaattccc aagacactga actctccttc    900
accatcactg gggacaatac caaatggaat gaaaatcaga acccacgcat gttcctggca    960
atgatcacat acataactag aaaccagcca gaatggttca gaaatgttct aagcattgca    1020
ccgattatgt tctcaaataa aatggcaaga ctggggaaag gatatatgtt tgaaagcaaa    1080
agtatgaaat tgagaactca ataccagca gaaatgctcg caagcattga tctgaaatat    1140
ttcaatgatt caacaaaaaa gaaaattgag aagatacgac cacaagccga attc          1194

<210> SEQ ID NO 45
<211> LENGTH: 673
<212> TYPE: DNA
<213> ORGANISM: Equine influenza virus H3N8
<220> FEATURE:
<221> NAME/KEY: CDS
<222> LOCATION: (36

```
atg gtg aca cag aga acc ata ggg aag aaa aaa caa cga tta aa          673
Met Val Thr Gln Arg Thr Ile Gly Lys Lys Lys Gln Arg Leu
    200             205             210
```

<210> SEQ ID NO 46
<211> LENGTH: 212
<212> TYPE: PRT
<213> ORGANISM: Equine influenza virus H3N8

<400> SEQUENCE: 46

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
    195                 200                 205

Lys Gln Arg Leu
    210
```

<210> SEQ ID NO 47
<211> LENGTH: 636
<212> TYPE: DNA
<213> ORGANISM: Equine influenza virus H3N8

<400> SEQUENCE: 47

```
atggatgtca atccgactct actcttctta aaggtgccag cgcaaaatgc tataagcaca      60 acattcccctt atactggaga tcctccctac agtcatggaa cagggacagg atacaccatg     120
gatactgtca acagaacaca tcaatactca gaaaagggga atggacaac aaacactgag      180 attggagcac cacaacttaa tccaatcgat ggaccgcttc ctgaagacaa tgaaccaagt     240
gggtacgccc aaacagattg tgtattggaa gcaatggctt ccttgaaga tcccatccc      300 ggaatctttg aaaattcgtg tcttgaaaca atggaggtgg ttcagcagac aagagtggac    360
aaactaacac aaggccgaca aacttacgat tggaccttga ataggaatca acctgccgca    420
acagcacttg ctaatacaat tgaagtgttc agatcaaatg atctgacttc cagtgagtca    480
```

-continued

```
gggagattaa tggacttcct caaagatgtc atggagtcca tgaacaagga agaaatggaa      540
ataacaacac acttccaacg gaagagaaga gtaagagaca acatgacaaa gagaatggtg      600
acacagagaa ccatagggaa gaaaaaacaa cgatta                                636
```

```
<210> SEQ ID NO 48
<211> LENGTH: 1225
<212> TYPE: DNA
<213> ORGANISM: Equine influenza virus H3N8
<220> FEATURE:
<221> NAME/KEY: CDS
<222> LOCATION: (34)..(1218)

<400> SEQUENCE: 48
```

```
gaattcagga gcaaaagcag gcaaactatt tga atg gat gtc aat ccg act cta       54
                                    Met Asp Val Asn Pro Thr Leu
                                     1               5 ctc ttc tta aag gtg cca gcg caa aat gct ata agc aca aca ttc cct       102
Leu Phe Leu Lys Val Pro Ala Gln Asn Ala Ile Ser Thr Thr Phe Pro
         10                  15                  20 tat act gga gat cct ccc tac agt cat gga aca ggg aca gga tac acc       150
Tyr Thr Gly Asp Pro Pro Tyr Ser His Gly Thr Gly Thr Gly Tyr Thr
 25                  30                  35 atg gat act gtc aac aga aca cat caa tac tca gaa aag ggg aaa tgg       198
Met Asp Thr Val Asn Arg Thr His Gln Tyr Ser Glu Lys Gly Lys Trp
 40                  45                  50                  55 aca aca aac act gag att gga gca cca caa ctt aat cca atc gat gga       246
Thr Thr Asn Thr Glu Ile Gly Ala Pro Gln Leu Asn Pro Ile Asp Gly
                 60                  65                  70 ccg ctt cct gaa gac aat gaa cca agt ggg tac gcc caa aca gat tgt       294
Pro Leu Pro Glu Asp Asn Glu Pro Ser Gly Tyr Ala Gln Thr Asp Cys
             75                  80                  85 gta ttg gaa gca atg gct ttc ctt gaa gaa tcc cat ccc gga atc ttt       342
Val Leu Glu Ala Met Ala Phe Leu Glu Glu Ser His Pro Gly Ile Phe
         90                  95                 100 gaa aat tcg tgt ctt gaa aca atg gag gtg gtt cag cag aca aga gtg       390
Glu Asn Ser Cys Leu Glu Thr Met Glu Val Val Gln Gln Thr Arg Val
    105                 110                 115 gac aaa cta aca caa ggc cga caa act tac gat tgg acc ttg aat agg       438
Asp Lys Leu Thr Gln Gly Arg Gln Thr Tyr Asp Trp Thr Leu Asn Arg
120                 125                 130                 135 aat caa cct gcc gca aca gca ctt gct aat aca att gaa gtg ttc aga       486
Asn Gln Pro Ala Ala Thr Ala Leu Ala Asn Thr Ile Glu Val Phe Arg
                140                 145                 150 tca aat gat ctg act tcc agt gag tca ggg aga tta atg gac ttc ctc       534
Ser Asn Asp Leu Thr Ser Ser Glu Ser Gly Arg Leu Met Asp Phe Leu
            155                 160                 165 aaa gat gtc atg gag tcc atg aac aag gaa gaa atg gaa ata aca aca       582
Lys Asp Val Met Glu Ser Met Asn Lys Glu Glu Met Glu Ile Thr Thr
        170                 175                 180 cac ttc caa cgg aag aga aga gta aga gac aac atg aca aag aga atg       630
His Phe Gln Arg Lys Arg Arg Val Arg Asp Asn Met Thr Lys Arg Met
    185                 190                 195 gtg aca cag aga acc ata ggg aag aaa aaa caa cga tta aac aga aag       678
Val Thr Gln Arg Thr Ile Gly Lys Lys Lys Gln Arg Leu Asn Arg Lys
200                 205                 210                 215 agc tat ctg atc agg gca tta acc tta aac aca atg acc aag gac gct       726
Ser Tyr Leu Ile Arg Ala Leu Thr Leu Asn Thr Met Thr Lys Asp Ala
                220                 225                 230 gag aga ggg aaa ttg aaa cga cga gca att gca acc cca gga atg cag       774
Glu Arg Gly Lys Leu Lys Arg Arg Ala Ile Ala Thr Pro Gly Met Gln
```

```
                   235                 240                 245
ata aga ggg ttt gta tat ttt gtt gaa aca tta gcc cga aga ata tgt      822
Ile Arg Gly Phe Val Tyr Phe Val Glu Thr Leu Ala Arg Arg Ile Cys
        250                 255                 260 gaa aag ctt gaa caa tca gga ttg cca gtt ggc ggt aat gag aaa aag      870
Glu Lys Leu Glu Gln Ser Gly Leu Pro Val Gly Gly Asn Glu Lys Lys
265                 270                 275 gcc aaa ctg gct aat gtc gtc aga aaa atg atg act aat tcc caa gac      918
Ala Lys Leu Ala Asn Val Val Arg Lys Met Met Thr Asn Ser Gln Asp
280                 285                 290                 295 act gaa ctc tcc ttc acc atc act ggg gac aat acc aaa tgg aat gaa      966
Thr Glu Leu Ser Phe Thr Ile Thr Gly Asp Asn Thr Lys Trp Asn Glu
                300                 305                 310 aat cag aac cca cgc atg ttc ctg gca atg atc aca tac ata act aga     1014
Asn Gln Asn Pro Arg Met Phe Leu Ala Met Ile Thr Tyr Ile Thr Arg
            315                 320                 325 aac cag cca gaa tgg ttc aga aat gtt cta agc att gca ccg att atg     1062
Asn Gln Pro Glu Trp Phe Arg Asn Val Leu Ser Ile Ala Pro Ile Met
        330                 335                 340 ttc tca aat aaa atg gca aga ctg ggg aaa gga tat atg ttt gaa agc     1110
Phe Ser Asn Lys Met Ala Arg Leu Gly Lys Gly Tyr Met Phe Glu Ser
    345                 350                 355 aaa agt atg aaa ttg aga act caa ata cca gca gaa atg ctc gca agc     1158
Lys Ser Met Lys Leu Arg Thr Gln Ile Pro Ala Glu Met Leu Ala Ser
360                 365                 370                 375 att gat ctg aaa tat ttc aat gat tca aca aaa aag aaa att gag aag     1206
Ile Asp Leu Lys Tyr Phe Asn Asp Ser Thr Lys Lys Lys Ile Glu Lys
                380                 385                 390 ata cga cca ccc tgaattc                                             1225
Ile Arg Pro Pro
        395

<210> SEQ ID NO 49
<211> LENGTH: 395
<212> TYPE: PRT
<213> ORGANISM: Equine influenza virus H3N8

<400> SEQUENCE: 49

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160
```

-continued

```
Gly Arg Leu Met Asp Phe Leu Lys Asp Val Met Glu Ser Met Asn Lys
                165                 170                 175
Glu Glu Met Glu Ile Thr Thr His Phe Gln Arg Lys Arg Arg Val Arg
            180                 185                 190
Asp Asn Met Thr Lys Arg Met Val Thr Gln Arg Thr Ile Gly Lys Lys
        195                 200                 205
Lys Gln Arg Leu Asn Arg Lys Ser Tyr Leu Ile Arg Ala Leu Thr Leu
    210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val Tyr Phe Val Glu
                245                 250                 255
Thr Leu Ala Arg Arg Ile Cys Glu Lys Leu Glu Gln Ser Gly Leu Pro
            260                 265                 270
Val Gly Gly Asn Glu Lys Lys Ala Lys Leu Ala Asn Val Val Arg Lys
        275                 280                 285
Met Met Thr Asn Ser Gln Asp Thr Glu Leu Ser Phe Thr Ile Thr Gly
    290                 295                 300
Asp Asn Thr Lys Trp Asn Glu Asn Gln Asn Pro Arg Met Phe Leu Ala
305                 310                 315                 320
Met Ile Thr Tyr Ile Thr Arg Asn Gln Pro Glu Trp Phe Arg Asn Val
                325                 330                 335
Leu Ser Ile Ala Pro Ile Met Phe Ser Asn Lys Met Ala Arg Leu Gly
            340                 345                 350
Lys Gly Tyr Met Phe Glu Ser Lys Ser Met Lys Leu Arg Thr Gln Ile
        355                 360                 365
Pro Ala Glu Met Leu Ala Ser Ile Asp Leu Lys Tyr Phe Asn Asp Ser
    370                 375                 380
Thr Lys Lys Lys Ile Glu Lys Ile Arg Pro Pro
385                 390                 395

<210> SEQ ID NO 50
<211> LENGTH: 1185
<212> TYPE: DNA
<213> ORGANISM: Equine influenza virus H3N8

<400> SEQUENCE: 50
atggatgtca atccgactct actcttctta aaggtgccag cgcaaaatgc tataagcaca      60
acattccctt atactggaga tcctccctac agtcatggaa cagggacagg atacaccatg     120
gatactgtca acagaacaca tcaatactca gaaaagggga aatggacaac aaacactgag     180
attggagcac cacaacttaa tccaatcgat ggaccgcttc ctgaagacaa tgaaccaagt     240
gggtacgccc aaacagattg tgtattggaa gcaatggctt tccttgaaga atcccatccc     300
ggaatctttg aaaattcgtg tcttgaaaca atggaggtgg ttcagcagac aagagtggac     360
aaactaacac aaggccgaca aacttacgat tggaccttga ataggaatca acctgccgca     420
acagcacttg ctaatacaat tgaagtgttc agatcaaatg atctgacttc cagtgagtca     480
gggagattaa tggacttcct caaagatgtc atggagtcca tgaacaagga agaaatggaa     540
ataacaacac acttccaacg gaagagaaga gtaagagaca acatgacaaa gagaatggtg     600
acacagagaa ccatagggaa gaaaaaacaa cgattaaaca gaaagagcta tctgatcagg     660
gcattaacct taaacacaat gaccaaggac gctgagagag ggaaattgaa acgacgagca     720
attgcaaccc caggaatgca gataagaggg tttgtatatt ttgttgaaac attagcccga     780
```

```
agaatatgtg aaaagcttga acaatcagga ttgccagttg gcggtaatga gaaaaaggcc    840
aaactggcta atgtcgtcag aaaaatgatg actaattccc aagacactga actctccttc    900
accatcactg gggacaatac caaatggaat gaaaatcaga acccacgcat gttcctggca    960
atgatcacat acataactag aaaccagcca gaatggttca gaaatgttct aagcattgca   1020
ccgattatgt tctcaaataa aatggcaaga ctggggaaag gatatatgtt tgaaagcaaa   1080
agtatgaaat tgagaactca ataccagca gaaatgctcg caagcattga tctgaaatat   1140
ttcaatgatt caacaaaaaa gaaaattgag aagatacgac caccc                  1185
```

<210> SEQ ID NO 51
<211> LENGTH: 1221
<212> TYPE: DNA
<213> ORGANISM: Equine influenza virus H3N8

<400> SEQUENCE: 51

```
gaattcagga aagcaggcaa actatttgaa tggatgtcaa tccgactcta ctcttcttaa     60
aggtgccagc gcaaaatgct ataagcacaa cattcccttta tactggagat cctccctaca   120
gtcatggaac agggacagga tacaccatgg atactgtcaa cagaacacat caatactcag   180
aaaaggggaa atggcaaca aacactgaga ttggagcacc acaacttaat ccaatcgatg    240
gaccgcttcc tgaagacaat gaaccaagtg ggtacgccca acagattgt gtattggaag    300 caatggcttt ccttgaagaa tcccatcccg gaatctttga aaattcgtgt cttgaaacaa    360
tggaggtggt tcagcagaca agagtggaca aactaacaca aggccgacaa acttacgatt    420 ggacccttgaa taggaatcaa cctgccgcaa cagcacttgc taatacaatt gaagtgttca   480
gatcaaatga tctgacttcc agtgagtcag ggagattaat ggacttcctc aaagatgtca   540
tggagtccat gaacaaggaa gaaatggaaa taacaacaca cttccaacgg aagagaagag   600
taagagacaa catgacaaag agaatggtga cacagagaac catagggaag aaaaaacaac   660
gattaaacag aaagagctat ctgatcaggg cattaacctt aaacacaatg accaaggacg   720
ctgagagagg gaaattgaaa cgacgagcaa ttgcaacccc aggaatgcag ataagagggt   780
ttgtatattt tgttgaaaca ttagcccgaa gaatatgtga aaagcttgaa caatcaggat   840
tgccagttgg cggtaatgag aaaaaggcca actggctaa tgtcgtcaga aaaatgatga   900
ctaattccca agacactgaa ctctccttca ccatcactgg ggacaatacc aaatggaatg   960
aaaatcagaa cccacgcatg ttcctggcaa tgatcacata cataactaga aaccagccag  1020
aatggttcag aaatgttcta agcattgcac cgattatgtt ctcaaataaa atggcaagac  1080
tggggaaagg atatatgttt gaaagcaaaa gtatgaaatt gagaactcaa ataccagcag  1140
aaatgctcgc aagcattgat ctgaaatatt tcaatgattc aacaaaaaag aaaattgaga  1200
agatacgacc accctgaatt c                                              1221
```

<210> SEQ ID NO 52
<211> LENGTH: 20
<212> TYPE: DNA
<213> ORGANISM: Artificial
<220> FEATURE:
<223> OTHER INFORMATION: Synthetic Primer

<400> SEQUENCE: 52

```
aaaacaagga ttttttcacg                                                 20
```

<210> SEQ ID NO 53

<211> LENGTH: 1234
<212> TYPE: DNA
<213> ORGANISM: Equine influenza virus H3N8
<220> FEATURE:
<221> NAME/KEY: CDS
<222> LOCATION: (1)..(1188)

<400> SEQUENCE: 53

| | | | | | | | | | | | | | | | | |
|---|---|---|---|---|---|---|---|---|---|---|---|---|---|---|---|---|
| atg | aaa | ttg | aga | act | caa | ata | cca | gca | gaa | atg | ctc | gca | agc | att | gat | 48 |
| Met | Lys | Leu | Arg | Thr | Gln | Ile | Pro | Ala | Glu | Met | Leu | Ala | Ser | Ile | Asp | |
| 1 | | | | 5 | | | | | 10 | | | | | 15 | | |
| ctg | aaa | tat | ttc | aat | gat | tca | aca | aaa | aag | aaa | att | gag | aag | ata | cga | 96 |
| Leu | Lys | Tyr | Phe | Asn | Asp | Ser | Thr | Lys | Lys | Lys | Ile | Glu | Lys | Ile | Arg | |
| | | | 20 | | | | | 25 | | | | | 30 | | | |
| cca | ctt | ctg | gtc | gat | ggg | act | gct | tca | ctg | agt | cct | ggc | atg | atg | atg | 144 |
| Pro | Leu | Leu | Val | Asp | Gly | Thr | Ala | Ser | Leu | Ser | Pro | Gly | Met | Met | Met | |
| | | 35 | | | | | 40 | | | | | 45 | | | | |
| gga | atg | ttc | aac | atg | ttg | agc | act | gta | cta | ggt | gta | tcc | ata | tta | aac | 192 |
| Gly | Met | Phe | Asn | Met | Leu | Ser | Thr | Val | Leu | Gly | Val | Ser | Ile | Leu | Asn | |
| | 50 | | | | | 55 | | | | | 60 | | | | | |
| ctg | ggc | cag | agg | aaa | tac | aca | aag | acc | aca | tac | tgg | tgg | gat | ggt | ctg | 240 |
| Leu | Gly | Gln | Arg | Lys | Tyr | Thr | Lys | Thr | Thr | Tyr | Trp | Trp | Asp | Gly | Leu | |
| 65 | | | | | 70 | | | | | 75 | | | | | 80 | |
| caa | tca | tcc | gat | gat | ttt | gct | ttg | ata | gtg | aat | gcg | cct | aat | cat | gaa | 288 |
| Gln | Ser | Ser | Asp | Asp | Phe | Ala | Leu | Ile | Val | Asn | Ala | Pro | Asn | His | Glu | |
| | | | | 85 | | | | | 90 | | | | | 95 | | |
| gga | ata | cag | gct | gga | gta | gac | aga | ttc | tat | aga | act | tgc | aaa | ctg | gtc | 336 |
| Gly | Ile | Gln | Ala | Gly | Val | Asp | Arg | Phe | Tyr | Arg | Thr | Cys | Lys | Leu | Val | |
| | | | 100 | | | | | 105 | | | | | 110 | | | |
| ggg | atc | aac | atg | agc | aaa | aag | aag | tcc | tac | ata | aat | aga | acc | ggc | aca | 384 |
| Gly | Ile | Asn | Met | Ser | Lys | Lys | Lys | Ser | Tyr | Ile | Asn | Arg | Thr | Gly | Thr | |
| | | 115 | | | | | 120 | | | | | 125 | | | | |
| ttc | gaa | ttc | aca | agc | ttt | ttc | tac | cgg | tat | ggt | ttt | gtc | gcc | aat | ttc | 432 |
| Phe | Glu | Phe | Thr | Ser | Phe | Phe | Tyr | Arg | Tyr | Gly | Phe | Val | Ala | Asn | Phe | |
| 130 | | | | | 135 | | | | | 140 | | | | | | |
| agc | atg | gag | cta | ccc | agt | ttt | ggg | gtt | tcc | ggg | ata | aat | gaa | tct | gca | 480 |
| Ser | Met | Glu | Leu | Pro | Ser | Phe | Gly | Val | Ser | Gly | Ile | Asn | Glu | Ser | Ala | |
| 145 | | | | | 150 | | | | | 155 | | | | | 160 | |
| gac | atg | agc | att | gga | atg | aca | gtt | atc | aaa | aac | aac | atg | ata | aat | aat | 528 |
| Asp | Met | Ser | Ile | Gly | Met | Thr | Val | Ile | Lys | Asn | Asn | Met | Ile | Asn | Asn | |
| | | | | 165 | | | | | 170 | | | | | 175 | | |
| gat | ctc | ggt | ccc | gcc | acg | gca | caa | atg | gca | ctc | caa | ctc | ttc | att | aag | 576 |
| Asp | Leu | Gly | Pro | Ala | Thr | Ala | Gln | Met | Ala | Leu | Gln | Leu | Phe | Ile | Lys | |
| | | | 180 | | | | | 185 | | | | | 190 | | | |
| gat | tat | cgg | tac | aca | tac | cgg | tgc | cat | aga | ggc | gat | acc | cag | ata | caa | 624 |
| Asp | Tyr | Arg | Tyr | Thr | Tyr | Arg | Cys | His | Arg | Gly | Asp | Thr | Gln | Ile | Gln | |
| | | 195 | | | | | 200 | | | | | 205 | | | | |
| acc | aga | aga | tcc | ttt | gag | ttg | aag | aaa | ctg | tgg | gaa | cag | act | cga | tca | 672 |
| Thr | Arg | Arg | Ser | Phe | Glu | Leu | Lys | Lys | Leu | Trp | Glu | Gln | Thr | Arg | Ser | |
| 210 | | | | | 215 | | | | | 220 | | | | | | |
| aag | act | ggt | cta | ctg | gta | tca | gat | ggg | ggt | cca | aac | cta | tac | aac | atc | 720 |
| Lys | Thr | Gly | Leu | Leu | Val | Ser | Asp | Gly | Gly | Pro | Asn | Leu | Tyr | Asn | Ile | |
| 225 | | | | | 230 | | | | | 235 | | | | | 240 | |
| aga | aac | cta | cac | atc | ccg | gaa | gtc | tgt | ttg | aaa | tgg | gag | ctg | atg | gat | 768 |
| Arg | Asn | Leu | His | Ile | Pro | Glu | Val | Cys | Leu | Lys | Trp | Glu | Leu | Met | Asp | |
| | | | | 245 | | | | | 250 | | | | | 255 | | |
| gaa | gat | tat | aaa | ggg | agg | cta | tgt | aat | cca | ttg | aat | cct | ttc | gtt | agc | 816 |
| Glu | Asp | Tyr | Lys | Gly | Arg | Leu | Cys | Asn | Pro | Leu | Asn | Pro | Phe | Val | Ser | |
| | | | 260 | | | | | 265 | | | | | 270 | | | |
| cac | aaa | gaa | att | gaa | tca | gtg | aac | agt | gca | gta | gta | atg | cct | gcg | cat | 864 |
| His | Lys | Glu | Ile | Glu | Ser | Val | Asn | Ser | Ala | Val | Val | Met | Pro | Ala | His | |

```
                      275                 280                 285
ggc cct gcc aaa agc atg gag tat gat gct gtt gca aca aca cac tct        912
Gly Pro Ala Lys Ser Met Glu Tyr Asp Ala Val Ala Thr Thr His Ser
        290                 295                 300 tgg atc ccc aag agg aac cgg tcc ata ttg aac aca agt caa agg gga        960
Trp Ile Pro Lys Arg Asn Arg Ser Ile Leu Asn Thr Ser Gln Arg Gly
305                 310                 315                 320 ata ctc gaa gat gag cag atg tat cag aaa tgc tgc aac ctg ttt gaa       1008
Ile Leu Glu Asp Glu Gln Met Tyr Gln Lys Cys Cys Asn Leu Phe Glu
                325                 330                 335 aaa ttc ttc ccc agc agc tca tac aga aga cca gtc gga att tct agt       1056
Lys Phe Phe Pro Ser Ser Ser Tyr Arg Arg Pro Val Gly Ile Ser Ser
            340                 345                 350 atg gtt gag gcc atg gtg tcc agg gcc cgc att gat gca cga att gac       1104
Met Val Glu Ala Met Val Ser Arg Ala Arg Ile Asp Ala Arg Ile Asp
        355                 360                 365 ttc gaa tct gga cgg ata aag aag gat gag ttc gct gag atc atg aag       1152
Phe Glu Ser Gly Arg Ile Lys Lys Asp Glu Phe Ala Glu Ile Met Lys
370                 375                 380 atc tgt tcc acc att gaa gag ctc aga cgg caa aaa tagtgaattt            1198
Ile Cys Ser Thr Ile Glu Glu Leu Arg Arg Gln Lys
385                 390                 395 agcttgatct tcgtgaaaaa atgccttgtt tctact                               1234

<210> SEQ ID NO 54
<211> LENGTH: 396
<212> TYPE: PRT
<213> ORGANISM: Equine influenza virus H3N8

<400> SEQUENCE: 54

Met Lys Leu Arg Thr Gln Ile Pro Ala Glu Met Leu Ala Ser Ile Asp
1               5                   10                  15

Leu Lys Tyr Phe Asn Asp Ser Thr Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Ser Tyr Ile Asn Arg Thr Gly Thr
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys His Arg Gly Asp Thr Gln Ile Gln
        195                 200                 205
```

-continued

```
Thr Arg Arg Ser Phe Glu Leu Lys Lys Leu Trp Gln Thr Arg Ser
    210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Arg Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395
```

<210> SEQ ID NO 55
<211> LENGTH: 20
<212> TYPE: DNA
<213> ORGANISM: Artificial
<220> FEATURE:
<223> OTHER INFORMATION: Synthetic Primer

<400> SEQUENCE: 55
taaatagaac cggcacattc                                           20

<210> SEQ ID NO 56
<211> LENGTH: 17
<212> TYPE: DNA
<213> ORGANISM: Artificial
<220> FEATURE:
<223> OTHER INFORMATION: Synthetic Primer

<400> SEQUENCE: 56
caaagaaatt gaatcag                                              17

<210> SEQ ID NO 57
<211> LENGTH: 18
<212> TYPE: DNA
<213> ORGANISM: Artificial
<220> FEATURE:
<223> OTHER INFORMATION: Synthetic Primer

<400> SEQUENCE: 57
caagcattac tactgcac                                             18

<210> SEQ ID NO 58
<211> LENGTH: 19
<212> TYPE: DNA
<213> ORGANISM: Artificial
<220> FEATURE:
<223> OTHER INFORMATION: Synthetic Primer -continued

<400> SEQUENCE: 58
agtctgttcc cacagtttc                                                19

<210> SEQ ID NO 59
<211> LENGTH: 20
<212> TYPE: DNA
<213> ORGANISM: Artificial
<220> FEATURE:
<223> OTHER INFORMATION: Synthetic Primer

<400> SEQUENCE: 59
gaattcgaat gtgccggttc                                               20

<210> SEQ ID NO 60
<211> LENGTH: 1188
<212> TYPE: DNA
<213> ORGANISM: Equine influenza virus H3N8

<400> SEQUENCE: 60
atgaaattga gaactcaaat accagcagaa atgctcgcaa gcattgatct gaaatatttc      60
aatgattcaa caaaaagaa aattgagaag atacgaccac ttctggtcga tgggactgct     120
tcactgagtc ctggcatgat gatgggaatg ttcaacatgt tgagcactgt actaggtgta    180
tccatattaa acctgggcca gaggaaatac acaaagacca catactggtg ggatggtctg    240
caatcatccg atgattttgc tttgatagtg aatgcgccta atcatgaagg aatacaggct    300
ggagtagaca gattctatag aacttgcaaa ctggtcggga tcaacatgag caaaaagaag    360
tcctacataa atagaaccgg cacattcgaa ttcacaagct ttttctaccg gtatggtttt    420
gtcgccaatt tcagcatgga gctacccagt tttggggttt ccgggataaa tgaatctgca    480
gacatgagca ttggaatgac agttatcaaa acaacatga taataatga tctcggtccc      540 gccacggcac aaatggcact ccaactcttc attaaggatt atcggtacac ataccggtgc    600
catagaggcg atacccagat acaaaccaga agatcctttg agttgaagaa actgtgggaa    660
cagactcgat caaagactgg tctactggta tcagatgggg gtccaaacct atacaacatc    720
agaaacctac acatcccgga gtctgttttg aaatgggagc tgatggatga agattataaa    780
gggaggctat gtaatccatt gaatccttttc gttagccaca agaaattga atcagtgaac    840 agtgcagtag taatgcctgc gcatggccct gccaaaagca tggagtatga tgctgttgca    900
acaacacact cttggatccc caagaggaac cggtccatat tgaacacaag tcaaaggga    960 atactcgaag atgagcagat gtatcagaaa tgctgcaacc tgtttgaaaa attcttcccc   1020
agcagctcat acagaagacc agtcggaatt tctagtatgg ttgaggccat ggtgtccagg   1080
gcccgcattg atgcacgaat tgacttcgaa tctggacgga taaagaagga tgagttcgct   1140
gagatcatga agatctgttc caccattgaa gagctcagac ggcaaaaa               1188

<210> SEQ ID NO 61
<211> LENGTH: 1240
<212> TYPE: DNA
<213> ORGANISM: Equine influenza virus H3N8
<220> FEATURE:
<221> NAME/KEY: CDS
<222> LOCATION: (8)..(1195)

<400> SEQUENCE: 61 caaaagt atg aaa ttg aga act caa ata cca gca gaa atg ctc gca agc      49
         Met Lys Leu Arg Thr Gln Ile Pro Ala Glu Met Leu Ala Ser
          1               5                  10

-continued

| | |
|---|---|
| att gat ctg aaa tat ttc aat gat tca aca aaa aag aaa att gag aag<br>Ile Asp Leu Lys Tyr Phe Asn Asp Ser Thr Lys Lys Lys Ile Glu Lys<br>15                    20                  25                  30 | 97 |
| ata cga cca ctt ctg gtc gat ggg act gct tca ctg agt cct ggc atg<br>Ile Arg Pro Leu Leu Val Asp Gly Thr Ala Ser Leu Ser Pro Gly Met<br>                  35                  40                  45 | 145 |
| atg atg gga atg ttc aac atg ttg agc act gta cta ggt gta tcc ata<br>Met Met Gly Met Phe Asn Met Leu Ser Thr Val Leu Gly Val Ser Ile<br>                  50                  55                  60 | 193 |
| tta aac ctg ggc cag agg aaa tac aca aag acc aca tac tgg tgg gat<br>Leu Asn Leu Gly Gln Arg Lys Tyr Thr Lys Thr Thr Tyr Trp Trp Asp<br>            65                  70                  75 | 241 |
| ggt ctg caa tca tcc gat gat ttt gct ttg ata gtg aat gcg cct aat<br>Gly Leu Gln Ser Ser Asp Asp Phe Ala Leu Ile Val Asn Ala Pro Asn<br>80                    85                  90 | 289 |
| cat gaa gga ata cag gct gga gta gac aga ttc tat aga act tgc aaa<br>His Glu Gly Ile Gln Ala Gly Val Asp Arg Phe Tyr Arg Thr Cys Lys<br>95                    100               105              110 | 337 |
| ctg gtc ggg atc aac atg agc aaa aag aag tcc tac ata aat aga acc<br>Leu Val Gly Ile Asn Met Ser Lys Lys Lys Ser Tyr Ile Asn Arg Thr<br>                 115               120              125 | 385 |
| ggc tca ttc gaa ttc aca agc ttt ttc tac cgg tat ggt ttt gtc gcc<br>Gly Ser Phe Glu Phe Thr Ser Phe Phe Tyr Arg Tyr Gly Phe Val Ala<br>               130               135              140 | 433 |
| aat ttc agc atg gag cta ccc agt ttt ggg gtt tcc ggg ata aat gaa<br>Asn Phe Ser Met Glu Leu Pro Ser Phe Gly Val Ser Gly Ile Asn Glu<br>             145               150              155 | 481 |
| tct gca gac atg agc att gga atg aca gtt atc aaa aac aac atg ata<br>Ser Ala Asp Met Ser Ile Gly Met Thr Val Ile Lys Asn Asn Met Ile<br>160                   165               170 | 529 |
| aat aat gat ctc ggt ccc gcc acg gca caa atg gca ctc caa ctc ttc<br>Asn Asn Asp Leu Gly Pro Ala Thr Ala Gln Met Ala Leu Gln Leu Phe<br>175                   180               185              190 | 577 |
| att aag gat tat cgg tac aca tac cgg tgc cat aga ggc gat acc cag<br>Ile Lys Asp Tyr Arg Tyr Thr Tyr Arg Cys His Arg Gly Asp Thr Gln<br>                   195               200              205 | 625 |
| ata caa acc aga aga tcc ttt gag ttg aag aaa ctg tgg gaa cag act<br>Ile Gln Thr Arg Arg Ser Phe Glu Leu Lys Lys Leu Trp Glu Gln Thr<br>               210               215              220 | 673 |
| cga tca aag act ggt cta ctg gta tca gat ggg ggt cca aac cta tac<br>Arg Ser Lys Thr Gly Leu Leu Val Ser Asp Gly Gly Pro Asn Leu Tyr<br>             225               230              235 | 721 |
| aac atc aga aac cta cac atc ccg gaa gtc tgt ttg aaa tgg gag ctg<br>Asn Ile Arg Asn Leu His Ile Pro Glu Val Cys Leu Lys Trp Glu Leu<br>240                   245               250 | 769 |
| atg gat gaa gat tat aaa ggg agg cta tgt aat cca ttg aat cct ttc<br>Met Asp Glu Asp Tyr Lys Gly Arg Leu Cys Asn Pro Leu Asn Pro Phe<br>255                   260               265              270 | 817 |
| gtt agc cac aaa gaa att gaa tca gtg aac agt gca gta gta atg cct<br>Val Ser His Lys Glu Ile Glu Ser Val Asn Ser Ala Val Val Met Pro<br>               275               280              285 | 865 |
| gcg cat ggc cct gcc aaa agc atg gag tat gat gct gtt gca aca aca<br>Ala His Gly Pro Ala Lys Ser Met Glu Tyr Asp Ala Val Ala Thr Thr<br>             290               295              300 | 913 |
| cac tct tgg atc ccc aag agg aac cgg tcc ata ttg aac aca agt caa<br>His Ser Trp Ile Pro Lys Arg Asn Arg Ser Ile Leu Asn Thr Ser Gln<br>305                   310               315 | 961 |
| agg gga ata ctc gaa gat gag cag atg tat cag aaa tgc tgc aac ctg<br>Arg Gly Ile Leu Glu Asp Glu Gln Met Tyr Gln Lys Cys Cys Asn Leu | 1009 |

-continued

```
             320                 325                 330
ttt gaa aaa ttc ttc ccc agc agc tca tac aga aga cca gtc gga att      1057
Phe Glu Lys Phe Phe Pro Ser Ser Ser Tyr Arg Arg Pro Val Gly Ile
335                 340                 345                 350 tct agt atg gtt gag gcc atg gtg tcc agg gcc cgc att gat gca cga      1105
Ser Ser Met Val Glu Ala Met Val Ser Arg Ala Arg Ile Asp Ala Arg
            355                 360                 365 att gac ttc gaa tct gga cgg ata aag aag gat gag ttc gct gag atc      1153
Ile Asp Phe Glu Ser Gly Arg Ile Lys Lys Asp Glu Phe Ala Glu Ile
        370                 375                 380 atg aag atc tgt tcc acc att gaa gag ctc aga cgg caa aaa              1195
Met Lys Ile Cys Ser Thr Ile Glu Glu Leu Arg Arg Gln Lys
    385                 390                 395 tagtgaattt agcttgatct tcgtgaaaaa atgccttgtt ctact                    1240
```

<210> SEQ ID NO 62
<211> LENGTH: 396
<212> TYPE: PRT
<213> ORGANISM: Equine influenza virus H3N8

<400> SEQUENCE: 62

```
Met Lys Leu Arg Thr Gln Ile Pro Ala Glu Met Leu Ala Ser Ile Asp
1               5                   10                  15

Leu Lys Tyr Phe Asn Asp Ser Thr Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Lys Ser Tyr Ile Asn Arg Thr Gly Ser
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys His Arg Gly Asp Thr Gln Ile Gln
        195                 200                 205

Thr Arg Arg Ser Phe Glu Leu Lys Lys Leu Trp Glu Gln Thr Arg Ser
    210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270
```

```
His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Arg Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
370                 375                 380

Ile Cys Ser Thr Ile Glu Glu Leu Arg Arg Gln Lys
385                 390                 395

<210> SEQ ID NO 63
<211> LENGTH: 1241
<212> TYPE: DNA
<213> ORGANISM: Equine influenza virus H3N8
<220> FEATURE:
<221> NAME/K

```
aat aat gat ctc ggt ccc gcc acg gca caa atg gca ctc caa ctc ttc     577
Asn Asn Asp Leu Gly Pro Ala Thr Ala Gln Met Ala Leu Gln Leu Phe
175                 180                 185                 190 att aag gat tat cgg tac aca tac cgg tgt caa aga ggc gat acc cag     625
Ile Lys Asp Tyr Arg Tyr Thr Tyr Arg Cys Gln Arg Gly Asp Thr Gln
            195                 200                 205 ata caa acc aga aga tcc ttt gag ttg aag aaa ctg tgg gaa cag act     673
Ile Gln Thr Arg Arg Ser Phe Glu Leu Lys Lys Leu Trp Glu Gln Thr
        210                 215                 220 cga tca aag act ggt cta ctg gta tca gat ggg gga cca aac cta tac     721
Arg Ser Lys Thr Gly Leu Leu Val Ser Asp Gly Gly Pro Asn Leu Tyr
    225                 230                 235 aac atc aga aac cta cac atc ccg gaa gtc tgt ttg aaa tgg gag ctg     769
Asn Ile Arg Asn Leu His Ile Pro Glu Val Cys Leu Lys Trp Glu Leu
240                 245                 250 atg gat gaa gat tat aaa ggg agg cta tgt aat cca ttg aat cct ttc     817
Met Asp Glu Asp Tyr Lys Gly Arg Leu Cys Asn Pro Leu Asn Pro Phe
255                 260                 265                 270 gtt agc cac aaa gaa att gaa tca gtg aac agt gca gta gta atg cct     865
Val Ser His Lys Glu Ile Glu Ser Val Asn Ser Ala Val Val Met Pro
            275                 280                 285 gcg cat ggc cct gcc aaa agc atg gag tat gat gct gtt gca aca aca     913
Ala His Gly Pro Ala Lys Ser Met Glu Tyr Asp Ala Val Ala Thr Thr
        290                 295                 300 cac tct tgg atc ccc aag agg aac cgg tcc ata ttg aac aca agt caa     961
His Ser Trp Ile Pro Lys Arg Asn Arg Ser Ile Leu Asn Thr Ser Gln
    305                 310                 315 agg gga ata ctc gaa gat gag cag atg tat cag aaa tgc tgc aac ctg    1009
Arg Gly Ile Leu Glu Asp Glu Gln Met Tyr Gln Lys Cys Cys Asn Leu
320                 325                 330 ttt gaa aaa ttc ttc ccc agc agc tca tac aga aaa cca gtc gga att    1057
Phe Glu Lys Phe Phe Pro Ser Ser Ser Tyr Arg Lys Pro Val Gly Ile
335                 340                 345                 350 tct agt atg gtt gag gcc atg gtg tcc agg gcc cgc att gat gca cga    1105
Ser Ser Met Val Glu Ala Met Val Ser Arg Ala Arg Ile Asp Ala Arg
            355                 360                 365 att gac ttc gaa tct gga cgg ata aag aag gat gag ttc gct gag atc    1153
Ile Asp Phe Glu Ser Gly Arg Ile Lys Lys Asp Glu Phe Ala Glu Ile
        370                 375                 380 atg aag atc tgt tcc acc att gaa gag ctc aga cgg caa aaa             1195
Met Lys Ile Cys Ser Thr Ile Glu Glu Leu Arg Arg Gln Lys
    385                 390                 395 tagtgaattt agcttgatct tcgtgaaaaa atgccttgtt tctact                 1241

<210> SEQ ID NO 64
<211> LENGTH: 396
<212> TYPE: PRT
<213> ORGANISM: Equine influenza virus H3N8

<400> SEQUENCE: 64

Met Lys Leu Arg Thr Gln Ile Pro Ala Glu Met Leu Ala Ser Ile Asp
1               5                   10                  15

Leu Lys Tyr Phe Asn Asp Ser Thr Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
```

```
                65                  70                  75                  80
        Gln Ser Ser Asp Asp Phe Ala Leu Ile Val Asn Ala Pro Asn His Glu
                        85                  90                  95

Gly Ile Gln Ala Gly Val Asp Arg Phe Tyr Arg Thr Cys Lys Leu Val
                    100                 105                 110

Gly Ile Asn Met Ser Lys Lys Ser Tyr Ile Asn Arg Thr Gly Thr
                    115                 120                 125

Phe Glu Phe Thr Ser Phe Phe Tyr Arg Tyr Gly Phe Val Ala Asn Phe
                    130                 135                 140

Ser Met Glu Leu Pro Ser Phe Gly Val Ser Gly Ile Asn Glu Ser Ala
        145                 150                 155                 160

Asp Met Ser Ile Gly Met Thr Val Ile Lys Asn Asn Met Ile Asn Asn
                        165                 170                 175

Asp Leu Gly Pro Ala Thr Ala Gln Met Ala Leu Gln Leu Phe Ile Lys
                    180                 185                 190

Asp Tyr Arg Tyr Thr Tyr Arg Cys Gln Arg Gly Asp Thr Gln Ile Gln
                    195                 200                 205

Thr Arg Arg Ser Phe Glu Leu Lys Lys Leu Trp Glu Gln Thr Arg Ser
            210                 215                 220

Lys Thr Gly Leu Leu Val Ser Asp Gly Gly Pro Asn Leu Tyr Asn Ile
        225                 230                 235                 240

Arg Asn Leu His Ile Pro Glu Val Cys Leu Lys Trp Glu Leu Met Asp
                        245                 250                 255

Glu Asp Tyr Lys Gly Arg Leu Cys Asn Pro Leu Asn Pro Phe Val Ser
                    260                 265                 270

His Lys Glu Ile Glu Ser Val Asn Ser Ala Val Val Met Pro Ala His
                    275                 280                 285

Gly Pro Ala Lys Ser Met Glu Tyr Asp Ala Val Ala Thr Thr His Ser
            290                 295                 300

Trp Ile Pro Lys Arg Asn Arg Ser Ile Leu Asn Thr Ser Gln Arg Gly
        305                 310                 315                 320

Ile Leu Glu Asp Glu Gln Met Tyr Gln Lys Cys Cys Asn Leu Phe Glu
                        325                 330                 335

Lys Phe Phe Pro Ser Ser Ser Tyr Arg Lys Pro Val Gly Ile Ser Ser
                    340                 345                 350

Met Val Glu Ala Met Val Ser Arg Ala Arg Ile Asp Ala Arg Ile Asp
                    355                 360                 365

Phe Glu Ser Gly Arg Ile Lys Lys Asp Glu Phe Ala Glu Ile Met Lys
            370                 375                 380

Ile Cys Ser Thr Ile Glu Glu Leu Arg Arg Gln Lys
        385                 390                 395

<210> SEQ ID NO 65
<211> LENGTH: 1188
<212> TYPE: DNA
<213> ORGANISM: Equine influenza virus H3N8

<400> SEQUENCE: 65
atgaaattga gaactcaaat accagcagaa atgctcgcaa gcattgatct gaaatatttc      60
aatgattcaa caaaaagaa aattgagaag atacgaccac ttctggtcga tgggactgct     120
tcactgagtc ctggcatgat gatgggaatg ttcaacatgt tgagcactgt actaggtgta     180
tccatattaa acctgggcca gaggaaatac acaaagacca catactggtg ggatggtctg     240
caatcatccg atgattttgc tttgatagtg aatgcgccta atcatgaagg aatacaggct     300
```

-continued

```
ggagtagaca gattctatag aacttgcaaa ctggtcggga tcaacatgag caaaaagaag    360
tcctacataa atagaaccgg cacattcgaa ttcacaagct ttttctaccg gtatggtttt    420
gtcgccaatt tcagcatgga gctacccagt tttggggttt ccgggataaa tgaatctgca    480
gacatgagca ttggaatgac agttatcaaa acaacatga taaataatga tctcggtccc    540
gccacggcac aaatggcact ccaactcttc attaaggatt atcggtacac ataccggtgt    600
caaagaggcg atacccagat acaaaccaga agatcctttg agttgaagaa actgtgggaa    660
cagactcgat caaagactgg tctactggta tcagatgggg gtccaaacct atacaacatc    720
agaaacctac acatcccgga agtctgtttg aaatgggagc tgatggatga agattataaa    780
gggaggctat gtaatccatt gaatcctttc gttagccaca agaaattga atcagtgaac    840
agtgcagtag taatgcctgc gcatggccct gccaaaagca tggagtatga tgctgttgca    900
acaacacact cttggatccc caagaggaac cggtccatat tgaacacaag tcaaagggga    960
atactcgaag atgagcagat gtatcagaaa tgctgcaacc tgtttgaaaa attcttcccc   1020
agcagctcat acagaaaacc agtcggaatt tctagtatgg ttgaggccat ggtgtccagg   1080
gcccgcattg atgcacgaat tgacttcgaa tctggacgga taaagaagga tgagttcgct   1140
gagatcatga agatctgttc caccattgaa gagctcagac ggcaaaaa               1188
```

```
<210> SEQ ID NO 66
<211> LENGTH: 1241
<212> TYPE: DNA
<213> ORGANISM: Equine influenza virus H3N8
<220> FEATURE:
<221> NAME/KEY: CDS
<222> LOCATION: (8)..(1195)

<400> SEQUENCE: 66
```

```
caaaagt atg aaa ttg aga act caa ata cca gca gaa atg ctc gca agc         49
        Met Lys Leu Arg Thr Gln Ile Pro Ala Glu Met Leu Ala Ser
        1               5                   10 att gat ctg aaa tat ttc aat gat tca aca aaa aag aaa att gag aag         97
Ile Asp Leu Lys Tyr Phe Asn Asp Ser Thr Lys Lys Lys Ile Glu Lys
15                  20                  25                  30 ata cga cca ctt ctg gtc gat ggg act gct tca ctg agt cct ggc atg        145
Ile Arg Pro Leu Leu Val Asp Gly Thr Ala Ser Leu Ser Pro Gly Met
                35                  40                  45 atg atg gga atg ttc aac atg ttg agc act gta cta ggt gta tcc ata        193
Met Met Gly Met Phe Asn Met Leu Ser Thr Val Leu Gly Val Ser Ile
            50                  55                  60 tta aac ctg ggc cag agg aaa tac aca aag acc aca tac tgg tgg gat        241
Leu Asn Leu Gly Gln Arg Lys Tyr Thr Lys Thr Thr Tyr Trp Trp Asp
65                  70                  75 ggt ctg caa tca tcc gat gat ttt gct ttg ata gtg aat gcg cct aat        289
Gly Leu Gln Ser Ser Asp Asp Phe Ala Leu Ile Val Asn Ala Pro Asn
80                  85                  90 cat gaa gga ata cag gct gga gta gac aga ttc tat aga act tgc aaa        337
His Glu Gly Ile Gln Ala Gly Val Asp Arg Phe Tyr Arg Thr Cys Lys
95                  100                 105                 110 ctg gtc ggg atc aac atg agc aaa aag aag tcc tac ata aat aga acc        385
Leu Val Gly Ile Asn Met Ser Lys Lys Lys Ser Tyr Ile Asn Arg Thr
                115                 120                 125 ggc aca ttc gaa ttc aca agc ttt ttc tac cgg tat ggt ttt gtc gcc        433
Gly Thr Phe Glu Phe Thr Ser Phe Phe Tyr Arg Tyr Gly Phe Val Ala
            130                 135                 140 aat ttc agc atg gag cta ccc agt ttt ggg gtt tcc ggg ata aat gaa        481
```

```

Asn Phe Ser Met Glu Leu Pro Ser Phe Gly Val Ser Gly Ile Asn Glu
            145                 150                 155 tct gca gac atg agc att gga atg aca gtt atc aaa aac aac atg ata      529
Ser Ala Asp Met Ser Ile Gly Met Thr Val Ile Lys Asn Asn Met Ile
        160                 165                 170 aat aat gat ctc ggt ccc gcc acg gca caa atg gca ctc caa ctc ttc      577
Asn Asn Asp Leu Gly Pro Ala Thr Ala Gln Met Ala Leu Gln Leu Phe
175                 180                 185                 190 att aag gat tat cgg tac aca tac cgg tgt caa aga ggc gat acc cag      625
Ile Lys Asp Tyr Arg Tyr Thr Tyr Arg Cys Gln Arg Gly Asp Thr Gln
                195                 200                 205 ata caa acc aga aga tcc ttt gag ttg aag aaa ctg tgg gaa cag act      673
Ile Gln Thr Arg Arg Ser Phe Glu Leu Lys Lys Leu Trp Glu Gln Thr
            210                 215                 220 cga tca aag act ggt cta ctg gta tca gat ggg ggt cca aac cta tac      721
Arg Ser Lys Thr Gly Leu Leu Val Ser Asp Gly Gly Pro Asn Leu Tyr
        225                 230                 235 aac atc aga aac cta cac atc ccg gaa gtc tgt ttg aaa tgg gag ctg      769
Asn Ile Arg Asn Leu His Ile Pro Glu Val Cys Leu Lys Trp Glu Leu
240                 245                 250 atg gat gaa gat tat aaa ggg agg cta tgt aat cca ttg aat cct ttc      817
Met Asp Glu Asp Tyr Lys Gly Arg Leu Cys Asn Pro Leu Asn Pro Phe
255                 260                 265                 270 gtt agc cac aaa gaa att gaa tca gtg aac agt gca gta gta atg cct      865
Val Ser His Lys Glu Ile Glu Ser Val Asn Ser Ala Val Val Met Pro
                275                 280                 285 gcg cat ggc cct gcc aaa agc atg gag tat gat gct gtt gca aca aca      913
Ala His Gly Pro Ala Lys Ser Met Glu Tyr Asp Ala Val Ala Thr Thr
            290                 295                 300 cac tct tgg atc ccc aag agg aac cgg tcc ata ttg aac aca agt caa      961
His Ser Trp Ile Pro Lys Arg Asn Arg Ser Ile Leu Asn Thr Ser Gln
        305                 310                 315 agg gga ata ctc gaa gat gag cag atg tat cag aaa tgc tgc aac ctg     1009
Arg Gly Ile Leu Glu Asp Glu Gln Met Tyr Gln Lys Cys Cys Asn Leu
320                 325                 330 ttt gaa aaa ttc ttc ccc agc agc tca tac aga aga cca gtc gga att     1057
Phe Glu Lys Phe Phe Pro Ser Ser Ser Tyr Arg Arg Pro Val Gly Ile
335                 340                 345                 350 tct agt atg gtt gag gcc atg gtg tcc agg gcc cgc att gat gca cga     1105
Ser Ser Met Val Glu Ala Met Val Ser Arg Ala Arg Ile Asp Ala Arg
                355                 360                 365 att gac ttc gaa tct gga cgg ata aag aag gat gag ttc gct gag atc     1153
Ile Asp Phe Glu Ser Gly Arg Ile Lys Lys Asp Glu Phe Ala Glu Ile
            370                 375                 380 atg aag atc tgt tcc acc att gaa gag ctc aga cgg caa aaa               1195
Met Lys Ile Cys Ser Thr Ile Glu Glu Leu Arg Arg Gln Lys
        385                 390                 395 tagtgaattt agcttgatct tcgtgaaaaa atgccttgtt tctact                   1241

<210> SEQ ID NO 67
<211> LENGTH: 396
<212> TYPE: PRT
<213> ORGANISM: Equine influenza virus H3N8

<400> SEQUENCE: 67

Met Lys Leu Arg Thr Gln Ile Pro Ala Glu Met Leu Ala Ser Ile Asp
1               5                   10                  15

Leu Lys Tyr Phe Asn Asp Ser Thr Lys Lys Ile Glu Lys Ile Arg
            20                  25                  30
```

```
Pro Leu Leu Val Asp Gly Thr Ala Ser Leu Ser Pro Gly Met Met Met
         35                  40                  45

Gly Met Phe Asn Met Leu Ser Thr Val Leu Gly Val Ser Ile Leu Asn
     50                  55                  60

Leu Gly Gln Arg Lys Tyr Thr Lys Thr Thr Tyr Trp Trp Asp Gly Leu
 65              70                  75                      80

Gln Ser Ser Asp Asp Phe Ala Leu Ile Val Asn Ala Pro Asn His Glu
                 85                  90                  95

Gly Ile Gln Ala Gly Val Asp Arg Phe Tyr Arg Thr Cys Lys Leu Val
             100                 105                 110

Gly Ile Asn Met Ser Lys Lys Lys Ser Tyr Ile Asn Arg Thr Gly Thr
             115                 120                 125

Phe Glu Phe Thr Ser Phe Phe Tyr Arg Tyr Gly Phe Val Ala Asn Phe
        130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys Gln Arg Gly Asp Thr Gln Ile Gln
            195                 200                 205

Thr Arg Arg Ser Phe Glu Leu Lys Lys Leu Trp Glu Gln Thr Arg Ser
        210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Arg Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
370                 375                 380

Ile Cys Ser Thr Ile Glu Glu Leu Arg Arg Gln Lys
385                 390                 395

<210> SEQ ID NO 68
<211> LENGTH: 2341
<212> TYPE: DNA
<213> ORGANISM: Equine influenza virus H3N8
<220> FEATURE:
<221> NAME/KEY: misc_feature
<222> LOCATION: (489)..(489)
<223> OTHER INFORMATION: The 'Xaa' at amino acid location 489 stands for
      Thr, or Ser.
```

```
<220> FEATURE:
<221> NAME/KEY: CDS
<222> LOCATION: (25)..(2295)

<400> SEQUENCE: 68
agcaaaagca ggcaaactat ttga atg gat gtc aat ccg act cta ctc ttc         51
                          Met Asp Val Asn Pro Thr Leu Leu Phe
                           1               5 tta aag gtg cca gcg caa aat gct ata agc aca aca ttc cct tat act        99
Leu Lys Val Pro Ala Gln Asn Ala Ile Ser Thr Thr Phe Pro Tyr Thr
 10              15                  20                  25 gga gat cct ccc tac agt cat gga aca ggg aca gga tac acc atg gat       147
Gly Asp Pro Pro Tyr Ser His Gly Thr Gly Thr Gly Tyr Thr Met Asp
                 30                  35                  40 act gtc aac aga aca cat caa tac tca gaa aag ggg aaa tgg aca aca       195
Thr Val Asn Arg Thr His Gln Tyr Ser Glu Lys Gly Lys Trp Thr Thr
             45                  50                  55 aac act gag att gga gca cca caa ctt aat cca atc gat gga ccg ctt       243
Asn Thr Glu Ile Gly Ala Pro Gln Leu Asn Pro Ile Asp Gly Pro Leu
         60                  65                  70 cct gaa gac aat gaa cca agt ggg tac gcc caa aca gat tgt gta ttg       291
Pro Glu Asp Asn Glu Pro Ser Gly Tyr Ala Gln Thr Asp Cys Val Leu
     75                  80                  85 gaa gca atg gct ttc ctt gaa gaa tcc cat ccc gga atc ttt gaa aat       339
Glu Ala Met Ala Phe Leu Glu Glu Ser His Pro Gly Ile Phe Glu Asn
 90                  95                 100                 105 tcg tgt ctt gaa aca atg gag gtg gtt cag cag aca aga gtg gac aaa       387
Ser Cys Leu Glu Thr Met Glu Val Val Gln Gln Thr Arg Val Asp Lys
                110                 115                 120 cta aca caa ggc cga caa act tac gat tgg acc ttg aat agg aat caa       435
Leu Thr Gln Gly Arg Gln Thr Tyr Asp Trp Thr Leu Asn Arg Asn Gln
            125                 130                 135 cct gcc gca aca gca ctt gct aat aca att gaa gtg ttc aga tca aat       483
Pro Ala Ala Thr Ala Leu Ala Asn Thr Ile Glu Val Phe Arg Ser Asn
        140                 145                 150 gat ctg act tcc agt gag tca ggg aga tta atg gac ttc ctc aaa gat       531
Asp Leu Thr Ser Ser Glu Ser Gly Arg Leu Met Asp Phe Leu Lys Asp
155                 160                 165 gtc atg gag tcc atg aac aag gaa gaa atg gaa ata aca aca cac ttc       579
Val Met Glu Ser Met Asn Lys Glu Glu Met Glu Ile Thr Thr His Phe
170                 175                 180                 185 caa cgg aag aga aga gta aga gac aac atg aca aag aga atg gtg aca       627
Gln Arg Lys Arg Arg Val Arg Asp Asn Met Thr Lys Arg Met Val Thr
                190                 195                 200 cag aga acc ata ggg aag aaa aaa caa cga tta aac aga aag agc tat       675
Gln Arg Thr Ile Gly Lys Lys Lys Gln Arg Leu Asn Arg Lys Ser Tyr
            205                 210                 215 ctg atc agg gca tta acc tta aac aca atg acc aag gac gct gag aga       723
Leu Ile Arg Ala Leu Thr Leu Asn Thr Met Thr Lys Asp Ala Glu Arg
        220                 225                 230 ggg aaa ttg aaa cga cga gca att gca acc cca gga atg cag ata aga       771
Gly Lys Leu Lys Arg Arg Ala Ile Ala Thr Pro Gly Met Gln Ile Arg
235                 240                 245 ggg ttt gta tat ttt gtt gaa aca tta gcc cga aga ata tgt gaa aag       819
Gly Phe Val Tyr Phe Val Glu Thr Leu Ala Arg Arg Ile Cys Glu Lys
250                 255                 260                 265 ctt gaa caa tca gga ttg cca gtt ggc ggt aat gag aaa aag gcc aaa       867
Leu Glu Gln Ser Gly Leu Pro Val Gly Gly Asn Glu Lys Lys Ala Lys
                270                 275                 280 ctg gct aat gtc gtc aga aaa atg atg act aat tcc caa gac act gaa       915
```

```
Leu Ala Asn Val Val Arg Lys Met Met Thr Asn Ser Gln Asp Thr Glu
            285                 290                 295 ctc tcc ttc acc atc act ggg gac aat acc aaa tgg aat gaa aat cag      963
Leu Ser Phe Thr Ile Thr Gly Asp Asn Thr Lys Trp Asn Glu Asn Gln
            300                 305                 310 aac cca cgc atg ttc ctg gca atg atc aca tac ata act aga aac cag     1011
Asn Pro Arg Met Phe Leu Ala Met Ile Thr Tyr Ile Thr Arg Asn Gln
315                 320                 325 cca gaa tgg ttc aga aat gtt cta agc att gca ccg att atg ttc tca     1059
Pro Glu Trp Phe Arg Asn Val Leu Ser Ile Ala Pro Ile Met Phe Ser
330                 335                 340                 345 aat aaa atg gca aga ctg ggg aaa gga tat atg ttt gaa agc aaa agt     1107
Asn Lys Met Ala Arg Leu Gly Lys Gly Tyr Met Phe Glu Ser Lys Ser
            350                 355                 360 atg aaa ttg aga act caa ata cca gca gaa atg ctc gca agc att gat     1155
Met Lys Leu Arg Thr Gln Ile Pro Ala Glu Met Leu Ala Ser Ile Asp
            365                 370                 375 ctg aaa tat ttc aat gat tca aca aaa aag aaa att gag aag ata cga     1203
Leu Lys Tyr Phe Asn Asp Ser Thr Lys Lys Lys Ile Glu Lys Ile Arg
            380                 385                 390 cca ctt ctg gtc gat ggg act gct tca ctg agt cct ggc atg atg atg     1251
Pro Leu Leu Val Asp Gly Thr Ala Ser Leu Ser Pro Gly Met Met Met
395                 400                 405 gga atg ttc aac atg ttg agc act gta cta ggt gta tcc ata tta aac     1299
Gly Met Phe Asn Met Leu Ser Thr Val Leu Gly Val Ser Ile Leu Asn
410                 415                 420                 425 ctg ggc cag agg aaa tac aca aag acc aca tac tgg tgg gat ggt ctg     1347
Leu Gly Gln Arg Lys Tyr Thr Lys Thr Thr Tyr Trp Trp Asp Gly Leu
            430                 435                 440 caa tca tcc gat gat ttt gct ttg ata gtg aat gcg cct aat cat gaa     1395
Gln Ser Ser Asp Asp Phe Ala Leu Ile Val Asn Ala Pro Asn His Glu
            445                 450                 455 gga ata cag gct gga gta gac aga ttc tat aga act tgc aaa ctg gtc     1443
Gly Ile Gln Ala Gly Val Asp Arg Phe Tyr Arg Thr Cys Lys Leu Val
            460                 465                 470 ggg atc aac atg agc aaa aag aag tcc tac ata aat aga acc ggc wca     1491
Gly Ile Asn Met Ser Lys Lys Lys Ser Tyr Ile Asn Arg Thr Gly Xaa
475                 480                 485 ttc gaa ttc aca agc ttt ttc tac cgg tat ggt ttt gtc gcc aat ttc     1539
Phe Glu Phe Thr Ser Phe Phe Tyr Arg Tyr Gly Phe Val Ala Asn Phe
490                 495                 500                 505 agc atg gag cta ccc agt ttt ggg gtt tcc ggg ata aat gaa tct gca     1587
Ser Met Glu Leu Pro Ser Phe Gly Val Ser Gly Ile Asn Glu Ser Ala
            510                 515                 520 gac atg agc att gga atg aca gtt atc aaa aac aac atg ata aat aat     1635
Asp Met Ser Ile Gly Met Thr Val Ile Lys Asn Asn Met Ile Asn Asn
            525                 530                 535 gat ctc ggt ccc gcc acg gca caa atg gca ctc caa ctc ttc att aag     1683
Asp Leu Gly Pro Ala Thr Ala Gln Met Ala Leu Gln Leu Phe Ile Lys
            540                 545                 550 gat tat cgg tac aca tac cgg tgc cat aga ggc gat acc cag ata caa     1731
Asp Tyr Arg Tyr Thr Tyr Arg Cys His Arg Gly Asp Thr Gln Ile Gln
            555                 560                 565 acc aga aga tcc ttt gag ttg aag aaa ctg tgg gaa cag act cga tca     1779
Thr Arg Arg Ser Phe Glu Leu Lys Lys Leu Trp Glu Gln Thr Arg Ser
570                 575                 580                 585 aag act ggt cta ctg gta tca gat ggg ggt cca aac cta tac aac atc     1827
Lys Thr Gly Leu Leu Val Ser Asp Gly Gly Pro Asn Leu Tyr Asn Ile
            590                 595                 600
```

```
                                                            -continued aga aac cta cac atc ccg gaa gtc tgt ttg aaa tgg gag ctg atg gat      1875
Arg Asn Leu His Ile Pro Glu Val Cys Leu Lys Trp Glu Leu Met Asp
            605                 610                 615 gaa gat tat aaa ggg agg cta tgt aat cca ttg aat cct ttc gtt agc      1923
Glu Asp Tyr Lys Gly Arg Leu Cys Asn Pro Leu Asn Pro Phe Val Ser
        620                 625                 630 cac aaa gaa att gaa tca gtg aac agt gca gta gta atg cct gcg cat      1971
His Lys Glu Ile Glu Ser Val Asn Ser Ala Val Val Met Pro Ala His
    635                 640                 645 ggc cct gcc aaa agc atg gag tat gat gct gtt gca aca aca cac tct      2019
Gly Pro Ala Lys Ser Met Glu Tyr Asp Ala Val Ala Thr Thr His Ser
650                 655                 660                 665 tgg atc ccc aag agg aac cgg tcc ata ttg aac aca agt caa agg gga      2067
Trp Ile Pro Lys Arg Asn Arg Ser Ile Leu Asn Thr Ser Gln Arg Gly
                670                 675                 680 ata ctc gaa gat gag cag atg tat cag aaa tgc tgc aac ctg ttt gaa      2115
Ile Leu Glu Asp Glu Gln Met Tyr Gln Lys Cys Cys Asn Leu Phe Glu
            685                 690                 695 aaa ttc ttc ccc agc agc tca tac aga aga cca gtc gga att tct agt      2163
Lys Phe Phe Pro Ser Ser Ser Tyr Arg Arg Pro Val Gly Ile Ser Ser
        700                 705                 710 atg gtt gag gcc atg gtg tcc agg gcc cgc att gat gca cga att gac      2211
Met Val Glu Ala Met Val Ser Arg Ala Arg Ile Asp Ala Arg Ile Asp
    715                 720                 725 ttc gaa tct gga cgg ata aag aag gat gag ttc gct gag atc atg aag      2259
Phe Glu Ser Gly Arg Ile Lys Lys Asp Glu Phe Ala Glu Ile Met Lys
730                 735                 740                 745 atc tgt tcc acc att gaa gag ctc aga cgg caa aaa tagtgaattt            2305
Ile Cys Ser Thr Ile Glu Glu Leu Arg Arg Gln Lys
                750                 755 agcttgatct tcgtgaaaaa atgccttgtt tctact                               2341

<210> SEQ ID NO 69
<211> LENGTH: 757
<212> TYPE: PRT
<213> ORGANISM: Equine influenza virus H3N8
<220> FEATURE:
<221> NAME/KEY: misc_feature
<222> LOCATION: (489)..(489)
<223> OTHER INFORMATION: The 'Xaa' at location 489 stands for Thr, or
      Ser.

<400> SEQUENCE: 69

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Ile Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125
```

-continued

```
Tyr Asp Trp Thr Leu Asn Arg Asn Gln Pro Ala Ala Thr Ala Leu Ala
130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Xaa Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Met Thr
        515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
```

```
                545                 550                 555                 560
Cys His Arg Gly Asp Thr Gln Ile Gln Thr Arg Arg Ser Phe Glu Leu
                    565                 570                 575
Lys Lys Leu Trp Glu Gln Thr Arg Ser Lys Thr Gly Leu Leu Val Ser
                580                 585                 590
Asp Gly Gly Pro Asn Leu Tyr Asn Ile Arg Asn Leu His Ile Pro Glu
            595                 600                 605
Val Cys Leu Lys Trp Glu Leu Met Asp Glu Asp Tyr Lys Gly Arg Leu
        610                 615                 620
Cys Asn Pro Leu Asn Pro Phe Val Ser His Lys Glu Ile Glu Ser Val
625                 630                 635                 640
Asn Ser Ala Val Val Met Pro Ala His Gly Pro Ala Lys Ser Met Glu
                645                 650                 655
Tyr Asp Ala Val Ala Thr Thr His Ser Trp Ile Pro Lys Arg Asn Arg
                660                 665                 670
Ser Ile Leu Asn Thr Ser Gln Arg Gly Ile Leu Glu Asp Glu Gln Met
            675                 680                 685
Tyr Gln Lys Cys Cys Asn Leu Phe Glu Lys Phe Phe Pro Ser Ser Ser
        690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Asp Glu Phe Ala Glu Ile Met Lys Ile Cys Ser Thr Ile Glu Glu
            740                 745                 750
Leu Arg Arg Gln Lys
        755

<210> SEQ ID NO 70
<211> LENGTH: 2271
<212> TYPE: DNA
<213> ORGANISM: Equine influenza virus H3N8

<400> SEQUENCE: 70
atggatgtca atccgactct actcttctta aaggtgccag cgcaaaatgc tataagcaca        60
acattccctt atactggaga tcctccctac agtcatggaa cagggacagg atacaccatg       120
gatactgtca acagaacaca tcaatactca gaaaagggga atggacaac aaacactgag        180 attggagcac acaacttaa tccaatcgat ggaccgcttc ctgaagacaa tgaaccaagt        240
gggtacgccc aaacagattg tgtattggaa gcaatggctt ccttgaaga tcccatccc        300 ggaatctttg aaaattcgtg tcttgaaaca atggaggtgg ttcagcagac aagagtggac       360
aaactaacac aaggccgaca aacttacgat tggaccttga ataggaatca acctgccgca       420
acagcacttg ctaatacaat tgaagtgttc agatcaaatg atctgacttc cagtgagtca       480
gggagattaa tggacttcct caaagatgtc atggagtcca tgaacaagga agaaatggaa       540
ataacaacac acttccaacg gaagagaaga gtaagagaca catgacaaa gagaatggtg        600 acacagagaa ccatagggaa gaaaaacaa cgattaaaca gaaagagcta tctgatcagg        660
gcattaacct aaacacaat gaccaaggac gctgagagag ggaaattgaa cgacgagca        720 attgcaaccc caggaatgca gataagaggg tttgtatatt ttgttgaaac attagcccga       780
agaatatgtg aaaagcttga acaatcagga ttgccagttg gcggtaatga aaaaggcc        840 aaactggcta atgtcgtcag aaaaatgatg actaattccc aagacactga actctccttc       900
```

-continued

```
accatcactg gggacaatac caaatggaat gaaaatcaga acccacgcat gttcctggca        960
atgatcacat acataactag aaaccagcca gaatggttca gaaatgttct aagcattgca       1020
ccgattatgt tctcaaataa aatggcaaga ctggggaaag gatatatgtt tgaaagcaaa       1080
agtatgaaat tgagaactca ataccagca gaaatgctcg caagcattga tctgaaatat        1140
ttcaatgatt caacaaaaaa gaaaattgag aagatacgac cacttctggt cgatgggact       1200
gcttcactga gtcctggcat gatgatggga atgttcaaca tgttgagcac tgtactaggt       1260
gtatccatat taaacctggg ccagaggaaa tacacaaaga ccacatactg gtgggatggt       1320
ctgcaatcat ccgatgattt tgctttgata gtgaatgcgc taatcatga aggaatacag        1380 gctggagtag acagattcta tagaacttgc aaactggtcg ggatcaacat gagcaaaaag       1440
aagtcctaca taaatagaac cggcwcattc gaattcacaa gcttttttcta ccggtatggt      1500 tttgtcgcca atttcagcat ggagctaccc agttttgggg tttccgggat aaatgaatct      1560
gcagacatga gcattggaat gacagttatc aaaaacaaca tgataaataa tgatctcggt      1620
cccgccacgg cacaaatggc actccaactc ttcattaagg attatcggta cacataccgg      1680
tgccatagag gcgataccca gatacaaacc agaagatcct ttgagttgaa gaaactgtgg      1740
gaacagactc gatcaaagac tggtctactg gtatcagatg ggggtccaaa cctatacaac      1800
atcagaaacc tacacatccc ggaagtctgt ttgaaatggg agctgatgga tgaagattat      1860
aaagggaggc tatgtaatcc attgaatcct ttcgttagcc acaaagaaat tgaatcagtg      1920
aacagtgcag tagtaatgcc tgcgcatggc cctgccaaaa gcatggagta tgatgctgtt     1980
gcaacaacac actcttggat ccccaagagg aaccggtcca tattgaacac aagtcaaagg      2040
ggaatactcg aagatgagca gatgtatcag aaatgctgca acctgtttga aaaattcttc      2100
cccagcagct catacagaag accagtcgga atttctagta tggttgaggc catggtgtcc      2160
agggcccgca ttgatgcacg aattgacttc gaatctggac ggataaagaa ggatgagttc      2220
gctgagatca tgaagatctg ttccaccatt gaagagctca gacggcaaaa a              2271
```

<210> SEQ ID NO 71
<211> LENGTH: 2341
<212> TYPE: DNA
<213> ORGANISM: Equine influenza virus H3N8
<220> FEATURE:
<221> NAME/KEY: misc_feature
<222> LOCATION: (707)..(707)
<223> OTHER INFORMATION: The 'Xaa' at amino acid location 707 stands for
      Arg, or Lys.
<220> FEATURE:
<221> NAME/KEY: CDS
<222> LOCATION: (25)..(2295)

<400> SEQUENCE: 71

```
agcaaaagca ggcaaactat ttga atg gat gtc aat ccg act cta ctc ttc           51
                         Met Asp Val Asn Pro Thr Leu Leu Phe
                           1               5 tta aag gtg cca gcg caa aat gct ata agc aca aca ttc cct tat act          99
Leu Lys Val Pro Ala Gln Asn Ala Ile Ser Thr Thr Phe Pro Tyr Thr
 10              15                  20                  25 gga gat cct ccc tac agt cat gga aca ggg aca gga tac acc atg gat         147
Gly Asp Pro Pro Tyr Ser His Gly Thr Gly Thr Gly Tyr Thr Met Asp
                 30                  35                  40 act gtc aac aga aca cat caa tac tca gaa aag ggg aaa tgg aca aca         195
Thr Val Asn Arg Thr His Gln Tyr Ser Glu Lys Gly Lys Trp Thr Thr
             45                  50                  55 aac act gag att gga gca cca caa ctt aat cca atc gat gga ccg ctt         243
```

-continued

```
                Asn Thr Glu Ile Gly Ala Pro Gln Leu Asn Pro Ile Asp Gly Pro Leu
                         60                  65                  70 cct gaa gac aat gaa cca agt ggg tac gcc caa aca gat tgt gta ttg         291
Pro Glu Asp Asn Glu Pro Ser Gly Tyr Ala Gln Thr Asp Cys Val Leu
     75                  80                  85 gaa gca atg gct ttc ctt gaa gaa tcc cat ccc gga atc ttt gaa aat         339
Glu Ala Met Ala Phe Leu Glu Glu Ser His Pro Gly Ile Phe Glu Asn
 90                  95                 100                 105 tcg tgt ctt gaa aca atg gag gtg gtt cag cag aca aga gtg gac aaa         387
Ser Cys Leu Glu Thr Met Glu Val Val Gln Gln Thr Arg Val Asp Lys
                 110                 115                 120 cta aca caa ggc cga caa act tac gat tgg acc ttg aat agg aat caa         435
Leu Thr Gln Gly Arg Gln Thr Tyr Asp Trp Thr Leu Asn Arg Asn Gln
                     125                 130                 135 cct gcc gca aca gca ctt gct aat aca att gaa gtg ttc aga tca aat         483
Pro Ala Ala Thr Ala Leu Ala Asn Thr Ile Glu Val Phe Arg Ser Asn
                 140                 145                 150 gat ctg act tcc agt gag tca ggg aga tta atg gac ttc ctc aaa gat         531
Asp Leu Thr Ser Ser Glu Ser Gly Arg Leu Met Asp Phe Leu Lys Asp
             155                 160                 165 gtc atg gag tcc atg aac aag gaa gaa atg gaa ata aca aca cac ttc         579
Val Met Glu Ser Met Asn Lys Glu Glu Met Glu Ile Thr Thr His Phe
170                 175                 180                 185 caa cgg aag aga aga gta aga gac aac atg aca aag aga atg gtg aca         627
Gln Arg Lys Arg Arg Val Arg Asp Asn Met Thr Lys Arg Met Val Thr
                 190                 195                 200 cag aga acc ata ggg aag aaa aaa caa cga tta aac aga aag agc tat         675
Gln Arg Thr Ile Gly Lys Lys Lys Gln Arg Leu Asn Arg Lys Ser Tyr
                 205                 210                 215 ctg atc agg gca tta acc tta aac aca atg acc aag gac gct gag aga         723
Leu Ile Arg Ala Leu Thr Leu Asn Thr Met Thr Lys Asp Ala Glu Arg
                 220                 225                 230 ggg aaa ttg aaa cga cga gca att gca acc cca gga atg cag ata aga         771
Gly Lys Leu Lys Arg Arg Ala Ile Ala Thr Pro Gly Met Gln Ile Arg
         235                 240                 245 ggg ttt gta tat ttt gtt gaa aca tta gcc cga aga ata tgt gaa aag         819
Gly Phe Val Tyr Phe Val Glu Thr Leu Ala Arg Arg Ile Cys Glu Lys
250                 255                 260                 265 ctt gaa caa tca gga ttg cca gtt ggc ggt aat gag aaa aag gcc aaa         867
Leu Glu Gln Ser Gly Leu Pro Val Gly Gly Asn Glu Lys Lys Ala Lys
                 270                 275                 280 ctg gct aat gtc gtc aga aaa atg atg act aat tcc caa gac act gaa         915
Leu Ala Asn Val Val Arg Lys Met Met Thr Asn Ser Gln Asp Thr Glu
             285                 290                 295 ctc tcc ttc acc atc act ggg gac aat acc aaa tgg aat gaa aat cag         963
Leu Ser Phe Thr Ile Thr Gly Asp Asn Thr Lys Trp Asn Glu Asn Gln
         300                 305                 310 aac cca cgc atg ttc ctg gca atg atc aca tac ata act aga aac cag        1011
Asn Pro Arg Met Phe Leu Ala Met Ile Thr Tyr Ile Thr Arg Asn Gln
     315                 320                 325 cca gaa tgg ttc aga aat gtt cta agc att gca ccg att atg ttc tca        1059
Pro Glu Trp Phe Arg Asn Val Leu Ser Ile Ala Pro Ile Met Phe Ser
330                 335                 340                 345 aat aaa atg gca aga ctg ggg aaa gga tat atg ttt gaa agc aaa agt        1107
Asn Lys Met Ala Arg Leu Gly Lys Gly Tyr Met Phe Glu Ser Lys Ser
                 350                 355                 360 atg aaa ttg aga act caa ata cca gca gaa atg ctc gca agc att gat        1155
Met Lys Leu Arg Thr Gln Ile Pro Ala Glu Met Leu Ala Ser Ile Asp
         365                 370                 375
```

```
ctg aaa tat ttc aat gat tca aca aaa aag aaa att gag aag ata cga        1203
Leu Lys Tyr Phe Asn Asp Ser Thr Lys Lys Lys Ile Glu Lys Ile Arg
        380                 385                 390 cca ctt ctg gtc gat ggg act gct tca ctg agt cct ggc atg atg atg        1251
Pro Leu Leu Val Asp Gly Thr Ala Ser Leu Ser Pro Gly Met Met Met
    395                 400                 405 gga atg ttc aac atg ttg agc act gta cta ggt gta tcc ata tta aac        1299
Gly Met Phe Asn Met Leu Ser Thr Val Leu Gly Val Ser Ile Leu Asn
410                 415                 420                 425 ctg ggc cag agg aaa tac aca aag acc aca tac tgg tgg gat ggt ctg        1347
Leu Gly Gln Arg Lys Tyr Thr Lys Thr Thr Tyr Trp Trp Asp Gly Leu
            430                 435                 440 caa tca tcc gat gat ttt gct ttg ata gtg aat gcg cct aat cat gaa        1395
Gln Ser Ser Asp Asp Phe Ala Leu Ile Val Asn Ala Pro Asn His Glu
                445                 450                 455 gga ata cag gct gga gta gac aga ttc tat aga act tgc aaa ctg gtc        1443
Gly Ile Gln Ala Gly Val Asp Arg Phe Tyr Arg Thr Cys Lys Leu Val
        460                 465                 470 ggg atc aac atg agc aaa aag aag tcc tac ata aat aga acc ggc aca        1491
Gly Ile Asn Met Ser Lys Lys Lys Ser Tyr Ile Asn Arg Thr Gly Thr
475                 480                 485 ttc gaa ttc aca agc ttt ttc tac cgg tat ggt ttt gtc gcc aat ttc        1539
Phe Glu Phe Thr Ser Phe Phe Tyr Arg Tyr Gly Phe Val Ala Asn Phe
490                 495                 500                 505 agc atg gag cta ccc agt ttt ggg gtt tcc ggg ata aat gaa tct gca        1587
Ser Met Glu Leu Pro Ser Phe Gly Val Ser Gly Ile Asn Glu Ser Ala
            510                 515                 520 gac atg agc att gga atg aca gtt atc aaa aac aac atg ata aat aat        1635
Asp Met Ser Ile Gly Met Thr Val Ile Lys Asn Asn Met Ile Asn Asn
                525                 530                 535 gat ctc ggt ccc gcc acg gca caa atg gca ctc caa ctc ttc att aag        1683
Asp Leu Gly Pro Ala Thr Ala Gln Met Ala Leu Gln Leu Phe Ile Lys
        540                 545                 550 gat tat cgg tac aca tac cgg tgt caa aga ggc gat acc cag ata caa        1731
Asp Tyr Arg Tyr Thr Tyr Arg Cys Gln Arg Gly Asp Thr Gln Ile Gln
555                 560                 565 acc aga aga tcc ttt gag ttg aag aaa ctg tgg gaa cag act cga tca        1779
Thr Arg Arg Ser Phe Glu Leu Lys Lys Leu Trp Glu Gln Thr Arg Ser
570                 575                 580                 585 aag act ggt cta ctg gta tca gat ggg ggt cca aac cta tac aac atc        1827
Lys Thr Gly Leu Leu Val Ser Asp Gly Gly Pro Asn Leu Tyr Asn Ile
            590                 595                 600 aga aac cta cac atc ccg gaa gtc tgt ttg aaa tgg gag ctg atg gat        1875
Arg Asn Leu His Ile Pro Glu Val Cys Leu Lys Trp Glu Leu Met Asp
                605                 610                 615 gaa gat tat aaa ggg agg cta tgt aat cca ttg aat cct ttc gtt agc        1923
Glu Asp Tyr Lys Gly Arg Leu Cys Asn Pro Leu Asn Pro Phe Val Ser
        620                 625                 630 cac aaa gaa att gaa tca gtg aac agt gca gta gta atg cct gcg cat        1971
His Lys Glu Ile Glu Ser Val Asn Ser Ala Val Val Met Pro Ala His
635                 640                 645 ggc cct gcc aaa agc atg gag tat gat gct gtt gca aca aca cac tct        2019
Gly Pro Ala Lys Ser Met Glu Tyr Asp Ala Val Ala Thr Thr His Ser
650                 655                 660                 665 tgg atc ccc aag agg aac cgg tcc ata ttg aac aca agt caa agg gga        2067
Trp Ile Pro Lys Arg Asn Arg Ser Ile Leu Asn Thr Ser Gln Arg Gly
            670                 675                 680 ata ctc gaa gat gag cag atg tat cag aaa tgc tgc aac ctg ttt gaa        2115
Ile Leu Glu Asp Glu Gln Met Tyr Gln Lys Cys Cys Asn Leu Phe Glu
                685                 690                 695
```

-continued

```
aaa ttc ttc ccc agc agc tca tac aga ara cca gtc gga att tct agt      2163
Lys Phe Phe Pro Ser Ser Ser Tyr Arg Xaa Pro Val Gly Ile Ser Ser
        700                 705                 710 atg gtt gag gcc atg gtg tcc agg gcc cgc att gat gca cga att gac      2211
Met Val Glu Ala Met Val Ser Arg Ala Arg Ile Asp Ala Arg Ile Asp
715                 720                 725 ttc gaa tct gga cgg ata aag aag gat gag ttc gct gag atc atg aag      2259
Phe Glu Ser Gly Arg Ile Lys Lys Asp Glu Phe Ala Glu Ile Met Lys
        730                 735                 740                 745 atc tgt tcc acc att gaa gag ctc aga cgg caa aaa tagtgaattt           2305
Ile Cys Ser Thr Ile Glu Glu Leu Arg Arg Gln Lys
                750                 755 agcttgatct tcgtgaaaaa atgccttgtt tctact                              2341
```

<210> SEQ ID NO 72
<211> LENGTH: 757
<212> TYPE: PRT
<213> ORGANISM: Equine influenza virus H3N8
<220> FEATURE:
<221> NAME/KEY: misc_feature
<222> LOCATION: (707)..(707)
<223> OTHER INFORMATION: The 'Xaa' at location 707 stands for Arg, or
      Lys.

<400> SEQUENCE: 72

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255
```

```
Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Met Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys Gln Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670
```

-continued

```
Ser Ile Leu Asn Thr Ser Gln Arg Gly Ile Leu Glu Asp Glu Gln Met
        675                 680                 685
Tyr Gln Lys Cys Cys Asn Leu Phe Glu Lys Phe Phe Pro Ser Ser Ser
    690                 695                 700
Tyr Arg Xaa Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Asp Glu Phe Ala Glu Ile Met Lys Ile Cys Ser Thr Ile Glu Glu
            740                 745                 750
Leu Arg Arg Gln Lys
        755
```

<210> SEQ ID NO 73
<211> LENGTH: 2271
<212> TYPE: DNA
<213> ORGANISM: Equine influenza virus H3N8

<400> SEQUENCE: 73

| | | | | | |
|---|---|---|---|---|---|
| atggatgtca | atccgactct | actcttctta | aaggtgccag | cgcaaaatgc | tataagcaca | 60 |
| acattccctt | atactggaga | tcctccctac | agtcatggaa | cagggacagg | atacaccatg | 120 |
| gatactgtca | acagaacaca | tcaatactca | gaaaagggga | atggacaac | aaacactgag | 180 |
| attggagcac | acaacttaa | tccaatcgat | ggaccgcttc | ctgaagacaa | tgaaccaagt | 240 |
| gggtacgccc | aaacagattg | tgtattgaa | gcaatggctt | tccttgaaga | atcccatccc | 300 |
| ggaatctttg | aaaattcgtg | tcttgaaaca | atggaggtgg | ttcagcagac | aagagtggac | 360 |
| aaactaacac | aaggccgaca | aacttacgat | tggaccttga | ataggaatca | acctgccgca | 420 |
| acagcacttg | ctaatacaat | tgaagtgttc | agatcaaatg | atctgacttc | cagtgagtca | 480 |
| gggagattaa | tggacttcct | caaagatgtc | atggagtcca | tgaacaagga | agaaatggaa | 540 |
| ataacaacac | acttccaacg | gaagagaaga | gtaagagaca | catgacaaa | gagaatggtg | 600 |
| acacagagaa | ccatagggaa | gaaaaaacaa | cgattaaaca | gaaagagcta | tctgatcagg | 660 |
| gcattaacct | taaacacaat | gaccaaggac | gctgagagag | ggaaattgaa | cgacgagca | 720 |
| attgcaaccc | caggaatgca | gataagaggg | tttgtatatt | ttgttgaaac | attagcccga | 780 |
| agaatatgtg | aaaagcttga | acaatcagga | ttgccagttg | gcggtaatga | aaaaaggcc | 840 |
| aaactggcta | atgtcgtcag | aaaaatgatg | actaattccc | aagacactga | actctccttc | 900 |
| accatcactg | gggacaatac | caaatggaat | gaaaatcaga | acccacgcat | gttcctggca | 960 |
| atgatcacat | acataactag | aaaccagcca | gaatggttca | gaaatgttct | aagcattgca | 1020 |
| ccgattatgt | tctcaaataa | aatggcaaga | ctggggaaag | gatatatgtt | tgaaagcaaa | 1080 |
| agtatgaaat | tgagaactca | ataccagcag | gaaatgctcg | caagcattga | tctgaaatat | 1140 |
| ttcaatgatt | caacaaaaaa | gaaaattgag | aagatacgac | cacttctggt | cgatgggact | 1200 |
| gcttcactga | gtcctggcat | gatgatggga | atgttcaaca | tgttgagcac | tgtactaggt | 1260 |
| gtatccatat | taaacctggg | ccagaggaaa | tacacaaaga | ccacatactg | gtgggatggt | 1320 |
| ctgcaatcat | ccgatgattt | tgctttgata | gtgaatgcgc | taatcatga | aggaatacag | 1380 |
| gctggagtag | acagattcta | tagaacttgc | aaactggtcg | ggatcaacat | gagcaaaaag | 1440 |
| aagtcctaca | taaatagaac | cggcacattc | gaattcacaa | gctttttcta | ccgtatggt | 1500 |
| tttgtcgcca | atttcagcat | ggagctaccc | agttttgggg | tttccgggat | aaatgaatct | 1560 |
| gcagacatga | gcattggaat | gacagttatc | aaaaacaaca | tgataaataa | tgatctcggt | 1620 |

-continued

```
cccgccacgg cacaaatggc actccaactc ttcattaagg attatcggta cacataccgg    1680
tgtcaaagag gcgataccca gatacaaacc agaagatcct ttgagttgaa gaaactgtgg    1740
gaacagactc gatcaaagac tggtctactg gtatcagatg ggggtccaaa cctatacaac    1800
atcagaaacc tacacatccc ggaagtctgt ttgaaatggg agctgatgga tgaagattat    1860
aaagggaggc tatgtaatcc attgaatcct ttcgttagcc acaaagaaat tgaatcagtg    1920
aacagtgcag tagtaatgcc tgcgcatggc cctgccaaaa gcatggagta tgatgctgtt    1980
gcaacaacac actcttggat ccccaagagg aaccggtcca tattgaacac aagtcaaagg    2040
ggaatactcg aagatgagca gatgtatcag aaatgctgca acctgtttga aaaattcttc    2100
cccagcagct catacagaar accagtcgga atttctagta tggttgaggc catggtgtcc    2160
agggcccgca ttgatgcacg aattgacttc gaatctggac ggataaagaa ggatgagttc    2220
gctgagatca tgaagatctg ttccaccatt gaagagctca gacggcaaaa a            2271
```

<210> SEQ ID NO 74
<211> LENGTH: 25
<212> TYPE: DNA
<213> ORGANISM: Artificial
<220> FEATURE:
<223> OTHER INFORMATION: Synthetic Primer

<400> SEQUENCE: 74

```
ggggcgggta cccaaactat ctcca                                           25
```

<210> SEQ ID NO 75
<211> LENGTH: 27
<212> TYPE: DNA
<213> ORGANISM: Artificial
<220> FEATURE:
<223> OTHER INFORMATION: Synthetic Primer

<400> SEQUENCE: 75

```
gggggctcga gtactttttt ggacagt                                         27
```

<210> SEQ ID NO 76
<211> LENGTH: 1228
<212> TYPE: DNA
<213> ORGANISM: Equine influenza virus H3N8
<220> FEATURE:
<221> NAME/KEY: CDS
<222> LOCATION: (3)..(1166)

<400> SEQUENCE: 76

```
gg ggc ggg tac cca aac tat ctc caa gct tgg aag caa gta tta gca      47
   Gly Gly Tyr Pro Asn Tyr Leu Gln Ala Trp Lys Gln Val Leu Ala
   1               5                  10                  15 gaa cta caa gac ctt gag aac gaa gaa aag acc cct aag acc aag aat    95
Glu Leu Gln Asp Leu Glu Asn Glu Glu Lys Thr Pro Lys Thr Lys Asn
                20                  25                  30 atg aaa aaa aca agc caa ttg aaa tgg gca ctc ggt gaa aat atg gca  143
Met Lys Lys Thr Ser Gln Leu Lys Trp Ala Leu Gly Glu Asn Met Ala
            35                  40                  45 cca gag aaa gtg gat ttt gag gat tgt aaa gac atc aat gat ttg aaa  191
Pro Glu Lys Val Asp Phe Glu Asp Cys Lys Asp Ile Asn Asp Leu Lys
        50                  55                  60 cag tat gac agt gat gag cca gaa aca agg tct ctt gca agt tgg att  239
Gln Tyr Asp Ser Asp Glu Pro Glu Thr Arg Ser Leu Ala Ser Trp Ile
    65                  70                  75 caa agt gag ttc aac aaa gct tgt gag ctg aca gat tca agc tgg ata  287
Gln Ser Glu Phe Asn Lys Ala Cys Glu Leu Thr Asp Ser Ser Trp Ile
```

-continued

| | | | | | | | | | | | | | | |
|---|---|---|---|---|---|---|---|---|---|---|---|---|---|---|
| Gln | Ser | Glu | Phe | Asn | Lys | Ala | Cys | Glu | Leu | Thr | Asp | Ser | Ser | Trp | Ile |
| 80 | | | | | 85 | | | | | 90 | | | | | 95 |

```
gag ctc gat gaa att ggg gag gat att gcc cca ata gaa tac att gcg      335
Glu Leu Asp Glu Ile Gly Glu Asp Ile Ala Pro Ile Glu Tyr Ile Ala
            100                 105                 110 agc atg agg aga aat tat ttt act gct gag gtt tcc cat tgt aga gca      383
Ser Met Arg Arg Asn Tyr Phe Thr Ala Glu Val Ser His Cys Arg Ala
                115                 120                 125 aca gaa tat ata atg aag gga gtg tac atc aac act gct cta ctc aat      431
Thr Glu Tyr Ile Met Lys Gly Val Tyr Ile Asn Thr Ala Leu Leu Asn
        130                 135                 140 gca tcc tgt gct gcg atg gat gaa ttc caa tta att ccg atg ata agc      479
Ala Ser Cys Ala Ala Met Asp Glu Phe Gln Leu Ile Pro Met Ile Ser
145                 150                 155 aaa tgc agg acc aaa gaa ggg aga agg aag aca aat tta tat gga ttc      527
Lys Cys Arg Thr Lys Glu Gly Arg Arg Lys Thr Asn Leu Tyr Gly Phe
160                 165                 170                 175 ata ata aag gga agg tcc cat tta agg aat gat acc gac gtg gta aac      575
Ile Ile Lys Gly Arg Ser His Leu Arg Asn Asp Thr Asp Val Val Asn
            180                 185                 190 ttt gta agt atg gaa ttt tct ctc act gat cca aga ttt gag cca cat      623
Phe Val Ser Met Glu Phe Ser Leu Thr Asp Pro Arg Phe Glu Pro His
                195                 200                 205 aaa tgg gaa aaa tac tgc gtt cta gaa att gga gac atg ctc cta agg      671
Lys Trp Glu Lys Tyr Cys Val Leu Glu Ile Gly Asp Met Leu Leu Arg
        210                 215                 220 act gct gta ggt caa gtg tca aga ccc atg ttt ttg tat gta agg aca      719
Thr Ala Val Gly Gln Val Ser Arg Pro Met Phe Leu Tyr Val Arg Thr
225                 230                 235 aat gga acc tct aaa att aaa atg aaa cgg gga atg gaa atg aga cgc      767
Asn Gly Thr Ser Lys Ile Lys Met Lys Arg Gly Met Glu Met Arg Arg
240                 245                 250                 255 tgc ctc ctt cag tct ctg caa cag att gaa agc atg atc gaa gct gag      815
Cys Leu Leu Gln Ser Leu Gln Gln Ile Glu Ser Met Ile Glu Ala Glu
            260                 265                 270 tcc tca gtc aaa gaa aag gac atg acc aaa gaa ttc ttt gag aac aaa      863
Ser Ser Val Lys Glu Lys Asp Met Thr Lys Glu Phe Phe Glu Asn Lys
                275                 280                 285 tca gag aca tgg cct ata gga gag tcc ccc aaa gga gtg gaa gag ggc      911
Ser Glu Thr Trp Pro Ile Gly Glu Ser Pro Lys Gly Val Glu Glu Gly
        290                 295                 300 tca atc ggg aag gtt tgc agg acc tta tta gca aaa tct gtg ttt aac      959
Ser Ile Gly Lys Val Cys Arg Thr Leu Leu Ala Lys Ser Val Phe Asn
305                 310                 315 agt ttg tat gca tct cca caa ctg gaa ggg ttt tca gct gaa tct agg     1007
Ser Leu Tyr Ala Ser Pro Gln Leu Glu Gly Phe Ser Ala Glu Ser Arg
320                 325                 330                 335 aaa tta ctt ctc att gtt cag gcc ctt agg gat aac ctg gaa cct gga     1055
Lys Leu Leu Leu Ile Val Gln Ala Leu Arg Asp Asn Leu Glu Pro Gly
            340                 345                 350 acc ttt gat att ggg ggg tta tat gaa tca att gag gag tgc ctg att     1103
Thr Phe Asp Ile Gly Gly Leu Tyr Glu Ser Ile Glu Glu Cys Leu Ile
                355                 360                 365 aat gat ccc tgg gtt ttg ctc aat gca tct tgg ttc aac tcc ttc ctt     1151
Asn Asp Pro Trp Val Leu Leu Asn Ala Ser Trp Phe Asn Ser Phe Leu
        370                 375                 380 aca cat gca ctg aag tagttgtagc aatgctacta tttgctatcc atactgtcca    1206
Thr His Ala Leu Lys
            385
```
aaaaagtact cgagccccca ag                                              1228

<210> SEQ ID NO 77
<211> LENGTH: 388
<212> TYPE: PRT
<213> ORGANISM: Equine influenza virus H3N8

<400> SEQUENCE: 77

Gly Gly Tyr Pro Asn Tyr Leu Gln Ala Trp Lys Gln Val Leu Ala Glu
1               5                   10                  15

Leu Gln Asp Leu Glu Asn Glu Glu Lys Thr Pro Lys Thr Lys Asn Met
            20                  25                  30

Lys Lys Thr Ser Gln Leu Lys Trp Ala Leu Gly Glu Asn Met Ala Pro
        35                  40                  45

Glu Lys Val Asp Phe Glu Asp Cys Lys Asp Ile Asn Asp Leu Lys Gln
    50                  55                  60

Tyr Asp Ser Asp Glu Pro Glu Thr Arg Ser Leu Ala Ser Trp Ile Gln
65                  70                  75                  80

Ser Glu Phe Asn Lys Ala Cys Glu Leu Thr Asp Ser Ser Trp Ile Glu
                85                  90                  95

Leu Asp Glu Ile Gly Glu Asp Ile Ala Pro Ile Glu Tyr Ile Ala Ser
            100                 105                 110

Met Arg Arg Asn Tyr Phe Thr Ala Glu Val Ser His Cys Arg Ala Thr
        115                 120                 125

Glu Tyr Ile Met Lys Gly Val Tyr Ile Asn Thr Ala Leu Leu Asn Ala
    130                 135                 140

Ser Cys Ala Ala Met Asp Glu Phe Gln Leu Ile Pro Met Ile Ser Lys
145                 150                 155                 160

Cys Arg Thr Lys Glu Gly Arg Arg Lys Thr Asn Leu Tyr Gly Phe Ile
                165                 170                 175

Ile Lys Gly Arg Ser His Leu Arg Asn Asp Thr Asp Val Val Asn Phe
            180                 185                 190

Val Ser Met Glu Phe Ser Leu Thr Asp Pro Arg Phe Glu Pro His Lys
        195                 200                 205

Trp Glu Lys Tyr Cys Val Leu Glu Ile Gly Asp Met Leu Leu Arg Thr
    210                 215                 220

Ala Val Gly Gln Val Ser Arg Pro Met Phe Leu Tyr Val Arg Thr Asn
225                 230                 235                 240

Gly Thr Ser Lys Ile Lys Met Lys Arg Gly Met Glu Met Arg Arg Cys
                245                 250                 255

Leu Leu Gln Ser Leu Gln Gln Ile Glu Ser Met Ile Glu Ala Glu Ser
            260                 265                 270

Ser Val Lys Glu Lys Asp Met Thr Lys Glu Phe Phe Glu Asn Lys Ser
        275                 280                 285

Glu Thr Trp Pro Ile Gly Glu Ser Pro Lys Gly Val Glu Glu Gly Ser
    290                 295                 300

Ile Gly Lys Val Cys Arg Thr Leu Leu Ala Lys Ser Val Phe Asn Ser
305                 310                 315                 320

Leu Tyr Ala Ser Pro Gln Leu Glu Gly Phe Ser Ala Glu Ser Arg Lys
                325                 330                 335

Leu Leu Leu Ile Val Gln Ala Leu Arg Asp Asn Leu Glu Pro Gly Thr
            340                 345                 350

Phe Asp Ile Gly Gly Leu Tyr Glu Ser Ile Glu Glu Cys Leu Ile Asn
        355                 360                 365

```
Asp Pro Trp Val Leu Leu Asn Ala Ser Trp Phe Asn Ser Phe Leu Thr
        370                 375                 380

His Ala Leu Lys
385

<210> SEQ ID NO 78
<211> LENGTH: 18
<212> TYPE: DNA
<213> ORGANISM: Artificial
<220> FEATURE:
<223> OTHER INFORMATION: Synthetic Primer

<400> SEQUENCE: 78
gcaaatgcag gaccaaag                                                    18

<210> SEQ ID NO 79
<211> LENGTH: 18
<212> TYPE: DNA
<213> ORGANISM: Artificial
<220> FEATURE:
<223> OTHER INFORMATION: Synthetic Primer

<400> SEQUENCE: 79
gactgaggac tcagcttc                                                    18

<210> SEQ ID NO 80
<211> LENGTH: 19
<212> TYPE: DNA
<213> ORGANISM: Artificial
<220> FEATURE:
<223> OTHER INFORMATION: Synthetic Primer

<400> SEQUENCE: 80
caatatcctc cccaatttc                                                   19

<210> SEQ ID NO 81
<211> LENGTH: 19
<212> TYPE: DNA
<213> ORGANISM: Artificial
<220> FEATURE:
<223> OTHER INFORMATION: Synthetic Primer

<400> SEQUENCE: 81
ggaaggtttg caggacctt                                                   19

<210> SEQ ID NO 82
<211> LENGTH: 1164
<212> TYPE: DNA
<213> ORGANISM: Equine influenza virus H3N8

<400> SEQUENCE: 82
ggcgggtacc caaactatct ccaagcttgg aagcaagtat tagcagaact acaagacctt      60
gagaacgaag aaaagacccc taagaccaag aatatgaaaa aaacaagcca attgaaatgg     120
gcactcggtg aaaatatggc accagagaaa gtggattttg aggattgtaa agacatcaat     180
gatttgaaac agtatgacag tgatgagcca gaaacaaggt ctcttgcaag ttggattcaa     240
agtgagttca acaaagcttg tgagctgaca gattcaagct ggatagagct cgatgaaatt     300
ggggaggata ttgccccaat agaatacatt gcgagcatga ggagaaatta ttttactgct     360
gaggtttccc attgtagagc aacagaatat ataatgaagg gagtgtacat caacactgct     420
ctactcaatg catcctgtgc tgcgatggat gaattccaat taattccgat gataagcaaa     480
tgcaggacca agaagggag aaggaagaca aatttatatg gattcataat aaagggaagg     540
```

-continued

```
tcccatttaa ggaatgatac cgacgtggta aactttgtaa gtatggaatt ttctctcact      600
gatccaagat ttgagccaca taaatgggaa aaatactgcg ttctagaaat tggagacatg      660
ctcctaagga ctgctgtagg tcaagtgtca agacccatgt ttttgtatgt aaggacaaat      720
ggaacctcta aaattaaaat gaaacgggga atggaaatga cgcctgcct ccttcagtct       780 ctgcaacaga ttgaaagcat gatcgaagct gagtcctcag tcaaagaaaa ggacatgacc      840
aaagaattct ttgagaacaa atcagagaca tggcctatag agagtcccc caaggagtg       900 gaagagggct caatcgggaa ggtttgcagg accttattag caaaatctgt gtttaacagt     960
ttgtatgcat ctccacaact ggaagggttt tcagctgaat ctaggaaatt acttctcatt    1020
gttcaggccc ttagggataa cctggaacct ggaacctttg atattggggg gttatatgaa    1080
tcaattgagg agtgcctgat taatgatccc tgggttttgc tcaatgcatc ttggttcaac    1140
tccttcctta cacatgcact gaag                                          1164
```

<210> SEQ ID NO 83
<211> LENGTH: 1223
<212> TYPE: DNA
<213> ORGANISM: Equine influenza virus H3N8

<400> SEQUENCE: 83

```
ggggcgggta cccaaactat ctccaagctt ggaagcaagt attagcagaa ctacaagacc      60
ttgagaacga agaaaagacc cctaagacca agaatatgaa aaaacaagc caattgaaat      120 gggcactcgg tgaaaatatg gcaccagaga agtggatttt tgaggattgt aaagacatca     180
atgatttgaa acagtatgac agtgatgagc cagaaacaag gtctcttgca agttggattc     240
aaagtgagtt caacaaagct tgtgagctga cagattcaag ctggatagag ctcgatgaaa    300
ttggggagga tattgcccca atagaataca ttgcgagcat gaggagaaat tattttactg     360
ctgaggtttc ccattgtaga gcaacagaat atataatgaa gggagtgtac atcaacactg    420
ctctactcaa tgcatcctgt gctgcgatgg atgaattcca attaattccg atgataagca    480
aatgcaggac caaagaaggg agaaggaaga caaatttata tggattcata taaagggaa     540 ggtcccattt aaggaatgat accgacgtgg taaactttgt aagtatggaa ttttctctca    600
ctgatccaag atttgagcca cataaatggg aaaaatactg cgttctagaa attggagaca    660
tgctcctaag gactgctgta ggtcaagtgt caagacccat gttttgtat gtaaggacaa     720 atggaacctc taaattaaaa tgaaatggg aatggaaat gagacgctgc ctccttcagt     780
ctctgcaaca gattgaaagc atgatcgaag ctgagtcctc agtcaaagaa aaggacatga    840
ccaaagaatt ctttgagaac aaatcagaga catggcctat aggagagtcc cccaaaggag    900
tggaagaggg ctcaatcggg aaggtttgca ggaccttatt agcaaaatct gtgtttaaca    960
gtttgtatgc atctccacaa ctggaagggt tttcagctga atctaggaaa ttacttctca   1020
ttgttcaggc ccttagggat aacctggaac ctggaacctt gatattggg gggttatatg    1080 aatcaattga ggagtgcctg attaatgatc cctgggtttt gctcaatgca tcttggttca    1140
actccttcct tacacatgca ctgaagtagt tgtagcaatg ctactatttg ctatccatac    1200
tgtccaaaaa agtactcgag ccc                                           1223
```

<210> SEQ ID NO 84
<211> LENGTH: 1233
<212> TYPE: DNA
<213> ORGANISM: Equine influenza virus H3N8
<220> FEATURE:

<221> NAME/KEY: CDS
<222> LOCATION: (3)..(1172)

<400> SEQUENCE: 84

| | | |
|---|---|---|
| at gaa aag ggt ata aac cca aac tat ctc caa gct tgg aag caa gta<br>   Glu Lys Gly Ile Asn Pro Asn Tyr Leu Gln Ala Trp Lys Gln Val<br>    1              5                   10              15 | 47 |
| tta gca gaa cta caa gac ctt gag aac gaa gaa aag acc cct aag acc<br>Leu Ala Glu Leu Gln Asp Leu Glu Asn Glu Glu Lys Thr Pro Lys Thr<br>                   20                   25                  30 | 95 |
| aag aat atg aaa aaa aca agc caa ttg aaa tgg gca ctc ggt gaa aat<br>Lys Asn Met Lys Lys Thr Ser Gln Leu Lys Trp Ala Leu Gly Glu Asn<br>           35                   40                 45 | 143 |
| atg gca cca gag aaa gtg gat ttt gag gat tgt aaa gac atc aat gat<br>Met Ala Pro Glu Lys Val Asp Phe Glu Asp Cys Lys Asp Ile Asn Asp<br>          50                   55                  60 | 191 |
| ttg aaa cag tat gac agt gat gag cca gaa aca agg tct ctt gca agt<br>Leu Lys Gln Tyr Asp Ser Asp Glu Pro Glu Thr Arg Ser Leu Ala Ser<br> 65                  70                  75 | 239 |
| tgg att caa agt gag ttc aac aaa gct tgt gag ctg aca gat tca agc<br>Trp Ile Gln Ser Glu Phe Asn Lys Ala Cys Glu Leu Thr Asp Ser Ser<br>80                  85                   90                  95 | 287 |
| tgg ata gag ctc gat gaa att ggg gag gat att gcc cca ata gaa tac<br>Trp Ile Glu Leu Asp Glu Ile Gly Glu Asp Ile Ala Pro Ile Glu Tyr<br>                 100                105              110 | 335 |
| att gcg agc atg agg aga aat tat ttt act gct gag gtt tcc cat tgt<br>Ile Ala Ser Met Arg Arg Asn Tyr Phe Thr Ala Glu Val Ser His Cys<br>              115                120              125 | 383 |
| aga gca aca gaa tat ata atg aag gga gtg tac atc aac act gct cta<br>Arg Ala Thr Glu Tyr Ile Met Lys Gly Val Tyr Ile Asn Thr Ala Leu<br>        130                135              140 | 431 |
| ctc aat gca tcc tgt gct gcg atg gat gaa ttc caa tta att ccg atg<br>Leu Asn Ala Ser Cys Ala Ala Met Asp Glu Phe Gln Leu Ile Pro Met<br>145                150                155 | 479 |
| ata agc aaa tgc agg acc aaa gaa ggg aga agg aag aca aat tta tat<br>Ile Ser Lys Cys Arg Thr Lys Glu Gly Arg Arg Lys Thr Asn Leu Tyr<br>160                 165                170              175 | 527 |
| gga ttc ata ata aag gga agg tcc cat tta agg aat gat acc gac gtg<br>Gly Phe Ile Ile Lys Gly Arg Ser His Leu Arg Asn Asp Thr Asp Val<br>              180                185              190 | 575 |
| gta aac ttt gta agt atg gaa ttt tct ctc act gat cca aga ttt gag<br>Val Asn Phe Val Ser Met Glu Phe Ser Leu Thr Asp Pro Arg Phe Glu<br>            195                200              205 | 623 |
| cca cat aaa tgg gaa aaa tac tgc gtt cta gaa att gga gac atg ctc<br>Pro His Lys Trp Glu Lys Tyr Cys Val Leu Glu Ile Gly Asp Met Leu<br>        210                215              220 | 671 |
| cta agg act gct gta ggt caa gtg tca aga ccc atg ttt ttg tat gta<br>Leu Arg Thr Ala Val Gly Gln Val Ser Arg Pro Met Phe Leu Tyr Val<br>225                230                235 | 719 |
| agg aca aat gga acc tct aaa att aaa atg aaa tgg gga atg gaa atg<br>Arg Thr Asn Gly Thr Ser Lys Ile Lys Met Lys Trp Gly Met Glu Met<br>240                 245                250              255 | 767 |
| aga cgc tgc ctc ctt cag tct ctg caa cag att gaa agc atg atc gaa<br>Arg Arg Cys Leu Leu Gln Ser Leu Gln Gln Ile Glu Ser Met Ile Glu<br>            260                265              270 | 815 |
| gct gag tcc tca gtc aaa gaa aag gac atg acc aaa gaa ttc ttt gag<br>Ala Glu Ser Ser Val Lys Glu Lys Asp Met Thr Lys Glu Phe Phe Glu<br>        275                280              285 | 863 |
| aac aaa tca gag aca tgg cct ata gga gag tcc ccc aaa gga gtg gaa<br>Asn Lys Ser Glu Thr Trp Pro Ile Gly Glu Ser Pro Lys Gly Val Glu | 911 |

-continued

```
                       290                 295                 300
gag ggc tca atc ggg aag gtt tgc agg acc tta tta gca aaa tct gtg      959
Glu Gly Ser Ile Gly Lys Val Cys Arg Thr Leu Leu Ala Lys Ser Val
305                 310                 315 ttt aac agt ttg tat gca tct cca caa ctg gaa ggg ttt tca gct gaa     1007
Phe Asn Ser Leu Tyr Ala Ser Pro Gln Leu Glu Gly Phe Ser Ala Glu
320                 325                 330                 335 tct agg aaa tta ctt ctc att gtt cag gcc ctt agg gat aac ctg gaa     1055
Ser Arg Lys Leu Leu Leu Ile Val Gln Ala Leu Arg Asp Asn Leu Glu
                340                 345                 350 cct gga acc ttt gat att ggg ggg tta tat gaa tca att gag gag tgc     1103
Pro Gly Thr Phe Asp Ile Gly Gly Leu Tyr Glu Ser Ile Glu Glu Cys
            355                 360                 365 ctg att aat gat ccc tgg gtt ttg ctc aat gca tct tgg ttc aac tcc     1151
Leu Ile Asn Asp Pro Trp Val Leu Leu Asn Ala Ser Trp Phe Asn Ser
        370                 375                 380 ttc ctt aca cat gca ctg aag tagttgtagc aatgctacta tttgctatcc        1202
Phe Leu Thr His Ala Leu Lys
    385                 390 atactgtcca aaaagtacc ttgtttctac t                                   1233
```

<210> SEQ ID NO 85
<211> LENGTH: 390
<212> TYPE: PRT
<213> ORGANISM: Equine influenza virus H3N8

<400> SEQUENCE: 85

```
Glu Lys Gly Ile Asn Pro Asn Tyr Leu Gln Ala Trp Lys Gln Val Leu
1               5                   10                  15

Ala Glu Leu Gln Asp Leu Glu Asn Glu Lys Thr Pro Lys Thr Lys
            20                  25                  30

Asn Met Lys Lys Thr Ser Gln Leu Lys Trp Ala Leu Gly Glu Asn Met
        35                  40                  45

Ala Pro Glu Lys Val Asp Phe Glu Asp Cys Lys Asp Ile Asn Asp Leu
    50                  55                  60

Lys Gln Tyr Asp Ser Asp Glu Pro Glu Thr Arg Ser Leu Ala Ser Trp
65                  70                  75                  80

Ile Gln Ser Glu Phe Asn Lys Ala Cys Glu Leu Thr Asp Ser Ser Trp
                85                  90                  95

Ile Glu Leu Asp Glu Ile Gly Glu Asp Ile Ala Pro Ile Glu Tyr Ile
            100                 105                 110

Ala Ser Met Arg Arg Asn Tyr Phe Thr Ala Glu Val Ser His Cys Arg
        115                 120                 125

Ala Thr Glu Tyr Ile Met Lys Gly Val Tyr Ile Asn Thr Ala Leu Leu
    130                 135                 140

Asn Ala Ser Cys Ala Ala Met Asp Glu Phe Gln Leu Ile Pro Met Ile
145                 150                 155                 160

Ser Lys Cys Arg Thr Lys Glu Gly Arg Arg Lys Thr Asn Leu Tyr Gly
                165                 170                 175

Phe Ile Ile Lys Gly Arg Ser His Leu Arg Asn Asp Thr Asp Val Val
            180                 185                 190

Asn Phe Val Ser Met Glu Phe Ser Leu Thr Asp Pro Arg Phe Glu Pro
        195                 200                 205

His Lys Trp Glu Lys Tyr Cys Val Leu Glu Ile Gly Asp Met Leu Leu
    210                 215                 220

Arg Thr Ala Val Gly Gln Val Ser Arg Pro Met Phe Leu Tyr Val Arg
```

```
            225                 230                 235                 240
Thr Asn Gly Thr Ser Lys Ile Lys Met Lys Trp Gly Met Glu Met Arg
                245                 250                 255
Arg Cys Leu Leu Gln Ser Leu Gln Gln Ile Glu Ser Met Ile Glu Ala
            260                 265                 270
Glu Ser Ser Val Lys Glu Lys Asp Met Thr Lys Glu Phe Phe Glu Asn
        275                 280                 285
Lys Ser Glu Thr Trp Pro Ile Gly Glu Ser Pro Lys Gly Val Glu Glu
    290                 295                 300
Gly Ser Ile Gly Lys Val Cys Arg Thr Leu Leu Ala Lys Ser Val Phe
305                 310                 315                 320
Asn Ser Leu Tyr Ala Ser Pro Gln Leu Glu Gly Phe Ser Ala Glu Ser
                325                 330                 335
Arg Lys Leu Leu Leu Ile Val Gln Ala Leu Arg Asp Asn Leu Glu Pro
            340                 345                 350
Gly Thr Phe Asp Ile Gly Gly Leu Tyr Glu Ser Ile Glu Glu Cys Leu
        355                 360                 365
Ile Asn Asp Pro Trp Val Leu Leu Asn Ala Ser Trp Phe Asn Ser Phe
    370                 375                 380
Leu Thr His Ala Leu Lys
385                 390

<210> SEQ ID NO 86
<211> LENGTH: 1170
<212> TYPE: DNA
<213> ORGANISM: Equine influenza virus H3N8

<400> SEQUENCE: 86
gaaaagggta taaacccaaa ctatctccaa gcttggaagc aagtattagc agaactacaa      60
gaccttgaga cgaagaaaaa gacccctaag accaagaata tgaaaaaaac aagccaattg     120
aaatgggcac tcggtgaaaa tatggcacca gagaaagtgg attttgagga ttgtaaagac     180
atcaatgatt tgaaacagta tgacagtgat gagccagaaa caaggtctct tgcaagttgg     240
attcaaagtg agttcaacaa agcttgtgag ctgacagatt caagctggat agagctcgat     300
gaaattgggg aggatattgc cccaatagaa tacattgcga gcatgaggag aaattatttt     360
actgctgagg tttcccattg tagagcaaca gaatatataa tgaagggagt gtacatcaac     420
actgctctac tcaatgcatc ctgtgctgcg atggatgaat ccaattaat tccgatgata     480 agcaaatgca ggaccaaaga agggagaagg aagacaaatt tatatggatt cataataaag     540
ggaaggtccc atttaaggaa tgataccgac gtggtaaact ttgtaagtat ggaattttct     600
ctcactgatc caagatttga gccacataaa tgggaaaaat actgcgttct agaaattgga     660
gacatgctcc taaggactgc tgtaggtcaa gtgtcaagac ccatgttttt gtatgtaagg     720
acaaatggaa cctctaaaat taaatgaaa tggggaatgg aaatgagacg ctgcctcctt     780
cagtctctgc aacagattga aagcatgatc gaagctgagt cctcagtcaa agaaaggac     840 atgaccaaag aattctttga gaacaaatca gagacatggc ctataggaga gtccccccaaa     900 ggagtggaag agggctcaat cgggaaggtt tgcaggacct tattagcaaa atctgtgttt     960
aacagtttgt atgcatctcc acaactggaa gggttttcag ctgaatctag gaaattactt    1020
ctcattgttc aggcccttag ggataacctg gaacctggaa cctttgatat tgggggggtta    1080 tatgaatcaa ttgaggagtg cctgattaat gatccctggg ttttgctcaa tgcatcttgg    1140
ttcaactcct tccttacaca tgcactgaag                                     1170
```

-continued

```
<210> SEQ ID NO 87
<211> LENGTH: 1478
<212> TYPE: DNA
<213> ORGANISM: Equine influenza virus H3N8
<220> FEATURE:
<221> NAME/KEY: CDS
<222> LOCATION: (29)..(1438)

<400> SEQUENCE: 87
gaattcagga gcaaagcagg agtttaaa atg aat cca aat caa aag ata ata       52
                               Met Asn Pro Asn Gln Lys Ile Ile
                               1               5 gca att gga tct gca tca ttg gga ata cta atc ctc aac gtc acc ctc     100
Ala Ile Gly Ser Ala Ser Leu Gly Ile Leu Ile Leu Asn Val Thr Leu
    10                  15                  20 cat gca gtc agc att ata gta aca gta ctg gtc ctc aat aac aat gga     148
His Ala Val Ser Ile Ile Val Thr Val Leu Val Leu Asn Asn Asn Gly
25                  30                  35                  40 aca ggt ctg aac tgc aac ggg acg atc ata aga gag tac aat gaa aca     196
Thr Gly Leu Asn Cys Asn Gly Thr Ile Ile Arg Glu Tyr Asn Glu Thr
                45                  50                  55 gta aga gta gaa aga att act caa tgg tat aat act agt aca att gag     244
Val Arg Val Glu Arg Ile Thr Gln Trp Tyr Asn Thr Ser Thr Ile Glu
            60                  65                  70 tac ata gag aga cct tca aat gaa tac tac atg aac aac acc gaa cca     292
Tyr Ile Glu Arg Pro Ser Asn Glu Tyr Tyr Met Asn Asn Thr Glu Pro
        75                  80                  85 ctt tgt gag gcc cag ggc ttt gca cca ttt tcc aaa gat aat gga ata     340
Leu Cys Glu Ala Gln Gly Phe Ala Pro Phe Ser Lys Asp Asn Gly Ile
    90                  95                  100 cga att ggg tcg aga ggc cat gtt ttt gta ata aga gaa cct ttt gtc     388
Arg Ile Gly Ser Arg Gly His Val Phe Val Ile Arg Glu Pro Phe Val
105                 110                 115                 120 tca tgt tcg ccc tca gaa tgt aga acc ttt ttc ctc aca cag ggc tca     436
Ser Cys Ser Pro Ser Glu Cys Arg Thr Phe Phe Leu Thr Gln Gly Ser
                125                 130                 135 tta ctc aat gac aaa cat tct aac ggc aca gtg aag gac cga agt cca     484
Leu Leu Asn Asp Lys His Ser Asn Gly Thr Val Lys Asp Arg Ser Pro
            140                 145                 150 tat agg act ttg atg agt gtc aaa ata ggg caa tca cct aat gtg tat     532
Tyr Arg Thr Leu Met Ser Val Lys Ile Gly Gln Ser Pro Asn Val Tyr
        155                 160                 165 caa gct agg ttt gaa tcg gtg gca tgg tca gca aca gca tgc cat gat     580
Gln Ala Arg Phe Glu Ser Val Ala Trp Ser Ala Thr Ala Cys His Asp
    170                 175                 180 gga aaa aaa tgg atg aca gtt gga gtc aca ggg ccc gat aat caa gca     628
Gly Lys Lys Trp Met Thr Val Gly Val Thr Gly Pro Asp Asn Gln Ala
185                 190                 195                 200 gtt gca gta gtg aac tat gga ggt gtt ccg gtt gat att att aat tca     676
Val Ala Val Val Asn Tyr Gly Gly Val Pro Val Asp Ile Ile Asn Ser
                205                 210                 215 tgg gca ggg gat atc tta aga acc caa gaa tcg tca tgc acc tgc att     724
Trp Ala Gly Asp Ile Leu Arg Thr Gln Glu Ser Ser Cys Thr Cys Ile
            220                 225                 230 aaa gga gac tgt tat tgg gtg atg act gat gga ccg gca aac aga caa     772
Lys Gly Asp Cys Tyr Trp Val Met Thr Asp Gly Pro Ala Asn Arg Gln
        235                 240                 245 gct aaa tat agg ata ttc aaa gca aaa gat gga aga ata att ggg cag     820
Ala Lys Tyr Arg Ile Phe Lys Ala Lys Asp Gly Arg Ile Ile Gly Gln
    250                 255                 260
```

```
act gat ata agt ttc aat ggg gga cac ata gag gag tgt tct tgt tac       868
Thr Asp Ile Ser Phe Asn Gly Gly His Ile Glu Glu Cys Ser Cys Tyr
265                 270                 275                 280 ccc aat gaa ggg aag gta gaa tgc ata tgc agg gac aac tgg act gga       916
Pro Asn Glu Gly Lys Val Glu Cys Ile Cys Arg Asp Asn Trp Thr Gly
            285                 290                 295 aca aat aga cca att ctg gta ata tct tct gat cta tcg tac aca gtc       964
Thr Asn Arg Pro Ile Leu Val Ile Ser Ser Asp Leu Ser Tyr Thr Val
        300                 305                 310 gga tat ttg tgt gct ggc att ccc act gac act cct agg gga gag gat      1012
Gly Tyr Leu Cys Ala Gly Ile Pro Thr Asp Thr Pro Arg Gly Glu Asp
    315                 320                 325 agt caa ttc aca ggc tca tgt aca agc cct ttg gga aat aaa gga tac      1060
Ser Gln Phe Thr Gly Ser Cys Thr Ser Pro Leu Gly Asn Lys Gly Tyr
330                 335                 340 ggt gta aaa ggt ttc ggg ttt cga caa gga aat gac gta tgg gcc gga      1108
Gly Val Lys Gly Phe Gly Phe Arg Gln Gly Asn Asp Val Trp Ala Gly
345                 350                 355                 360 agg aca att agt agg act tca aga tca gga ttc gaa ata ata aaa atc      1156
Arg Thr Ile Ser Arg Thr Ser Arg Ser Gly Phe Glu Ile Ile Lys Ile
            365                 370                 375 agg aat ggt tgg aca cag aac agt aaa gac caa atc aga agg caa gtg      1204
Arg Asn Gly Trp Thr Gln Asn Ser Lys Asp Gln Ile Arg Arg Gln Val
        380                 385                 390 att att gat aac cca aat tgg tca gga tat agc ggt tct ttc aca ttg      1252
Ile Ile Asp Asn Pro Asn Trp Ser Gly Tyr Ser Gly Ser Phe Thr Leu
    395                 400                 405 ccg gtt gaa cta aca aaa aag gga tgt tta gtc ccc tgt ttc tgg gtt      1300
Pro Val Glu Leu Thr Lys Lys Gly Cys Leu Val Pro Cys Phe Trp Val
410                 415                 420 gaa atg att aga ggt aaa cct gaa gaa aca aca ata tgg acc tct agc      1348
Glu Met Ile Arg Gly Lys Pro Glu Glu Thr Thr Ile Trp Thr Ser Ser
425                 430                 435                 440 agc tcc att gtg atg tgt gga gta gat cat aaa att gcc agt tgg tca      1396
Ser Ser Ile Val Met Cys Gly Val Asp His Lys Ile Ala Ser Trp Ser
            445                 450                 455 tgg cac gat gga gct att ctt ccc ttt gac atc gat aag atg               1438
Trp His Asp Gly Ala Ile Leu Pro Phe Asp Ile Asp Lys Met
        460                 465                 470 taatttacga aaaaaactcc ttgtttctac tcctgaattc                          1478

<210> SEQ ID NO 88
<211> LENGTH: 470
<212> TYPE: PRT
<213> ORGANISM: Equine influenza virus H3N8

<400> SEQUENCE: 88

Met Asn Pro Asn Gln Lys Ile Ile Ala Ile Gly Ser Ala Ser Leu Gly
1               5                   10                  15

Ile Leu Ile Leu Asn Val Thr Leu His Ala Val Ser Ile Ile Val Thr
            20                  25                  30

Val Leu Val Leu Asn Asn Asn Gly Thr Gly Leu Asn Cys Asn Gly Thr
        35                  40                  45

Ile Ile Arg Glu Tyr Asn Glu Thr Val Arg Val Glu Arg Ile Thr Gln
    50                  55                  60

Trp Tyr Asn Thr Ser Thr Ile Glu Tyr Ile Glu Arg Pro Ser Asn Glu
65                  70                  75                  80

Tyr Tyr Met Asn Asn Thr Glu Pro Leu Cys Glu Ala Gln Gly Phe Ala
```

-continued

```
             85                  90                  95
Pro Phe Ser Lys Asp Asn Gly Ile Arg Ile Gly Ser Arg Gly His Val
            100                 105                 110
Phe Val Ile Arg Glu Pro Phe Val Ser Cys Ser Pro Ser Glu Cys Arg
            115                 120                 125
Thr Phe Phe Leu Thr Gln Gly Ser Leu Leu Asn Asp Lys His Ser Asn
            130                 135                 140
Gly Thr Val Lys Asp Arg Ser Pro Tyr Arg Thr Leu Met Ser Val Lys
145                 150                 155                 160
Ile Gly Gln Ser Pro Asn Val Tyr Gln Ala Arg Phe Glu Ser Val Ala
                165                 170                 175
Trp Ser Ala Thr Ala Cys His Asp Gly Lys Lys Trp Met Thr Val Gly
                180                 185                 190
Val Thr Gly Pro Asp Asn Gln Ala Val Ala Val Val Asn Tyr Gly Gly
                195                 200                 205
Val Pro Val Asp Ile Ile Asn Ser Trp Ala Gly Asp Ile Leu Arg Thr
210                 215                 220
Gln Glu Ser Ser Cys Thr Cys Ile Lys Gly Asp Cys Tyr Trp Val Met
225                 230                 235                 240
Thr Asp Gly Pro Ala Asn Arg Gln Ala Lys Tyr Arg Ile Phe Lys Ala
                245                 250                 255
Lys Asp Gly Arg Ile Ile Gly Gln Thr Asp Ile Ser Phe Asn Gly Gly
                260                 265                 270
His Ile Glu Glu Cys Ser Cys Tyr Pro Asn Glu Gly Lys Val Glu Cys
                275                 280                 285
Ile Cys Arg Asp Asn Trp Thr Gly Thr Asn Arg Pro Ile Leu Val Ile
290                 295                 300
Ser Ser Asp Leu Ser Tyr Thr Val Gly Tyr Leu Cys Ala Gly Ile Pro
305                 310                 315                 320
Thr Asp Thr Pro Arg Gly Glu Asp Ser Gln Phe Thr Gly Ser Cys Thr
                325                 330                 335
Ser Pro Leu Gly Asn Lys Gly Tyr Gly Val Lys Gly Phe Gly Phe Arg
                340                 345                 350
Gln Gly Asn Asp Val Trp Ala Gly Arg Thr Ile Ser Arg Thr Ser Arg
                355                 360                 365
Ser Gly Phe Glu Ile Ile Lys Ile Arg Asn Gly Trp Thr Gln Asn Ser
370                 375                 380
Lys Asp Gln Ile Arg Arg Gln Val Ile Ile Asp Asn Pro Asn Trp Ser
385                 390                 395                 400
Gly Tyr Ser Gly Ser Phe Thr Leu Pro Val Glu Leu Thr Lys Lys Gly
                405                 410                 415
Cys Leu Val Pro Cys Phe Trp Val Glu Met Ile Arg Gly Lys Pro Glu
                420                 425                 430
Glu Thr Thr Ile Trp Thr Ser Ser Ser Ile Val Met Cys Gly Val
                435                 440                 445
Asp His Lys Ile Ala Ser Trp Ser Trp His Asp Gly Ala Ile Leu Pro
450                 455                 460
Phe Asp Ile Asp Lys Met
465                 470

<210> SEQ ID NO 89
<211> LENGTH: 1410
<212> TYPE: DNA
<213> ORGANISM: Equine influenza virus H3N8
```

<400> SEQUENCE: 89

```
atgaatccaa atcaaaagat aatagcaatt ggatctgcat cattgggaat actaatcctc    60
aacgtcaccc tccatgcagt cagcattata gtaacagtac tggtcctcaa taacaatgga   120
acaggtctga actgcaacgg gacgatcata agagagtaca atgaaacagt aagagtagaa   180
agaattactc aatggtataa tactagtaca attgagtaca tagagagacc ttcaaatgaa   240
tactacatga caacaccga accactttgt gaggcccagg gctttgcacc attttccaaa   300
gataatggaa tacgaattgg gtcgagaggc catgttttg taataagaga acctttgtc    360
tcatgttcgc cctcagaatg tagaaccttt ttcctcacac agggctcatt actcaatgac   420
aaacattcta acggcacagt gaaggaccga agtccatata ggactttgat gagtgtcaaa   480
ataggggcaat cacctaatgt gtatcaagct aggtttgaat cggtggcatg gtcagcaaca   540
gcatgccatg atggaaaaaa atggatgaca gttggagtca cagggcccga taatcaagca   600
gttgcagtag tgaactatgg aggtgttccg gttgatatta ttaattcatg ggcaggggat   660
atcttaagaa cccaagaatc gtcatgcacc tgcattaaag gagactgtta ttgggtgatg   720
actgatggac cggcaaacag acaagctaaa tataggatat tcaaagcaaa agatggaaga   780
ataattgggc agactgatat aagtttcaat ggggggacaca tagaggagtg ttcttgttac   840
cccaatgaag ggaaggtaga atgcatatgc aggacaact ggactggaac aaatagacca    900
attctggtaa tatcttctga tctatcgtac acagtcggat atttgtgtgc tggcattccc   960
actgacactc ctagggagga ggatagtcaa ttcacaggct catgtacaag ccctttggga  1020
aataaaggat acgtgtaaa aggtttcggg tttcgacaag gaaatgacgt atgggccgga  1080
aggacaatta gtaggacttc aagatcagga ttcgaaataa taaaaatcag gaatggttgg  1140
acacagaaca gtaaagacca aatcagaagg caagtgatta ttgataaccc aaattggtca  1200
ggatatagcg gttcttttca cattgccggtt gaactaacaa aaaagggatg tttagtcccc  1260
tgtttctggg ttgaaatgat tagaggtaaa cctgaagaaa caacaatatg gacctctagc  1320
agctccattg tgatgtgtgg agtagatcat aaaaattgcca gttggtcatg gcacgatgga  1380
gctattcttc cctttgacat cgataagatg                                    1410
```

<210> SEQ ID NO 90
<211> LENGTH: 17
<212> TYPE: DNA
<213> ORGANISM: Artificial
<220> FEATURE:
<223> OTHER INFORMATION: Synthetic Primer

<400> SEQUENCE: 90

```
gtgacttggg tcctcaa                                                    17
```

<210> SEQ ID NO 91
<211> LENGTH: 19
<212> TYPE: DNA
<213> ORGANISM: Artificial
<220> FEATURE:
<223> OTHER INFORMATION: Synthetic Primer

<400> SEQUENCE: 91

```
accccgacca ctcaagatg                                                  19
```

<210> SEQ ID NO 92
<211> LENGTH: 20
<212> TYPE: DNA

<213> ORGANISM: Artificial
<220> FEATURE:
<223> OTHER INFORMATION: Synthetic Primer

<400> SEQUENCE: 92
catatactac ctggagaagg        20

<210> SEQ ID NO 93
<211> LENGTH: 19
<212> TYPE: DNA
<213> ORGANISM: Artificial
<220> FEATURE:
<223> OTHER INFORMATION: Synthetic Primer

<400> SEQUENCE: 93
atagtccgct tttgtagcc         19

<210> SEQ ID NO 94
<211> LENGTH: 1216
<212> TYPE: DNA
<213> ORGANISM: Equine influenza virus H3N8

<400> SEQUENCE: 94

| | | | | | |
|---|---|---|---|---|---|
| agcaaaagca | ggtatgatcc | aaaatggaag | actttgtgcg | acagtgcttc | aatccaatga | 60 |
| tcgtcgagct | tgcggaaaag | gcaatgaaag | aatatggaga | ggacccgaaa | attgaaacaa | 120 |
| acaaatttgc | agcaatatgc | actcacttgg | aagtctgctt | catgtactcg | gatttccact | 180 |
| ttattaatga | actgggtgag | tcagtgatca | tagagtctgg | tgatccaaat | gctcttttga | 240 |
| aacacagatt | tgaaatcatt | gaagggagag | atcgaacaat | ggcatggaca | gtagtaaaca | 300 |
| gcatctgcaa | caccacaaga | gctgaaaaac | ccaagtttct | cccagattta | tacgactata | 360 |
| aggagaacag | atttgttgaa | attggtgtga | caaggagaga | agttcacata | tactacctgg | 420 |
| agaaggccaa | caaaataaag | tctgagaaaa | cacatatcca | cattttctca | tttacaggag | 480 |
| aggaaatggc | tacaaaagcg | gactatactc | ttgatgaaga | gagtagagcc | aggatcaaga | 540 |
| ccagactatt | caccataaga | caagaaatgg | ccagtagagg | cctctgggat | tcctttcgtc | 600 |
| agtccgagag | aggcgaagag | acaattgaag | aaagatttga | aatcacaggg | acgatgcgca | 660 |
| ggcttgccaa | ttacagtctc | ccaccgaact | tctccagcct | tgaaaatttt | agagtctatg | 720 |
| tggatggatt | cgaaccgaac | ggctgcattg | agagtaagct | ttctcaaatg | tccaaagaag | 780 |
| taaatgccag | aatcgagcca | ttttcaaaga | caacaccccg | accactcaag | atgccaggtg | 840 |
| gtccaccctg | ccatcagcga | tctaaattct | tgctaatgga | tgctctgaaa | ttgagtattg | 900 |
| aggacccaag | tcacgaggga | gagggaatac | cactatatga | tgctatcaaa | tgcatgaaaa | 960 |
| ctttctttgg | atggaaagag | cccagtgttg | ttaaaccaca | tgaaaagggt | ataaacccaa | 1020 |
| actatctcca | agcttggaag | caagtattag | cagaactaca | agaccttgag | aacgaagaaa | 1080 |
| agaccccctaa | gaccaagaat | atgaaaaaaa | caagccaatt | gaaatgggca | ctcggtgaaa | 1140 |
| atatggcacc | agagaaagtg | gattttgagg | attgtaaaga | catcaatgat | ttgaaacagt | 1200 |
| atgacagtga | tgagcc | | | | | 1216 |

<210> SEQ ID NO 95
<211> LENGTH: 1193
<212> TYPE: DNA
<213> ORGANISM: Equine influenza virus H3N8
<220> FEATURE:
<221> NAME/KEY: CDS
<222> LOCATION: (1)..(1191)

<400> SEQUENCE: 95

```
atg gaa gac ttt gtg cga cag tgc ttc aat cca atg atc gtc gag ctt       48
Met Glu Asp Phe Val Arg Gln Cys Phe Asn Pro Met Ile Val Glu Leu
1               5                  10                  15 gcg gaa aag gca atg aaa gaa tat gga gag gac ccg aaa att gaa aca       96
Ala Glu Lys Ala Met Lys Glu Tyr Gly Glu Asp Pro Lys Ile Glu Thr
            20                  25                  30 aac aaa ttt gca gca ata tgc act cac ttg gaa gtc tgc ttc atg tac      144
Asn Lys Phe Ala Ala Ile Cys Thr His Leu Glu Val Cys Phe Met Tyr
        35                  40                  45 tcg gat ttc cac ttt att aat gaa ctg ggt gag tca gtg atc ata gag      192
Ser Asp Phe His Phe Ile Asn Glu Leu Gly Glu Ser Val Ile Ile Glu
    50                  55                  60 tct ggt gat cca aat gct ctt ttg aaa cac aga ttt gaa atc att gaa      240
Ser Gly Asp Pro Asn Ala Leu Leu Lys His Arg Phe Glu Ile Ile Glu
65                  70                  75                  80 ggg aga gat cga aca atg gca tgg aca gta gta aac agc atc tgc aac      288
Gly Arg Asp Arg Thr Met Ala Trp Thr Val Val Asn Ser Ile Cys Asn
                85                  90                  95 acc aca aga gct gaa aaa ccc aag ttt ctc cca gat tta tac gac tat      336
Thr Thr Arg Ala Glu Lys Pro Lys Phe Leu Pro Asp Leu Tyr Asp Tyr
            100                 105                 110 aag gag aac aga ttt gtt gaa att ggt gtg aca agg aga gaa gtt cac      384
Lys Glu Asn Arg Phe Val Glu Ile Gly Val Thr Arg Arg Glu Val His
        115                 120                 125 ata tac tac ctg gag aag gcc aac aaa ata aag tct gag aaa aca cat      432
Ile Tyr Tyr Leu Glu Lys Ala Asn Lys Ile Lys Ser Glu Lys Thr His
    130                 135                 140 atc cac att ttc tca ttt aca gga gag gaa atg gct aca aaa gcg gac      480
Ile His Ile Phe Ser Phe Thr Gly Glu Glu Met Ala Thr Lys Ala Asp
145                 150                 155                 160 tat act ctt gat gaa gag agt aga gcc agg atc aag acc aga cta ttc      528
Tyr Thr Leu Asp Glu Glu Ser Arg Ala Arg Ile Lys Thr Arg Leu Phe
                165                 170                 175 acc ata aga caa gaa atg gcc agt aga ggc ctc tgg gat tcc ttt cgt      576
Thr Ile Arg Gln Glu Met Ala Ser Arg Gly Leu Trp Asp Ser Phe Arg
            180                 185                 190 cag tcc gag aga ggc gaa gag aca att gaa gaa aga ttt gaa atc aca      624
Gln Ser Glu Arg Gly Glu Glu Thr Ile Glu Glu Arg Phe Glu Ile Thr
        195                 200                 205 ggg acg atg cgc agg ctt gcc aat tac agt ctc cca ccg aac ttc tcc      672
Gly Thr Met Arg Arg Leu Ala Asn Tyr Ser Leu Pro Pro Asn Phe Ser
    210                 215                 220 agc ctt gaa aat ttt aga gtc tat gtg gat gga ttc gaa ccg aac ggc      720
Ser Leu Glu Asn Phe Arg Val Tyr Val Asp Gly Phe Glu Pro Asn Gly
225                 230                 235                 240 tgc att gag agt aag ctt tct caa atg tcc aaa gaa gta aat gcc aga      768
Cys Ile Glu Ser Lys Leu Ser Gln Met Ser Lys Glu Val Asn Ala Arg
                245                 250                 255 atc gag cca ttt tca aag aca aca ccc cga cca ctc aag atg cca ggt      816
Ile Glu Pro Phe Ser Lys Thr Thr Pro Arg Pro Leu Lys Met Pro Gly
            260                 265                 270 ggt cca ccc tgc cat cag cga tct aaa ttc ttg cta atg gat gct ctg      864
Gly Pro Pro Cys His Gln Arg Ser Lys Phe Leu Leu Met Asp Ala Leu
        275                 280                 285 aaa ttg agt att gag gac cca agt cac gag gga gag gga ata cca cta      912
Lys Leu Ser Ile Glu Asp Pro Ser His Glu Gly Glu Gly Ile Pro Leu
    290                 295                 300 tat gat gct atc aaa tgc atg aaa act ttc ttt gga tgg aaa gag ccc      960
Tyr Asp Ala Ile Lys Cys Met Lys Thr Phe Phe Gly Trp Lys Glu Pro
```

-continued

```
Tyr Asp Ala Ile Lys Cys Met Lys Thr Phe Phe Gly Trp Lys Glu Pro
305                 310                 315                 320 agt gtt gtt aaa cca cat gaa aag ggt ata aac cca aac tat ctc caa        1008
Ser Val Val Lys Pro His Glu Lys Gly Ile Asn Pro Asn Tyr Leu Gln
                325                 330                 335 gct tgg aag caa gta tta gca gaa cta caa gac ctt gag aac gaa gaa        1056
Ala Trp Lys Gln Val Leu Ala Glu Leu Gln Asp Leu Glu Asn Glu Glu
        340                 345                 350 aag acc cct aag acc aag aat atg aaa aaa aca agc caa ttg aaa tgg        1104
Lys Thr Pro Lys Thr Lys Asn Met Lys Lys Thr Ser Gln Leu Lys Trp
            355                 360                 365 gca ctc ggt gaa aat atg gca cca gag aaa gtg gat ttt gag gat tgt        1152
Ala Leu Gly Glu Asn Met Ala Pro Glu Lys Val Asp Phe Glu Asp Cys
370                 375                 380 aaa gac atc aat gat ttg aaa cag tat gac agt gat gag cc                 1193
Lys Asp Ile Asn Asp Leu Lys Gln Tyr Asp Ser Asp Glu
385                 390                 395
```

<210> SEQ ID NO 96
<211> LENGTH: 397
<212> TYPE: PRT
<213> ORGANISM: Equine influenza virus H3N8

<400> SEQUENCE: 96

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Ile Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Arg
                245                 250                 255
```

-continued

```
Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Val Val Lys Pro His Glu Lys Gly Ile Asn Pro Asn Tyr Leu Gln
                325                 330                 335

Ala Trp Lys Gln Val Leu Ala Glu Leu Gln Asp Leu Glu Asn Glu Glu
            340                 345                 350

Lys Thr Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu
385                 390                 395
```

<210> SEQ ID NO 97
<211> LENGTH: 1217
<212> TYPE: DNA
<213> ORGANISM: Equine influenza virus H3N8

<400> SEQUENCE: 97

| | | | | |
|---|---|---|---|---|
| agcaaaagca | ggtactgatc | caaaatggaa | gactttgtgc | gacagtgctt caatccaatg | 60 |
| atcgtcgagc | ttgcggaaaa | ggcaatgaaa | gaatatggag | aggacccgaa aattgaaaca | 120 |
| aacaaatttg | cagcaatatg | cactcacttg | gaagtctgct | tcatgtactc ggatttccac | 180 |
| tttattaatg | aactgggtaa | gtcagtgatc | atagagtctg | gtgatccaaa tgctctttg | 240 |
| aaacacagat | ttgaaatcat | gaagggaga | gatcgaacaa | tggcatggac agtagtaaac | 300 |
| agcatctgca | acaccacaag | agctgaaaaa | cccaagtttc | tcccagattt atacgactat | 360 |
| aaggagaaca | gatttgttga | aattggtgtg | acaaggagag | aagttcacat atactacctg | 420 |
| gagaaggcca | caaaataaa | gtctgagaaa | acacatatcc | acattttctc atttacagga | 480 |
| gaggaaatga | ctacaaaagc | ggactatact | cttgatgaag | agagtagagc caggatcaag | 540 |
| accagactat | tcaccataag | acaagaaatg | gccagtagag | gcctctggga ttcctttcgt | 600 |
| cagtccgaga | gaggcgaaga | gacaattgaa | gaaagatttg | aaatcacagg gacgatgcgc | 660 |
| aggcttgcca | attacagtct | cccaccgaac | ttctccagcc | ttgaaaattt tagagtctat | 720 |
| gtggatggat | tcgaaccgaa | cggctgcatt | gagagtaagc | tttctcaaat gtccaaagaa | 780 |
| gtaaatgcca | gaatcgagcc | attttcaaag | acaacacccc | gaccactcaa gatgccaggt | 840 |
| ggtccaccct | gccatcagcg | atctaaattc | ttgctaatgg | atgctctgaa attaagtatt | 900 |
| gaggacccaa | gtcacgaggg | agagggaata | ccactatatg | atgctatcaa atgcatgaaa | 960 |
| actttctttg | gatggaaaga | gcccagtgtt | gttaaaccac | atgaaaaggg tataaaccca | 1020 |
| aactatctcc | aagcttggaa | gcaagtatta | gcagaactac | aagaccttga gaacgaagaa | 1080 |
| aagacccta | agaccaagaa | tatgaaaaaa | acaagccaat | tgaaatgggc actcggtgaa | 1140 |
| aatatggcac | cagagaaagt | ggatttttgag | gattgtaaag | acatcaatga tttgaaacag | 1200 |
| tatgacagtg | atgagcc | | | | 1217 |

<210> SEQ ID NO 98

```
<211> LENGTH: 1193
<212> TYPE: DNA
<213> ORGANISM: Equine influenza virus H3N8
<220> FEATURE:
<221> NAME/KEY: CDS
<222> LOCATION: (1)..(1191)

<400> SEQUENCE: 98 atg gaa gac ttt gtg cga cag tgc ttc aat cca atg atc gtc gag ctt     48
Met Glu Asp Phe Val Arg Gln Cys Phe Asn Pro Met Ile Val Glu Leu
1               5                  10                  15 gcg gaa aag gca atg aaa gaa tat gga gag gac ccg aaa att gaa aca     96
Ala Glu Lys Ala Met Lys Glu Tyr Gly Glu Asp Pro Lys Ile Glu Thr
            20                  25                  30 aac aaa ttt gca gca ata tgc act cac ttg gaa gtc tgc ttc atg tac    144
Asn Lys Phe Ala Ala Ile Cys Thr His Leu Glu Val Cys Phe Met Tyr
        35                  40                  45 tcg gat ttc cac ttt att aat gaa ctg ggt aag tca gtg atc ata gag    192
Ser Asp Phe His Phe Ile Asn Glu Leu Gly Lys Ser Val Ile Ile Glu
    50                  55                  60 tct ggt gat cca aat gct ctt ttg aaa cac aga ttt gaa atc att gaa    240
Ser Gly Asp Pro Asn Ala Leu Leu Lys His Arg Phe Glu Ile Ile Glu
65                  70                  75                  80 ggg aga gat cga aca atg gca tgg aca gta gta aac agc atc tgc aac    288
Gly Arg Asp Arg Thr Met Ala Trp Thr Val Val Asn Ser Ile Cys Asn
                85                  90                  95 acc aca aga gct gaa aaa ccc aag ttt ctc cca gat tta tac gac tat    336
Thr Thr Arg Ala Glu Lys Pro Lys Phe Leu Pro Asp Leu Tyr Asp Tyr
            100                 105                 110 aag gag aac aga ttt gtt gaa att ggt gtg aca agg aga gaa gtt cac    384
Lys Glu Asn Arg Phe Val Glu Ile Gly Val Thr Arg Arg Glu Val His
        115                 120                 125 ata tac tac ctg gag aag gcc aac aaa ata aag tct gag aaa aca cat    432
Ile Tyr Tyr Leu Glu Lys Ala Asn Lys Ile Lys Ser Glu Lys Thr His
    130                 135                 140 atc cac att ttc tca ttt aca gga gag gaa atg act aca aaa gcg gac    480
Ile His Ile Phe Ser Phe Thr Gly Glu Glu Met Thr Thr Lys Ala Asp
145                 150                 155                 160 tat act ctt gat gaa gag agt aga gcc agg atc aag acc aga cta ttc    528
Tyr Thr Leu Asp Glu Glu Ser Arg Ala Arg Ile Lys Thr Arg Leu Phe
                165                 170                 175 acc ata aga caa gaa atg gcc agt aga ggc ctc tgg gat tcc ttt cgt    576
Thr Ile Arg Gln Glu Met Ala Ser Arg Gly Leu Trp Asp Ser Phe Arg
            180                 185                 190 cag tcc gag aga ggc gaa gag aca att gaa gaa aga ttt gaa atc aca    624
Gln Ser Glu Arg Gly Glu Glu Thr Ile Glu Glu Arg Phe Glu Ile Thr
        195                 200                 205 ggg acg atg cgc agg ctt gcc aat tac agt ctc cca ccg aac ttc tcc    672
Gly Thr Met Arg Arg Leu Ala Asn Tyr Ser Leu Pro Pro Asn Phe Ser
    210                 215                 220 agc ctt gaa aat ttt aga gtc tat gtg gat gga ttc gaa ccg aac ggc    720
Ser Leu Glu Asn Phe Arg Val Tyr Val Asp Gly Phe Glu Pro Asn Gly
225                 230                 235                 240 tgc att gag agt aag ctt tct caa atg tcc aaa gaa gta aat gcc aga    768
Cys Ile Glu Ser Lys Leu Ser Gln Met Ser Lys Glu Val Asn Ala Arg
                245                 250                 255 atc gag cca ttt tca aag aca aca ccc cga cca ctc aag atg cca ggt    816
Ile Glu Pro Phe Ser Lys Thr Thr Pro Arg Pro Leu Lys Met Pro Gly
            260                 265                 270 ggt cca ccc tgc cat cag cga tct aaa ttc ttg cta atg gat gct ctg    864
Gly Pro Pro Cys His Gln Arg Ser Lys Phe Leu Leu Met Asp Ala Leu
```

```
                    275                 280                 285
aaa tta agt att gag gac cca agt cac gag gga gag gga ata cca cta        912
Lys Leu Ser Ile Glu Asp Pro Ser His Glu Gly Glu Gly Ile Pro Leu
    290                 295                 300 tat gat gct atc aaa tgc atg aaa act ttc ttt gga tgg aaa gag ccc        960
Tyr Asp Ala Ile Lys Cys Met Lys Thr Phe Phe Gly Trp Lys Glu Pro
305                 310                 315                 320 agt gtt gtt aaa cca cat gaa aag ggt ata aac cca aac tat ctc caa       1008
Ser Val Val Lys Pro His Glu Lys Gly Ile Asn Pro Asn Tyr Leu Gln
                325                 330                 335 gct tgg aag caa gta tta gca gaa cta caa gac ctt gag aac gaa gaa       1056
Ala Trp Lys Gln Val Leu Ala Glu Leu Gln Asp Leu Glu Asn Glu Glu
            340                 345                 350 aag acc cct aag acc aag aat atg aaa aaa aca agc caa ttg aaa tgg       1104
Lys Thr Pro Lys Thr Lys Asn Met Lys Lys Thr Ser Gln Leu Lys Trp
        355                 360                 365 gca ctc ggt gaa aat atg gca cca gag aaa gtg gat ttt gag gat tgt       1152
Ala Leu Gly Glu Asn Met Ala Pro Glu Lys Val Asp Phe Glu Asp Cys
370                 375                 380 aaa gac atc aat gat ttg aaa cag tat gac agt gat gag cc                1193
Lys Asp Ile Asn Asp Leu Lys Gln Tyr Asp Ser Asp Glu
385                 390                 395

<210> SEQ ID NO 99
<211> LENGTH: 397
<212> TYPE: PRT
<213> ORGANISM: Equine influenza virus H3N8

<400> SEQUENCE: 99

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Lys Ser Val Ile Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Thr Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asn Tyr Ser Leu Pro Pro Asn Phe Ser
    210                 215                 220
```

-continued

```
Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Arg
            245                 250                 255

Ile Glu Pro Phe Ser Lys Thr Thr Pro Arg Pro Leu Lys Met Pro Gly
        260                 265                 270

Gly Pro Pro Cys His Gln Arg Ser Lys Phe Leu Leu Met Asp Ala Leu
    275                 280                 285

Lys Leu Ser Ile Glu Asp Pro Ser His Glu Gly Glu Gly Ile Pro Leu
290                 295                 300

Tyr Asp Ala Ile Lys Cys Met Lys Thr Phe Phe Gly Trp Lys Glu Pro
305                 310                 315                 320

Ser Val Val Lys Pro His Glu Lys Gly Ile Asn Pro Asn Tyr Leu Gln
            325                 330                 335

Ala Trp Lys Gln Val Leu Ala Glu Leu Gln Asp Leu Glu Asn Glu Glu
        340                 345                 350

Lys Thr Pro Lys Thr Lys Asn Met Lys Lys Thr Ser Gln Leu Lys Trp
    355                 360                 365

Ala Leu Gly Glu Asn Met Ala Pro Glu Lys Val Asp Phe Glu Asp Cys
370                 375                 380

Lys Asp Ile Asn Asp Leu Lys Gln Tyr Asp Ser Asp Glu
385                 390                 395
```

```
<210> SEQ ID NO 100
<211> LENGTH: 2148
<212> TYPE: DNA
<213> ORGANISM: Equine influenza virus H3N8
<220> FEATURE:
<221> NAME/KEY: misc_feature
<222> LOCATION: (577)..(577)
<223> OTHER INFORMATION: The 'Xaa' at amino acid location 577 stands for
      Arg, or Trp.
<220> FEATURE:
<221> NAME/KEY: CDS
<222> LOCATION: (1)..(2148)

<400> SEQUENCE: 100
```

```
atg gaa gac ttt gtg cga cag tgc ttc aat cca atg atc gtc gag ctt      48
Met Glu Asp Phe Val Arg Gln Cys Phe Asn Pro Met Ile Val Glu Leu
1               5                   10                  15 gcg gaa aag gca atg aaa gaa tat gga gag gac ccg aaa att gaa aca      96
Ala Glu Lys Ala Met Lys Glu Tyr Gly Glu Asp Pro Lys Ile Glu Thr
            20                  25                  30 aac aaa ttt gca gca ata tgc act cac ttg gaa gtc tgc ttc atg tac     144
Asn Lys Phe Ala Ala Ile Cys Thr His Leu Glu Val Cys Phe Met Tyr
        35                  40                  45 tcg gat ttc cac ttt att aat gaa ctg ggt gag tca gtg atc ata gag     192
Ser Asp Phe His Phe Ile Asn Glu Leu Gly Glu Ser Val Ile Ile Glu
    50                  55                  60 tct ggt gat cca aat gct ctt ttg aaa cac aga ttt gaa atc att gaa     240
Ser Gly Asp Pro Asn Ala Leu Leu Lys His Arg Phe Glu Ile Ile Glu
65                  70                  75                  80 ggg aga gat cga aca atg gca tgg aca gta gta aac agc atc tgc aac     288
Gly Arg Asp Arg Thr Met Ala Trp Thr Val Val Asn Ser Ile Cys Asn
                85                  90                  95 acc aca aga gct gaa aaa ccc aag ttt ctc cca gat tta tac gac tat     336
Thr Thr Arg Ala Glu Lys Pro Lys Phe Leu Pro Asp Leu Tyr Asp Tyr
            100                 105                 110 aag gag aac aga ttt gtt gaa att ggt gtg aca agg aga gaa gtt cac     384
```

```
                                                       -continued

Lys Glu Asn Arg Phe Val Glu Ile Gly Val Thr Arg Glu Val His
        115                 120                 125 ata tac tac ctg gag aag gcc aac aaa ata aag tct gag aaa aca cat         432
Ile Tyr Tyr Leu Glu Lys Ala Asn Lys Ile Lys Ser Glu Lys Thr His
130                 135                 140 atc cac att ttc tca ttt aca gga gag gaa atg gct aca aaa gcg gac         480
Ile His Ile Phe Ser Phe Thr Gly Glu Glu Met Ala Thr Lys Ala Asp
145                 150                 155                 160 tat act ctt gat gaa gag agt aga gcc agg atc aag acc aga cta ttc         528
Tyr Thr Leu Asp Glu Glu Ser Arg Ala Arg Ile Lys Thr Arg Leu Phe
                165                 170                 175 acc ata aga caa gaa atg gcc agt aga ggc ctc tgg gat tcc ttt cgt         576
Thr Ile Arg Gln Glu Met Ala Ser Arg Gly Leu Trp Asp Ser Phe Arg
            180                 185                 190 cag tcc gag aga ggc gaa gag aca att gaa gaa aga ttt gaa atc aca         624
Gln Ser Glu Arg Gly Glu Glu Thr Ile Glu Glu Arg Phe Glu Ile Thr
        195                 200                 205 ggg acg atg cgc agg ctt gcc aat tac agt ctc cca ccg aac ttc tcc         672
Gly Thr Met Arg Arg Leu Ala Asn Tyr Ser Leu Pro Pro Asn Phe Ser
    210                 215                 220 agc ctt gaa aat ttt aga gtc tat gtg gat gga ttc gaa ccg aac ggc         720
Ser Leu Glu Asn Phe Arg Val Tyr Val Asp Gly Phe Glu Pro Asn Gly
225                 230                 235                 240 tgc att gag agt aag ctt tct caa atg tcc aaa gaa gta aat gcc aga         768
Cys Ile Glu Ser Lys Leu Ser Gln Met Ser Lys Glu Val Asn Ala Arg
                245                 250                 255 atc gag cca ttt tca aag aca aca ccc cga cca ctc aag atg cca ggt         816
Ile Glu Pro Phe Ser Lys Thr Thr Pro Arg Pro Leu Lys Met Pro Gly
            260                 265                 270 ggt cca ccc tgc cat cag cga tct aaa ttc ttg cta atg gat gct ctg         864
Gly Pro Pro Cys His Gln Arg Ser Lys Phe Leu Leu Met Asp Ala Leu
        275                 280                 285 aaa ttg agt att gag gac cca agt cac gag gga gag gga ata cca cta         912
Lys Leu Ser Ile Glu Asp Pro Ser His Glu Gly Glu Gly Ile Pro Leu
    290                 295                 300 tat gat gct atc aaa tgc atg aaa act ttc ttt gga tgg aaa gag ccc         960
Tyr Asp Ala Ile Lys Cys Met Lys Thr Phe Phe Gly Trp Lys Glu Pro
305                 310                 315                 320 agt gtt gtt aaa cca cat gaa aag ggt ata aac cca aac tat ctc caa        1008
Ser Val Val Lys Pro His Glu Lys Gly Ile Asn Pro Asn Tyr Leu Gln
                325                 330                 335 gct tgg aag caa gta tta gca gaa cta caa gac ctt gag aac gaa gaa        1056
Ala Trp Lys Gln Val Leu Ala Glu Leu Gln Asp Leu Glu Asn Glu Glu
            340                 345                 350 aag acc cct aag acc aag aat atg aaa aaa aca agc caa ttg aaa tgg        1104
Lys Thr Pro Lys Thr Lys Asn Met Lys Lys Thr Ser Gln Leu Lys Trp
        355                 360                 365 gca ctc ggt gaa aat atg gca cca gag aaa gtg gat ttt gag gat tgt        1152
Ala Leu Gly Glu Asn Met Ala Pro Glu Lys Val Asp Phe Glu Asp Cys
    370                 375                 380 aaa gac atc aat gat ttg aaa cag tat gac agt gat gag cca gaa aca        1200
Lys Asp Ile Asn Asp Leu Lys Gln Tyr Asp Ser Asp Glu Pro Glu Thr
385                 390                 395                 400 agg tct ctt gca agt tgg att caa agt gag ttc aac aaa gct tgt gag        1248
Arg Ser Leu Ala Ser Trp Ile Gln Ser Glu Phe Asn Lys Ala Cys Glu
                405                 410                 415 ctg aca gat tca agc tgg ata gag ctc gat gaa att ggg gag gat att        1296
Leu Thr Asp Ser Ser Trp Ile Glu Leu Asp Glu Ile Gly Glu Asp Ile
            420                 425                 430
```

-continued

| | |
|---|---|
| gcc cca ata gaa tac att gcg agc atg agg aga aat tat ttt act gct<br>Ala Pro Ile Glu Tyr Ile Ala Ser Met Arg Arg Asn Tyr Phe Thr Ala<br>435 440 445 | 1344 |
| gag gtt tcc cat tgt aga gca aca gaa tat ata atg aag gga gtg tac<br>Glu Val Ser His Cys Arg Ala Thr Glu Tyr Ile Met Lys Gly Val Tyr<br>450 455 460 | 1392 |
| atc aac act gct cta ctc aat gca tcc tgt gct gcg atg gat gaa ttc<br>Ile Asn Thr Ala Leu Leu Asn Ala Ser Cys Ala Ala Met Asp Glu Phe<br>465 470 475 480 | 1440 |
| caa tta att ccg atg ata agc aaa tgc agg acc aaa gaa ggg aga agg<br>Gln Leu Ile Pro Met Ile Ser Lys Cys Arg Thr Lys Glu Gly Arg Arg<br>485 490 495 | 1488 |
| aag aca aat tta tat gga ttc ata ata aag gga agg tcc cat tta agg<br>Lys Thr Asn Leu Tyr Gly Phe Ile Ile Lys Gly Arg Ser His Leu Arg<br>500 505 510 | 1536 |
| aat gat acc gac gtg gta aac ttt gta agt atg gaa ttt tct ctc act<br>Asn Asp Thr Asp Val Val Asn Phe Val Ser Met Glu Phe Ser Leu Thr<br>515 520 525 | 1584 |
| gat cca aga ttt gag cca cat aaa tgg gaa aaa tac tgc gtt cta gaa<br>Asp Pro Arg Phe Glu Pro His Lys Trp Glu Lys Tyr Cys Val Leu Glu<br>530 535 540 | 1632 |
| att gga gac atg ctc cta agg act gct gta ggt caa gtg tca aga ccc<br>Ile Gly Asp Met Leu Leu Arg Thr Ala Val Gly Gln Val Ser Arg Pro<br>545 550 555 560 | 1680 |
| atg ttt ttg tat gta agg aca aat gga acc tct aaa att aaa atg aaa<br>Met Phe Leu Tyr Val Arg Thr Asn Gly Thr Ser Lys Ile Lys Met Lys<br>565 570 575 | 1728 |
| ygg gga atg gaa atg aga cgc tgc ctc ctt cag tct ctg caa cag att<br>Xaa Gly Met Glu Met Arg Arg Cys Leu Leu Gln Ser Leu Gln Gln Ile<br>580 585 590 | 1776 |
| gaa agc atg atc gaa gct gag tcc tca gtc aaa gaa aag gac atg acc<br>Glu Ser Met Ile Glu Ala Glu Ser Ser Val Lys Glu Lys Asp Met Thr<br>595 600 605 | 1824 |
| aaa gaa ttc ttt gag aac aaa tca gag aca tgg cct ata gga gag tcc<br>Lys Glu Phe Phe Glu Asn Lys Ser Glu Thr Trp Pro Ile Gly Glu Ser<br>610 615 620 | 1872 |
| ccc aaa gga gtg gaa gag ggc tca atc ggg aag gtt tgc agg acc tta<br>Pro Lys Gly Val Glu Glu Gly Ser Ile Gly Lys Val Cys Arg Thr Leu<br>625 630 635 640 | 1920 |
| tta gca aaa tct gtg ttt aac agt ttg tat gca tct cca caa ctg gaa<br>Leu Ala Lys Ser Val Phe Asn Ser Leu Tyr Ala Ser Pro Gln Leu Glu<br>645 650 655 | 1968 |
| ggg ttt tca gct gaa tct agg aaa tta ctt ctc att gtt cag gcc ctt<br>Gly Phe Ser Ala Glu Ser Arg Lys Leu Leu Leu Ile Val Gln Ala Leu<br>660 665 670 | 2016 |
| agg gat aac ctg gaa cct gga acc ttt gat att ggg ggg tta tat gaa<br>Arg Asp Asn Leu Glu Pro Gly Thr Phe Asp Ile Gly Gly Leu Tyr Glu<br>675 680 685 | 2064 |
| tca att gag gag tgc ctg att aat gat ccc tgg gtt ttg ctc aat gca<br>Ser Ile Glu Glu Cys Leu Ile Asn Asp Pro Trp Val Leu Leu Asn Ala<br>690 695 700 | 2112 |
| tct tgg ttc aac tcc ttc ctt aca cat gca ctg aag<br>Ser Trp Phe Asn Ser Phe Leu Thr His Ala Leu Lys<br>705 710 715 | 2148 |

<210> SEQ ID NO 101
<211> LENGTH: 716
<212> TYPE: PRT
<213> ORGANISM: Equine influenza virus H3N8
<220> FEATURE:
<221> NAME/KEY: misc_feature

```
<222> LOCATION: (577)..(577)
<223> OTHER INFORMATION: The 'Xaa' at location 577 stands for Arg, or
      Trp.

<400> SEQUENCE: 101
```

| | | | | | | | | | | | | | | |
|---|---|---|---|---|---|---|---|---|---|---|---|---|---|---|
| Met | Glu | Asp | Phe | Val | Arg | Gln | Cys | Phe | Asn | Pro | Met | Ile | Val | Glu | Leu |
| 1 | | | | 5 | | | | | 10 | | | | | 15 | |

| Ala | Glu | Lys | Ala | Met | Lys | Glu | Tyr | Gly | Glu | Asp | Pro | Lys | Ile | Glu | Thr |
|---|---|---|---|---|---|---|---|---|---|---|---|---|---|---|---|
| | | | 20 | | | | | 25 | | | | | 30 | | |

| Asn | Lys | Phe | Ala | Ala | Ile | Cys | Thr | His | Leu | Glu | Val | Cys | Phe | Met | Tyr |
|---|---|---|---|---|---|---|---|---|---|---|---|---|---|---|---|
| | | 35 | | | | | 40 | | | | | 45 | | | |

| Ser | Asp | Phe | His | Phe | Ile | Asn | Glu | Leu | Gly | Glu | Ser | Val | Ile | Ile | Glu |
|---|---|---|---|---|---|---|---|---|---|---|---|---|---|---|---|
| | 50 | | | | | 55 | | | | | 60 | | | | |

| Ser | Gly | Asp | Pro | Asn | Ala | Leu | Leu | Lys | His | Arg | Phe | Glu | Ile | Ile | Glu |
|---|---|---|---|---|---|---|---|---|---|---|---|---|---|---|---|
| 65 | | | | 70 | | | | | 75 | | | | | 80 | |

| Gly | Arg | Asp | Arg | Thr | Met | Ala | Trp | Thr | Val | Val | Asn | Ser | Ile | Cys | Asn |
|---|---|---|---|---|---|---|---|---|---|---|---|---|---|---|---|
| | | | | 85 | | | | | 90 | | | | | 95 | |

| Thr | Thr | Arg | Ala | Glu | Lys | Pro | Lys | Phe | Leu | Pro | Asp | Leu | Tyr | Asp | Tyr |
|---|---|---|---|---|---|---|---|---|---|---|---|---|---|---|---|
| | | | 100 | | | | | 105 | | | | | 110 | | |

| Lys | Glu | Asn | Arg | Phe | Val | Glu | Ile | Gly | Val | Thr | Arg | Arg | Glu | Val | His |
|---|---|---|---|---|---|---|---|---|---|---|---|---|---|---|---|
| | | 115 | | | | | 120 | | | | | 125 | | | |

| Ile | Tyr | Tyr | Leu | Glu | Lys | Ala | Asn | Lys | Ile | Lys | Ser | Glu | Lys | Thr | His |
|---|---|---|---|---|---|---|---|---|---|---|---|---|---|---|---|
| 130 | | | | | 135 | | | | | 140 | | | | | |

| Ile | His | Ile | Phe | Ser | Phe | Thr | Gly | Glu | Glu | Met | Ala | Thr | Lys | Ala | Asp |
|---|---|---|---|---|---|---|---|---|---|---|---|---|---|---|---|
| 145 | | | | | 150 | | | | | 155 | | | | | 160 |

| Tyr | Thr | Leu | Asp | Glu | Glu | Ser | Arg | Ala | Arg | Ile | Lys | Thr | Arg | Leu | Phe |
|---|---|---|---|---|---|---|---|---|---|---|---|---|---|---|---|
| | | | | 165 | | | | | 170 | | | | | 175 | |

| Thr | Ile | Arg | Gln | Glu | Met | Ala | Ser | Arg | Gly | Leu | Trp | Asp | Ser | Phe | Arg |
|---|---|---|---|---|---|---|---|---|---|---|---|---|---|---|---|
| | | | 180 | | | | | 185 | | | | | 190 | | |

| Gln | Ser | Glu | Arg | Gly | Glu | Glu | Thr | Ile | Glu | Glu | Arg | Phe | Glu | Ile | Thr |
|---|---|---|---|---|---|---|---|---|---|---|---|---|---|---|---|
| | | 195 | | | | | 200 | | | | | 205 | | | |

| Gly | Thr | Met | Arg | Arg | Leu | Ala | Asn | Tyr | Ser | Leu | Pro | Pro | Asn | Phe | Ser |
|---|---|---|---|---|---|---|---|---|---|---|---|---|---|---|---|
| 210 | | | | | 215 | | | | | 220 | | | | | |

| Ser | Leu | Glu | Asn | Phe | Arg | Val | Tyr | Val | Asp | Gly | Phe | Glu | Pro | Asn | Gly |
|---|---|---|---|---|---|---|---|---|---|---|---|---|---|---|---|
| 225 | | | | | 230 | | | | | 235 | | | | | 240 |

| Cys | Ile | Glu | Ser | Lys | Leu | Ser | Gln | Met | Ser | Lys | Glu | Val | Asn | Ala | Arg |
|---|---|---|---|---|---|---|---|---|---|---|---|---|---|---|---|
| | | | | 245 | | | | | 250 | | | | | 255 | |

| Ile | Glu | Pro | Phe | Ser | Lys | Thr | Thr | Pro | Arg | Pro | Leu | Lys | Met | Pro | Gly |
|---|---|---|---|---|---|---|---|---|---|---|---|---|---|---|---|
| | | | 260 | | | | | 265 | | | | | 270 | | |

| Gly | Pro | Pro | Cys | His | Gln | Arg | Ser | Lys | Phe | Leu | Leu | Met | Asp | Ala | Leu |
|---|---|---|---|---|---|---|---|---|---|---|---|---|---|---|---|
| | | 275 | | | | | 280 | | | | | 285 | | | |

| Lys | Leu | Ser | Ile | Glu | Asp | Pro | Ser | His | Glu | Gly | Glu | Gly | Ile | Pro | Leu |
|---|---|---|---|---|---|---|---|---|---|---|---|---|---|---|---|
| | 290 | | | | | 295 | | | | | 300 | | | | |

| Tyr | Asp | Ala | Ile | Lys | Cys | Met | Lys | Thr | Phe | Phe | Gly | Trp | Lys | Glu | Pro |
|---|---|---|---|---|---|---|---|---|---|---|---|---|---|---|---|
| 305 | | | | | 310 | | | | | 315 | | | | | 320 |

| Ser | Val | Val | Lys | Pro | His | Glu | Lys | Gly | Ile | Asn | Pro | Asn | Tyr | Leu | Gln |
|---|---|---|---|---|---|---|---|---|---|---|---|---|---|---|---|
| | | | | 325 | | | | | 330 | | | | | 335 | |

| Ala | Trp | Lys | Gln | Val | Leu | Ala | Glu | Leu | Gln | Asp | Leu | Glu | Asn | Glu | Glu |
|---|---|---|---|---|---|---|---|---|---|---|---|---|---|---|---|
| | | | 340 | | | | | 345 | | | | | 350 | | |

| Lys | Thr | Pro | Lys | Thr | Lys | Asn | Met | Lys | Lys | Thr | Ser | Gln | Leu | Lys | Trp |
|---|---|---|---|---|---|---|---|---|---|---|---|---|---|---|---|
| | | 355 | | | | | 360 | | | | | 365 | | | |

| Ala | Leu | Gly | Glu | Asn | Met | Ala | Pro | Glu | Lys | Val | Asp | Phe | Glu | Asp | Cys |
|---|---|---|---|---|---|---|---|---|---|---|---|---|---|---|---|
| 370 | | | | | 375 | | | | | 380 | | | | | |

| Lys | Asp | Ile | Asn | Asp | Leu | Lys | Gln | Tyr | Asp | Ser | Asp | Glu | Pro | Glu | Thr |
|---|---|---|---|---|---|---|---|---|---|---|---|---|---|---|---|

```
                385                 390                 395                 400

Arg Ser Leu Ala Ser Trp Ile Gln Ser Glu Phe Asn Lys Ala Cys Glu
                            405                 410                 415

Leu Thr Asp Ser Ser Trp Ile Glu Leu Asp Glu Ile Gly Glu Asp Ile
                            420                 425                 430

Ala Pro Ile Glu Tyr Ile Ala Ser Met Arg Arg Asn Tyr Phe Thr Ala
                            435                 440                 445

Glu Val Ser His Cys Arg Ala Thr Glu Tyr Ile Met Lys Gly Val Tyr
                            450                 455                 460

Ile Asn Thr Ala Leu Leu Asn Ala Ser Cys Ala Ala Met Asp Glu Phe
            465                 470                 475                 480

Gln Leu Ile Pro Met Ile Ser Lys Cys Arg Thr Lys Glu Gly Arg Arg
                            485                 490                 495

Lys Thr Asn Leu Tyr Gly Phe Ile Ile Lys Gly Arg Ser His Leu Arg
                            500                 505                 510

Asn Asp Thr Asp Val Val Asn Phe Val Ser Met Glu Phe Ser Leu Thr
                            515                 520                 525

Asp Pro Arg Phe Glu Pro His Lys Trp Glu Lys Tyr Cys Val Leu Glu
                            530                 535                 540

Ile Gly Asp Met Leu Leu Arg Thr Ala Val Gly Gln Val Ser Arg Pro
            545                 550                 555                 560

Met Phe Leu Tyr Val Arg Thr Asn Gly Thr Ser Lys Ile Lys Met Lys
                            565                 570                 575

Xaa Gly Met Glu Met Arg Arg Cys Leu Leu Gln Ser Leu Gln Gln Ile
                            580                 585                 590

Glu Ser Met Ile Glu Ala Glu Ser Val Lys Glu Lys Asp Met Thr
                            595                 600                 605

Lys Glu Phe Phe Glu Asn Lys Ser Glu Thr Trp Pro Ile Gly Glu Ser
                            610                 615                 620

Pro Lys Gly Val Glu Glu Gly Ser Ile Gly Lys Val Cys Arg Thr Leu
            625                 630                 635                 640

Leu Ala Lys Ser Val Phe Asn Ser Leu Tyr Ala Ser Pro Gln Leu Glu
                            645                 650                 655

Gly Phe Ser Ala Glu Ser Arg Lys Leu Leu Leu Ile Val Gln Ala Leu
                            660                 665                 670

Arg Asp Asn Leu Glu Pro Gly Thr Phe Asp Ile Gly Gly Leu Tyr Glu
                            675                 680                 685

Ser Ile Glu Glu Cys Leu Ile Asn Asp Pro Trp Val Leu Leu Asn Ala
                            690                 695                 700

Ser Trp Phe Asn Ser Phe Leu Thr His Ala Leu Lys
            705                 710                 715

<210> SEQ ID NO 102
<211> LENGTH: 2148
<212> TYPE: DNA
<213> ORGANISM: Equine influenza virus H3N8
<220> FEATURE:
<221> NAME/KEY: CDS
<222> LOCATION: (1)..(2148)

<400> SEQUENCE: 102 atg gaa gac ttt gtg cga cag tgc ttc aat cca atg atc gtc gag ctt     48
Met Glu Asp Phe Val Arg Gln Cys Phe Asn Pro Met Ile Val Glu Leu
1               5                   10                  15 gcg gaa aag gca atg aaa gaa tat gga gag gac ccg aaa att gaa aca     96
Ala Glu Lys Ala Met Lys Glu Tyr Gly Glu Asp Pro Lys Ile Glu Thr
```

```
                    20                  25                  30
aac aaa ttt gca gca ata tgc act cac ttg gaa gtc tgc ttc atg tac       144
Asn Lys Phe Ala Ala Ile Cys Thr His Leu Glu Val Cys Phe Met Tyr
             35                  40                  45 tcg gat ttc cac ttt att aat gaa ctg ggt aag tca gtg atc ata gag       192
Ser Asp Phe His Phe Ile Asn Glu Leu Gly Lys Ser Val Ile Ile Glu
 50                  55                  60 tct ggt gat cca aat gct ctt ttg aaa cac aga ttt gaa atc att gaa       240
Ser Gly Asp Pro Asn Ala Leu Leu Lys His Arg Phe Glu Ile Ile Glu
 65                  70                  75                  80 ggg aga gat cga aca atg gca tgg aca gta gta aac agc atc tgc aac       288
Gly Arg Asp Arg Thr Met Ala Trp Thr Val Val Asn Ser Ile Cys Asn
                     85                  90                  95 acc aca aga gct gaa aaa ccc aag ttt ctc cca gat tta tac gac tat       336
Thr Thr Arg Ala Glu Lys Pro Lys Phe Leu Pro Asp Leu Tyr Asp Tyr
            100                 105                 110 aag gag aac aga ttt gtt gaa att ggt gtg aca agg aga gaa gtt cac       384
Lys Glu Asn Arg Phe Val Glu Ile Gly Val Thr Arg Arg Glu Val His
        115                 120                 125 ata tac tac ctg gag aag gcc aac aaa ata aag tct gag aaa aca cat       432
Ile Tyr Tyr Leu Glu Lys Ala Asn Lys Ile Lys Ser Glu Lys Thr His
    130                 135                 140 atc cac att ttc tca ttt aca gga gag gaa atg act aca aaa gcg gac       480
Ile His Ile Phe Ser Phe Thr Gly Glu Glu Met Thr Thr Lys Ala Asp
145                 150                 155                 160 tat act ctt gat gaa gag agt aga gcc agg atc aag acc aga cta ttc       528
Tyr Thr Leu Asp Glu Glu Ser Arg Ala Arg Ile Lys Thr Arg Leu Phe
                165                 170                 175 acc ata aga caa gaa atg gcc agt aga ggc ctc tgg gat tcc ttt cgt       576
Thr Ile Arg Gln Glu Met Ala Ser Arg Gly Leu Trp Asp Ser Phe Arg
            180                 185                 190 cag tcc gag aga ggc gaa gag aca att gaa gaa aga ttt gaa atc aca       624
Gln Ser Glu Arg Gly Glu Glu Thr Ile Glu Glu Arg Phe Glu Ile Thr
        195                 200                 205 ggg acg atg cgc agg ctt gcc aat tac agt ctc cca ccg aac ttc tcc       672
Gly Thr Met Arg Arg Leu Ala Asn Tyr Ser Leu Pro Pro Asn Phe Ser
    210                 215                 220 agc ctt gaa aat ttt aga gtc tat gtg gat gga ttc gaa ccg aac ggc       720
Ser Leu Glu Asn Phe Arg Val Tyr Val Asp Gly Phe Glu Pro Asn Gly
225                 230                 235                 240 tgc att gag agt aag ctt tct caa atg tcc aaa gaa gta aat gcc aga       768
Cys Ile Glu Ser Lys Leu Ser Gln Met Ser Lys Glu Val Asn Ala Arg
                245                 250                 255 atc gag cca ttt tca aag aca aca ccc cga cca ctc aag atg cca ggt       816
Ile Glu Pro Phe Ser Lys Thr Thr Pro Arg Pro Leu Lys Met Pro Gly
            260                 265                 270 ggt cca ccc tgc cat cag cga tct aaa ttc ttg cta atg gat gct ctg       864
Gly Pro Pro Cys His Gln Arg Ser Lys Phe Leu Leu Met Asp Ala Leu
        275                 280                 285 aaa tta agt att gag gac cca agt cac gag gga gag gga ata cca cta       912
Lys Leu Ser Ile Glu Asp Pro Ser His Glu Gly Glu Gly Ile Pro Leu
    290                 295                 300 tat gat gct atc aaa tgc atg aaa act ttc ttt gga tgg aaa gag ccc       960
Tyr Asp Ala Ile Lys Cys Met Lys Thr Phe Phe Gly Trp Lys Glu Pro
305                 310                 315                 320 agt gtt gtt aaa cca cat gaa aag ggt ata aac cca aac tat ctc caa      1008
Ser Val Val Lys Pro His Glu Lys Gly Ile Asn Pro Asn Tyr Leu Gln
                325                 330                 335 gct tgg aag caa gta tta gca gaa cta caa gac ctt gag aac gaa gaa      1056
```

```
Ala Trp Lys Gln Val Leu Ala Glu Leu Gln Asp Leu Glu Asn Glu Glu
            340                 345                 350 aag acc cct aag acc aag aat atg aaa aaa aca agc caa ttg aaa tgg         1104
Lys Thr Pro Lys Thr Lys Asn Met Lys Lys Thr Ser Gln Leu Lys Trp
        355                 360                 365 gca ctc ggt gaa aat atg gca cca gag aaa gtg gat ttt gag gat tgt         1152
Ala Leu Gly Glu Asn Met Ala Pro Glu Lys Val Asp Phe Glu Asp Cys
370                 375                 380 aaa gac atc aat gat ttg aaa cag tat gac agt gat gag cca gaa aca         1200
Lys Asp Ile Asn Asp Leu Lys Gln Tyr Asp Ser Asp Glu Pro Glu Thr
385                 390                 395                 400 agg tct ctt gca agt tgg att caa agt gag ttc aac aaa gct tgt gag         1248
Arg Ser Leu Ala Ser Trp Ile Gln Ser Glu Phe Asn Lys Ala Cys Glu
            405                 410                 415 ctg aca gat tca agc tgg ata gag ctc gat gaa att ggg gag gat att         1296
Leu Thr Asp Ser Ser Trp Ile Glu Leu Asp Glu Ile Gly Glu Asp Ile
            420                 425                 430 gcc cca ata gaa tac att gcg agc atg agg aga aat tat ttt act gct         1344
Ala Pro Ile Glu Tyr Ile Ala Ser Met Arg Arg Asn Tyr Phe Thr Ala
            435                 440                 445 gag gtt tcc cat tgt aga gca aca gaa tat ata atg aag gga gtg tac         1392
Glu Val Ser His Cys Arg Ala Thr Glu Tyr Ile Met Lys Gly Val Tyr
        450                 455                 460 atc aac act gct cta ctc aat gca tcc tgt gct gcg atg gat gaa ttc         1440
Ile Asn Thr Ala Leu Leu Asn Ala Ser Cys Ala Ala Met Asp Glu Phe
465                 470                 475                 480 caa tta att ccg atg ata agc aaa tgc agg acc aaa gaa ggg aga agg         1488
Gln Leu Ile Pro Met Ile Ser Lys Cys Arg Thr Lys Glu Gly Arg Arg
            485                 490                 495 aag aca aat tta tat gga ttc ata ata aag gga agg tcc cat tta agg         1536
Lys Thr Asn Leu Tyr Gly Phe Ile Ile Lys Gly Arg Ser His Leu Arg
            500                 505                 510 aat gat acc gac gtg gta aac ttt gta agt atg gaa ttt tct ctc act         1584
Asn Asp Thr Asp Val Val Asn Phe Val Ser Met Glu Phe Ser Leu Thr
        515                 520                 525 gat cca aga ttt gag cca cat aaa tgg gaa aaa tac tgc gtt cta gaa         1632
Asp Pro Arg Phe Glu Pro His Lys Trp Glu Lys Tyr Cys Val Leu Glu
530                 535                 540 att gga gac atg ctc cta agg act gct gta ggt caa gtg tca aga ccc         1680
Ile Gly Asp Met Leu Leu Arg Thr Ala Val Gly Gln Val Ser Arg Pro
545                 550                 555                 560 atg ttt ttg tat gta agg aca aat gga acc tct aaa att aaa atg aaa         1728
Met Phe Leu Tyr Val Arg Thr Asn Gly Thr Ser Lys Ile Lys Met Lys
            565                 570                 575 tgg gga atg gaa atg aga cgc tgc ctc ctt cag tct ctg caa cag att         1776
Trp Gly Met Glu Met Arg Arg Cys Leu Leu Gln Ser Leu Gln Gln Ile
            580                 585                 590 gaa agc atg atc gaa gct gag tcc tca gtc aaa gaa aag gac atg acc         1824
Glu Ser Met Ile Glu Ala Glu Ser Ser Val Lys Glu Lys Asp Met Thr
        595                 600                 605 aaa gaa ttc ttt gag aac aaa tca gag aca tgg cct ata gga gag tcc         1872
Lys Glu Phe Phe Glu Asn Lys Ser Glu Thr Trp Pro Ile Gly Glu Ser
610                 615                 620 ccc aaa gga gtg gaa gag ggc tca atc ggg aag gtt tgc agg acc tta         1920
Pro Lys Gly Val Glu Glu Gly Ser Ile Gly Lys Val Cys Arg Thr Leu
625                 630                 635                 640 tta gca aar tct gtg ttt aac agt ttg tat gca tct cca caa ctg gaa         1968
Leu Ala Lys Ser Val Phe Asn Ser Leu Tyr Ala Ser Pro Gln Leu Glu
            645                 650                 655
```

```
ggg ttt tca gct gaa tct agg aaa tta ctt ctc att gtt cag gcc ctt    2016
Gly Phe Ser Ala Glu Ser Arg Lys Leu Leu Leu Ile Val Gln Ala Leu
        660                 665                 670 agg gat aac ctg gaa cct gga acc ttt gat att ggg ggg tta tat gaa    2064
Arg Asp Asn Leu Glu Pro Gly Thr Phe Asp Ile Gly Gly Leu Tyr Glu
    675                 680                 685 tca att gag gag tgc ctg att aat gat ccc tgg gtt ttg ctc aat gca    2112
Ser Ile Glu Glu Cys Leu Ile Asn Asp Pro Trp Val Leu Leu Asn Ala
690                 695                 700 tct tgg ttc aac tcc ttc ctt aca cat gca ctg aag                    2148
Ser Trp Phe Asn Ser Phe Leu Thr His Ala Leu Lys
705                 710                 715

<210> SEQ ID NO 103
<211> LENGTH: 716
<212> TYPE: PRT
<213> ORGANISM: Equine influenza virus H3N8

<400> SEQUENCE: 103

Met Glu Asp Phe Val Arg G

-continued

```
            290                 295                 300
Tyr Asp Ala Ile Lys Cys Met Lys Thr Phe Phe Gly Trp Lys Glu Pro
305                 310                 315                 320

Ser Val Val Lys Pro His Glu Lys Gly Ile Asn Pro Asn Tyr Leu Gln
                325                 330                 335

Ala Trp Lys Gln Val Leu Ala Glu Leu Gln Asp Leu Glu Asn Glu Glu
                340                 345                 350

Lys Thr Pro Lys Thr Lys Asn Met Lys Lys Thr Ser Gln Leu Lys Trp
            355                 360                 365

Ala Leu Gly Glu Asn Met Ala Pro Glu Lys Val Asp Phe Glu Asp Cys
370                 375                 380

Lys Asp Ile Asn Asp Leu Lys Gln Tyr Asp Ser Asp Glu Pro Glu Thr
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Ile
                420                 425                 430

Ala Pro Ile Glu Tyr Ile Ala Ser Met Arg Arg Asn Tyr Phe Thr Ala
            435                 440                 445

Glu Val Ser His Cys Arg Ala Thr Glu Tyr Ile Met Lys Gly Val Tyr
        450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Phe Glu Pro His Lys Trp Glu Lys Tyr Cys Val Leu Glu
        530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
        610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Ile Val Gln Ala Leu
            660                 665                 670

Arg Asp Asn Leu Glu Pro Gly Thr Phe Asp Ile Gly Gly Leu Tyr Glu
            675                 680                 685

Ser Ile Glu Glu Cys Leu Ile Asn Asp Pro Trp Val Leu Leu Asn Ala
        690                 695                 700

Ser Trp Phe Asn Ser Phe Leu Thr His Ala Leu Lys
705                 710                 715
```

<210> SEQ ID NO 104
<211> LENGTH: 738
<212> TYPE: DNA
<213> ORGANISM: Equine influenza virus H3N8
<220> FEATURE:
<221> NAME/KEY: CDS
<222> LOCATION: (1)..(738)

<400> SEQUENCE: 104

| | | | | | | | | | | | | | | | | |
|---|---|---|---|---|---|---|---|---|---|---|---|---|---|---|---|---|
| agc | aaa | agc | agg | gta | gat | aat | cac | tca | ctg | agt | gac | atc | aaa | atc | atg | 48 |
| Ser | Lys | Ser | Arg | Val | Asp | Asn | His | Ser | Leu | Ser | Asp | Ile | Lys | Ile | Met | |
| 1 | | | | 5 | | | | | 10 | | | | | 15 | | |
| gcg | tct | caa | ggc | acc | aaa | cga | tct | tat | gag | cag | atg | gaa | act | gat | ggg | 96 |
| Ala | Ser | Gln | Gly | Thr | Lys | Arg | Ser | Tyr | Glu | Gln | Met | Glu | Thr | Asp | Gly | |
| | | | 20 | | | | | 25 | | | | | 30 | | | |
| gaa | cgc | caa | aat | gca | act | gaa | atc | aga | gca | tct | gtc | gga | agg | atg | gtg | 144 |
| Glu | Arg | Gln | Asn | Ala | Thr | Glu | Ile | Arg | Ala | Ser | Val | Gly | Arg | Met | Val | |
| | | | 35 | | | | | 40 | | | | | 45 | | | |
| gga | gga | atc | ggt | cgg | ttt | tat | gtt | cag | atg | tgt | act | gag | ctt | aaa | cta | 192 |
| Gly | Gly | Ile | Gly | Arg | Phe | Tyr | Val | Gln | Met | Cys | Thr | Glu | Leu | Lys | Leu | |
| | 50 | | | | | 55 | | | | | 60 | | | | | |
| aac | gac | cat | gaa | ggg | cgg | ctg | att | cag | aac | agc | ata | aca | ata | gaa | agg | 240 |
| Asn | Asp | His | Glu | Gly | Arg | Leu | Ile | Gln | Asn | Ser | Ile | Thr | Ile | Glu | Arg | |
| 65 | | | | | 70 | | | | | 75 | | | | | 80 | |
| atg | gta | ctt | tcg | gca | ttc | gac | gaa | aga | aga | aac | aag | tac | ctc | gag | gag | 288 |
| Met | Val | Leu | Ser | Ala | Phe | Asp | Glu | Arg | Arg | Asn | Lys | Tyr | Leu | Glu | Glu | |
| | | | | 85 | | | | | 90 | | | | | 95 | | |
| cat | ccc | agt | gct | ggg | aaa | gac | cct | aag | aaa | acg | gga | ggc | ccg | ata | tac | 336 |
| His | Pro | Ser | Ala | Gly | Lys | Asp | Pro | Lys | Lys | Thr | Gly | Gly | Pro | Ile | Tyr | |
| | | | 100 | | | | | 105 | | | | | 110 | | | |
| aga | agg | aaa | gat | ggg | aaa | tgg | atg | aga | gaa | ctc | atc | ctc | cat | gat | aaa | 384 |
| Arg | Arg | Lys | Asp | Gly | Lys | Trp | Met | Arg | Glu | Leu | Ile | Leu | His | Asp | Lys | |
| | | | 115 | | | | | 120 | | | | | 125 | | | |
| gaa | gaa | atc | atg | agg | atc | tgg | cgt | cag | gcc | aac | aat | ggt | gaa | gac | gct | 432 |
| Glu | Glu | Ile | Met | Arg | Ile | Trp | Arg | Gln | Ala | Asn | Asn | Gly | Glu | Asp | Ala | |
| | 130 | | | | | 135 | | | | | 140 | | | | | |
| act | gct | ggt | ctt | act | cat | atg | atg | atc | tgg | cac | tcc | aat | ctc | aat | gac | 480 |
| Thr | Ala | Gly | Leu | Thr | His | Met | Met | Ile | Trp | His | Ser | Asn | Leu | Asn | Asp | |
| 145 | | | | | 150 | | | | | 155 | | | | | 160 | |
| acc | aca | tac | cac | aga | aca | agg | gct | ctt | gtt | cgg | act | ggg | atg | gat | ccc | 528 |
| Thr | Thr | Tyr | His | Arg | Thr | Arg | Ala | Leu | Val | Arg | Thr | Gly | Met | Asp | Pro | |
| | | | | 165 | | | | | 170 | | | | | 175 | | |
| aga | atg | tgc | tct | ctg | atg | caa | gga | tca | acc | ctc | cca | cgg | aga | tct | gga | 576 |
| Arg | Met | Cys | Ser | Leu | Met | Gln | Gly | Ser | Thr | Leu | Pro | Arg | Arg | Ser | Gly | |
| | | | 180 | | | | | 185 | | | | | 190 | | | |
| gct | gct | ggt | gct | gca | gta | aaa | ggt | gtt | gga | aca | atg | gta | atg | gaa | ctc | 624 |
| Ala | Ala | Gly | Ala | Ala | Val | Lys | Gly | Val | Gly | Thr | Met | Val | Met | Glu | Leu | |
| | | | 195 | | | | | 200 | | | | | 205 | | | |
| atc | aga | atg | atc | aaa | cgc | ggg | ata | aat | gat | cga | aat | ttc | tgg | aga | ggt | 672 |
| Ile | Arg | Met | Ile | Lys | Arg | Gly | Ile | Asn | Asp | Arg | Asn | Phe | Trp | Arg | Gly | |
| | 210 | | | | | 215 | | | | | 220 | | | | | |
| gaa | aat | ggt | cga | aga | acc | aga | att | gcc | tat | gaa | aga | atg | tgc | aat | atc | 720 |
| Glu | Asn | Gly | Arg | Arg | Thr | Arg | Ile | Ala | Tyr | Glu | Arg | Met | Cys | Asn | Ile | |
| 225 | | | | | 230 | | | | | 235 | | | | | 240 | |
| ctc | aaa | ggg | aaa | ttt | cag | | | | | | | | | | | 738 |
| Leu | Lys | Gly | Lys | Phe | Gln | | | | | | | | | | | |
| | | | | 245 | | | | | | | | | | | | |

<210> SEQ ID NO 105
<211> LENGTH: 246

-continued

```
<212> TYPE: PRT
<213> ORGANISM: Equine influenza virus H3N8

<400> SEQUENCE: 105

Ser Lys Ser Arg Val Asp Asn His Ser Leu Ser Asp Ile Lys Ile Met
1               5                   10                  15

Ala Ser Gln Gly Thr Lys Arg Ser Tyr Glu Gln Met Glu Thr Asp Gly
            20                  25                  30

Glu Arg Gln Asn Ala Thr Glu Ile Arg Ala Ser Val Gly Arg Met Val
        35                  40                  45

Gly Gly Ile Gly Arg Phe Tyr Val Gln Met Cys Thr Glu Leu Lys Leu
    50                  55                  60

Asn Asp His Glu Gly Arg Leu Ile Gln Asn Ser Ile Thr Ile Glu Arg
65                  70                  75                  80

Met Val Leu Ser Ala Phe Asp Glu Arg Arg Asn Lys Tyr Leu Glu Glu
                85                  90                  95

His Pro Ser Ala Gly Lys Asp Pro Lys Lys Thr Gly Gly Pro Ile Tyr
            100                 105                 110

Arg Arg Lys Asp Gly Lys Trp Met Arg Glu Leu Ile Leu His Asp Lys
        115                 120                 125

Glu Glu Ile Met Arg Ile Trp Arg Gln Ala Asn Asn Gly Glu Asp Ala
    130                 135                 140

Thr Ala Gly Leu Thr His Met Met Ile Trp His Ser Asn Leu Asn Asp
145                 150                 155                 160

Thr Thr Tyr His Arg Thr Arg Ala Leu Val Arg Thr Gly Met Asp Pro
                165                 170                 175

Arg Met Cys Ser Leu Met Gln Gly Ser Thr Leu Pro Arg Arg Ser Gly
            180                 185                 190

Ala Ala Gly Ala Ala Val Lys Gly Val Gly Thr Met Val Met Glu Leu
        195                 200                 205

Ile Arg Met Ile Lys Arg Gly Ile Asn Asp Arg Asn Phe Trp Arg Gly
    210                 215                 220

Glu Asn Gly Arg Arg Thr Arg Ile Ala Tyr Glu Arg Met Cys Asn Ile
225                 230                 235                 240

Leu Lys Gly Lys Phe Gln
                245

<210> SEQ ID NO 106
<211> LENGTH: 693
<212> TYPE: DNA
<213> ORGANISM: Equine influenza virus H3N8
<220> FEATURE:
<221> NAME/KEY: CDS
<222> LOCATION: (1)..(693)

<400> SEQUENCE: 106 atg gcg tct caa ggc acc aaa cga tct tat gag cag atg gaa act gat      48
Met Ala Ser Gln Gly Thr Lys Arg Ser Tyr Glu Gln Met Glu Thr Asp
1               5                   10                  15 ggg gaa cgc caa aat gca act gaa atc aga gca tct gtc gga agg atg      96
Gly Glu Arg Gln Asn Ala Thr Glu Ile Arg Ala Ser Val Gly Arg Met
            20                  25                  30 gtg gga gga atc ggt cgg ttt tat gtt cag atg tgt act gag ctt aaa     144
Val Gly Gly Ile Gly Arg Phe Tyr Val Gln Met Cys Thr Glu Leu Lys
        35                  40                  45 cta aac gac cat gaa ggg cgg ctg att cag aac agc ata aca ata gaa     192
Leu Asn Asp His Glu Gly Arg Leu Ile Gln Asn Ser Ile Thr Ile Glu
    50                  55                  60
```

```
agg atg gta ctt tcg gca ttc gac gaa aga aga aac aag tac ctc gag        240
Arg Met Val Leu Ser Ala Phe Asp Glu Arg Arg Asn Lys Tyr Leu Glu
 65              70                  75                  80 gag cat ccc agt gct ggg aaa gac cct aag aaa acg gga ggc ccg ata        288
Glu His Pro Ser Ala Gly Lys Asp Pro Lys Lys Thr Gly Gly Pro Ile
                 85                  90                  95 tac aga agg aaa gat ggg aaa tgg atg aga gaa ctc atc ctc cat gat        336
Tyr Arg Arg Lys Asp Gly Lys Trp Met Arg Glu Leu Ile Leu His Asp
                100                 105                 110 aaa gaa gaa atc atg agg atc tgg cgt cag gcc aac aat ggt gaa gac        384
Lys Glu Glu Ile Met Arg Ile Trp Arg Gln Ala Asn Asn Gly Glu Asp
            115                 120                 125 gct act gct ggt ctt act cat atg atg atc tgg cac tcc aat ctc aat        432
Ala Thr Ala Gly Leu Thr His Met Met Ile Trp His Ser Asn Leu Asn
130                 135                 140 gac acc aca tac cac aga aca agg gct ctt gtt cgg act ggg atg gat        480
Asp Thr Thr Tyr His Arg Thr Arg Ala Leu Val Arg Thr Gly Met Asp
145                 150                 155                 160 ccc aga atg tgc tct ctg atg caa gga tca acc ctc cca cgg aga tct        528
Pro Arg Met Cys Ser Leu Met Gln Gly Ser Thr Leu Pro Arg Arg Ser
                165                 170                 175 gga gct gct ggt gct gca gta aaa ggt gtt gga aca atg gta atg gaa        576
Gly Ala Ala Gly Ala Ala Val Lys Gly Val Gly Thr Met Val Met Glu
            180                 185                 190 ctc atc aga atg atc aaa cgc ggg ata aat gat cga aat ttc tgg aga        624
Leu Ile Arg Met Ile Lys Arg Gly Ile Asn Asp Arg Asn Phe Trp Arg
        195                 200                 205 ggt gaa aat ggt cga aga acc aga att gcc tat gaa aga atg tgc aat        672
Gly Glu Asn Gly Arg Arg Thr Arg Ile Ala Tyr Glu Arg Met Cys Asn
210                 215                 220 atc ctc aaa ggg aaa ttt cag                                            693
Ile Leu Lys Gly Lys Phe Gln
225                 230

<210> SEQ ID NO 107
<211> LENGTH: 231
<212> TYPE: PRT
<213> ORGANISM: Equine influenza virus H3N8

<400> SEQUENCE: 107

Met Ala Ser Gln Gly Thr Lys Arg Ser Tyr Glu Gln Met Glu Thr Asp
 1               5                  10                  15

Gly Glu Arg Gln Asn Ala Thr Glu Ile Arg Ala Ser Val Gly Arg Met
                20                  25                  30

Val Gly Gly Ile Gly Arg Phe Tyr Val Gln Met Cys Thr Glu Leu Lys
            35                  40                  45

Leu Asn Asp His Glu Gly Arg Leu Ile Gln Asn Ser Ile Thr Ile Glu
 50                  55                  60

Arg Met Val Leu Ser Ala Phe Asp Glu Arg Arg Asn Lys Tyr Leu Glu
 65              70                  75                  80

Glu His Pro Ser Ala Gly Lys Asp Pro Lys Lys Thr Gly Gly Pro Ile
                 85                  90                  95

Tyr Arg Arg Lys Asp Gly Lys Trp Met Arg Glu Leu Ile Leu His Asp
                100                 105                 110

Lys Glu Glu Ile Met Arg Ile Trp Arg Gln Ala Asn Asn Gly Glu Asp
            115                 120                 125

Ala Thr Ala Gly Leu Thr His Met Met Ile Trp His Ser Asn Leu Asn
130                 135                 140
```

```
Asp Thr Thr Tyr His Arg Thr Arg Ala Leu Val Arg Thr Gly Met Asp
145                 150                 155                 160

Pro Arg Met Cys Ser Leu Met Gln Gly Ser Thr Leu Pro Arg Ser
            165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
        210                 215                 220

Ile Leu Lys Gly Lys Phe Gln
225                 230

<210> SEQ ID NO 108
<211> LENGTH: 738
<212> TYPE: DNA
<213> ORGANISM: Equine influenza virus H3N8
<220> FEATURE:
<221> NAME/KEY: CDS
<222> LOCATION: (1)..(738)

<400> SEQUENCE: 108 agc aaa agc agg gta gat aat cac tca ctg agt gac atc aaa atc atg      48
Ser Lys Ser Arg Val Asp Asn His Ser Leu Ser Asp Ile Lys Ile Met
1               5                   10                  15 gcg tct caa ggc acc aaa cga tct tat gag cag atg gaa act gat ggg      96
Ala Ser Gln Gly Thr Lys Arg Ser Tyr Glu Gln Met Glu Thr Asp Gly
            20                  25                  30 gaa cgc caa aat gca act gaa atc aga gca tct gtc gga agg atg gtg     144
Glu Arg Gln Asn Ala Thr Glu Ile Arg Ala Ser Val Gly Arg Met Val
        35                  40                  45 gga gga atc ggt cgg ttt tat gtt cag atg tgt act gag ctt aaa cta     192
Gly Gly Ile Gly Arg Phe Tyr Val Gln Met Cys Thr Glu Leu Lys Leu
    50                  55                  60 aac gac cat gaa ggg cgg ctg att cag aac agc ata aca ata gaa agg     240
Asn Asp His Glu Gly Arg Leu Ile Gln Asn Ser Ile Thr Ile Glu Arg
65                  70                  75                  80 atg gta ctt tcg gca ttc gac gaa aga aga aac aag tac ctc gag gag     288
Met Val Leu Ser Ala Phe Asp Glu Arg Arg Asn Lys Tyr Leu Glu Glu
                85                  90                  95 cat ccc agt gct ggg aaa gac cct aag aaa acg gga ggc ccg ata tac     336
His Pro Ser Ala Gly Lys Asp Pro Lys Lys Thr Gly Gly Pro Ile Tyr
            100                 105                 110 aga agg aaa gat ggg aaa tgg atg aga gaa ctc atc ctc cat gat aaa     384
Arg Arg Lys Asp Gly Lys Trp Met Arg Glu Leu Ile Leu His Asp Lys
        115                 120                 125 gaa gaa atc atg agg atc tgg cgt cag gcc aac aat ggt gaa gac gct     432
Glu Glu Ile Met Arg Ile Trp Arg Gln Ala Asn Asn Gly Glu Asp Ala
    130                 135                 140 act gct ggt ctt act cat atg atg atc tgg cac tcc aat ctc aat gac     480
Thr Ala Gly Leu Thr His Met Met Ile Trp His Ser Asn Leu Asn Asp
145                 150                 155                 160 acc aca tac caa aga aca agg gct ctt gtt cgg act ggg atg gat ccc     528
Thr Thr Tyr Gln Arg Thr Arg Ala Leu Val Arg Thr Gly Met Asp Pro
                165                 170                 175 aga atg tgc tct ctg atg caa gga tca acc ctc cca cgg aga tct gga     576
Arg Met Cys Ser Leu Met Gln Gly Ser Thr Leu Pro Arg Arg Ser Gly
            180                 185                 190 gct gct ggt gct gca gta aaa ggt gtt gga aca atg gta atg gaa ctc     624
Ala Ala Gly Ala Ala Val Lys Gly Val Gly Thr Met Val Met Glu Leu
```

| | | | | | | | | | | | | |
|---|---|---|---|---|---|---|---|---|---|---|---|---|
| Ala | Ala | Gly | Ala | Ala | Val | Lys | Gly | Val | Gly | Thr | Met | Val | Met | Glu | Leu |
| | | 195 | | | | 200 | | | | | 205 | |

```
atc aga atg atc aaa cgc ggg ata aat gat cga aat ttc tgg aga ggt     672
Ile Arg Met Ile Lys Arg Gly Ile Asn Asp Arg Asn Phe Trp Arg Gly
210                 215                 220 gaa aat ggt cga aga acc aga att gcc tat gaa aga atg tgc aat atc     720
Glu Asn Gly Arg Arg Thr Arg Ile Ala Tyr Glu Arg Met Cys Asn Ile
225                 230                 235                 240 ctc aaa ggg aaa ttt cag                                             738
Leu Lys Gly Lys Phe Gln
            245
```

<210> SEQ ID NO 109
<211> LENGTH: 246
<212> TYPE: PRT
<213> ORGANISM: Equine influenza virus H3N8

<400> SEQUENCE: 109

Ser Lys Ser Arg Val Asp Asn His Ser Leu Ser Asp Ile Lys Ile Met
1               5                   10                  15

Ala Ser Gln Gly Thr Lys Arg Ser Tyr Glu Gln Met Glu Thr Asp Gly
            20                  25                  30

Glu Arg Gln Asn Ala Thr Glu Ile Arg Ala Ser Val Gly Arg Met Val
        35                  40                  45

Gly Gly Ile Gly Arg Phe Tyr Val Gln Met Cys Thr Glu Leu Lys Leu
    50                  55                  60

Asn Asp His Glu Gly Arg Leu Ile Gln Asn Ser Ile Thr Ile Glu Arg
65                  70                  75                  80

Met Val Leu Ser Ala Phe Asp Glu Arg Arg Asn Lys Tyr Leu Glu Glu
                85                  90                  95

His Pro Ser Ala Gly Lys Asp Pro Lys Lys Thr Gly Gly Pro Ile Tyr
            100                 105                 110

Arg Arg Lys Asp Gly Lys Trp Met Arg Glu Leu Ile Leu His Asp Lys
        115                 120                 125

Glu Glu Ile Met Arg Ile Trp Arg Gln Ala Asn Asn Gly Glu Asp Ala
    130                 135                 140

Thr Ala Gly Leu Thr His Met Met Ile Trp His Ser Asn Leu Asn Asp
145                 150                 155                 160

Thr Thr Tyr Gln Arg Thr Arg Ala Leu Val Arg Thr Gly Met Asp Pro
                165                 170                 175

Arg Met Cys Ser Leu Met Gln Gly Ser Thr Leu Pro Arg Arg Ser Gly
            180                 185                 190

Ala Ala Gly Ala Ala Val Lys Gly Val Gly Thr Met Val Met Glu Leu
        195                 200                 205

Ile Arg Met Ile Lys Arg Gly Ile Asn Asp Arg Asn Phe Trp Arg Gly
    210                 215                 220

Glu Asn Gly Arg Arg Thr Arg Ile Ala Tyr Glu Arg Met Cys Asn Ile
225                 230                 235                 240

Leu Lys Gly Lys Phe Gln
            245

<210> SEQ ID NO 110
<211> LENGTH: 693
<212> TYPE: DNA
<213> ORGANISM: Equine influenza virus H3N8
<220> FEATURE:
<221> NAME/KEY: CDS
<222> LOCATION: (1)..(693)

```
<400> SEQUENCE: 110 atg gcg tct caa ggc acc aaa cga tct tat gag cag atg gaa act gat       48
Met Ala Ser Gln Gly Thr Lys Arg Ser Tyr Glu Gln Met Glu Thr Asp
1               5                   10                  15 ggg gaa cgc caa aat gca act gaa atc aga gca tct gtc gga agg atg       96
Gly Glu Arg Gln Asn Ala Thr Glu Ile Arg Ala Ser Val Gly Arg Met
            20                  25                  30 gtg gga gga atc ggt cgg ttt tat gtt cag atg tgt act gag ctt aaa      144
Val Gly Gly Ile Gly Arg Phe Tyr Val Gln Met Cys Thr Glu Leu Lys
        35                  40                  45 cta aac gac cat gaa ggg cgg ctg att cag aac agc ata aca ata gaa      192
Leu Asn Asp His Glu Gly Arg Leu Ile Gln Asn Ser Ile Thr Ile Glu
50                  55                  60 agg atg gta ctt tcg gca ttc gac gaa aga aga aac aag tac ctc gag      240
Arg Met Val Leu Ser Ala Phe Asp Glu Arg Arg Asn Lys Tyr Leu Glu
65                  70                  75                  80 gag cat ccc agt gct ggg aaa gac cct aag aaa acg gga ggc ccg ata      288
Glu His Pro Ser Ala Gly Lys Asp Pro Lys Lys Thr Gly Gly Pro Ile
                85                  90                  95 tac aga agg aaa gat ggg aaa tgg atg aga gaa ctc atc ctc cat gat      336
Tyr Arg Arg Lys Asp Gly Lys Trp Met Arg Glu Leu Ile Leu His Asp
            100                 105                 110 aaa gaa gaa atc atg agg atc tgg cgt cag gcc aac aat ggt gaa gac      384
Lys Glu Glu Ile Met Arg Ile Trp Arg Gln Ala Asn Asn Gly Glu Asp
        115                 120                 125 gct act gct ggt ctt act cat atg atg atc tgg cac tcc aat ctc aat      432
Ala Thr Ala Gly Leu Thr His Met Met Ile Trp His Ser Asn Leu Asn
130                 135                 140 gac acc aca tac caa aga aca agg gct ctt gtt cgg act ggg atg gat      480
Asp Thr Thr Tyr Gln Arg Thr Arg Ala Leu Val Arg Thr Gly Met Asp
145                 150                 155                 160 ccc aga atg tgc tct ctg atg caa gga tca acc ctc cca cgg aga tct      528
Pro Arg Met Cys Ser Leu Met Gln Gly Ser Thr Leu Pro Arg Arg Ser
                165                 170                 175 gga gct gct ggt gct gca gta aaa ggt gtt gga aca atg gta atg gaa      576
Gly Ala Ala Gly Ala Ala Val Lys Gly Val Gly Thr Met Val Met Glu
            180                 185                 190 ctc atc aga atg atc aaa cgc ggg ata aat gat cga aat ttc tgg aga      624
Leu Ile Arg Met Ile Lys Arg Gly Ile Asn Asp Arg Asn Phe Trp Arg
        195                 200                 205 ggt gaa aat ggt cga aga acc aga att gcc tat gaa aga atg tgc aat      672
Gly Glu Asn Gly Arg Arg Thr Arg Ile Ala Tyr Glu Arg Met Cys Asn
    210                 215                 220 atc ctc aaa ggg aaa ttt cag                                          693
Ile Leu Lys Gly Lys Phe Gln
225                 230

<210> SEQ ID NO 111
<211> LENGTH: 231
<212> TYPE: PRT
<213> ORGANISM: Equine influenza virus H3N8

<400> SEQUENCE: 111

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45
```

-continued

```
Leu Asn Asp His Glu Gly Arg Leu Ile Gln Asn Ser Ile Thr Ile Glu
     50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Lys Asp Gly Lys Trp Met Arg Glu Leu Ile Leu His Asp
                100                 105                 110

Lys Glu Glu Ile Met Arg Ile Trp Arg Gln Ala Asn Asn Gly Glu Asp
                115                 120                 125

Ala Thr Ala Gly Leu Thr His Met Met Ile Trp His Ser Asn Leu Asn
130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
                195                 200                 205

Gly Glu Asn Gly Arg Arg Thr Arg Ile Ala Tyr Glu Arg Met Cys Asn
                210                 215                 220

Ile Leu Lys Gly Lys Phe Gln
225                 230

<210> SEQ ID NO 112
<211> LENGTH: 245
<212> TYPE: PRT
<213> ORGANISM: Equine influenza virus H3N8

<400> SEQUENCE: 112

Ser Lys Ser Arg Val Asp Asn His Ser Leu Ser Asp Ile Lys Ile Met
 1               5                  10                  15

Ala Ser Gln Gly Thr Lys Arg Ser Tyr Glu Gln Met Glu Thr Asp Gly
                20                  25                  30

Glu Arg Gln Asn Ala Thr Glu Ile Arg Ala Ser Val Gly Arg Met Val
             35                  40                  45

Val Gly Ile Gly Arg Phe Tyr Val Gln Met Cys Thr Glu Leu Lys Leu
 50                  55                  60

Asn Asp His Glu Gly Arg Leu Ile Gln Asn Ser Met Thr Ile Glu Arg
 65                  70                  75                  80

Met Val Leu Ser Ala Phe Asp Glu Arg Arg Asn Lys Tyr Leu Glu Glu
                 85                  90                  95

His Pro Ser Ala Gly Lys Asp Pro Lys Lys Thr Gly Gly Pro Ile Tyr
                100                 105                 110

Arg Arg Lys Asp Gly Lys Trp Met Arg Glu Leu Ile Leu His Asp Lys
                115                 120                 125

Glu Glu Ile Met Arg Ile Trp Arg Gln Ala Asn Asn Gly Glu Asp Ala
                130                 135                 140

Thr Ala Gly Leu Thr His Met Met Ile Trp His Ser Asn Leu Asn Asp
145                 150                 155                 160

Thr Thr Tyr Gln Arg Thr Arg Ala Leu Val Arg Thr Gly Met Asp Pro
                165                 170                 175

Arg Met Cys Ser Met Met Gln Gly Ser Thr Leu Pro Arg Arg Ser Gly
```

```
                    180             185              190
Ala Ala Gly Ala Ala Val Lys Gly Val Gly Thr Met Val Met Glu Leu
        195             200             205

Ile Arg Met Ile Lys Arg Gly Ile Asn Asp Arg Asn Phe Trp Arg Ser
    210              215             220

Glu Asn Gly Arg Arg Thr Arg Ile Ala Tyr Glu Arg Met Cys Asn Ile
225             230             235             240

Leu Lys Gly Lys Phe
            245

<210> SEQ ID NO 113
<211> LENGTH: 690
<212> TYPE: DNA
<213> ORGANISM: Equine influenza virus H3N8
<220> FEATURE:
<221> NAME/KEY: CDS
<222> LOCATION: (1)..(690)

<400> SEQUENCE: 113 atg gcg tct caa ggc acc aaa cga tct tat gag cag atg gaa act gat     48
Met Ala Ser Gln Gly Thr Lys Arg Ser Tyr Glu Gln Met Glu Thr Asp
1               5                   10                  15 ggg gaa cgc caa aat gca act gaa atc aga gca tct gtc gga agg atg     96
Gly Glu Arg Gln Asn Ala Thr Glu Ile Arg Ala Ser Val Gly Arg Met
            20                  25                  30 gtg gta gga atc ggt cgg ttt tat gtt cag atg tgt act gag ctt aaa    144
Val Val Gly Ile Gly Arg Phe Tyr Val Gln Met Cys Thr Glu Leu Lys
        35                  40                  45 cta aac gac cat gaa ggg cgg ctg att cag aac agc atg aca ata gaa    192
Leu Asn Asp His Glu Gly Arg Leu Ile Gln Asn Ser Met Thr Ile Glu
    50                  55                  60 agg atg gta ctt tcg gca ttc gac gaa aga aga aac aag tac ctc gag    240
Arg Met Val Leu Ser Ala Phe Asp Glu Arg Arg Asn Lys Tyr Leu Glu
65                  70                  75                  80 gag cat ccc agt gct ggg aaa gac cct aag aaa acg gga ggc ccg ata    288
Glu His Pro Ser Ala Gly Lys Asp Pro Lys Lys Thr Gly Gly Pro Ile
                85                  90                  95 tac aga agg aaa gat ggg aaa tgg atg aga gaa ctc atc ctc cat gat    336
Tyr Arg Arg Lys Asp Gly Lys Trp Met Arg Glu Leu Ile Leu His Asp
            100                 105                 110 aaa gaa gaa atc atg agg atc tgg cgt cag gcc aac aat ggt gaa gac    384
Lys Glu Glu Ile Met Arg Ile Trp Arg Gln Ala Asn Asn Gly Glu Asp
        115                 120                 125 gct act gct ggt ctt act cat atg atg atc tgg cac tcc aat ctc aat    432
Ala Thr Ala Gly Leu Thr His Met Met Ile Trp His Ser Asn Leu Asn
    130                 135                 140 gac acc aca tac caa aga aca agg gct ctt gtt cgg act ggg atg gat    480
Asp Thr Thr Tyr Gln Arg Thr Arg Ala Leu Val Arg Thr Gly Met Asp
145                 150                 155                 160 ccc aga atg tgc tct atg atg caa gga tca acc ctc cca cgg aga tct    528
Pro Arg Met Cys Ser Met Met Gln Gly Ser Thr Leu Pro Arg Arg Ser
                165                 170                 175 gga gct gct ggt gct gca gta aaa ggt gtt gga aca atg gta atg gaa    576
Gly Ala Ala Gly Ala Ala Val Lys Gly Val Gly Thr Met Val Met Glu
            180                 185                 190 ctc atc aga atg atc aaa cgc gga ata aat gat cga aat ttc tgg aga    624
Leu Ile Arg Met Ile Lys Arg Gly Ile Asn Asp Arg Asn Phe Trp Arg
        195                 200                 205 agt gaa aat ggt cga aga acc aga att gcc tat gaa aga atg tgc aat    672
Ser Glu Asn Gly Arg Arg Thr Arg Ile Ala Tyr Glu Arg Met Cys Asn
```

```
        210                 215                 220
atc ctc aaa ggg aaa ttt                                              690
Ile Leu Lys Gly Lys Phe
225                 230
```

<210> SEQ ID NO 114
<211> LENGTH: 230
<212> TYPE: PRT
<213> ORGANISM: Equine influenza virus H3N8

<400> SEQUENCE: 114

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
                20                  25                  30

Val Val Gly Ile Gly Arg Phe Tyr Val Gln Met Cys Thr Glu Leu Lys
            35                  40                  45

Leu Asn Asp His Glu Gly Arg Leu Ile Gln Asn Ser Met Thr Ile Glu
        50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Met Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Ser Glu Asn Gly Arg Arg Thr Arg Ile Ala Tyr Glu Arg Met Cys Asn
    210                 215                 220

Ile Leu Lys Gly Lys Phe
225                 230
```

<210> SEQ ID NO 115
<211> LENGTH: 735
<212> TYPE: DNA
<213> ORGANISM: Equine influenza virus H3N8
<220> FEATURE:
<221> NAME/KEY: CDS
<222> LOCATION: (1)..(735)

<400> SEQUENCE: 115

```
agc aaa agc agg gta gat aat cac tca ctg agt gac atc aaa atc atg    48
Ser Lys Ser Arg Val Asp Asn His Ser Leu Ser Asp Ile Lys Ile Met
1               5                   10                  15 gcg tct caa ggc acc aaa cga tct tat gag cag atg gaa act gat ggg    96
Ala Ser Gln Gly Thr Lys Arg Ser Tyr Glu Gln Met Glu Thr Asp Gly
                20                  25                  30 gaa cgc caa aat gca act gaa atc aga gca tct gtc gga agg atg gtg   144
```

```
                                                              -continued

Glu Arg Gln Asn Ala Thr Glu Ile Arg Ala Ser Val Gly Arg Met Val
        35                  40                  45 gta gga atc ggt cgg ttt tat gtt cag atg tgt act gag ctt aaa cta        192
Val Gly Ile Gly Arg Phe Tyr Val Gln Met Cys Thr Glu Leu Lys Leu
 50                  55                  60 aac gac cat gaa ggg cgg ctg att cag aac agc atg aca ata gaa agg        240
Asn Asp His Glu Gly Arg Leu Ile Gln Asn Ser Met Thr Ile Glu Arg
65                  70                  75                  80 atg gta ctt tcg gca ttc gac gaa aga aga aac aag tac ctc gag gag        288
Met Val Leu Ser Ala Phe Asp Glu Arg Arg Asn Lys Tyr Leu Glu Glu
                85                  90                  95 cat ccc agt gct ggg aaa gac cct aag aaa acg gga ggc ccg ata tac        336
His Pro Ser Ala Gly Lys Asp Pro Lys Lys Thr Gly Gly Pro Ile Tyr
            100                 105                 110 aga agg aaa gat ggg aaa tgg atg aga gaa ctc atc ctc cat gat aaa        384
Arg Arg Lys Asp Gly Lys Trp Met Arg Glu Leu Ile Leu His Asp Lys
        115                 120                 125 gaa gaa atc atg agg atc tgg cgt cag gcc aac aat ggt gaa gac gct        432
Glu Glu Ile Met Arg Ile Trp Arg Gln Ala Asn Asn Gly Glu Asp Ala
    130                 135                 140 act gct ggt ctt act cat atg atg atc tgg cac tcc aat ctc aat gac        480
Thr Ala Gly Leu Thr His Met Met Ile Trp His Ser Asn Leu Asn Asp
145                 150                 155                 160 acc aca tac caa aga aca agg gct ctt gtt cgg act ggg atg gat ccc        528
Thr Thr Tyr Gln Arg Thr Arg Ala Leu Val Arg Thr Gly Met Asp Pro
                165                 170                 175 aga atg tgc tct ctg atg caa gga tca acc ctc cca cgg aga tct gga        576
Arg Met Cys Ser Leu Met Gln Gly Ser Thr Leu Pro Arg Arg Ser Gly
            180                 185                 190 gct gct ggt gct gca gta aaa ggt gtt gga aca atg gta atg gaa ctc        624
Ala Ala Gly Ala Ala Val Lys Gly Val Gly Thr Met Val Met Glu Leu
        195                 200                 205 atc aga atg atc aaa cgc gga ata aat gat cga aat ttc tgg aga agt        672
Ile Arg Met Ile Lys Arg Gly Ile Asn Asp Arg Asn Phe Trp Arg Ser
    210                 215                 220 gaa aat ggt cga aga acc aga att gcc tat gaa aga atg tgc aat atc        720
Glu Asn Gly Arg Arg Thr Arg Ile Ala Tyr Glu Arg Met Cys Asn Ile
225                 230                 235                 240 ctc aaa ggg aaa ttt                                                    735
Leu Lys Gly Lys Phe
                245

<210> SEQ ID NO 116
<211> LENGTH: 245
<212> TYPE: PRT
<213> ORGANISM: Equine influenza virus H3N8

<400> SEQUENCE: 116

Ser Lys Ser Arg Val Asp As

```
                             85                   90                   95
His Pro Ser Ala Gly Lys Asp Pro Lys Lys Thr Gly Gly Pro Ile Tyr
            100                 105                 110

Arg Arg Lys Asp Gly Lys Trp Met Arg Glu Leu Ile Leu His Asp Lys
        115                 120                 125

Glu Glu Ile Met Arg Ile Trp Arg Gln Ala Asn Asn Gly Glu Asp Ala
    130                 135                 140

Thr Ala Gly Leu Thr His Met Met Ile Trp His Ser Asn Leu Asn Asp
145                 150                 155                 160

Thr Thr Tyr Gln Arg Thr Arg Ala Leu Val Arg Thr Gly Met Asp Pro
                165                 170                 175

Arg Met Cys Ser Leu Met Gln Gly Ser Thr Leu Pro Arg Arg Ser Gly
            180                 185                 190

Ala Ala Gly Ala Ala Val Lys Gly Val Gly Thr Met Val Met Glu Leu
        195                 200                 205

Ile Arg Met Ile Lys Arg Gly Ile Asn Asp Arg Asn Phe Trp Arg Ser
    210                 215                 220

Glu Asn Gly Arg Arg Thr Arg Ile Ala Tyr Glu Arg Met Cys Asn Ile
225                 230                 235                 240

Leu Lys Gly Lys Phe
                245

<210> SEQ ID NO 117
<211> LENGTH: 690
<212> TYPE: DNA
<213> ORGANISM: Equine influenza virus H3N8
<220> FEATURE:
<221> NAME/KEY: CDS
<222> LOCATION: (1)..(690)

<400> SEQUENCE: 117 atg gcg tct caa ggc acc aaa cga tct tat gag cag atg gaa act gat        48
Met Ala Ser Gln Gly Thr Lys Arg Ser Tyr Glu Gln Met Glu Thr Asp
1               5                   10                  15 ggg gaa cgc caa aat gca act gaa atc aga gca tct gtc gga agg atg        96
Gly Glu Arg Gln Asn Ala Thr Glu Ile Arg Ala Ser Val Gly Arg Met
            20                  25                  30 gtg gta gga atc ggt cgg ttt tat gtt cag atg tgt act gag ctt aaa       144
Val Val Gly Ile Gly Arg Phe Tyr Val Gln Met Cys Thr Glu Leu Lys
        35                  40                  45 cta aac gac cat gaa ggg cgg ctg att cag aac agc atg aca ata gaa       192
Leu Asn Asp His Glu Gly Arg Leu Ile Gln Asn Ser Met Thr Ile Glu
    50                  55                  60 agg atg gta ctt tcg gca ttc gac gaa aga aga aac aag tac ctc gag       240
Arg Met Val Leu Ser Ala Phe Asp Glu Arg Arg Asn Lys Tyr Leu Glu
65                  70                  75                  80 gag cat ccc agt gct ggg aaa gac cct aag aaa acg gga ggc ccg ata       288
Glu His Pro Ser Ala Gly Lys Asp Pro Lys Lys Thr Gly Gly Pro Ile
                85                  90                  95 tac aga agg aaa gat ggg aaa tgg atg aga gaa ctc atc ctc cat gat       336
Tyr Arg Arg Lys Asp Gly Lys Trp Met Arg Glu Leu Ile Leu His Asp
            100                 105                 110 aaa gaa gaa atc atg agg atc tgg cgt cag gcc aac aat ggt gaa gac       384
Lys Glu Glu Ile Met Arg Ile Trp Arg Gln Ala Asn Asn Gly Glu Asp
        115                 120                 125 gct act gct ggt ctt act cat atg atg atc tgg cac tcc aat ctc aat       432
Ala Thr Ala Gly Leu Thr His Met Met Ile Trp His Ser Asn Leu Asn
    130                 135                 140
```

```
gac acc aca tac caa aga aca agg gct ctt gtt cgg act ggg atg gat    480
Asp Thr Thr Tyr Gln Arg Thr Arg Ala Leu Val Arg Thr Gly Met Asp
145                 150                 155                 160 ccc aga atg tgc tct ctg atg caa gga tca acc ctc cca cgg aga tct    528
Pro Arg Met Cys Ser Leu Met Gln Gly Ser Thr Leu Pro Arg Arg Ser
            165                 170                 175 gga gct gct ggt gct gca gta aaa ggt gtt gga aca atg gta atg gaa    576
Gly Ala Ala Gly Ala Ala Val Lys Gly Val Gly Thr Met Val Met Glu
        180                 185                 190 ctc atc aga atg atc aaa cgc gga ata aat gat cga aat ttc tgg aga    624
Leu Ile Arg Met Ile Lys Arg Gly Ile Asn Asp Arg Asn Phe Trp Arg
    195                 200                 205 agt gaa aat ggt cga aga acc aga att gcc tat gaa aga atg tgc aat    672
Ser Glu Asn Gly Arg Arg Thr Arg Ile Ala Tyr Glu Arg Met Cys Asn
210                 215                 220 atc ctc aaa ggg aaa ttt                                            690
Ile Leu Lys Gly Lys Phe
225             230

<210> SEQ ID NO 118
<211> LENGTH: 230
<212> TYPE: PRT
<213> ORGANISM: Equine influenza virus H3N8

<400> SEQUENCE: 118

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Val Gly Ile Gly Arg Phe Tyr Val Gln Met Cys Thr Glu Leu Lys
        35                  40                  45

Leu Asn Asp His Glu Gly Arg Leu Ile Gln Asn Ser Met Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Ser Glu Asn Gly Arg Arg Thr Arg Ile Ala Tyr Glu Arg Met Cys Asn
    210                 215                 220

Ile Leu Lys Gly Lys Phe
225             230

<210> SEQ ID NO 119
```

<211> LENGTH: 679
<212> TYPE: DNA
<213> ORGANISM: Equine influenza virus H3N8

<400> SEQUENCE: 119

```
atggccttgc agtaaccagt gggtatgact tgagaagga aggatactct ctggttggaa      60
ttgatccttt caaactactc cagaacagcc aaattttcag tctaatcaga ccgaaagaaa     120
acccagcaca aagagccag ttggtgtgga tggcatgcca ttctgcagca tttgaggacc     180
tgagagtttt gaatttcatt agaggaacca agtaatccc aagaggacag ttagcaacca     240
gaggagtgca aattgcttca atgaaaaca tggacaat agattctagc acactcgaac      300
tgagaagcaa atattgggca ataaggacca gaagtggagg aaacaccagt caacagagag     360
catctgcagg acagataagt gtgcaaccta ctttctcagt gcagagaaat cttcccttg     420
aaagagcaac cattatggct gcattcactg gaacactga ggggaggact tccgacatga     480
gaacggaaat cataaggatg atggaaaatg ccaaatcaga agatgtgtct ttccaggggc     540
ggggagtctt cgagctctcg gacgaaaagg caacgaaccc gatcgtgcct tcctttgaca     600
tgagcaatga agggtcttat ttcttcggag acaatgctga ggagtttgac agttaaagaa     660
aaatacccttt gtttctact                                                 679
```

<210> SEQ ID NO 120
<211> LENGTH: 225
<212> TYPE: PRT
<213> ORGANISM: Equine influenza virus H3N8
<220> FEATURE:
<221> NAME/KEY: MISC_FEATURE
<222> LOCATION: (225)..(225)
<223> OTHER INFORMATION: Xaa = unknown

<400> SEQUENCE: 120

```
Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Lys Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln
        115                 120                 125

Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
                165                 170                 175

Phe Gln Gly Arg Gly Val Phe Glu Leu Ser Asp Glu Lys Ala Thr Asn
            180                 185                 190

Pro Ile Val Pro Ser Phe Asp Met Ser Asn Glu Gly Ser Tyr Phe Phe
```

Gly Asp Asn Ala Glu Glu Phe Asp Ser Arg Lys Ile Pro Leu Phe Leu
    210                 215                 220

Xaa
225

<210> SEQ ID NO 121
<211> LENGTH: 656
<212> TYPE: DNA
<213> ORGANISM: Equine influenza virus H3N8

<400> SEQUENCE: 121
atggccttgc agtaaccagt gggtatgact ttgagaagga aggatactct ctggttggaa     60
ttgatccttt caaactactc cagaacagcc aaattttcag tctaatcaga ccgaaagaaa    120
acccagcaca agagccag ttggtgtgga tggcatgcca ttctgcagca tttgaggacc    180
tgagagtttt gaatttcatt agaggaacca agtaatccc aagaggacag ttagcaacca    240
gaggagtgca aattgcttca atgaaaaca tggagacaat agattctagc acactcgaac    300
tgagaagcaa atattggca ataaggacca gaagtggagg aaacaccagt caacagagag    360
catctgcagg acagataagt gtgcaaccta ctttctcagt gcagagaaat cttcccttg    420
aaagagcaac cattatggct gcattcactg ggaacactga ggggaggact tccgacatga    480
gaacggaaat cataaggatg atggaaaatg ccaaatcaga agatgtgtct ttccaggggc    540
ggggagtctt cgagctctcg gacgaaaagg caacgaaccc gatcgtgcct tcctttgaca    600
tgagcaatga agggtcttat ttcttcggag acaatgctga ggagtttgac agttaa       656

<210> SEQ ID NO 122
<211> LENGTH: 217
<212> TYPE: PRT
<213> ORGANISM: Equine influenza virus H3N8

<400> SEQUENCE: 122

Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Lys Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln
        115                 120                 125

Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
                165                 170                 175

-continued

Phe Gln Gly Arg Gly Val Phe Glu Leu Ser Asp Glu Lys Ala Thr Asn
                180                 185                 190

Pro Ile Val Pro Ser Phe Asp Met Ser Asn Glu Gly Ser Tyr Phe Phe
            195                 200                 205

Gly Asp Asn Ala Glu Glu Phe Asp Ser
        210                 215

<210> SEQ ID NO 123
<211> LENGTH: 679
<212> TYPE: DNA
<213> ORGANISM: Equine influenza virus H3N8

<400> SEQUENCE: 123
atggccttgc agtaaccagt gggtatgact tgagaagga aggatactct ctggttggaa        60
ttgatccttt caaactactc cagaacagcc aaattttcag tctaatcaga ccgaaagaaa       120
acccagcaca caggagccag ttggtgtgga tggcatgcca ttctgcagca tttgaggacc       180
tgagagtttt gaatttcatt agaggaacca agtaatccc aagaggacag ttagcaacca       240
gaggagtgca aattgcttca atgaaaaca tggagacaat agattctagc acactcgaac       300
tgagaagcaa atattgggca ataaggacca gaagtggagg aaacaccagt caacagagag       360
catctgcagg acagataagt gtgcaaccta ctttctcagt gcagagaaat cttcccttg       420 aaagagcaac cattatggct gcattcactg gaacactga ggggaggact tccgacatga       480
gaacggaaat cataaggatg atggaaaatg ccaaatcaga agatgtgtct ttccaggggc       540
ggggagtctt cgagctctcg gacgaaaagg caacgaaccc gatcgtgcct tcctttgaca       600
tgagcaatga aggtcttat ttcttcggag acaatgctga ggagtttgac agttaaagaa       660
aaataccctt gtttctact                                                   679

<210> SEQ ID NO 124
<211> LENGTH: 225
<212> TYPE: PRT
<213> ORGANISM: Equine influenza virus H3N8
<220> FEATURE:
<221> NAME/KEY: MISC_FEATURE
<222> LOCATION: (225)..(225)
<223> OTHER INFORMATION: Xaa = unknown

<400> SEQUENCE: 124

Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Arg Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln
        115                 120                 125

Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
            165                 170                 175

Phe Gln Gly Arg Gly Val Phe Glu Leu Ser Asp Glu Lys Ala Thr Asn
        180                 185                 190

Pro Ile Val Pro Ser Phe Asp Met Ser Asn Glu Gly Ser Tyr Phe Phe
    195                 200                 205

Gly Asp Asn Ala Glu Glu Phe Asp Ser Arg Lys Ile Pro Leu Phe Leu
210                 215                 220

Xaa
225

<210> SEQ ID NO 125
<211> LENGTH: 656
<212> TYPE: DNA
<213> ORGANISM: Equine influenza virus H3N8

<400> SEQUENCE: 125
atggccttgc agtaaccagt gggtatgact ttgagaagga aggatactct ctggttggaa      60
ttgatccttt caaactactc cagaacagcc aaattttcag tctaatcaga ccgaaagaaa     120
acccagcaca caggagccag ttggtgtgga tggcatgcca ttctgcagca tttgaggacc     180
tgagagtttt gaatttcatt agaggaacca agtaatccc aagaggacag ttagcaacca     240
gaggagtgca aattgcttca atgaaaaca tggagacaat agattctagc acactcgaac     300
tgagaagcaa atattgggca ataaggacca gaagtggagg aaacaccagt caacagagag     360
catctgcagg acagataagt gtgcaaccta ctttctcagt gcagagaaat cttcccttg     420 aaagagcaac cattatggct gcattcactg gaacactga ggggaggact tccgacatga     480
gaacggaaat cataaggatg atggaaaatg ccaaatcaga gatgtgtct ttccaggggc     540 ggggagtctt cgagctctcg gacgaaaagg caacgaaccc gatcgtgcct tcctttgaca     600
tgagcaatga agggtcttat ttcttcggag acaatgctga ggagtttgac agttaa        656

<210> SEQ ID NO 126
<211> LENGTH: 217
<212> TYPE: PRT
<213> ORGANISM: Equine influenza virus H3N8

<400> SEQUENCE: 126

Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Arg Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln

-continued

```
              115                 120                 125
Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
                165                 170                 175

Phe Gln Gly Arg Gly Val Phe Glu Leu Ser Asp Glu Lys Ala Thr Asn
            180                 185                 190

Pro Ile Val Pro Ser Phe Asp Met Ser Asn Glu Gly Ser Tyr Phe Phe
        195                 200                 205

Gly Asp Asn Ala Glu Glu Phe Asp Ser
    210                 215
```

<210> SEQ ID NO 127
<211> LENGTH: 665
<212> TYPE: DNA
<213> ORGANISM: Equine influenza virus H3N8

<400> SEQUENCE: 127

```
accagtgggt atgactttga gaaggaagga tactctctgg ttggaattga tcctttcaaa      60
ctactccaga acagccaaat tttcagtcta atcagaccga agaaaaccc agcacacagg     120
agccagttgg tgtggatggc atgccattct gcagcatttg aggacctgag agttttgaat     180
ttcattagag gaaccaaagt aatcccaaga ggacagttag caaccagagg agtgcaaatt     240
gcttcaaatg aaaacatgga gacaatagat tctagcacac tcgaactgag aagcaaatat     300
tgggcaataa ggaccagaag tggaggaaac accagtcaac agagagcatc tgcaggacag     360
ataagtgtgc aacctacttt ctcagtgcag agaaatcttc cctttgaaag agcaaccatt     420
atggctgcat tcactgggaa cactgagggg aggacttccg acatgagaac ggaaatcata     480
aggatgatgg aaaatgccaa atcagaagat gtgtctttcc aggggcgggg agtcttcgag     540
ctctcggacg aaaaggcaac gaacccgatc gtgccttcct ttgacatgag caatgaaggg     600
tcttatttct tcggagacaa tgctgaggag tttgacagtt aaagaaaaat acccttgttt     660
ctact                                                                 665
```

<210> SEQ ID NO 128
<211> LENGTH: 221
<212> TYPE: PRT
<213> ORGANISM: Equine influenza virus H3N8
<220> FEATURE:
<221> NAME/KEY: MISC_FEATURE
<222> LOCATION: (221)..(221)
<223> OTHER INFORMATION: Xaa = unknown

<400> SEQUENCE: 128

```
Thr Ser Gly Tyr Asp Phe Glu Lys Glu Gly Tyr Ser Leu Val Gly Ile
1               5                  10                  15

Asp Pro Phe Lys Leu Leu Gln Asn Ser Gln Ile Phe Ser Leu Ile Arg
            20                  25                  30

Pro Lys Glu Asn Pro Ala His Arg Ser Gln Leu Val Trp Met Ala Cys
        35                  40                  45

His Ser Ala Ala Phe Glu Asp Leu Arg Val Leu Asn Phe Ile Arg Gly
    50                  55                  60

Thr Lys Val Ile Pro Arg Gly Gln Leu Ala Thr Arg Gly Val Gln Ile
65                  70                  75                  80
```

```
Ala Ser Asn Glu Asn Met Glu Thr Ile Asp Ser Ser Thr Leu Glu Leu
                85                  90                  95

Arg Ser Lys Tyr Trp Ala Ile Arg Thr Arg Ser Gly Gly Asn Thr Ser
            100                 105                 110

Gln Gln Arg Ala Ser Ala Gly Gln Ile Ser Val Gln Pro Thr Phe Ser
        115                 120                 125

Val Gln Arg Asn Leu Pro Phe Glu Arg Ala Thr Ile Met Ala Ala Phe
    130                 135                 140

Thr Gly Asn Thr Glu Gly Arg Thr Ser Asp Met Arg Thr Glu Ile Ile
145                 150                 155                 160

Arg Met Met Glu Asn Ala Lys Ser Glu Asp Val Ser Phe Gln Gly Arg
                165                 170                 175

Gly Val Phe Glu Leu Ser Asp Glu Lys Ala Thr Asn Pro Ile Val Pro
            180                 185                 190

Ser Phe Asp Met Ser Asn Glu Gly Ser Tyr Phe Phe Gly Asp Asn Ala
        195                 200                 205

Glu Glu Phe Asp Ser Arg Lys Ile Pro Leu Phe Leu Xaa
    210                 215                 220

<210> SEQ ID NO 129
<211> LENGTH: 642
<212> TYPE: DNA
<213> ORGANISM: Equine influenza virus H3N8

<400> SEQUENCE: 129
accagtgggt atgactttga aaggaagga tactctctgg ttggaattga tcctttcaaa      60
ctactccaga acagccaaat tttcagtcta atcagaccga agaaaaccc agcacacagg     120 agccagttgg tgtggatggc atgccattct gcagcatttg aggacctgag agttttgaat     180
ttcattagag gaaccaaagt aatcccaaga ggacagttag caaccagagg agtgcaaatt     240
gcttcaaatg aaaacatgga gacaatagat tctagcacac tcgaactgag aagcaaatat     300
tgggcaataa ggaccagaag tggaggaaac accagtcaac agagagcatc tgcaggacag     360
ataagtgtgc aacctacttt ctcagtgcag agaaatcttc cctttgaaag agcaaccatt     420
atggctgcat tcactgggaa cactgagggg aggacttccg acatgagaac ggaaatcata     480
aggatgatgg aaaatgccaa atcagaagat gtgtctttcc aggggcgggg agtcttcgag     540
ctctcggacg aaaaggcaac gaacccgatc gtgccttcct ttgacatgag caatgaaggg     600
tcttatttct tcggagacaa tgctgaggag tttgacagtt aa                         642

<210> SEQ ID NO 130
<211> LENGTH: 213
<212> TYPE: PRT
<213> ORGANISM: Equine influenza virus H3N8

<400> SEQUENCE: 130

Thr Ser Gly Tyr Asp Phe Glu Lys Glu Gly Tyr Ser Leu Val Gly Ile
1               5                   10                  15

Asp Pro Phe Lys Leu Leu Gln Asn Ser Gln Ile Phe Ser Leu Ile Arg
            20                  25                  30

Pro Lys Glu Asn Pro Ala His Arg Ser Gln Leu Val Trp Met Ala Cys
        35                  40                  45

His Ser Ala Ala Phe Glu Asp Leu Arg Val Leu Asn Phe Ile Arg Gly
    50                  55                  60

Thr Lys Val Ile Pro Arg Gly Gln Leu Ala Thr Arg Gly Val Gln Ile
65                  70                  75                  80
```

-continued

```
Ala Ser Asn Glu Asn Met Glu Thr Ile Asp Ser Ser Thr Leu Glu Leu
             85                  90                  95

Arg Ser Lys Tyr Trp Ala Ile Arg Thr Arg Ser Gly Gly Asn Thr Ser
            100                 105                 110

Gln Gln Arg Ala Ser Ala Gly Gln Ile Ser Val Gln Pro Thr Phe Ser
            115                 120                 125

Val Gln Arg Asn Leu Pro Phe Glu Arg Ala Thr Ile Met Ala Ala Phe
        130                 135                 140

Thr Gly Asn Thr Glu Gly Arg Thr Ser Asp Met Arg Thr Glu Ile Ile
145                 150                 155                 160

Arg Met Met Glu Asn Ala Lys Ser Glu Asp Val Ser Phe Gln Gly Arg
                165                 170                 175

Gly Val Phe Glu Leu Ser Asp Glu Lys Ala Thr Asn Pro Ile Val Pro
            180                 185                 190

Ser Phe Asp Met Ser Asn Glu Gly Ser Tyr Phe Phe Gly Asp Asn Ala
        195                 200                 205

Glu Glu Phe Asp Ser
    210
```